US012692510B2

(12) United States Patent
Larue et al.

(10) Patent No.: US 12,692,510 B2
(45) Date of Patent: Jul. 28, 2026

(54) METHODS AND COMPOSITIONS FOR GENE EXPRESSION IN PLANTS

(71) Applicant: Monsanto Technology LLC, St. Louis, MO (US)

(72) Inventors: Clayton T. Larue, Chesterfield, MO (US); Joel E. Ream, Edmonds, WA (US); Aabid Shariff, Durham, NC (US); Yuanji Zhang, Weldon Spring, MO (US); Xuefeng Zhou, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 390 days.

(21) Appl. No.: 18/182,009

(22) Filed: Mar. 10, 2023

(65) Prior Publication Data

US 2023/0340519 A1     Oct. 26, 2023

Related U.S. Application Data

(62) Division of application No. 16/931,427, filed on Jul. 16, 2020, now Pat. No. 11,629,358, which is a division of application No. 15/660,660, filed on Jul. 26, 2017, now Pat. No. 10,745,712.

(60) Provisional application No. 62/368,840, filed on Jul. 29, 2016.

(51) Int. Cl.
*C12N 15/82*         (2006.01)
*C12N 9/02*          (2006.01)

(52) U.S. Cl.
CPC ......... *C12N 15/8274* (2013.01); *C12N 9/001* (2013.01); *C12N 15/8221* (2013.01); *C12Y 103/03004* (2013.01)

(58) Field of Classification Search
None
See application file for complete search history.

(56) References Cited

U.S. PATENT DOCUMENTS

| | | | |
|---|---|---|---|
| 5,767,373 A | 6/1998 | Ward et al. |
| 5,939,602 A | 8/1999 | Volrath et al. |
| 6,023,012 A | 2/2000 | Volrath |
| 6,084,155 A | 7/2000 | Volrath et al. |
| 6,905,852 B1 | 6/2005 | Horikoshi et al. |
| 7,250,561 B1 | 7/2007 | Pallett et al. |
| 7,586,023 B1 | 9/2009 | Boynton et al. |
| 10,370,677 B2 | 8/2019 | Evdokimov et al. |
| 10,378,023 B2 | 8/2019 | Evdokimov et al. |
| 10,745,712 B2 | 8/2020 | Larue et al. |
| 11,124,803 B2 | 9/2021 | Larue et al. |
| 11,198,886 B2 | 12/2021 | Evdokimov et al. |
| 11,319,551 B2 | 5/2022 | Evdokimov et al. |
| 11,629,358 B2 | 4/2023 | Larue et al. |
| 12,123,009 B2 | 10/2024 | Evdokimov et al. |

| | | | |
|---|---|---|---|
| 2002/0042932 A1 | 4/2002 | Back et al. |
| 2003/0233675 A1 | 12/2003 | Cao et al. |
| 2004/0088753 A1 | 5/2004 | Shimizu et al. |
| 2007/0050863 A1 | 3/2007 | Tranel et al. |
| 2010/0100988 A1 | 4/2010 | Tranel et al. |
| 2012/0304336 A1 | 11/2012 | Bourett et al. |
| 2013/0007924 A1 | 1/2013 | Meade et al. |
| 2014/0123340 A1 | 5/2014 | Aponte et al. |
| 2014/0259212 A1 | 9/2014 | Plesch et al. |
| 2015/0252379 A1 | 9/2015 | Hutzler et al. |
| 2016/0029644 A1 | 2/2016 | Tao |
| 2016/0194655 A1 | 7/2016 | Aponte et al. |
| 2016/0345606 A1 | 12/2016 | Fruhauf et al. |
| 2016/0374339 A1 | 12/2016 | Aponte et al. |
| 2017/0037427 A1 | 2/2017 | Evdokimov et al. |
| 2017/0058290 A1 | 3/2017 | Evdokimov et al. |
| 2017/0175131 A1 | 6/2017 | Ellis et al. |
| 2019/0185873 A1 | 6/2019 | Larue et al. |
| 2022/0033839 A1 | 2/2022 | Larue et al. |
| 2022/0127634 A1 | 4/2022 | Evdokimov et al. |
| 2025/0092413 A1 | 3/2025 | Evdokimov et al. |

FOREIGN PATENT DOCUMENTS

| | | |
|---|---|---|
| JP | H1118775 | 1/1999 |
| JP | 2015/519913 | 7/2015 |
| KR | 20050099705 | 3/2006 |
| WO | 199534659 | 6/1995 |
| WO | 1995034659 | 12/1995 |
| WO | 1997041228 | 11/1997 |
| WO | 199833927 | 1/1998 |
| WO | 1998033927 | 8/1998 |
| WO | 2001026458 | 4/2001 |
| WO | 01/68826 | 9/2001 |
| WO | 2011075586 | 6/2011 |

(Continued)

OTHER PUBLICATIONS

Larue et al, Pest. Manag. Sci. (2020) 756:1031-1038.*
Lee et al, Plant Physiology (2006) 140: 466-483.*
GenBank Accession No. XM_021983162, submitted on Aug. 1, 2017.*
UniProt Accession No. A0A085G3K7, submitted on Oct. 29, 2014.*
USPTO: Response to Final Office Action regarding U.S. Appl. No. 17/404,857, filed Feb. 1, 2024.
USPTO: Advisory Action regarding U.S. Appl. No. 17/404,857, mailed Feb. 8, 2024.
GenBank Accession No. EHT98690.1, dated Feb. 22, 2012.
Myouga, et al., "An *Arabidopsis* chloroplast-targeted Hsp101 homologue, APG6, has an essential role in chloroplast development as well as heat-stress response," *Plant J.*, 48(2):249-260, 2006.

(Continued)

*Primary Examiner* — Mykola V. Kovalenko
(74) *Attorney, Agent, or Firm* — Dentons US LLP; Elizabeth Millard

(57)          ABSTRACT

The invention provides recombinant DNA molecules useful for providing efficient expression of proteins in transgenic plants, as well as compositions and methods for using the recombinant DNA molecules. In particular embodiments, the invention provides recombinant DNA molecules and constructs comprising sequences encoding transit peptides and operably linked sequences conferring herbicide tolerance.

31 Claims, No Drawings
Specification includes a Sequence Listing.

(56)        References Cited

FOREIGN PATENT DOCUMENTS

| WO | 2012021797 | 2/2012 |
|----|-----------|--------|
| WO | 2012080975 | 6/2012 |
| WO | 2012/158535 | 11/2012 |
| WO | 2013012788 | 1/2013 |
| WO | 2013/189984 | 12/2013 |
| WO | 2015/022640 | 2/2015 |
| WO | 2015/023846 | 2/2015 |
| WO | 2015022636 | 2/2015 |
| WO | 2015092706 | 6/2015 |
| WO | 2016099153 | 6/2016 |
| WO | 2016203377 | 12/2016 |
| WO | 2017198859 | 11/2017 |

OTHER PUBLICATIONS

Taverniers, et al., "Gene stacking in transgenic plants: towards compliance between definitions, terminology, and detection within the EU regulatory framework," Environ. Biosafety Res., 7:197-218, 2008.
USPTO: Non-Final Office Action regarding U.S. Appl. No. 17/404,857, mailed Apr. 14, 2023.
USPTO: Notice of Allowance regarding U.S. Appl. No. 16/218,822, dated May 14, 2021.
Extended European Search Report regarding European App. No. 20200866.0, dated May 26, 2021.
Response to Restriction Requirement regarding U.S. Appl. No. 17/404,857, filed Jan. 23, 2023.
GenBank Accession No. AFR01602, dated Jan. 30, 2014.
GenBank Accession No. AFI92445, dated Jan. 19, 2018.
Restriction Requirement regarding U.S. Appl. No. 17/404,857, mailed Nov. 30, 2022.
GenBank Accession No. XP_010456129.1, dated Nov. 29, 2016.
UniProt Accession No. A0A0D2V233, submitted Apr. 29, 2015.
Laure et al.; U.S. Appl. No. 16/218,822, filed Dec. 13, 2018.
Evdokimov et al.; U.S. Appl. No. 16/452,305, filed Jun. 25, 2019.
Evdokimov et al.; U.S. Appl. No. 16/452,327, filed Jun. 25, 2019.
Evdokimov et al.; U.S. Appl. No. 16/452,349, filed Jun. 25, 2019.
International Search Report and Written Opinion regarding International Application No. PCT/US2017/043990, dated Nov. 27, 2017.
USPTO: Non-Final Office Action regarding U.S. Appl. No. 15/224,276, dated Feb. 15, 2019.
Response to Non-Final Office Action regarding U.S. Appl. No. 15/224,276, dated Apr. 5, 2019.
USPTO: Non-Final Office Action regarding U.S. Appl. No. 15/228,993, dated Feb. 27, 2019.
Response to Non-Final Office Action regarding U.S. Appl. No. 15/228,993, dated Apr. 5, 2019.
USPTO: Notice of Allowance regarding U.S. Appl. No. 15/224,276, dated May 1, 2019.
USPTO: Notice of Allowance regarding U.S. Appl. No. 15/228,993, dated May 1, 2019.
Partial Supplementary European Search Report regarding Europe Application No. 17835219.1 dated Dec. 17, 2019.
Emanuelsson et al., "Predicting Subcellular Localization of Proteins Based on their N-Terminal Amino Acid Sequence", J. Mol. Biol. 300(4):1005-1016, 2000.
Uni Prot Accession No. R0H9S5 9BRAS, submitted on Jun. 26, 2013.
Demarco et al., Biochem. Biophys. Res. Comm. (2003) 309:873-878.
USPTO: Notice of Allowance regarding U.S. Appl. No. 16/452,327, dated Aug. 13, 2021.
GenBank Accession No. AB029492, Pinacia oleracea SO-POX1 mRNA for photoporphyrinogen oxidase (Protox-I), 2000.
USPTO: Notice of Allowance regarding U.S. Appl. No. 16/452,349, dated Jan. 12, 2022.

Becker et al., The cab-m7 gene: a light-inducible, mesophyll-specific gene of maize, Plant Mol Biol, 20:49-60, 1992.
Boynton et al., Identification of Escherichia coli HemG as a novel, menadione-dependent flavodoxin with oxidase Activity, Biochemistry 48(29):6705-6711, 2009.
Boynton et al., Discovery of a gene involved in a third bacterial protoporphyrinogen oxidase activity through genomic analysis and functional complementation, Appl Environ Microbiol, 77:4795-4801, 2011.
Creissen et al., Simultaneous targeting of pea glutathione reductase and of a bacterial fusion protein to chloroplasts mitochondria, Plant J, 8:167-175, 1995.
Dailey et al., Expression of a cloned protoporphyrinogen oxidase, J Biol Chem, 269(2):813-815, 1994.
De Castro Silva Filho et al., Mitochondria! and chloroplast targeting sequences in tandem modify protein import in plant organelles, Plant Mol Biol, 30:769-780, 1996.
Della-Cioppa et al., Translocation of the precursor of 5-enolpyruvylshikimate-3-phosphate synthase into of higher plants in vitro, PNAS USA, 83:6873-6877, 1986.
EBI Accession No. ACU63901 dated Aug. 21, 2009.
Ecogene Accession No. EG11485, retrieved from the database Jan. 31, 2017.
GenBank Accession No. ABD52326, dated Aug. 18, 2006.
GenBank Accession No. CP001699, dated Dec. 24, 2013.
GenBank Accession No. CP002505, dated Jan. 7, 2015.
GenBank Accession No. JMPJ01000000.1, dated Jul. 28, 2014.
GenBank Accession No. ORJ22714.1, dated Apr. 14, 2017.
GenBank Accession No. WP_021498199, dated Jun. 2, 2019.
GenBank Accession No. WP_034794962, dated Jun. 20, 2019.
Glavina Del Rio et al., Complete genome sequence of Chitinophaga pinesis type strain (UQM 2034T), Stand Sci, 2(1):87-95, 2010.
Grossman et al., The herbicide Saflufenacil (Kixorlm) is a new inhibitor of protoporphyrinogen IX oxidase activity, Sci, 58:1-9, 2010.
Guo et al., Protein tolerance to random amino acid change, PNAS USA, 101:9205-9210, 2004.
Hansson et al., Cloning and characterization of the Bacillus subtilis hemEHY gene cluster, which encodes IX biosynthetic enzymes, J Bacteriol, 174:8081-8093, 1992.
Hao et al., Protoporphyrinogen oxidase inhibitor: An ideal target for herbicide discovery, Chimia (Aarau), 65:961-969, 2011.
Hara et al., The complete genome sequence of Pantoea ananatis AJ13355, an organism with great biological Appl. Microbiol. Biotechnol 93(1): 331-341, 2012.
U.S. Appl. No. 18/816,876, filed Aug. 27, 2024, Evdokimov et al.
USPTO: Response to Non-Final Office action regarding U.S. Appl. No. 17/404,857, filed Aug. 22, 2025.
USPTO: Notice of Allowance regarding U.S. Appl. No. 17/522,737, dated May 22, 2024.
GenBank Accession No. EOA20353.1, dated Mar. 21, 2015.
USPTO: Response to Non-Final Office Action regarding U.S. Appl. No. 17/404,857, filed Jul. 14, 2023.
USPTO: Final Office Action regarding U.S. Appl. No. 17/404,857, dated Nov. 1, 2023.
USPTO: Response to Non-Final Office Action regarding U.S. Appl. No. 17/522,737, filed Feb. 20, 2024.
USPTO: Non-Final Office Action regarding U.S. Appl. No. 17/522,737, mailed Nov. 21, 2023.
Evdokimov et al.; U.S. Appl. No. 17/522,737, filed Sep. 11, 2021.
Larue et al.; U.S. Appl. No. 17/404,857, filed Aug. 17, 2021.
Jacobs et al., Measurement of protoporphyrinogen oxidase activity, Curr Protoc Toxicol, 8.5.1-8.5.13, 1999.
Keskin et al., A new, structurally nonredundant, diverse data set of protein-protein interfaces and its implications, Sci., 13:1043-1055, 2004.
Klee et al., Cloning of an Arabidopsis thaliana gene encoding 5-enolpyruvylshikimate-3-phosphate synthase: analysis and manipulation to obtain glyphosate-tolerant plants, Mol Gen Genet, 210:437-442, 1987.
Matsumoto et al., Porphyrin intermediate involved in herbicidal action of delta-aminolevulinic acid on duckweed pauciostata Hegelm. ), Pestic Biochem Physiol, 48:214-221, 1994.

(56) References Cited

OTHER PUBLICATIONS

Nishimura et al., Cloning and identification of the hemG Gene Encoding protoporphyrinogen oxidase (PPO) of *coli* K-12, DNA Res, 2(1):1-8,1995.

Patzoldt et al., A codon deletion confers resistance to herbicides inhibiting protoporphyrinogen oxidase, Proc Natl Sci USA, 103:12329-12334, 2006.

USPTO: Notice of Allowance regarding U.S. Appl. No. 16/452,305, dated Sep. 28, 2021.

Sasarman et al., Mapping of a new hem gene in *Escherichia coli* K12, J Gen Microbiol, 113:297-303, 1979.

Sasarman et al., Nucleotide sequence of the hemG gene involved in the protoporphyrinogen oxidase activity of *coli* K12, Can J Microbiol, 39:1155-1161, 1993.

Thorton et al., From structure to function: approaches and limitations, Nat Struct Biol, Suppl:991-994, 2000.

UniProtKB Accession No. A0A093V7L1, dated Nov. 26, 2014.

UniProtKB Accession No. C6DHI2, dated Sep. 1, 2009.

UniProtKB Accession No. C7PKZ1, dated Oct. 13, 2009.

USPTO: Non-Final Office Action regarding U.S. Appl. No. 16/452,305, dated Apr. 6, 2021.

USPTO: Non-Final Office Action regarding U.S. Appl. No. 16/452,349, dated May 21, 2021.

USPTO: Response to Non-Final Office Action regarding U.S. Appl. No. 16/452,305, Jun. 17, 2021.

USPTO: Response to Non-Final Office Action regarding U.S. Appl. No. 16/452,349, Aug. 6, 2021.

USPTO: Final Office Action regarding U.S. Appl. No. 16/452,305, issued Jul. 14, 2021.

USPTO: Final Office Action regarding U.S. Appl. No. 16/452,349, dated Sep. 20, 2021.

USPTO: Response to Final Office Action regarding U.S. Appl. No. 16/452,305, filed Sep. 14, 2021.

USPTO: Response to Final Office Action regarding U.S. Appl. No. 16/452,349, filed Dec. 17, 2021.

Zwerschke et al., Leishmania major possesses a unique HemG-type protoporphyrinogen IX oxidase, BioSci Rep art:300124, 2014.

USPTO: Response to Final Office Action regarding U.S. Appl. No. 17/404,857, filed Feb. 14, 2025.

USPTO: Non-Final Office Action regarding U.S. Appl. No. 17/404,857, mailed Apr. 25, 2025.

USPTO: Final Office Action regarding U.S. Appl. No. 17/404,857, mailed Nov. 14, 2024.

GenBank Accession No. XP_012459125.1. chaperone protein ClpB3, chloroplastic [Gossypium raimondii], (2022).

UniProt Accession No. X2GVR1, dated Jun. 11, 2014.

UniProt Accession No. Q8EKR5, dated Mar. 1, 2003.

UniProt Accession No. A9DOK0, dated Feb. 5, 2008.

UniProt Accession No. X7E5G9, dated Jun. 11, 2014.

USPTO: Final Office Action regarding U.S. Appl. No. 17/404,857, mailed Dec. 12, 2025.

GenBank Accession No. ADD75372, dated Jan. 30, 2014.

USPTO: Response to Final Office Action regarding U.S. Appl. No. 17/404,857, filed Mar. 12, 2026.

* cited by examiner

SEQUENCE LISTING

```
Sequence total quantity: 297
SEQ ID NO: 1            moltype = AA  length = 68
FEATURE                 Location/Qualifiers
source                  1..68
                        mol_type = protein
                        organism = Arabidopsis thaliana
SEQUENCE: 1
MATATTTATA AFSGVVSVGT ETRRIYSFSH LQPSAAFPAK PSSFKSLKLK QSARLTRRLD   60
HRPFVVRC                                                            68

SEQ ID NO: 2            moltype = AA  length = 68
FEATURE                 Location/Qualifiers
source                  1..68
                        mol_type = protein
                        note = Recombinant
                        organism = synthetic construct
SEQUENCE: 2
MASSTTTATA AFSGVVSVGT ETRRIYSFSH LQPSAAFPAK PSSFKSLKLK QSARLTRRLD   60
HRPFVVRC                                                            68

SEQ ID NO: 3            moltype = AA  length = 35
FEATURE                 Location/Qualifiers
source                  1..35
                        mol_type = protein
```

-continued

```
                        organism = Gossypium raimondii
SEQUENCE: 3
MLNIAPSCVL ASGISKPVTK MASTENKDDH SSAKR                                        35

SEQ ID NO: 4            moltype = AA  length = 45
FEATURE                 Location/Qualifiers
source                  1..45
                        mol_type = protein
                        organism = Canavalia rosea
SEQUENCE: 4
MVAVFNDVVF PPSQTLLRPS FHSPTFFFSS PTPKFTRTRP NRILR                             45

SEQ ID NO: 5            moltype = AA  length = 60
FEATURE                 Location/Qualifiers
source                  1..60
                        mol_type = protein
                        organism = Senna obtusifolia
SEQUENCE: 5
MPAIAMASLT DLPSLSPTQT LVHSNTSFIS SRTCFVCPII PFPSRSQLNR RIACIRSNVR  60

SEQ ID NO: 6            moltype = AA  length = 55
FEATURE                 Location/Qualifiers
source                  1..55
                        mol_type = protein
                        organism = Nicotiana benthamiana
SEQUENCE: 6
MTTTPVANHP NIFTHRSPPS SSSSSPSAFL TRTSFLPFSS ICKRNSVNCN GWRTR                  55

SEQ ID NO: 7            moltype = AA  length = 34
FEATURE                 Location/Qualifiers
source                  1..34
                        mol_type = protein
                        organism = Brassica napus
SEQUENCE: 7
MDFSLLRPAS TQPFLSPFSN PFPRSRPYKP LNLR                                         34

SEQ ID NO: 8            moltype = AA  length = 37
FEATURE                 Location/Qualifiers
source                  1..37
                        mol_type = protein
                        organism = Adansonia digitata
SEQUENCE: 8
MAILIDLSLL RSSPSVFSFS KPNHRIPPRI YKPFKLR                                      37

SEQ ID NO: 9            moltype = AA  length = 47
FEATURE                 Location/Qualifiers
source                  1..47
                        mol_type = protein
                        note = cultivar = osiana
                        organism = Rosa hybrida
SEQUENCE: 9
MTTLSRLADL PSFAAPPPLL THRPPPSVFL TPKPTKPSPP HHFFKLR                           47

SEQ ID NO: 10           moltype = AA  length = 46
FEATURE                 Location/Qualifiers
source                  1..46
                        mol_type = protein
                        organism = Xanthium strumarium
SEQUENCE: 10
MSSLTDLPSL NHYRTCSPRP FPISRQTSSS INPNNLTTSN RWRRFR                            46

SEQ ID NO: 11           moltype = AA  length = 35
FEATURE                 Location/Qualifiers
source                  1..35
                        mol_type = protein
                        organism = Conyza canadensis
SEQUENCE: 11
MTSLTNFTPL KLTNPNYLNT TTTYNHRKLS NFRFR                                        35

SEQ ID NO: 12           moltype = AA  length = 45
FEATURE                 Location/Qualifiers
source                  1..45
                        mol_type = protein
                        organism = Amaranthus palmeri
SEQUENCE: 12
MSAMALSSSI LQCPPHSDIS FRFSAYTATR SPFFFGRPRK LSYIH                             45

SEQ ID NO: 13           moltype = AA  length = 47
FEATURE                 Location/Qualifiers
```

-continued

```
source                   1..47
                         mol_type = protein
                         organism = Spinacia oleracea
SEQUENCE: 13
MSAMALSSTM ALSLPQSSMS LSHCRHNRIT ILIPSSSLRR RGGSSIR                 47

SEQ ID NO: 14            moltype = AA  length = 61
FEATURE                  Location/Qualifiers
source                   1..61
                         mol_type = protein
                         organism = Kochia scoparia
SEQUENCE: 14
MSAMASPSII PQSFLQRSPT SLQSRSNYSK NHIIISISTP CSHGKNQRRF LRKTTHFRSI   60
H                                                                   61

SEQ ID NO: 15            moltype = AA  length = 34
FEATURE                  Location/Qualifiers
source                   1..34
                         mol_type = protein
                         organism = Setaria italica
SEQUENCE: 15
MVAAAMATAP SAGVPPLRGT RGPARFRIRG VSVR                               34

SEQ ID NO: 16            moltype = AA  length = 27
FEATURE                  Location/Qualifiers
source                   1..27
                         mol_type = protein
                         organism = Allium cepa
SEQUENCE: 16
MATTTAAAAV TISIPKKPVF IRRPRLR                                       27

SEQ ID NO: 17            moltype = AA  length = 33
FEATURE                  Location/Qualifiers
source                   1..33
                         mol_type = protein
                         organism = Digitaria sanguinalis
SEQUENCE: 17
MLSSTATASS ASSHHPYRSA SARASSTRLR PVL                                33

SEQ ID NO: 18            moltype = AA  length = 49
FEATURE                  Location/Qualifiers
source                   1..49
                         mol_type = protein
                         organism = Amaranthus palmeri
SEQUENCE: 18
MVIQSITHLS PKLALPSPLS ISAKNYPVAV MGNISEREEP TSAKRVAVV               49

SEQ ID NO: 19            moltype = AA  length = 48
FEATURE                  Location/Qualifiers
source                   1..48
                         mol_type = protein
                         organism = Spinacia oleracea
SEQUENCE: 19
MVILPVSQLS TNLGLSLVSP TKNNPVMGNV SERNQVNQPI SAKRVAVV                48

SEQ ID NO: 20            moltype = AA  length = 51
FEATURE                  Location/Qualifiers
source                   1..51
                         mol_type = protein
                         organism = Sedum album
SEQUENCE: 20
MLSLSSSHSS ATTYSLRQRY STTTKGSLNQ PEMASAENPS SKGSGKRGAV V            51

SEQ ID NO: 21            moltype = AA  length = 38
FEATURE                  Location/Qualifiers
source                   1..38
                         mol_type = protein
                         organism = Camelina sativa
SEQUENCE: 21
MELSLLRPST QSLLPSFSKP NLRLHVYKPL KLRCSVAG                           38

SEQ ID NO: 22            moltype = AA  length = 43
FEATURE                  Location/Qualifiers
source                   1..43
                         mol_type = protein
                         organism = Cucumis melo
SEQUENCE: 22
MATGATLLTD LPFRRPHPLT LLRPSDIPSF YPLHISLQNN RLR                     43
```

-continued

```
SEQ ID NO: 23          moltype = AA   length = 30
FEATURE                Location/Qualifiers
source                 1..30
                       mol_type = protein
                       organism = Eragrostis tef
SEQUENCE: 23
MVAAAATMAT AAPPLRAPQT LARPRRGSVR                                     30

SEQ ID NO: 24          moltype = AA   length = 32
FEATURE                Location/Qualifiers
source                 1..32
                       mol_type = protein
                       organism = Canavalia rosea
SEQUENCE: 24
MYVSPASNNP RACLKLSQEM ASSAADGNPR SV                                  32

SEQ ID NO: 25          moltype = AA   length = 42
FEATURE                Location/Qualifiers
source                 1..42
                       mol_type = protein
                       organism = Eragrostis tef
SEQUENCE: 25
MLSSAATASS ASAHPYRPAS ARASRSVLAM AGSDDTRAAP AR                       42

SEQ ID NO: 26          moltype = AA   length = 41
FEATURE                Location/Qualifiers
source                 1..41
                       mol_type = protein
                       organism = Andropogon gerardii
SEQUENCE: 26
MVAATAMATA ASAAAPLLNG TRRPARLRHR GLRVRCAAVA G                        41

SEQ ID NO: 27          moltype = AA   length = 24
FEATURE                Location/Qualifiers
source                 1..24
                       mol_type = protein
                       organism = Digitaria sanguinalis
SEQUENCE: 27
MLSSTATASS ASSHHPYRSA SARA                                           24

SEQ ID NO: 28          moltype = AA   length = 23
FEATURE                Location/Qualifiers
source                 1..23
                       mol_type = protein
                       organism = Eragrostis tef
SEQUENCE: 28
MLSSAATASS ASAHPYRPAS ARA                                            23

SEQ ID NO: 29          moltype = AA   length = 28
FEATURE                Location/Qualifiers
source                 1..28
                       mol_type = protein
                       organism = Amaranthus graecizans
SEQUENCE: 29
MSAMALSSSI LQCPPHSDIS FRFFAHTR                                       28

SEQ ID NO: 30          moltype = AA   length = 13
FEATURE                Location/Qualifiers
source                 1..13
                       mol_type = protein
                       organism = Ambrosia trifida
SEQUENCE: 30
MASPTIVDNQ KPA                                                       13

SEQ ID NO: 31          moltype = AA   length = 14
FEATURE                Location/Qualifiers
source                 1..14
                       mol_type = protein
                       organism = Brassica napus
SEQUENCE: 31
MASNAAADHD KLSG                                                      14

SEQ ID NO: 32          moltype = AA   length = 13
FEATURE                Location/Qualifiers
source                 1..13
                       mol_type = protein
                       note = cultivar = osiana
                       organism = Rosa hybrida
SEQUENCE: 32
```

-continued

```
MASPSPGDKH SSV                                                        13

SEQ ID NO: 33           moltype = AA   length = 55
FEATURE                 Location/Qualifiers
source                  1..55
                        mol_type = protein
                        organism = Amaranthus cruentus
SEQUENCE: 33
MKGRKRRITR ESAREMSAMA LSSSILQCPP HSDISFRFSA HSPTHSPIFF GRPRK          55

SEQ ID NO: 34           moltype = AA   length = 45
FEATURE                 Location/Qualifiers
source                  1..45
                        mol_type = protein
                        organism = Taraxacum officinale
SEQUENCE: 34
MTYLTDVGSL NCYRSWPSLP APGTVGALTS KNPRYLITYG PAHRK                     45

SEQ ID NO: 35           moltype = AA   length = 67
FEATURE                 Location/Qualifiers
source                  1..67
                        mol_type = protein
                        organism = Canavalia rosea
SEQUENCE: 35
MVAVFNDVVF PPSQTLLRPS FHSPTFFFSS PTPKFTRTRP NRILRCSIAQ ESTTSPSQSR    60
ESAPLDC                                                              67

SEQ ID NO: 36           moltype = AA   length = 52
FEATURE                 Location/Qualifiers
source                  1..52
                        mol_type = protein
                        organism = Eragrostis tef
SEQUENCE: 36
MVAAAATMAT AAPPLRAPQT LARPRRGSVR CAVVSDAAEA PAAPGARLSA DC             52

SEQ ID NO: 37           moltype = AA   length = 51
FEATURE                 Location/Qualifiers
source                  1..51
                        mol_type = protein
                        organism = Allium cepa
SEQUENCE: 37
MATTTAAAAV TISIPKKPVF IRRPRLRCSA VASDAIISNE APTGTTISAD C              51

SEQ ID NO: 38           moltype = AA   length = 77
FEATURE                 Location/Qualifiers
source                  1..77
                        mol_type = protein
                        organism = Taraxacum officinale
SEQUENCE: 38
MTYLTDVGSL NCYRSWPSLP APGTVGALTS KNPRYLITYG PAHRKCNSWR FRCSIAKDSP    60
ITPPISNESN SQPLLDC                                                   77

SEQ ID NO: 39           moltype = AA   length = 71
FEATURE                 Location/Qualifiers
source                  1..71
                        mol_type = protein
                        organism = Cucumis melo
SEQUENCE: 39
MATGATLLTD LPFRRPHPLT LLRPSDIPSF YPLHISLQNN RLRSHFRCSI AEGSTALSPS    60
NASSQSSILD C                                                         71

SEQ ID NO: 40           moltype = AA   length = 71
FEATURE                 Location/Qualifiers
source                  1..71
                        mol_type = protein
                        organism = Xanthium strumarium
SEQUENCE: 40
MSSLTDLPSL NHYRTCSPRP FPISRQTSSS INPNNLTTSN RWRRFRCSIA NDTPISPPIS    60
SDSTSHPFLD C                                                         71

SEQ ID NO: 41           moltype = AA   length = 38
FEATURE                 Location/Qualifiers
source                  1..38
                        mol_type = protein
                        organism = Camelina sativa
SEQUENCE: 41
MELSLLRPST QSLLPSFSKP NLRLHVYKPL KLRCSVAG                             38

SEQ ID NO: 42           moltype = AA   length = 45
```

```
FEATURE           Location/Qualifiers
source            1..45
                  mol_type = protein
                  organism = Taraxacum officinale
SEQUENCE: 42
MTYLTDVGSL NCYRSWPSLP APGTVGALTS KNPRYLITYG PAHRK              45

SEQ ID NO: 43     moltype = AA  length = 65
FEATURE           Location/Qualifiers
source            1..65
                  mol_type = protein
                  organism = Taraxacum officinale
SEQUENCE: 43
MTYLTDVGSL NCYRSWPSLP APGTVGALTS KNPRYLITYG PAHRKDSPIT PPISNESNSQ  60
PLLDC                                                         65

SEQ ID NO: 44     moltype = AA  length = 60
FEATURE           Location/Qualifiers
source            1..60
                  mol_type = protein
                  organism = Senna obtusifolia
SEQUENCE: 44
MPAIAIASLT DLPSLSPTQT LVHSNTSFIS SRTCFVCPII PFPSRSQLNR RIACIRSNVR  60

SEQ ID NO: 45     moltype = AA  length = 19
FEATURE           Location/Qualifiers
source            1..19
                  mol_type = protein
                  organism = Eragrostis tef
SEQUENCE: 45
MVAAAEAPAA PGARLSADC                                          19

SEQ ID NO: 46     moltype = AA  length = 25
FEATURE           Location/Qualifiers
source            1..25
                  mol_type = protein
                  organism = Allium cepa
SEQUENCE: 46
MATTTASDAI ISNEAPTGTT ISADC                                   25

SEQ ID NO: 47     moltype = AA  length = 12
FEATURE           Location/Qualifiers
source            1..12
                  mol_type = protein
                  organism = Allium cepa
SEQUENCE: 47
MATTGTTISA DC                                                 12

SEQ ID NO: 48     moltype = AA  length = 19
FEATURE           Location/Qualifiers
source            1..19
                  mol_type = protein
                  organism = Cucumis melo
SEQUENCE: 48
MATALSPSNA SSQSSILDC                                          19

SEQ ID NO: 49     moltype = AA  length = 32
FEATURE           Location/Qualifiers
source            1..32
                  mol_type = protein
                  organism = Xanthium strumarium
SEQUENCE: 49
MSSLTDLPSL NHYRTCSPPI SSDSTSHPFL DC                           32

SEQ ID NO: 50     moltype = DNA  length = 204
FEATURE           Location/Qualifiers
source            1..204
                  mol_type = other DNA
                  note = Recombinant
                  organism = synthetic construct
SEQUENCE: 50
atggccaccg ccaccactac cgccaccgct gcgttctccg gcgtggtgag cgtcggcact  60
gagacgcgca ggatctactc cttcagccac ctccagcctt ctgctgcgtt ccccgctaag  120
ccgtcttcgt tcaagagcct gaagctgaaa cagtccgcac gccttacccg gcgcctggac  180
cataggccat tcgttgtcag gtgc                                   204

SEQ ID NO: 51     moltype = DNA  length = 204
FEATURE           Location/Qualifiers
source            1..204
```

```
                              mol_type = other DNA
                              note = Recombinant
                              organism = synthetic construct
SEQUENCE: 51
atggcgacgg ctacgacgac tgctacggcg gcgtttagtg gtgtagtcag tgtaggaacg     60
gagactcgaa ggatttattc gttttctcat cttcaacctt ctgcggcttt tccggcgaag    120
cctagttcct tcaaatctct caaattaaag cagagcgcga ggctcacacg gcggcttgat    180
catcggccgt tcgttgtccg atgt                                           204

SEQ ID NO: 52                 moltype = DNA   length = 204
FEATURE                       Location/Qualifiers
source                        1..204
                              mol_type = other DNA
                              note = Recombinant
                              organism = synthetic construct
SEQUENCE: 52
atggcttcct ccacgacgac tgctacggcg gcgtttagtg gtgtagtcag tgtaggaacg     60
gagactcgaa ggatttattc gttttctcat cttcaacctt ctgcggcttt tccggcgaag    120
cctagttcct tcaaatctct caaattaaag cagagcgcga ggctcacacg gcggcttgat    180
catcggccgt tcgttgtccg atgt                                           204

SEQ ID NO: 53                 moltype = DNA   length = 105
FEATURE                       Location/Qualifiers
source                        1..105
                              mol_type = other DNA
                              note = Recombinant
                              organism = synthetic construct
SEQUENCE: 53
atgcttaaca ttgcgccgag ttgtgttttg gccagcggga tctctaagcc cgtgaccaag     60
atggctagca cggagaacaa ggacgaccac agcagcgcca agagg                    105

SEQ ID NO: 54                 moltype = DNA   length = 135
FEATURE                       Location/Qualifiers
source                        1..135
                              mol_type = other DNA
                              note = Recombinant
                              organism = synthetic construct
SEQUENCE: 54
atggtggctg tgttcaacga cgtagtgttc cctccttcgc agacccttct tcgcccctcc     60
ttccacagcc cgacgttctt ttttagcagc cccacaccaa agttcacgcg tacgaggccg    120
aatagaatac tgcgg                                                     135

SEQ ID NO: 55                 moltype = DNA   length = 180
FEATURE                       Location/Qualifiers
source                        1..180
                              mol_type = other DNA
                              note = Recombinant
                              organism = synthetic construct
SEQUENCE: 55
atgccggcga tagcaatggc ttctttaact gatctgccgt cgttgagccc cacacagacc     60
ctcgttcact cgaacacgag cttcatttca tcgagaacct gcttcgtctg tccgatcatc    120
cccttcccat cgaggtcgca actgaaccgc cgcatcgcct gcatcaggtc caacgtaagg    180

SEQ ID NO: 56                 moltype = DNA   length = 165
FEATURE                       Location/Qualifiers
source                        1..165
                              mol_type = other DNA
                              note = Recombinant
                              organism = synthetic construct
SEQUENCE: 56
atgaccacaa ccccggtagc aaaccacccc aatatcttca ctcaccgaag ccctccgtca     60
tcttcctcgt cctcacccag cgcgtttctg acccgcacct cctttctgcc cttctctagc    120
atctgcaaaa ggaactctgt gaactgcaat gggtggcgaa cccgg                    165

SEQ ID NO: 57                 moltype = DNA   length = 102
FEATURE                       Location/Qualifiers
source                        1..102
                              mol_type = other DNA
                              note = Recombinant
                              organism = synthetic construct
SEQUENCE: 57
atggacttca gtctccttag gcccgcttcg acgcagccgt tcctctcacc cttctccaat     60
cccttcccac ggagtaggcc atacaagcca cttaatctga gg                       102

SEQ ID NO: 58                 moltype = DNA   length = 111
FEATURE                       Location/Qualifiers
source                        1..111
                              mol_type = other DNA
                              note = Recombinant
```

```
                              organism = synthetic construct
SEQUENCE: 58
atggccatct tgattgacct ctccctcctg aggtcctctc cgtcggtctt ctccttctcc    60
aagccgaacc acaggatacc accgcggatc tacaagccgt tcaagttgag g             111

SEQ ID NO: 59                 moltype = DNA   length = 141
FEATURE                       Location/Qualifiers
source                        1..141
                              mol_type = other DNA
                              note = Recombinant
                              organism = synthetic construct
SEQUENCE: 59
atgaccacgc tttccaggct cgctgacctt ccttcttttg ctgccctcc tcctctcttg     60
acccaccggc cccctccttc agttttcctg actccgaagc cgacaaagcc gtcacctcca   120
catcacttct ttaaactgcg c                                             141

SEQ ID NO: 60                 moltype = DNA   length = 138
FEATURE                       Location/Qualifiers
source                        1..138
                              mol_type = other DNA
                              note = Recombinant
                              organism = synthetic construct
SEQUENCE: 60
atgtcgtccc taacggacct cccctccctg aatcactata ggacgtgcag cccgcgccca    60
ttccccatct ccaggcagac cagttcatca attaacccaa acaacttgac gaccagtaac   120
cgttggcgca ggttcagg                                                 138

SEQ ID NO: 61                 moltype = DNA   length = 105
FEATURE                       Location/Qualifiers
source                        1..105
                              mol_type = other DNA
                              note = Recombinant
                              organism = synthetic construct
SEQUENCE: 61
atgacgagtc tcaccaactt caccccgctc aagctgacga accccaacta cctcaacacg    60
accaccacct acaaccaccg taagctctcc aacttccggt tccgc                   105

SEQ ID NO: 62                 moltype = DNA   length = 135
FEATURE                       Location/Qualifiers
source                        1..135
                              mol_type = other DNA
                              note = Recombinant
                              organism = synthetic construct
SEQUENCE: 62
atgtcggcca tggcgctgtc cagcagcatt ctacagtgcc cgcctcactc agacatatcc    60
ttccgcttct cggcatacac tgccacccgc tcacctttct tcttcgggag gccaaggaaa   120
ctatcttaca tccac                                                    135

SEQ ID NO: 63                 moltype = DNA   length = 141
FEATURE                       Location/Qualifiers
source                        1..141
                              mol_type = other DNA
                              note = Recombinant
                              organism = synthetic construct
SEQUENCE: 63
atgtcggcca tggcattgag ctccaccatg gccctcagcc tgccacaatc tagcatgtcc    60
ttgagccact gcagacacaa tagaataact attctgatcc cctcgagctc gttacggcga   120
cggggaggtt cctcgatccg c                                             141

SEQ ID NO: 64                 moltype = DNA   length = 183
FEATURE                       Location/Qualifiers
source                        1..183
                              mol_type = other DNA
                              note = Recombinant
                              organism = synthetic construct
SEQUENCE: 64
atgtctgcta tggcgagccc ctccatcatc ccgcagtcgt tcctccagcg aagcccgacc    60
tccttgcaat ctcgatccaa ctactcgaag aaccacatca tcatctccat cagcacccg   120
tgctctcatg ggaagaacca gcgacgtttc ttgcgaaaga ccacccactt ccgatccatc   180
cac                                                                 183

SEQ ID NO: 65                 moltype = DNA   length = 102
FEATURE                       Location/Qualifiers
source                        1..102
                              mol_type = other DNA
                              note = Recombinant
                              organism = synthetic construct
SEQUENCE: 65
atggtcgccg ctgcaatggc tacagcccct tccgctggag tccctcctct tagagggaca    60
```

```
aggggtccag caaggtttag aatccgggga gtgtcagtgc gt                      102

SEQ ID NO: 66          moltype = DNA   length = 81
FEATURE                Location/Qualifiers
source                 1..81
                       mol_type = other DNA
                       note = Recombinant
                       organism = synthetic construct
SEQUENCE: 66
atggccacta ccacagcagc cgcggcggtc accatcagca ttcctaaaaa gcctgttttt   60
atccgccgcc cacgacttcg t                                             81

SEQ ID NO: 67          moltype = DNA   length = 99
FEATURE                Location/Qualifiers
source                 1..99
                       mol_type = other DNA
                       note = Recombinant
                       organism = synthetic construct
SEQUENCE: 67
atgttgtcta gcactgctac tgcaagttct gcatcctcac accacccota ccgttcagct   60
tctgcaaggg cttcgtcgac acgtctccgc ccggtcctt                         99

SEQ ID NO: 68          moltype = DNA   length = 147
FEATURE                Location/Qualifiers
source                 1..147
                       mol_type = other DNA
                       note = Recombinant
                       organism = synthetic construct
SEQUENCE: 68
atggtcattc agtcaattac gcatctttct cccaagctcg cactgccctc tccgctgtcg   60
atctcggcta agaactaccc ggtggccgtg atggggaata tcagcgagag ggaggagcca   120
acttctgcta aaagggtggc cgtggtg                                      147

SEQ ID NO: 69          moltype = DNA   length = 144
FEATURE                Location/Qualifiers
source                 1..144
                       mol_type = other DNA
                       note = Recombinant
                       organism = synthetic construct
SEQUENCE: 69
atggtcattc tacccgtgtc ccagctctcg actaatttgg ggctttccct tgttagtcca   60
acgaagaaca acccggtgat gggcaacgtg tccgagagga accaggtgaa ccagccaatc   120
tccgccaagc gcgttgctgt cgtg                                         144

SEQ ID NO: 70          moltype = DNA   length = 153
FEATURE                Location/Qualifiers
source                 1..153
                       mol_type = other DNA
                       note = Recombinant
                       organism = synthetic construct
SEQUENCE: 70
atgctctcac tgagcagctc ccactcatcc gcgacaacgt attctctccg gcaacggtac   60
tctacaacga ccaaaggttc gttgaaccag cctgagatgg ccagcgccga aaacccttcc   120
agcaagggat caggtaagag aggagcagtg gtg                               153

SEQ ID NO: 71          moltype = DNA   length = 114
FEATURE                Location/Qualifiers
source                 1..114
                       mol_type = other DNA
                       note = Recombinant
                       organism = synthetic construct
SEQUENCE: 71
atggagctga gcctcctaag accgtctact cagtcattgc tcccctcgtt cagcaagcct   60
aatttgcggc tccacgtgta caagcccctt aagctccgat gcagcgtagc cggt        114

SEQ ID NO: 72          moltype = DNA   length = 129
FEATURE                Location/Qualifiers
source                 1..129
                       mol_type = other DNA
                       note = Recombinant
                       organism = synthetic construct
SEQUENCE: 72
atggcgacag gagccaccct gctaacagac ctgccgttcc gtaggccgca cccgcttacg   60
ctcttacgtc cgagcgatat cccgtccttt tacccactac acataagcct acagaacaat   120
cgtttgagg                                                          129

SEQ ID NO: 73          moltype = DNA   length = 90
FEATURE                Location/Qualifiers
source                 1..90
```

-continued

```
                          mol_type = other DNA
                          note = Recombinant
                          organism = synthetic construct
SEQUENCE: 73
atggtggctg ctgcggcaac gatggctacc gccgcaccac cattaagagc gcctcaaact  60
cttgcacgac cgcgaagagg tagtgtgaga                                    90

SEQ ID NO: 74            moltype = DNA   length = 96
FEATURE                  Location/Qualifiers
source                   1..96
                          mol_type = other DNA
                          note = Recombinant
                          organism = synthetic construct
SEQUENCE: 74
atgtatgtgt cgcccgcctc gaacaaccca cgagcatgcc tcaagctgtc acaggaaatg  60
gcgtcttcag cagcagacgg caacccaaga tccgtt                             96

SEQ ID NO: 75            moltype = DNA   length = 126
FEATURE                  Location/Qualifiers
source                   1..126
                          mol_type = other DNA
                          note = Recombinant
                          organism = synthetic construct
SEQUENCE: 75
atgttgtcta gcgcagcgac agctagcagc gcaagtgctc atccttatcg acctgcttct  60
gcccgggcga gtaggagcgt gttggctatg gctggatcag acgatactag ggcagctcct 120
gcccgg                                                            126

SEQ ID NO: 76            moltype = DNA   length = 123
FEATURE                  Location/Qualifiers
source                   1..123
                          mol_type = other DNA
                          note = Recombinant
                          organism = synthetic construct
SEQUENCE: 76
atggtggctg cgaccgcaat ggccaccgct gcttcggctg ctgcgcctct cctaaacgga  60
acgagacgac cggcacgatt gagacataga ggtttacgtg ttaggtgtgc tgcagtagca 120
gga                                                               123

SEQ ID NO: 77            moltype = DNA   length = 72
FEATURE                  Location/Qualifiers
source                   1..72
                          mol_type = other DNA
                          note = Recombinant
                          organism = synthetic construct
SEQUENCE: 77
atgctttcta gcactgccac agcttcctca gcttctagcc accaccgta tcgttcagct   60
tcggcacgtg cc                                                       72

SEQ ID NO: 78            moltype = DNA   length = 69
FEATURE                  Location/Qualifiers
source                   1..69
                          mol_type = other DNA
                          note = Recombinant
                          organism = synthetic construct
SEQUENCE: 78
atgcttagct cagcagctac ggcctctagt gcttctgccc atccataccg tcccgcatct  60
gctcgagca                                                           69

SEQ ID NO: 79            moltype = DNA   length = 84
FEATURE                  Location/Qualifiers
source                   1..84
                          mol_type = other DNA
                          note = Recombinant
                          organism = synthetic construct
SEQUENCE: 79
atgagcgcga tggcgctttc ttctagcatc ttgcaatgcc cccccactc tgacatttct   60
ttccgcttct tcgcccacac tcgc                                          84

SEQ ID NO: 80            moltype = DNA   length = 39
FEATURE                  Location/Qualifiers
source                   1..39
                          mol_type = other DNA
                          note = Recombinant
                          organism = synthetic construct
SEQUENCE: 80
atggcgagtc ccacgatcgt tgacaaccag aagccagcg                          39

SEQ ID NO: 81            moltype = DNA   length = 42
```

```
FEATURE              Location/Qualifiers
source               1..42
                     mol_type = other DNA
                     note = Recombinant
                     organism = synthetic construct
SEQUENCE: 81
atggctagta acgccgctgc tgaccacgat aagctctcgg gt                          42

SEQ ID NO: 82        moltype = DNA  length = 39
FEATURE              Location/Qualifiers
source               1..39
                     mol_type = other DNA
                     note = Recombinant
                     organism = synthetic construct
SEQUENCE: 82
atggcgtcgc cgtccccagg cgacaaacat tcgtctgta                              39

SEQ ID NO: 83        moltype = DNA  length = 165
FEATURE              Location/Qualifiers
source               1..165
                     mol_type = other DNA
                     note = Recombinant
                     organism = synthetic construct
SEQUENCE: 83
atgaagggqc ggaagagacg gatcacgcgg gagtctgcaa gggagatgtc agcgatggca      60
ttgtcttcga gcatactcca gtgccctcct cactccgaca tctctttccg ttttagcgct      120
cactcaccga cacacagccc tatcttcttt gggcgtccca ggaaa                      165

SEQ ID NO: 84        moltype = DNA  length = 135
FEATURE              Location/Qualifiers
source               1..135
                     mol_type = other DNA
                     note = Recombinant
                     organism = synthetic construct
SEQUENCE: 84
atgacctacc tcactgatgt gggtagtctc aattgctaca ggtcctggcc tagcctaccg      60
gcccctggga cggtcggagc attgacttct aagaaccccc gctacttgat cacatacggt      120
ccggctcacc gaaag                                                       135

SEQ ID NO: 85        moltype = DNA  length = 201
FEATURE              Location/Qualifiers
source               1..201
                     mol_type = other DNA
                     note = Recombinant
                     organism = synthetic construct
SEQUENCE: 85
atggtggctg tgttcaacga cgtagtgttc cctccttcgc agacccttct tcgcccctcc      60
ttccacagcc cgacgttctt ttttagcagc cccacaccaa agttcacgcg tacgaggccg      120
aatagaaatac tgcggtgctc gattgcgcag gagtctacaa catcgccgtc gcagtcgcga     180
gagtcagctc cactcgattg t                                                201

SEQ ID NO: 86        moltype = DNA  length = 156
FEATURE              Location/Qualifiers
source               1..156
                     mol_type = other DNA
                     note = Recombinant
                     organism = synthetic construct
SEQUENCE: 86
atggtggctg ctgcggcaac gatggctacc gccgcaccac cattaagagc gcctcaaact      60
cttgcacgac cgcgaagagg tagtgtgaga tgtgccgtcg ttagcgatgc tgcagaagct      120
ccggctgctc ctggcgctag actctctgca gattgc                                156

SEQ ID NO: 87        moltype = DNA  length = 153
FEATURE              Location/Qualifiers
source               1..153
                     mol_type = other DNA
                     note = Recombinant
                     organism = synthetic construct
SEQUENCE: 87
atggccacta ccacagcagc cgcggcggtc accatcagca ttcctaaaaa gcctgttttt      60
atccgccgcc cacgacttcg ttgctcggca gttgcatccg acgcaatcat ctccaacgag      120
gcccctacag ggacgacaat ctcggctgac tgt                                   153

SEQ ID NO: 88        moltype = DNA  length = 231
FEATURE              Location/Qualifiers
source               1..231
                     mol_type = other DNA
                     note = Recombinant
                     organism = synthetic construct
```

-continued

```
SEQUENCE: 88
atgacctacc tcactgatgt gggtagtctc aattgctaca ggtcctggcc tagcctaccg    60
gcccctggga cggtcggagc attgacttct aagaaccccc gctacttgat cacatacggt   120
ccggctcacc gaaagtgcaa cagctggcgc ttccggtgct ctattgcaaa ggactcccc    180
atcacgcccc caatttcgaa cgagagcaat tcacagcccc tgctagactg c            231

SEQ ID NO: 89            moltype = DNA   length = 213
FEATURE                  Location/Qualifiers
source                   1..213
                         mol_type = other DNA
                         note = Recombinant
                         organism = synthetic construct
SEQUENCE: 89
atggcgacag gagccaccct gctaacagac ctgccgttcc gtaggccgca cccgcttacg    60
ctcttacgtc cgagcgatat cccgtccttt tacccactac acataagcct acagaacaat   120
cgtttgagga gtcatttcag gtgctcaatc gccgagggct cgacggcact gagcccatct   180
aacgcatcgt cgcaatcgag tatcttggac tgc                                213

SEQ ID NO: 90            moltype = DNA   length = 213
FEATURE                  Location/Qualifiers
source                   1..213
                         mol_type = other DNA
                         note = Recombinant
                         organism = synthetic construct
SEQUENCE: 90
atgtcgtccc taacggacct cccctccctg aatcactata ggacgtgcag cccgcgccca    60
ttccccatct ccaggcagac cagttcatca attaacccaa acaacttgac gaccagtaac   120
cgttggcgca ggttcaggtg ctctattgcg aacgacaccc cgatcagccc gccgatttcc   180
agcgactcta cttcccaccc tttcttggac tgt                                213

SEQ ID NO: 91            moltype = DNA   length = 114
FEATURE                  Location/Qualifiers
source                   1..114
                         mol_type = other DNA
                         note = Recombinant
                         organism = synthetic construct
SEQUENCE: 91
atggagctaa gcctcctaag accgtctact cagtcattgc tcccctcgtt cagcaagcct    60
aatttgcggc tccacgtgta caagcccctt aagctccgat gcagcgtagc cggt         114

SEQ ID NO: 92            moltype = DNA   length = 135
FEATURE                  Location/Qualifiers
source                   1..135
                         mol_type = other DNA
                         note = Recombinant
                         organism = synthetic construct
SEQUENCE: 92
atgacctacc tcactgatgt gggtagtctc aattgctaca ggtcttggcc tagcctaccg    60
gcccctggga cggtcggagc attgacttct aagaaccccc gctacttgat cacatacggt   120
ccggctcacc gaaag                                                    135

SEQ ID NO: 93            moltype = DNA   length = 195
FEATURE                  Location/Qualifiers
source                   1..195
                         mol_type = other DNA
                         note = Recombinant
                         organism = synthetic construct
SEQUENCE: 93
atgacctacc tcactgatgt gggtagtctc aattgctaca ggtcctggcc tagcctaccg    60
gcccctggga cggtcggagc attgacttct aagaaccccc gctacttgat cacatacggt   120
ccggctcacc gaaaggactc ccccatcacg cccccaattt cgaacgagag caattcacag   180
cccctgctag actgc                                                    195

SEQ ID NO: 94            moltype = DNA   length = 180
FEATURE                  Location/Qualifiers
source                   1..180
                         mol_type = other DNA
                         note = Recombinant
                         organism = synthetic construct
SEQUENCE: 94
atgccggcga tagcaatagc ttctttaact gatctgccgt cgttgagccc cacacagacc    60
ctcgttcact cgaacacgag cttcatttca tcgagaacct gcttcgtctg tccgatcatc   120
cccttcccat cgaggtcgca actgaaccgc cgcatcgcct gcatcaggtc caacgtaagg   180

SEQ ID NO: 95            moltype = DNA   length = 57
FEATURE                  Location/Qualifiers
source                   1..57
                         mol_type = other DNA
                         note = Recombinant
```

-continued

```
                           organism = synthetic construct
SEQUENCE: 95
atggtggctg ctgcggaagc tccggctgct cctggcgcta gactctctgc agattgc       57

SEQ ID NO: 96            moltype = DNA   length = 75
FEATURE                 Location/Qualifiers
source                  1..75
                        mol_type = other DNA
                        note = Recombinant
                        organism = synthetic construct
SEQUENCE: 96
atggccacta ccacagcatc cgacgcaatc atctccaacg aggcccctac agggacgaca       60
atctcggctg actgt                                                       75

SEQ ID NO: 97            moltype = DNA   length = 36
FEATURE                 Location/Qualifiers
source                  1..36
                        mol_type = other DNA
                        note = Recombinant
                        organism = synthetic construct
SEQUENCE: 97
atggccacta cagggacgac aatctcggct gactgt                                36

SEQ ID NO: 98            moltype = DNA   length = 57
FEATURE                 Location/Qualifiers
source                  1..57
                        mol_type = other DNA
                        note = Recombinant
                        organism = synthetic construct
SEQUENCE: 98
atggcgacgg cactgagccc atctaacgca tcgtcgcaat cgagtatctt ggactgc         57

SEQ ID NO: 99            moltype = DNA   length = 96
FEATURE                 Location/Qualifiers
source                  1..96
                        mol_type = other DNA
                        note = Recombinant
                        organism = synthetic construct
SEQUENCE: 99
atgtcgtccc taacggacct cccctccctg aatcactata ggacgtgcag cccgccgatt       60
tccagcgact ctacttccca ccctttcttg gactgt                                96

SEQ ID NO: 100           moltype = AA   length = 179
FEATURE                 Location/Qualifiers
source                  1..179
                        mol_type = protein
                        organism = Enterobacter cloacae
SEQUENCE: 100
MKALVLYSTR DGQTHAIASY IASCMKEKAE CDVIDLTHGE HVNLTQYDQV LIGASIRYGH       60
FNAVLDKFIK RNVDQLNNMP SAFFCVNLTA RKPEKRTPQT NPYVRKFLLA TPWQPALCGV      120
FAGALRYPRY RWIDKVMIQL IMRMTGGETD TSKEVEYTDW EQVKKFAEDF AKLSYKKAL      179

SEQ ID NO: 101           moltype = AA   length = 178
FEATURE                 Location/Qualifiers
source                  1..178
                        mol_type = protein
                        organism = Pantoea ananatis
SEQUENCE: 101
MKALILFSTR DGQTQKIASA IADEIKGQQS CDVINIQDAK TLDWQQYDRV LIGASIRYGH       60
FQPVVNEFVK HNLLALQQRV SGFFSVNLTA RKPEKRSPET NAYTVKFLAQ SPWQPDCCAV      120
FAGALYYPRY RWFDRVMIQF IMRMTGGETD ASKEVEYTDW QQVQRFARDF AQLPGKSY       178

SEQ ID NO: 102           moltype = AA   length = 177
FEATURE                 Location/Qualifiers
source                  1..177
                        mol_type = protein
                        organism = Pantoea stewartii
SEQUENCE: 102
MKALILYSTR DGQTRKIASS IADVIRQQQQ CDVLNIKDAS LPDWAQYDRV LIGASIRYGH       60
FQPVVDKFVK QHLHELQQRT SGFFSVNLTA RKPEKRSPET NAYTQKFLAH SPWQPDCCAV      120
FAGALYYPRY RWFDRVMIQL IMRMTGGETD STKEVEYTDW QQVSTFANDF AQLPGKS        177

SEQ ID NO: 103           moltype = AA   length = 181
FEATURE                 Location/Qualifiers
source                  1..181
                        mol_type = protein
                        organism = Escherichia coli
SEQUENCE: 103
MKTLILFSTR DGQTREIASY LASELKELGI QADVANVHRI EEPQWENYDR VVIGASIRYG       60
```

```
HYHSAFQEFV KKHATRLNSM PSAFYSVNLV ARKPEKRTPQ TNSYARKFLM NSQWRPDRCA 120
VIAGALRYPR YRWYDRFMIK LIMKMSGGET DTRKEVVYTD WEQVANFARE IAHLTDKPTL 180
K                                                                181

SEQ ID NO: 104           moltype = AA   length = 178
FEATURE                  Location/Qualifiers
source                   1..178
                         mol_type = protein
                         organism = Erwinia toletana
SEQUENCE: 104
MKALILFSSR EGQTREIASY IANSIKEEME CDVFNILRVE QIDWSQYDRV LIGGSIHYGH 60
FHPAVAKFVK RHLHELQQRS SGFFCVNLTA RKADKRTPQT NAYMRKFLLQ SPWQPDCCAV 120
FAGALRYTRY RWFDRVMIQL IMRMTGGETD TSKEVEYTDW TQVARFAQEF AHLPGKTQ   178

SEQ ID NO: 105           moltype = AA   length = 179
FEATURE                  Location/Qualifiers
source                   1..179
                         mol_type = protein
                         organism = Pectobacterium carotovorum
SEQUENCE: 105
MKALIVFSSR DGQTRAIASY IANTLKGTLE CDVVNVLNAN DIDLSQYDRV AIGASIRYGR 60
FHPAVNQFIR KHLTSLQQLP SAFFSVNLTA RKPEKRTIQT NAYTRKFLLN SPWQPDCCV 120
FAGALRYPRY RWFDRVMIQL IMRITGGETD STKEIEYTDW QQVARFAQDF AQLAAKNPA  179

SEQ ID NO: 106           moltype = AA   length = 179
FEATURE                  Location/Qualifiers
source                   1..179
                         mol_type = protein
                         organism = Shimwellia blattae
SEQUENCE: 106
MKTLILFSTR DGQTHKIARH IAGVLEEQGK ACELVDLLQP GEPDWSTVEC VVLGASIRYG 60
HFHKSFIRFV NTHAQRLNNM PGALFTVNLV ARKPEKQSPQ TNSYTRKFLA ASPWQPQRCQ 120
VFAGALRYPR YSWYDRMMIR LIMKMAGGET DTRKEVEYTD WQSVTRFARE IAQLPGETR  179

SEQ ID NO: 107           moltype = AA   length = 178
FEATURE                  Location/Qualifiers
source                   1..178
                         mol_type = protein
                         organism = Pantoea stewartii
SEQUENCE: 107
MKALILFSSR DGQTQLIASS IAKELEGKQA CDVLNILDTT NVEWTQYDRV LIGASIRYGH 60
FHPAVAEFVK RHQRELQQRS SGFFSVNLTA RKPEKRSPET NAYTAKFLNQ SPWQPDCCAV 120
FAGALRYPRY RWFDRIMIQL IMRMTGGETD SSKEVEYTDW QQVTRFAQEF ARLPGKTS   178

SEQ ID NO: 108           moltype = AA   length = 180
FEATURE                  Location/Qualifiers
source                   1..180
                         mol_type = protein
                         organism = Enterobacter cloacae
SEQUENCE: 108
MKTLILFSTR DGQTREIAAF LASELKEQGI YADVINLNRT EEIAWQEYDR VVIGASIRYG 60
HFHPAVDRFV KKHTETLNSL PGAFFSVNLV ARKAEKRTPQ TNSYTRKFLL NSPWKPAACA 120
VFAGALRYPR YRWYDRFMIR LIMKMTGGET DTRKEVVYTD WSQVASFARE IVQLTRSSRL 180

SEQ ID NO: 109           moltype = AA   length = 177
FEATURE                  Location/Qualifiers
source                   1..177
                         mol_type = protein
                         organism = Enterobacter mori
SEQUENCE: 109
MKILILFSTR DGQTREIAAS LASELKEQAF DVDVVNLHRA ENIAWEEYDG VVIGASIRYG 60
HFHSTLNSFV KKHQQALKKL PGAFYSVNLV ARKPEKRTPQ TNSYTRKFLL DSPWQPDLSA 120
VFAGALRYPR YNWYDRIMIR LIMKITGGET DTRKEVVYTD WQQVTHFAHE IVQLVRK    177

SEQ ID NO: 110           moltype = AA   length = 178
FEATURE                  Location/Qualifiers
source                   1..178
                         mol_type = protein
                         organism = Enterobacter cloacae
SEQUENCE: 110
KALVLYSTRD GQTHAIASYI ASCMKEKAEC DVIDLTHGEH VNLTQYDQVL IGASIRYGHF 60
NAVLDKFIKR NVDQLNNMPS AFFCVNLTAR KPEKRTPQTN PYVRKFLLAT PWQPALCGVF 120
AGALRYPRYR WIDKVMIQLI MRMTGGETDT SKEVEYTDWE QVKKFAEDFA KLSYKKAL   178

SEQ ID NO: 111           moltype = AA   length = 177
FEATURE                  Location/Qualifiers
source                   1..177
                         mol_type = protein
                         organism = Pantoea ananatis
```

```
SEQUENCE: 111
KALILFSTRD GQTQKIASAI ADEIKGQQSC DVINIQDAKT LDWQQYDRVL IGASIRYGHF   60
QPVVNEFVKH NLLALQQRVS GFFSVNLTAR KPEKRSPETN AYTVKFLAQS PWQPDCCAVF  120
AGALYYPRYR WFDRVMIQFI MRMTGGETDA SKEVEYTDWQ QVQRFARDFA QLPGKSY     177

SEQ ID NO: 112          moltype = AA  length = 180
FEATURE                 Location/Qualifiers
source                  1..180
                        mol_type = protein
                        organism = Escherichia coli
SEQUENCE: 112
KTLILFSTRD GQTREIASYL ASELKELGIQ ADVANVHRIE EPQWENYDRV VIGASIRYGH   60
YHSAFQEFVK KHATRLNSMP SAFYSVNLVA RKPEKRTPQT NSYARKFLMN SQWRPDRCAV  120
IAGALRYPRY RWYDRFMIKL IMKMSGGETD TRKEVVYTDW EQVANFAREI AHLTDKPTLK  180

SEQ ID NO: 113          moltype = AA  length = 177
FEATURE                 Location/Qualifiers
source                  1..177
                        mol_type = protein
                        organism = Erwinia toletana
SEQUENCE: 113
KALILFSSRE GQTREIASYI ANSIKEEMEC DVFNILRVEQ IDWSQYDRVL IGGSIHYGHF   60
HPAVAKFVKR HLHELQQRSS GFFCVNLTAR KADKRTPQTN AYMRKFLLQS PWQPDCCAVF  120
AGALRYTRYR WFDRVMIQLI MRMTGGETDT SKEVEYTDWT QVARFAQEFA HLPGKTQ     177

SEQ ID NO: 114          moltype = AA  length = 178
FEATURE                 Location/Qualifiers
source                  1..178
                        mol_type = protein
                        organism = Pectobacterium carotovorum
SEQUENCE: 114
KALIVFSSRD GQTRAIASYI ANTLKGTLEC DVVNVLNAND IDLSQYDRVA IGASIRYGRF   60
HPAVNQFIRK HLTSLQQLPS AFFSVNLTAR KPEKRTIQTN AYTRKFLLNS PWQPDLCCVF  120
AGALRYPRYR WFDRVMIQLI MRITGGETDS TKEIEYTDWQ QVARFAQDFA QLAAKNPA    178

SEQ ID NO: 115          moltype = AA  length = 178
FEATURE                 Location/Qualifiers
source                  1..178
                        mol_type = protein
                        organism = Shimwellia blattae
SEQUENCE: 115
KTLILFSTRD GQTHKIARHI AGVLEEQGKA CELVDLLQPG EPDWSTVECV VLGASIRYGH   60
FHKSFIRFVN THAQRLNNMP GALFTVNLVA RKPEKQSPQT NSYTRKFLAA SPWQPQRCQV  120
FAGALRYPRY SWYDRMMIRL IMKMAGGETD TRKEVEYTDW QSVTRFAREI AQLPGETR    178

SEQ ID NO: 116          moltype = AA  length = 179
FEATURE                 Location/Qualifiers
source                  1..179
                        mol_type = protein
                        organism = Enterobacter cloacae
SEQUENCE: 116
KTLILFSTRD GQTREIAAFL ASELKEQGIY ADVINLNRTE EIAWQEYDRV VIGASIRYGH   60
FHPAVDRFVK KHTETLNSLP GAFFSVNLVA RKAEKRTPQT NSYTRKFLLN SPWKPAACAV  120
FAGALRYPRY RWYDRFMIRL IMKMTGGETD TRKEVVYTDW SQVASFAREI VQLTRSSRL   179

SEQ ID NO: 117          moltype = AA  length = 178
FEATURE                 Location/Qualifiers
source                  1..178
                        mol_type = protein
                        note = Recombinant
                        organism = synthetic construct
SEQUENCE: 117
KALVLYSTRD GQTHAIASYI ASCMKEKAEC DVIDLTHGEH VNLTQYDQVL IGANIRYGHF   60
NAVLDKFIKR NVDQLNNMPS AFFCVNLTAR KPEKRTPQTN PYVRKFLLAT PWQPALCGVF  120
AGALRYPRYR WIDKVMIQLI MRMTGGETDT SKEVEYTDWE QVKKFAEDFA KLSYKKAL    178

SEQ ID NO: 118          moltype = AA  length = 172
FEATURE                 Location/Qualifiers
source                  1..172
                        mol_type = protein
                        note = Recombinant
                        organism = synthetic construct
SEQUENCE: 118
KALVLYSTRD GQTHAIASYI ASCMKEKAEC DVIDLTHGEH VNLTQYDQVL IGASIRYGHF   60
NAVLDKFIKR NVDQLNNMPS AFFCVNLTAR KPEKRTPQTN PYVRKFLLAT PWQPALCGVF  120
AGALRYPRYR WIDKVMIQLI MRMTGGETDT SKEVEYTDWE QVKKFAEDFA KL          172

SEQ ID NO: 119          moltype = AA  length = 179
FEATURE                 Location/Qualifiers
```

```
source                   1..179
                         mol_type = protein
                         note = Recombinant
                         organism = synthetic construct
SEQUENCE: 119
KTLILFSTRD GQTREIAAFL ASELKEQGIY ADVINLNRTE EIAWQEYDRV VIGASIRYGH   60
FHPAVDRFVK KHTETLNSLP GAFFSVNLVA RKAEKRTPQT NSYTRKFLLN SPWKPAACAV  120
FAGALRYPRY RWYDRFMIRL IMKMTGGETD TRKEVVYTDW SQIASFAREI VQLTRSSRL   179

SEQ ID NO: 120          moltype = AA  length = 504
FEATURE                 Location/Qualifiers
source                  1..504
                        mol_type = protein
                        organism = Amaranthus tuberculatus
SEQUENCE: 120
MGNISEREEP TSAKRVAVVG AGVSGLAAAY KLKSHGLSVT LFEADSRAGG KLKTVKKDGF   60
IWDEGANTMT ESEAEVSSLI DDLGLREKQQ LPISQNKRYI ARDGLPVLLP SNPAALLTSN  120
ILSAKSKLQI MLEPFLWRKH NATELSDEHV QESVGEFFER HFGKEFVDYV IDPFVAGTCG  180
GDPQSLSMHH TFPEVWNIEK RFGSVFAGLI QSTLLSKKEK GGENASIKKP RVRGSFSFQG  240
GMQTLVDTMC KQLGEDELKL QCEVLSLSYN QKGIPSLGNW SVSSMSNNTS EDQSYDAVVV  300
TAPIRNVKEM KIMKFGNPFS LDFIPEVTYV PLSVMITAFK KDKVKRPLEG FGVLIPSKEQ  360
HNGLKTLGTL FSSMMFPDRA PSDMCLFTTF VGGSRNRKLA NASTDELKQI VSSDLQQLLG  420
TEDEPSFVNH LFWSNAFPLY GHNYDSVLRA IDKMEKDLPG FFYAGNHKGG LSVGKAMASG  480
CKAAELVISY LDSHIYVKMD EKTA                                         504

SEQ ID NO: 121          moltype = DNA  length = 537
FEATURE                 Location/Qualifiers
source                  1..537
                        mol_type = other DNA
                        note = Recombinant
                        organism = synthetic construct
SEQUENCE: 121
atgaaagcgc tggtgctgta tagcacccgc gatggccaga cccatgcgat tgcgagctat   60
attgcgagct gcatgaaaga aaaagcggaa tgcgatgtga ttgatctgac ccatggcgaa  120
catgtgaacc tgacccagta tgatcaggtg ctgattgcg cgagcattcg ctatggccat  180
tttaacgcgg tgctggataa atttattaaa cgcaacgtgg atcagctgaa caacatgccg  240
agcgcgtttt tttgcgtgaa cctgaccgcg cgcaaaccgg aaaaacgcac cccgcagacc  300
aacccgtatg tgcgcaaatt tctgctggcg accccgtggc agccggcgct gtgcggcgtg  360
tttgcgggcg cgctgcgcta tccgcgctat cgctggattg ataaagtgat gattcagctg  420
attatgcgca tgaccggcgg cgaaaccgat accagcaaag aagtggaata taccgattgg  480
gaacaggtga aaaaatttgc ggaagatttt gcgaaactga ctataaaaa agcgctg       537

SEQ ID NO: 122          moltype = DNA  length = 534
FEATURE                 Location/Qualifiers
source                  1..534
                        mol_type = other DNA
                        note = Recombinant
                        organism = synthetic construct
SEQUENCE: 122
atgaaagcgc tgattctgtt tagcacccgc gatggccaga cccagaaaat tgcgagcgcg   60
attgcggatg aaattaaagg ccagcagagc tgcgatgtga ttaacattca ggatgcgaaa  120
accctggatt ggcagcagta tgatcgcgtg ctgattggcg cgagcattcg ctatggccat  180
tttcagccgg tggtgaacga atttgtgaaa cataacctgc tggcgctgca gcagcgcgtg  240
agcggctttt ttagcgtgaa cctgaccgcg cgcaaaccgg aaaaacgcag cccggaaacc  300
aacgcgtata ccgtgaaatt tctggcgcag agcccggtgc agccggattg ctgcgcggtg  360
tttgcgggcg cgctgtatta tccgcgctat cgctggtttg atcgcgtgat gattcagttg  420
attatgcgca tgaccggcgg cgaaaccgat gcgagcaaag aagtggaata taccgattgg  480
cagcaggtgc agcgctttgc gcgcgatttt gcgcagctgc cgggcaaaag ctat        534

SEQ ID NO: 123          moltype = DNA  length = 531
FEATURE                 Location/Qualifiers
source                  1..531
                        mol_type = other DNA
                        note = Recombinant
                        organism = synthetic construct
SEQUENCE: 123
atgaaagcgc tgattctgta tagcacccgc gatggccaga cccgcaaaat tgcgagcagc   60
attgcggatg tgattcgcca gcagcagcag tgcgatgtgc tgaacattaa agatgcgagc  120
ctgccggatt gggcgcagta tgatccgtg ctgattggcg cgagcattcg ctatggccat  180
tttcagccgg tggtggataa atttgtgaaa cagcatctgc atgaactgca gcagcgcacc  240
agcggctttt ttagcgtgaa cctgaccgcg cgcaaaccgg aaaaacgcag cccggaaacc  300
aacgcgtata cccagaaatt tctggcgcat agcccgtggc agccggattg ctgcgcggtg  360
tttgcgggcg cgctgtatta tccgcgctat cgctggtttg atcgcgtgat gattcagctg  420
attatgcgca tgaccggcgg cgaaaccgat agcaccaaag aagtggaata taccgattgg  480
cagcaggtga gcacctttgc gaacgatttt gcgcagctgc cgggcaaaag c            531

SEQ ID NO: 124          moltype = DNA  length = 546
FEATURE                 Location/Qualifiers
source                  1..546
```

```
                                mol_type = genomic DNA
                                organism = Escherichia coli
SEQUENCE: 124
gtgaaaacat taattctttt ctcaacaagg gacggacaaa cgcgcgagat tgcctcctac    60
ctggcttcgg aactgaaaga actggggatc caggcggatg tcgccaatgt gcaccgcatt   120
gaagaaccac agtgggaaaa ctatgaccgt gtggtcattg gtgcttctat tcgctatggt   180
cactaccatt cagcgttcca ggaatttgtc aaaaaacatg cgacgcggct gaattcgatg   240
ccgagcgcct tttactccgt gaatctggtg gcgcgcaaac cggagaagcg tactccacag   300
accaacagct acgcgcgcaa gtttctgatg aactcgcaat ggcgtcccga tcgctgcgcg   360
gtcattgccg gggcgctgcg ttacccacgt tatcgctggt acgaccgttt tatgatcaag   420
ctgattatga agatgtcagg cggtgaaacg gatacgcgca aagaagttgt ctataccgat   480
tgggagcagg tggcgaattt cgcccgagaa atcgcccatt taaccgacaa accgacgctg   540
aaataa                                                             546

SEQ ID NO: 125              moltype = DNA   length = 534
FEATURE                     Location/Qualifiers
source                      1..534
                            mol_type = other DNA
                            note = Recombinant
                            organism = synthetic construct
SEQUENCE: 125
atgaaagcgc tgattctgtt tagcagccgc gaaggccaga cccgcgaaat tgcgagctat    60
attgcgaaca gcattaaaga agaaatggaa tgcgatgtgt ttaacattct gcgcgtggaa   120
cagattgatt ggagccagta tgatcgcgtg ctgattggcg gcagcattca ttatggccat   180
tttcatccgg cggtggcgaa atttgtgaaa cgccatctgc atgaactgca gcagcgcagc   240
agcggctttt tttgcgtgaa cctgaccgcg cgcaaagcgg ataaacgcac cccgcagacc   300
aacgcgtata tgcgcaaatt tctgctgcag agcccgtggc agccggattg ctgcgcggtg   360
tttgcgggcg cgctgcgcta tacccgctat cgctggtttg atcgcgtgat gattcagctg   420
attatgcgca tgaccggcgg cgaaaccgat accagcaaag aagtggaata taccgattgg   480
acccaggtgg cgcgctttgc gcaggaattt gcgcatctgc cgggcaaaac ccag         534

SEQ ID NO: 126              moltype = DNA   length = 537
FEATURE                     Location/Qualifiers
source                      1..537
                            mol_type = other DNA
                            note = Recombinant
                            organism = synthetic construct
SEQUENCE: 126
atgaaagcgc tgattgtgtt tagcagccgc gatggccaga cccgcgcgat tgcgagctat    60
attgcgaaca ccctgaaagg caccctggaa tgcgatgtgg tgaacgtgct gaacgcgaac   120
gatattgatc tgagccagta tgatcgcgtg gcgattggcg cgagcattcg ctatggccgc   180
tttcatccgg cggtgaacca gtttattcgc aaacatctga ccagcctgca gcagctgccg   240
agcggctttt ttagcgtgaa cctgaccgcg cgcaaaccgg aaaaacgcac cattcagacc   300
aacgcgtata cccgcaaatt tctgctgaac agcccggggc agccggatct gtgctgcgtg   360
tttgcgggcg cgctgcgcta tccgcgctat cgctggtttg atcgcgtgat gattcagctg   420
attatgcgca ttaccggcgg cgaaaccgat agcaccaaag aaattgaata taccgattgg   480
cagcaggtgg cgcgctttgc gcaggatttt gcgcagctgg cggcgaaaaa cccggcg      537

SEQ ID NO: 127              moltype = DNA   length = 537
FEATURE                     Location/Qualifiers
source                      1..537
                            mol_type = other DNA
                            note = Recombinant
                            organism = synthetic construct
SEQUENCE: 127
atgaagacct tgatcctatt ctccaccagg gacggccaaa cacacaagat cgcaaggcac    60
atcgcaggag tcctcgaaga gcaggggaag gcctgcgagt tggtcgatct gttacagccc   120
ggcgaaccaa ctggagtac cgttgaatgc gtcgttctag gggccagcat tagatatggt   180
cacttccata agtctttcat caggttcgta aacactcacg cgcagcgctt gaataatatg   240
ccaggcgccc tttttcacagt taacttagtc gcccgaaagc ccgagaagca gagtccacag   300
acgaactctt acacccgcaa gtttctcgc gcctcccctt ggcagccaca gcgatgccaa   360
gttttcgcgg gcgctttgag gtaccctagg tactcgtggt acgacagaat gatgatacgt   420
ttgataatga agatggccgg gggcgagact gacacaagga aggaggttga gtacactgac   480
tggcagtcgg tgactcggtt cgcgaggag atcgctcagc tgccgggaga gacgcgg      537

SEQ ID NO: 128              moltype = DNA   length = 534
FEATURE                     Location/Qualifiers
source                      1..534
                            mol_type = other DNA
                            note = Recombinant
                            organism = synthetic construct
SEQUENCE: 128
atgaaagcgc tgattctgtt tagcagccgc gatggccaga cccagctgat tgcgagcagc    60
attgcgaaag aactggaagg caaacaggcg tgcgatgtgc tgaacattct ggataccacc   120
aacgtggaat ggacccagta tgatcgcgtg ctgattggcg cgagcattcg ctatggccat   180
tttcatccgg cggtggcgga atttgtgaaa cgccatcagc gcgaactgca gcagcgcagc   240
agcggctttt ttagcgtgaa cctgaccgcg cgcaaaccgg aaaaacgcag cccggaaacc   300
aacgcgtata ccgcgaaatt tctgaaccag agcccgtggc agccggattg ctgcgcggtg   360
tttgcgggcg cgctgcgcta tccgcgctat cgctggtttg atcgcattat gattcagctg   420
```

```
attatgcgca tgaccggcgg cgaaaccgat agcagcaaag aagtggaata taccgattgg   480
cagcaggtga cccgctttgc gcaggaattt gcgcgcctgc cgggcaaaac cagc          534

SEQ ID NO: 129           moltype = DNA   length = 540
FEATURE                  Location/Qualifiers
source                   1..540
                         mol_type = other DNA
                         note = Recombinant
                         organism = synthetic construct
SEQUENCE: 129
atgaaaaccc tgattctgtt tagcacccgc gatggccaga cccgcgaaat tgcggcgttt   60
ctggcgagcg aactgaaaga acagggcatt tatgcggatg tgattaacct gaaccgcacc   120
gaagaaattg cgtggcagga atatgatcgc gtggtgattg gcgcgagcat tcgctatggc   180
cattttcatc cggccggtgga tcgctttgtg aaaaaacata ccgaaaccct gaacagcctg   240
ccgggcgcgt tttttagcgt gaacctggtg gcgcgcaaag cggaaaaacg cacccccgcag   300
accaacagct atacccgcaa atttctgctg aacagcccgt ggaaaccggc ggcgtgcgcg   360
gtgtttgcgg gcgcgctgcg ctatccgcgc tatcgctggt atgatcgctt tatgattcgc   420
ctgattatga aaatgaccgg cggcgaaacc gatacccgca aagaagtggt gtataccgat   480
tggagccagg tggcgagctt tgcgcgcgaa attgtgcagc tgacccgcag cagccgcctg   540

SEQ ID NO: 130           moltype = DNA   length = 531
FEATURE                  Location/Qualifiers
source                   1..531
                         mol_type = other DNA
                         note = Recombinant
                         organism = synthetic construct
SEQUENCE: 130
atgaaaattc tgattctgtt tagcacccgc gatggccaga cccgcgaaat tgcggcgagc   60
ctggcgagcg aactgaaaga acaggcgttt gatgtggatg tggtgaacct gcatcgcgcg   120
gaaaacattg cgtgggaaga atatgatggc gtggtgattg gcgcgagcat tcgctatggc   180
cattttcata gcacccctgaa cagctttgtg aaaaaacatc agcaggcgct gaaaaaactg   240
ccgggcgcgt tttatagcgt gaacctggtg gcgcgcaaac cggaaaaacg cacccccgcag   300
accaacagct atacccgcaa atttctgctg gatagcccgt ggcagccgga tctgagcgcg   360
gtgtttgcgg gcgcgctgcg ctatccgcgc tataactggt atgatcgcat tatgattcgc   420
ctgattatga aaattaccgg cggcgaaacc gatacccgca aagaagtggt gtataccgat   480
tggcagcagg tgacccattt tgcgcatgaa attgtgcagc tggtgcgcaa a             531

SEQ ID NO: 131           moltype = DNA   length = 540
FEATURE                  Location/Qualifiers
source                   1..540
                         mol_type = other DNA
                         note = Recombinant
                         organism = synthetic construct
SEQUENCE: 131
atgaaggcct tggtactgta ctcgacgcgg gacggccaga cccacgcaat tgcttcatac   60
atcgcctcct gcatgaagga gaaggccgaa tgcgacgtga tcgacctcac ccacgggggag   120
cacgtgaacc tcacccaata cgatcaggtg ctaatcggcg cgagtattcg ttacgggcac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta cccgcgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540

SEQ ID NO: 132           moltype = DNA   length = 537
FEATURE                  Location/Qualifiers
source                   1..537
                         mol_type = other DNA
                         note = Recombinant
                         organism = synthetic construct
SEQUENCE: 132
atgaaggcct tgatcctgtt ctctacacgc gacggacaga cacagaagat cgcatctgcc   60
atcgctgatg agataaaggg gcagcaatcg tgcgacgtga ttaacataca ggatgccaaa   120
accctcgact ggcagcagta cgaccgggta ctcatcggcg cctccattcg ttacgggcat   180
ttccagcccg ttgtgaatga gtttgtcaag cacaacctct tggccctaca gcagagagtt   240
tccggattct tctccgtgaa cttgacagcc cgaaagccag agaagcggag ccccgagact   300
aacgcttata cagtcaaatt cttggcgcag tcaccctggc aaccggactg ctgcgctgtt   360
tttgcggggg ccctgtacta cccacggtac cggtggttcg ataggggtgat gatacagttc   420
ataatgcgaa tgacgggggg agagaccgac gcatcgaaag aggtggagta cactgactgg   480
cagcaggtgc agcggttcgc gcgagacttc gcgcagttac cgggtaagtc ctactga      537

SEQ ID NO: 133           moltype = DNA   length = 534
FEATURE                  Location/Qualifiers
source                   1..534
                         mol_type = other DNA
                         note = Recombinant
                         organism = synthetic construct
SEQUENCE: 133
atgaaggcgc tgatcttgta ctcaaccagg gacggtcaga ctcgcaagat tgcaagtagc   60
```

-continued

```
attgcggacg tcatcaggca gcagcagcag tgcgacgtct taaacattaa agacgcatca   120
cttcctgact gggcccaata tgaccgagtg ctcatcggag ctagcatccg ttacgggcat   180
ttccagcccg ttgtagacaa gttcgtgaag cagcacttgc acgagcttca gcagcggacc   240
tccggcttct tctccgtgaa cctgacggcg aggaagcctg aaaaaaggag ccctgagacc   300
aatgcctaca cccagaaatt cttggcgcac tccccttggc agcccgattg ctgtgccgtt   360
ttcgcggggg ccctttacta ccccaggtac cgttggttcg accgggtgat gatccagttg   420
attatgcgca tgactggtgg agagaccgac tctaccaagg aagtggagta cactgactgg   480
cagcaggtga gtaccttcgc caacgatttt gcccagcttc caggcaagag ctaa         534
```

SEQ ID NO: 134        moltype = DNA  length = 546
FEATURE              Location/Qualifiers
source                1..546
                        mol_type = other DNA
                        note = Recombinant
                        organism = synthetic construct
SEQUENCE: 134

```
atgaagacct tgattctatt ctccacaagg gacggccaga ctagggagat cgcttcctac   60
ctggccagcg agctaaagga gcttggcatt caggcagacg tggctaacgt gcaccgaatt   120
gaggagccgc agtgggagaa ctacgatcgg gtcgtgatcg gcgccagcat ccggtatgga   180
cactaccaca gcgcgttcca ggagttcgtg aaaaagcacg cgacccgtct gaatagcatg   240
ccatcagcgt tctactcggt caacctcgtg gctcgtaagc ccgagaagcg gacaccccag   300
accaactcgt atgccaggaa gttccttatg aactcgcagt ggcgaccgga ccgctgcgcg   360
gtgatcgccg gtgcgctcag gtaccctcgt tataggtggt acgacaggta tatgattaaa   420
cttataatga aaatgagcgg cggagagacc gacaccagaa aagaggtggt ttacacagac   480
tgggagcagg tagcaaactt cgctagggag attgctcacc tcaccgacaa gccgaccttg   540
aagtaa                                                               546
```

SEQ ID NO: 135        moltype = DNA  length = 537
FEATURE              Location/Qualifiers
source                1..537
                        mol_type = other DNA
                        note = Recombinant
                        organism = synthetic construct
SEQUENCE: 135

```
atgaaggccc ttatactgtt cagttccaga gaaggccaga cgagggagat agcgagttac   60
attgccaact cgataaagga ggaaatggaa tgcgacgtgt tcaacatcct tcgtgtggag   120
cagatcgact ggtctcaata cgaccgcgtc ctgatcgggg gctcgataca ctacggccat   180
ttccacccag cggtggcaaa atttgtcaag aggcacctcc atgagttgca acagaggtct   240
tccggctttt tctgcgtcaa cctgacggcc aggaaggccg acaagcggac tccccagacc   300
aatgcctaca tgagaaagtt cttgttgcag tccccatggc aacccgattg ctgcgccgtg   360
tttgcggggg cccttaggta cacccgttac aggtggttcg acagggtaat gattcagctg   420
atcatgagga tgacgggcgg agagactgac acatcgaagg aggtggagta cacagactgg   480
acgcaggtcg cccgcttcgc gcaggagttc gcccatttgc ccggcaaaac tcagtga      537
```

SEQ ID NO: 136        moltype = DNA  length = 540
FEATURE              Location/Qualifiers
source                1..540
                        mol_type = other DNA
                        note = Recombinant
                        organism = synthetic construct
SEQUENCE: 136

```
atgaaggctc ttatcgtatt ctcttcgagg gatggccaaa cccgagcgat cgcgtcttat   60
attgctaata ccctcaaagg gaccctagag tgcgacgtcg tcaacgtcct caatgctaac   120
gacattgatt tgagccagta cgaccgtgtg gccattggcg cctccattcg ctacgggagg   180
ttccacccag ctgttaacca gtttatccgg aagcacctta cgagcctcca gcagctacca   240
tctgcgttct tctccgtgaa cctcacagct cggaagcccg agaagaggac tatacaaacc   300
aacgcgtaca ctaggaagtt tctactgaac tcgccgtggc agccggacct gtgctgcgtg   360
ttcgcgggag cccttcgcta tccccgttac aggtggtttg accgagtgat gattcaactc   420
ataatgcgca taacgggggg cgagacagac tccaccaagg agatcgagta caccgactgg   480
cagcaggtcg cgcgattcgc ccaggatttt gcacagcttg ccgcaaagaa cccggcatga   540
```

SEQ ID NO: 137        moltype = DNA  length = 540
FEATURE              Location/Qualifiers
source                1..540
                        mol_type = other DNA
                        note = Recombinant
                        organism = synthetic construct
SEQUENCE: 137

```
atgaagacct tgatcctatt ctccaccagg gacggccaaa cacacaagat cgcaaggcac   60
atcgcaggag tcctcgaaga gcaggggaag gcctgcgagt tggtcgatct gttacagccc   120
ggcgaaccag actggagtac cgttgaatgc gtcgttctag gggccagcat tagatatggt   180
cacttccata agtctttcat caggttcgta aacactcacg cgcagcgctt gaataatatg   240
ccaggcgccc ttttcacagt taacttagtc gcccgaaagc ccgagaagca gagtccacag   300
acgaactctt acacccgcaa gtttctcgcc gcctcccctt ggcagccaca gcgatgccaa   360
gttttcgcgc gcgctttgag gtaccctagg tactccgtgg acgacagaat gatgatacgt   420
ttgataatga agatggccgg gggcgagact gacacaagga aggaggttga gtacactgac   480
tggcagtcgg tgactcggtt cgcgagggag atcgctcagc tgccgggaga gacgcggtag   540
```

SEQ ID NO: 138        moltype = DNA  length = 537

```
FEATURE               Location/Qualifiers
source                1..537
                      mol_type = other DNA
                      note = Recombinant
                      organism = synthetic construct
SEQUENCE: 138
atgaaggccc taatttatt cagtagtagg gacggccaga cccagcttat agcatcgtct   60
atcgccaagg agctcgaagg gaagcaggcg tgcgacgtgt tgaatatcct cgacacgact  120
aatgtggagt ggacccagta cgaccgcgtg ctgattggag catccatccg gtacgggcac  180
tttcaccctg cggtcgccga gttcgtaaag cgtcaccagc gagagctaca gcagagaagt  240
agtggctttt tctctgtgaa cttgacggcc cgtaagccgg aaaagaggtc ccccgagact  300
aacgcctata ccgccaagtt ccttaaccaa agtccatggc agcctgactg ttcgcgctgtg 360
ttcgctgggg ctttgcgata ccctcggtac cgctggttcg acagaattat gatccagcta  420
atcatgcgga tgactggggg tgagacagat tcttcaaagg aggtcgagta caccgactgg  480
cagcaggtga cccgcttcgc gcaagagttc gccaggcttc cgggaaagac cagttga      537

SEQ ID NO: 139          moltype = DNA   length = 543
FEATURE               Location/Qualifiers
source                1..543
                      mol_type = other DNA
                      note = Recombinant
                      organism = synthetic construct
SEQUENCE: 139
atgaagaccc taatactgtt ctctacccgc gacgggcaga caagggagat cgccgcgttc   60
cttgcctcgg agctgaagga gcaggggatt tacgctgacg tcataaacct taaccggacg  120
gaggagatag cttggcagga gtatgataga gtcgtaatcg gggcgtcgat ccgatacggg  180
catttccacc ctgctgtcga ccgcttcgtg aagaagcaca cagagacact caactcactg  240
cccggcgcct ttttctctgt aaaccttgtt gcccggaaag ccgagaagag aacgccgcag  300
acgaactcat acaccaggaa gttcctatta aacagcccgt ggaagccagc ggcctgcgcg  360
gtctttgctg gggccctccg ctaccctaga taccgctggt acgacaggtt catgatacga  420
ctgattatga aaatgacagg cggggagacg gatacccgaa aggaggtagt ctacactgac  480
tggtcgcagg tcgcgtcgtt tgccagagag atagtccagt tgaccaggtc atcgcgcttg  540
tga                                                                 543

SEQ ID NO: 140          moltype = DNA   length = 534
FEATURE               Location/Qualifiers
source                1..534
                      mol_type = other DNA
                      note = Recombinant
                      organism = synthetic construct
SEQUENCE: 140
atgaagatat taatcctttt ctccacccgt gacggccaaa cccgtgagat tgcggcgtcc   60
ttggcgtccg aactcaagga gcaggcattc gacgtggacg tcgtcaacct tcaccgggcc  120
gagaacatcg catgggagga gtacgacggt gttgtcatcg gagcgtccat caggtacggc  180
cactttcata gtaccctgaa ctcatttgtc aagaagcatc agcaggctct taagaagctt  240
cccgggcctt tctacagcgt gaacctcgtc gcccggaagc ctgagaagcg cacaccgcag  300
accaatagct acacccgcaa gttcctcttg gattcccgt gcgagcccga cctttcagcc  360
gtgttcgccg gggcactcag gtaccctcgg tacaattggt acgaccgtat catgattaga  420
cttatcatga agattacagg cggcgagact gataccagga aggaagtagt ctacacagac  480
tggcagcagg tcactcactt tgctcacgag atcgtccagc tcgtgcggaa gtag         534

SEQ ID NO: 141          moltype = DNA   length = 537
FEATURE               Location/Qualifiers
source                1..537
                      mol_type = other DNA
                      note = Recombinant
                      organism = synthetic construct
SEQUENCE: 141
aaggccttgg tactgtactc gacgcgggac ggccagaccc acgcaattgc ttcatacatc   60
gcctcctgca tgaaggagaa ggccgaatgc gacgtgatcg acctcaccca cggggagcac  120
gtgaacctca cccaatacga tcaggtgcta atcggtgcga gtattcgtta cggccacttc  180
aacgccgtgc ttgacaagtt catcaagaga aacgtggatc agctgaacaa catgccaagc  240
gcgttcttct gcgtaaacct cacagcaagg aagcccgaga agcgtactcc ccagacaaac  300
ccttatgtcc gaaaattctt gcttgctacc ccctggcagc ccgcgttgtg gggagtgttc  360
gcagggcccc ttcggtaccc gcgataccgg tggatcgaca aggtgatgat ccagctaata  420
atgcggatga ctgggggaga gacagacacg agcaaggagg tcgagtacac ggattgggag  480
caggttaaga agttcgcgga ggattttgca aagctatcgt acaagaaggc cctctag      537

SEQ ID NO: 142          moltype = DNA   length = 534
FEATURE               Location/Qualifiers
source                1..534
                      mol_type = other DNA
                      note = Recombinant
                      organism = synthetic construct
SEQUENCE: 142
aaggccttga tcctgttctc tacacgcgac ggacagacac agaagatcgc atctgccatc   60
gctgatgaga taaaggggca gcaatcgtgc gacgtgatta acatacagga tgccaaaacc  120
ctcgactggc agcagtacga ccgggtactc atcggcgcct ccattcgtta cggcggcatttc  180
cagcccgttg tgaatgagtt tgtcaagcac aacctccttg ccctacagca gagagtttcc  240
```

-continued

```
ggattcttct ccgtgaactt gacagcccga aagccagaga agcggagccc cgagactaac   300
gcttatacag tcaaattctt ggcgcagtca ccctggcaac cggactgctg cgctgttttt   360
gcggggggccc tgtactaccc acggtaccgg tggttcgata gggtgatgat acagttcata   420
atgcgaatga cgggggggaga gaccgacgca tcgaaagagg tggagtacac tgactggcag   480
caggtgcagc ggttcgcgcg agacttcgcg cagttaccgg gtaagtccta ctga           534
```

SEQ ID NO: 143          moltype = DNA   length = 543
FEATURE                 Location/Qualifiers
source                  1..543
                        mol_type = other DNA
                        note = Recombinant
                        organism = synthetic construct
SEQUENCE: 143
```
aagaccttga ttctattctc cacaagggac ggccagacta gggagatcgc ttcctacctg   60
gccagcgagc taaaggagct tggcattcag gcagacgtgg ctaacgtgca ccgaattgag   120
gagccgcagt gggagaacta cgatcgggtc gtgatcggcg ccagcatccg gtatggacac   180
taccacagcg cgtccagga gttcgtgaaa aagcacgcga cccgtctgaa tagcatgcca   240
tcagcgttct actcggtcaa cctcgtggct cgtaagcccg agaagcggac accccagacc   300
aactcgtatg ccaggaagtt ccttatgaac tcgcagtggc gaccggaccg ctgcgcggtg   360
atcgccggtg cgctcaggta ccctcgttat aggtggtacg acaggtttat gattaaactt   420
ataatgaaaa tgagcggcgg agagaccgac accagaaaag aggtggttta cacagactgg   480
gagcaggtag caaacttcgc tagggagatt gctcacctca ccgacaagcc gaccttgaag   540
taa                                                                  543
```

SEQ ID NO: 144          moltype = DNA   length = 534
FEATURE                 Location/Qualifiers
source                  1..534
                        mol_type = other DNA
                        note = Recombinant
                        organism = synthetic construct
SEQUENCE: 144
```
aaggccctta tactgttcag ttccagagaa ggccagacga gggagatagc gagttacatt   60
gccaactcga taaaggagga aatggaatgc gacgtgttca acatccttcg tgtggagcag   120
atcgactggt ctcaatacga ccgcgtcctg atcgggggct cgatacacta cggccatttc   180
cacccagcgg tggcaaaatt tgtcaagagg cacctccatg agttgcaaca gaggtcttcc   240
ggcttttttct gcgtcaacct gacggccagg aaggccgaca agcggactcc ccagaccaat   300
gcctacatga gaaagttctt gttgcagtcc ccatggcaac ccgattgctg cgccgtgttt   360
gcggggggccc ttaggtacac ccgttacagg tggttcgaca gggtaatgat tcagctgatc   420
atgaggatga cgggcggaga gactgacaca tcgaaggagg tggagtacac agactggacg   480
caggtcgccc gcttcgcgca ggagttcgcc catttgcccg gcaaaactca gtga           534
```

SEQ ID NO: 145          moltype = DNA   length = 537
FEATURE                 Location/Qualifiers
source                  1..537
                        mol_type = other DNA
                        note = Recombinant
                        organism = synthetic construct
SEQUENCE: 145
```
aaggctctta tcgtattctc ttcgagggat ggccaaaccc gagcgatcgc gtcttatatt   60
gctaataccc tcaaagggac cctagagtgc gacgtcgtca acgtcctcaa tgctaacgac   120
attgatttga gccagtacga ccgtgtggcc attggcgcct ccattcgcta cgggaggttc   180
cacccagctg ttaaccagtt tatccggaag caccttacga gcctccagca gctaccatct   240
gcgttcttct ccgtgaacct cacagctcgg aagcccgaga agaggactat acaaaccaac   300
gcgtacacta ggaagtttct actgaactcg ccgtggcagc cggacctgtg ctgcgtgttc   360
gcgggagccc ttcgctatcc ccgttacagg tggtttgacc gagtgatgat tcaactcata   420
atgcgcataa cggggggcga gacagactcc accaaggaga tcgagtacac cgactggcag   480
caggtcgcgc gattcgccca ggattttgca cagcttgccg caaagaaccc ggcatga       537
```

SEQ ID NO: 146          moltype = DNA   length = 537
FEATURE                 Location/Qualifiers
source                  1..537
                        mol_type = other DNA
                        note = Recombinant
                        organism = synthetic construct
SEQUENCE: 146
```
aagaccttga tcctattctc caccagggac ggccaaacac acaagatcgc aaggcacatc   60
gcaggagtcc tcgaagagca gggggaaggcc tgcgagttgg tcgatctgtt acagcccggc   120
gaaccagact ggagtaccgt tgaatgcgtc gttctagggg ccagcattag atatggtcac   180
ttccataagt ctttcatcag gttcgtaaac actcacgcgc agcgcttgaa taatatgcca   240
ggcgcccttt tcacagttaa cttagtcgcc cgaaagcccg agaagcagag tccacagacg   300
aactcttaca cccgcaagtt tctgcccgcc tccccttggc agccacacgcg atgccaagtt   360
ttcgcgggcg ctttgaggta ccctaggtac tcgtggtacg acagaatgat gatacgtttg   420
ataatgaaga tggccggggg cgagactgac acaaggaagg aggttgagta cactgactgg   480
cagtcggtga ctcggttcgc gagggagatc gctcagctgc cggagagagc gcggtag        537
```

SEQ ID NO: 147          moltype = DNA   length = 540
FEATURE                 Location/Qualifiers
source                  1..540
                        mol_type = other DNA -continued

```
                            note = Recombinant
                            organism = synthetic construct
SEQUENCE: 147
aagaccctaa tactgttctc tacccgcgac gggcagacaa gggagatcgc cgcgttcctt    60
gcctcggagc tgaaggagca ggggatttac gctgacgtca taaaccttaa ccggacggag   120
gagatagctt ggcaggagta tgatagagtc gtaatcgggg cgtcgatccg atacgggcat   180
ttccaccctg ctgtcgaccg cttcgtgaag aagcacacag agacactcaa ctcactgccc   240
ggcgcctttt tctctgtaaa ccttgttgcc cggaaagccg agaagagaac gccgcagacg   300
aactcataca ccaggaagtt cctattaaac agcccgtgga agccagcggc ctgcgcggtc   360
tttgctgggg ccctccgcta ccctagatac cgctggtacg acaggttcat gatacgactg   420
attatgaaaa tgacaggcgg gggagacggat acccgaaagg aggtagtcta cactgactgg   480
tcgcaggtcg cgtcgtttgc cagagagata gtccagttga ccaggtcatc gcgcttgtga   540

SEQ ID NO: 148        moltype = DNA  length = 537
FEATURE               Location/Qualifiers
source                1..537
                      mol_type = other DNA
                      note = Recombinant
                      organism = synthetic construct
SEQUENCE: 148
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga gtattcgtta cggccacttc   180
aacgccgtgc ttgacaagtt catcaagaga aacgtggatc agctgaacaa catgccaagc   240
gcgttcttct gcgtaaacct cacggcaagg aagcccgaga agcgtactcc ccagacaaac   300
ccttatgtcc gaaaattctt gcttgctacc ccctggcaac ccgcgttgtg cggagtgttc   360
gcaggggccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatcgt acaagaaggc cctctag      537

SEQ ID NO: 149        moltype = DNA  length = 537
FEATURE               Location/Qualifiers
source                1..537
                      mol_type = other DNA
                      note = Recombinant
                      organism = synthetic construct
SEQUENCE: 149
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga atattcgtta cggccacttc   180
aacgccgtgc ttgacaagtt catcaagaga aacgtggatc agctgaacaa catgccaagc   240
gcgttcttct gcgtaaacct cacagcaagg aagcccgaga agcgtactcc ccagacaaac   300
ccttatgtcc gaaaattctt gcttgctacc ccctggcaac ccgcgttgtg cggagtgttc   360
gcaggggccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatcgt acaagaaggc cctctag      537

SEQ ID NO: 150        moltype = DNA  length = 537
FEATURE               Location/Qualifiers
source                1..537
                      mol_type = other DNA
                      note = Recombinant
                      organism = synthetic construct
SEQUENCE: 150
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga gtattcgtta cggccacttc   180
aacgccgtgc ttgacaagtt catcaagaga aacgtggatc agctgaacaa catgccaagc   240
gcgttcttct gcgtaaacct cacagcaagg aagcccgaga agcgtactcc ccagacaaac   300
ccttatgtcc gaaaattctt gcttgctacc ccctggcagc ccgcgttgtg cggagtgttc   360
gcaggggccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatagt acaagaaggc cctctag      537

SEQ ID NO: 151        moltype = DNA  length = 534
FEATURE               Location/Qualifiers
source                1..534
                      mol_type = other DNA
                      note = Recombinant
                      organism = synthetic construct
SEQUENCE: 151
aaggccttga tcctgttctc tacacgcgac ggacagacac agaagatcgc atctgccatc    60
gctgatgaga taaaggggca gcaatcgtgc gacgtgatta acatacagga tgccaaaacc   120
ctcgactggc agcagtacga ccgggtactc atcggcgcct ccattcgtta cgggcatttc   180
cagcccgttg tgaatgagtt tgtcaagcac aacctcttgg ccctacagca gagagtttcc   240
ggattcttct ccgtgaactt gacagcccga aagccagaga agcggagccc cgagactaac   300
gcttatacag tcaaattctt ggcgcagtca ccctggcaac cggactgctg cgctgttttt   360
gcggggggcc tgtactaccc acggtaccgg tggttcgata gggtgatgat acagttcata   420
atgcgaatga cgggggggga gaccgacgca tcgaaagagg tggagtacac tgactggcag   480
```

```
caggtgcagc ggttcgcgcg agacttcgcg cagttaccgg gtaagtccta ctga          534

SEQ ID NO: 152           moltype = DNA   length = 540
FEATURE                  Location/Qualifiers
source                   1..540
                         mol_type = other DNA
                         note = Recombinant
                         organism = synthetic construct
SEQUENCE: 152
aagaccctaa tactgttctc tacccgcgac gggcagacaa gggagatcgc cgcgttcctt     60
gcctcggagc tgaaggagca ggggatttac gctgacgtca taaaccttaa ccggacggag     120
gagatagctt ggcaggagta tgatagagtc gtaatcgggg cgtcgatccg atacgggcat     180
ttccaccctg ctgtcgaccg cttcgtgaag aagcacacag agacactcaa ctcactgccc     240
ggcgcctttt tctctgtaaa ccttgttgcc cggaaagccg agaagagaac gccgcagacg     300
aactcataca ccaggaagtt cctattaaac agcccgtgga agccagcggc ctgcgcggtc     360
tttgctgggg ccctccgcta ccctagatac cgctggtacg acaggttcat gatacgactg     420
attatgaaaa tgacaggcgg gggagacggat acccgaaagg aggtagtcta cactgactgg     480
tcgcagatcg cgtcgtttgc cagagagata gtccagttga ccaggtcatc gcgcttgtga     540

SEQ ID NO: 153           moltype = DNA   length = 540
FEATURE                  Location/Qualifiers
source                   1..540
                         mol_type = other DNA
                         note = Recombinant
                         organism = synthetic construct
SEQUENCE: 153
atgaaggcgc tcgtgctcta cagcacacgc gacggccaga ctcatgcgat cgcctcttac     60
atcgcgtcct gtatgaagga gaaggccgag tgcgacgtca tcgatctcac gcacggggag     120
cacgtgaatc ttacgcagta cgaccaagtg ctgataggcg cctctatccg ttacggccat     180
tttaacgccg tcctcgacaa attcatcaag cgcaatgtag accagctgaa caacatgccc     240
tccgcgttct tttgcgtgaa cctgacggct cggaagcctg agaagcgaac acctgcgacc     300
aacccatacg tgcggaaatt cctactcgca acgccatggc agcccgccct gtgcggggtt     360
ttcgcagggg cgctacgcta tccgcgttac cgctggatcg ataaggtgat gatccagcta     420
ataatgcgca tgaccggcgg cgagacagac acatcgaagg aagtcgaata cacagactgg     480
gaacaggtga agaagtttgc agaggatttc gccaagctct catacaaaaa ggcattgtga     540

SEQ ID NO: 154           moltype = DNA   length = 537
FEATURE                  Location/Qualifiers
source                   1..537
                         mol_type = other DNA
                         note = Recombinant
                         organism = synthetic construct
SEQUENCE: 154
atgaaggcgc ttatactgtt ctcgacacgc gacggtcaga cgcagaaaat cgcctcagcc     60
atcgccgacg agatcaaggg ccagcagagc tgcgatgtga tcaatattca ggacgccaaa     120
actctcgact ggcagcagta tgaccgcgtg ctcattggcg catcaatccg ctacgggcat     180
ttccagccag tcgtcaatga gtttgtgaaa cataacctct tggcattgca gcagcgggtg     240
tctggcttct tctccgtgaa ccttacagct agaaaaccag agaagcggtc gcccgagact     300
aacgcctaca ccgttaagtt ccttgcgcag tcaccgtggc agcctgattg ctgcgcggtc     360
ttcgccgggg cactgtacta ccctcgatac cggtggtttg ataggtaat gatccagttc      420
ataatgcgca tgaccggtgg gggagaccgac gcaagtaaag aagttgagta cacggattgg     480
cagcaggtgc aaaggttcgc acgcgacttc gcgcagctcc cgggcaagtc ttactga        537

SEQ ID NO: 155           moltype = DNA   length = 534
FEATURE                  Location/Qualifiers
source                   1..534
                         mol_type = other DNA
                         note = Recombinant
                         organism = synthetic construct
SEQUENCE: 155
atgaaagccc tgatcctcta ttccaccagg gacggccaga cccgcaagat agcctcctcc     60
atcgctgatg tcatccgcca gcagcagcag tgcgacgttt aaacattaa ggacgcttca      120
ctgcctgatt gggcccagta tgaccgcgtc ctgatcggcg cgtcgattcg gtacggccac     180
ttccagcctg tggttgacaa gttcgtcaag cagcacctgc atgagctgca gcagcgaact     240
agcgggttct tcagtgtgaa cctgacagct agaaagcccg aaaagagatc cccagaaacc     300
aacgcctata cgcagaaatt ccttgctcac tcaccctggc agcctgactg ttgtgccgtc     360
ttcgcgggc ccttgtacta tccccgctac cgctggttcg ataggtgat gatccagctg       420
attatgagaa tgacgggagg gggagaccgat tcgaccaagg aggtagagta cactgactgg     480
caacaggtgt caactttcgc aaacgacttc gcacaactac ccggtaagtc ttga            534

SEQ ID NO: 156           moltype = DNA   length = 546
FEATURE                  Location/Qualifiers
source                   1..546
                         mol_type = other DNA
                         note = Recombinant
                         organism = synthetic construct
SEQUENCE: 156
atgaaaaccc taatactgtt ctcgacccgc gacggccaga cgcgtgagat tgcgagctac      60
ctggcctccg agctcaagga gctggggatc caagccgatg tcgcgaacgt gcaccgcatt     120
```

-continued

```
gaggagccgc agtgggagaa ttacgatcgc gttgtgatag gggccagcat ccgctatggc  180
cactaccact cggcctttca ggagtttgta aagaaacacg ccacaagatt aaactccatg  240
cctagcgcct tctactccgt caaccttgtc gcgcgcaagc cggagaagcg gacacctcag  300
acgaactcct acgcgcggaa gttcctgatg aacagccagt ggcggccgga cagatgtgct  360
gttattgcgg gagccctgag atacccgagg taccggtcag acgataggtt tatgattaaa  420
cttattatga agatgtctgg tggggagact gacaccagga aggaggtggt atatacagac  480
tgggagcagg tcgccaattt cgctcgggaa atcgcgcatc tgacagacaa gcctacactg  540
aagtag                                                                546

SEQ ID NO: 157          moltype = DNA   length = 537
FEATURE                 Location/Qualifiers
source                  1..537
                        mol_type = other DNA
                        note = Recombinant
                        organism = synthetic construct SEQUENCE: 157
atgaaggccc tgatcctctt tagctctagg gagggccaga cccgcgagat cgcgtcatat  60
atcgcgaatt ccataaagga ggagatggag tgcgatgtgt ttaacatcct tagggtggag  120
caaatagact ggtctcagta tgaccgtgtg ctcatagggg ggagcatcca ctacggccac  180
tttcacccgg ccgtggcgaa attcgtcaag cgacacctcc acgagcttca gcagcgctcc  240
tcagggttct tctgcgtcaa cctgacagca agaaaggcag ataaacgcac cccgcagacg  300
aacgcctaca tgaggaagtt ccttctgcag tctccttgcg tctcctggag cactgcgcta  360
ttcgccggtg cactgcgcta tacgcgctat agatggtttg atagagtcat gattcagctc  420
atcatgcgga tgaccggcgg ggaaacggat actagtaagg aggtggagta cacggactgg  480
acccaggtgg cacgtttcgc ccaggagttt gcacatcttc ctgggaagac ccaatga     537

SEQ ID NO: 158          moltype = DNA   length = 540
FEATURE                 Location/Qualifiers
source                  1..540
                        mol_type = other DNA
                        note = Recombinant
                        organism = synthetic construct SEQUENCE: 158
atgaaggcgc taattgtgtt cagctccagg gatggccaga cgagggctat agcatcctat  60
atcgccaata ccttgaaagg aacgctcgag tgtgacgtgg tcaacgtctt gaacgccaat  120
gacattgacc tttcccagta cgaccgagtt gccataggcg cgtcgatccg ctacgggcga  180
tttcaccctg cagtcaacca gtttatacgg aagcatttga cctcgctgca gcagctcccg  240
tcagccttct tctctgtgaa tttaaccgcg cggaagcctg agaaacggac gatccaaaca  300
aacgcctata cccgaaagtt cctcctgaac agcccagtgg agccagacct gtgctgtgtc  360
ttcgccggcg cgttgcggta tccccgctac aggtggttcg atagagtgat gatccagctc  420
atcatgagga tcaccggggg agagaccgat agtaccaagg agatcgagta cacggactgg  480
cagcaggtgg ctcgcttcgc ccaggacttc gctcagttgg ccgcaaagaa tccagcataa  540

SEQ ID NO: 159          moltype = DNA   length = 540
FEATURE                 Location/Qualifiers
source                  1..540
                        mol_type = other DNA
                        note = Recombinant
                        organism = synthetic construct SEQUENCE: 159
atgaagacac tgatcctgtt ctcgactcga gatggccaga ctcataaaat tgcgcgccac  60
attgcggggg tcctggagga gcagggcaaa gcgtgcgagc tcgtggactt actccagccc  120
ggggagccgg actggagcac ggtggagtgc gtcgttctgg gcgcttccat acgttacggg  180
catttccaca aaagtttcat ccggttcgtc aacacccacg ctcaacggct gaacaacatg  240
cctggcgcgc tattcactgt taacttagtg gctcgtaagc ccgagaagca gtctccgcag  300
actaactcct acacaaggaa atttctagca gcaagcccat ggcaaccgca gcggtgccag  360
gtggttcgctg gagctctgcg ctatcctagg tacagttggt acgacagaat gatgatacgg  420
ttgattatga agatggcagg cggggagacg gacaccagga aagaggtcga atacactgac  480
tggcaatcag tcactcggtt tgctagagag atcgcgcaat taccaggtga gacgcggtaa  540

SEQ ID NO: 160          moltype = DNA   length = 537
FEATURE                 Location/Qualifiers
source                  1..537
                        mol_type = other DNA
                        note = Recombinant
                        organism = synthetic construct SEQUENCE: 160
atgaaggctc tcatactgtt cagctcgaga gacgggcaga cccagctgat cgcctcctcc  60
atagcaaagg agctagaggg caagcaagcc tgcgacgtgc tcaatattct cgacacaacc  120
aacgtggagt ggactcagta cgacagagtc ctaatcggcg cgtccatcag atacggccac  180
ttccatcccg ccgtcgctga attcgtgaaa cgccaccagc gtgagctcca gcagcgcagc  240
agcggcttct tcagcgtgaa tcttactgcg agaaagccgg aaaagcggag tcccgagact  300
aacgcttata cggcaaagtt cctcaaccaa tctccctggc aaccagactg ctgtgccgtg  360
ttcgctgggg cactgaggta tccgcgctat cggtggttcg atagaatcat gatacagctg  420
ataatgcgta tgactggtgg ggagacggat tccagtaaag aggtagagta tactgattgg  480
cagcaggtca ctaggttcgc gcaggagttt gctaggctgc cggcaagac atcctga      537

SEQ ID NO: 161          moltype = DNA   length = 543
FEATURE                 Location/Qualifiers
```

```
source                  1..543
                        mol_type = other DNA
                        note = Recombinant
                        organism = synthetic construct
SEQUENCE: 161
atgaaaacct taatcttgtt cagcacccgc gacggccaga cgcgtgaaat cgcagcgttc  60
ctcgcttcgg agctcaagga acagggaatt tacgccgacg tcattaacct aaaccgtacc  120
gaagagattg cgtggcagga gtatgaccgc gtggtgattg cgcgcttctat ccgctatggc  180
cacttccacc cggctgttga ccggttcgtg aagaagcaca cggagacctt gaactcactg  240
ccggggggcat tctttagcgt aaatctggtg gcgcgcaagg ccgagaagcg caccccccag  300
acgaacagct cacaccgcaa attttttactt aactcccccat ggaaacctgc ggcctgcgca  360
gtgttcgcag gagctctccg ctatcctcgc tatcgatggt acgatcggtt catgattcgg  420
ctgattatga aaatgacggg cggcgagacg gatacgcgaa aggaagttgt ctacactgac  480
tggtcccagg tggcctcgtt tgcaagggag atcgtacagc tcactcgatc tagtaggctc  540
tga                                                               543

SEQ ID NO: 162         moltype = DNA  length = 534
FEATURE                Location/Qualifiers
source                  1..534
                        mol_type = other DNA
                        note = Recombinant
                        organism = synthetic construct
SEQUENCE: 162
atgaagattc tcatcttatt ttccacccga gacggccaaa cccgcgagat tgcggcgtcc  60
ctcgcctccg agttgaagga gcaggcgttt gatgtggatg tggtcaacct ccaccgcgca  120
gaaaacatag cgtgggagga gtacgatggg gtcgtcatcg gagcgtcaat ccgctacgga  180
catttccact caacgctgaa ttcatttgtg aagaagcacc aacaagcgct caagaagctg  240
cccggagcat tctacagcgt caacctcgtg gctcggaagc cggaaaagcg cacccccgcaa  300
acaaacagct cacacgcaa gtttctgctc gactcgccct ggcaacccga cctgagtgcc  360
gttttcgccg gggcactgcg ctatcccccgt tacaactggt acgatcgcat aatgattcga  420
ctgatcatga agattacagg cggggaaacc gatactcgga aggaggtggt gtatacagac  480
tggcagcagg ttacccactt cgcccacgag atcgtccagc tcgttcgtaa gtga        534

SEQ ID NO: 163         moltype = AA  length = 442
FEATURE                Location/Qualifiers
source                  1..442
                        mol_type = protein
                        organism = Xanthomonas campestris
SEQUENCE: 163
MQTQPVIIAG AGIAGLSIAY ELQQKGIPYE IMEASSYAGG VVKSLHIDGY ELDAGPNSLA  60
ASAAFMAYID QLGLQDQVLE AAAASKNRFL VRNDKLHAVS PHPFKILQSA YISGGAKWRL  120
FTERFRKAAA PEGEETVSSF VTRRFGKEIN DYLFEPVLSG IYAGNPDLMS VGEVLPMLPQ  180
WEQKYGSVTQ GLLKNKGAMG GRKIIAFKGG NATLTNRLQS LLSGKIRFNC AVTGVTRGAD  240
DYIVQYTENG NTAMLNASRV IFTTPAYSTA VAIQALDASL ATHLSDVPYP RMGVLHLGFG  300
AEARQKAPAG FGFLVPHAAG KHFLGAICNS AIFPSRVPTG KVLFTVFLGG ARQEQLFDQL  360
GPEKLQQTVV KELMELLGLT TPPEMQRFSE WNRAIPQLNV GYAQTRQQIG VFEQRYPGIR  420
LAGNYVTGVA VPAIIQAAKG YC                                           442

SEQ ID NO: 164         moltype = AA  length = 439
FEATURE                Location/Qualifiers
source                  1..439
                        mol_type = protein
                        organism = Xanthomonas campestris
SEQUENCE: 164
QPVIIAGAGI AGLSIAYELQ QKGIPYEIME ASSYAGGVVK SLHIDGYELD AGPNSLAASA  60
AFMAYIDQLG LQDQVLEAAA ASKNRFLVRN DKLHAVSPHP FKILQSAYIS GGAKWRLFTE  120
RFRKAAAPEG EETVSSFVTR RFGKEINDYL FEPVLSGIYA GNPDLMSVGE VLPMLPQWEQ  180
KYGSVTQGLL KNKGAMGGRK IIAFKGGNAT LTNRLQSLLS GKIRFNCAVT GVTRGADDYI  240
VQYTENGNTA MLNASRVIFT TPAYSTAVAI QALDASLATH LSDVPYPRMG VLHLGFGAEA  300
RQKAPAGFGF LVPHAAGKHF LGAICNSAIF PSRVPTGKVL FTVFLGGARQ EQLFDQLGPE  360
KLQQTVVKEL MELLGLTTPP EMQRFSEWNR AIPQLNVGYA QTRQQIGVFE QRYPGIRLAG  420
NYVTGVAVPA IIQAAKGYC                                               439

SEQ ID NO: 165         moltype = AA  length = 448
FEATURE                Location/Qualifiers
source                  1..448
                        mol_type = protein
                        organism = Chitinophaga pinensis
SEQUENCE: 165
MSDQPVLIVG AGLSGLSIAY ELQKLQVPYQ VLEVSGHSGG VMKSLRKDGF ELDAGANTIA  60
ASPEILAYFT SLGLENEILQ ATAASKHRFL VRRQLHAVS PHPFKIMSSP YLSRGSKWRL  120
FTERFRKPVV ASGEETVTDF ITRRFNREIA EYVFDPVLSG IYAGNPDQMS IAEVLPALPR  180
WEREYGSVTK GLMKDKGAMG GRKIISFKGG NQLLTNRLQQ LLTTPVRFNC KVTGITASNG  240
GYIVSAVEDG VSESYTASRV ILTTPAYSAA ATITNLDAAT AALLNEIHYP RMGVLHLGFD  300
ATALPQPLDG FGFLVPNAEN MHFLGAICNA AIFPDKAPPG KILFTVFLGG ARQESLFDQM  360
TPEALQQVV SEVMSLLHLS APPVMQHFSS WNKAIPQLNV GHVKLRRAVE AFEKKYPGIH  420
LSGNYLQGVA IPALLQHAAA LAASLKKN                                     448

SEQ ID NO: 166         moltype = AA  length = 445
```

```
FEATURE                   Location/Qualifiers
source                    1..445
                          mol_type = protein
                          note = Recombinant
                          organism = synthetic construct
SEQUENCE: 166
QPVLIVGAGL SGLSIAYELQ KLQVPYQVLE VSGHSGGVMK SLRKDGFELD AGANTIATSP     60
EILAYFTSLG LENEILQATA TSKHRFLVRR RQLHAVSPHP FKIMSSPYLC RGSKWRLFTE    120
RFRKPVVASG EETVTDFITR RFNREIAEYV FDPVLSGIYA GNPDQMSIAE VLPALPRWER    180
EYGSVTKGLM KDKGAMGGRK IISFKGGNQL LTNRLQQLLT TPVRFNCKVT GITASNGGYI    240
VSAVEDGVSE SYTASRVILT TPAYSAAATI TNLDAATAAL LNEIHYPRMG VLHLGFDATA    300
LPQPLDGFGF LVPNAENMHF LGAICNAAIF PDKAPPGKIL FTVFLGGARQ ESLFDQMTPE    360
ALQQQVVSEV MSLLHLSAPP VMQHFSSWNK AIPQLNVGHV KLRRAVEAFE KKYPGIHLSG    420
NYLQGVAIPA LLQHAAALAA SLKKN                                          445

SEQ ID NO: 167          moltype = AA   length = 470
FEATURE                   Location/Qualifiers
source                    1..470
                          mol_type = protein
                          organism = Bacillus subtilis
SEQUENCE: 167
MSDGKKHVVI IGGGITGLAA AFYMEKEIKE KNLPLELTLV EASPRVGGKI QTVKKDGYII     60
ERGPDSFLER KKSAPQLVKD LGLEHLLVNN ATGQSYVLVN RTLHPMPKGA VMGIPTKIAP    120
FVSTGLFSLS GKARAAMDFI LPASKTKDDQ SLGEFFRRRV GDEVVENLIE PLLSGIYAGD    180
IDKLSLMSTF PQFYQTEQKH RSLILGMKKT RPQGSGQQLT AKKQGQFQTL STGLQTLVEE    240
IEKQLKLTKV YKGTKVTKLS HSGSGYSLEL DNGVTLDADS VIVTAPHKAA AGMLSELPAI    300
SHLKNMHSTS VANVALGFPE GSVQMEHEGT GFVISRNSDF AITACTWTNK KWPHAAPEGK    360
TLLRAYVGKA GDESIVDLSD NDIINIVLED LKKVMNINGE PEMTCVTRWH ESMPQYHVGH    420
KQRIKELREA LASAYPGVYM TGASFEGVGI PDCIDQGKAA VSDALTYLFS               470

SEQ ID NO: 168          moltype = AA   length = 470
FEATURE                   Location/Qualifiers
source                    1..470
                          mol_type = protein
                          organism = Bacillus pumilus
SEQUENCE: 168
MHDNQKHLVI IGGGITGLAA AFYLEKEVEE KGLPIQISLI EASPRLGGKI QTLYKDGYII     60
ERGPDSFLER KVSGPQLAKD VGLSDQLVNN ETGQAYVLVN EKLHPMPKGA VMGIPTQISP    120
FITTGLFSVA GKARAAMDFV LPKSKQTEDQ SLGEFFRRRV GDEVVENLIE PLLSGIYAGD    180
IDRLSLMSTF PQFYQTEQQH RSLILGMKKS QQHAKAQQVT AKKQGQFQTI NQGLQSLVEA    240
VEGKLKLTTV YKGTKVKQIE KTDGGYGLQL DSGQTLFADS AIVTTPHQSI YSMFPKEAGL    300
EYLHDMTSTS VATVALGFKD EDVHNEYDGT GFVISRNSDF SITACTWTNK KWPHTAPKGK    360
TLLRAYVGKA GDESIVEQSD SQIVSIVLED LKKIMDIKAD PELTTVTRWK TSMPQYHVGH    420
QKAISNMRET FKQSYPGVYI TGAAFEGVGI PDCIDQGKAA ISEAVSYLFS               470

SEQ ID NO: 169          moltype = AA   length = 470
FEATURE                   Location/Qualifiers
source                    1..470
                          mol_type = protein
                          organism = Bacillus pumilus
SEQUENCE: 169
MHDNQKHLVI IGGGITGLAA AFYLEKEVEE KGLPIQISLI EASPRLGGKI QTLYKDGYII     60
ERGPDSFLER KVSGPQLAKD VGLSDQLVNN ETGQAYVLVN ETLHPMPKGA VMGIPTQISP    120
FITTGLFSVA GKARAAMDFV LPKSKQTEDQ SLGEFFRRRV GDEVVENLIE PLLSGIYAGD    180
IDRLSLMSTF PQFYQTEQKH RSLILGMKKS QQHAKAQQVT AKKQGQFQTI NQGLQALVEA    240
VESKLKLTTI YKGTKVKQIE KTDGGYGVQL DSGQTLLADS AIVTTPHQSI YSMFPKEAGL    300
EYLHDMTSTS VATVALGFKE EDVHNEYDGT GFVISRNSDF SITACTWTNK KWPHTAPKGK    360
TLLRAYVGKA GDESIVEQSD HQIVSIVLED LKKIMDIKAD PELTTVTRWK TSMPQYHVGH    420
QKAISNMRET FKQSYPGVYI TGAAFEGVGI PDCIDQGKAA ISEAVSYLFS               470

SEQ ID NO: 170          moltype = AA   length = 477
FEATURE                   Location/Qualifiers
source                    1..477
                          mol_type = protein
                          organism = Paenibacillus macerans
SEQUENCE: 170
MSKKIAVIGG GITGLSVAYY VRKLLREQGV NAGVTLVEQS DRLGGKIRSL RRDGFTIEQG     60
PDSMIARKPA ALELIRELGL EDKLAGTNPQ AKRSYILHRG KFHPMPPGLM LGIPTQMWPM    120
VKTGLLSPAG KLRAAMDLLL PARRGGGDES LGGFIRRRLG REVLEQMTEP LLAGIYAGDT    180
EQLSLKATFP QFMEMERKHR SLILGLLAGK KQPPRPGGSQ VPLPKAAQTS MFLTLTGGLE    240
GLTEALEESL SEEKIITGQA VTGLSQQEAG YELNLSGGER LNADGVILAV PAFAAARLLD    300
GVPEAAYLER IRYVSVANLA FAYRREDVPH DLNGSGVLIP RGEGRMITAI TWVSSKWLHS    360
APGDKALLRA YIGRLGDEAW TAMCRADIER RVAAELRDLL GIAASPLFCE LAALPESMPQ    420
YPVGHVERLE ALRGALCRAK PGLLLCGAGY AGVGIPDCIR QGKEAAESMA AYLRDGR      477

SEQ ID NO: 171          moltype = AA   length = 493
FEATURE                   Location/Qualifiers
source                    1..493
                          mol_type = protein
```

```
                              organism = Paenibacillus thiaminolyticus
SEQUENCE: 171
MKALRKLVVI GGGITGLSAA FYALKQADEE GQPISVTIIE QSDRLGGKIQ TLRKEGCVIE    60
KGPDSFLARK LPMIDLARDL GMDSELVATN PHAKKTYILR RGKLYRMPPG LVLGIPTELG   120
PPFAKTGLISP WGKLRAAMDL FIKPHPADED ESVGAFLDRR LGREVTEHIA EPLLAGIYAG  180
DLQOALSLQAT FPQFAQVERK HGGLIRGMKA SRQAGQSVPG LPDVAKGTMF LTFRNGLTSL  240
VERLEETLRD RAELCLGIGA EGFEKREDGT YLVRLSDGSR LQADAVIVTT PSYHAASLLE   300
EHVDASALQA IRHVSVANVV SVFDRKQVNN QFDGTGFVIS RREGRAITAC TWTSVKWPHT   360
SRGDKLIIRC YIGRAGDEER VDWPDEALKR TVRSELRELL DIDIDPEFVE ITRLRHSMPQ   420
YPVGHVQAIR SLRDEVGRTL PGVFLAGQPY EGVGMPDCVR SGRDAAEAAV SAMQAMSTEP   480
EAPAEDAATG TAG                                                      493

SEQ ID NO: 172            moltype = AA  length = 474
FEATURE                   Location/Qualifiers
source                    1..474
                          mol_type = protein
                          organism = Paenibacillus polymyxa
SEQUENCE: 172
MGDKKRRVVV VGGGLTGLSA AFYIRKHYRE AGVEPVITLV EKSSSMGGMI ETLHRDGFVI    60
EKGPDSFLAR KTAMIDLAKE LEIDHELVSQ NPESKKTYIM QRGKLHPMPA GLVLGIPTEL   120
RPFLRSGLVS PAGKLRALMD FVIPPRRTTE DESLGYMIER RLGAEVLENL TEPLLAGIYA   180
GDMRRLSLQA TFPQFGEVER DYGSLIRGMM TGRKPAETHT GTKRSAFLNF RQGLQSLVHA   240
LVHELQDVDQ RLNTAVKSLQ RLDGAQTRYR VELGNGEMLE ADDVVVTVPT YVASELLKPH   300
VDTAALDAIN YVSVANVVLA FEKKEVEHVF DGSGFLVPRK EGRNITACTW TSTKWLHTSP   360
DDKVLLRCYV GRSGDEQNVE LPDEALTNLV LKDLRETMGI EAVPIFSEIT RLRKSMPQYP   420
VGHLQHIAAL REELGSKLPG VYIAGAGYEG VGLPDCIRQA KEMSVQATQE LAAD          474

SEQ ID NO: 173            moltype = AA  length = 470
FEATURE                   Location/Qualifiers
source                    1..470
                          mol_type = protein
                          organism = Bacillus atrophaeus
SEQUENCE: 173
MSDGKKHLVI IGGGITGLAS AFYMEKEIRE KNLPLSVTLV EASPRVGGKI QTARKDGYII    60
ERGPDSFLER KKSAPELVED LGLEHLLVNN ATGQSYVLVN ETLHPMPKGA VMGIPTKIAP   120
FMSTGLFSFS GKARAAMDFV LPASKPKEDQ SLGEFFRRRV GDEVVENLIE PLLSGIYAGD   180
IDRLSLMSTF PQFYQTEQKH RSLILGMKKT RPQGSGQRLT AKKQGQFQTL KTGLQTLVEE   240
LENQLKLTKV YKGTKVTNIS RGEKGCSIAL DNGMTLDADA AIVTSPHKSA AGMFPDLPAV   300
SQLKDMHSTS VANVALGFPQ EAVQMEHEGT GFVISRNSDF SITACTWTNK KWPHSAPEGK   360
TLLRAYVGKA GDESIVELSD NEIIKIVLED LKKVMKIKGE PEMTCVTRWN ESMPQYHVGH   420
KQRIKKVREA LAASYPGVYM TGASFEGVGI PDCIDQGKSA VSDVLAYLFG               470

SEQ ID NO: 174            moltype = AA  length = 470
FEATURE                   Location/Qualifiers
source                    1..470
                          mol_type = protein
                          organism = Bacillus atrophaeus
SEQUENCE: 174
MSDGKKHLVI IGGGITGLAS AFYMEKEIRE KNLPLSVTLV EASPRVGGKI QTARKDGYII    60
ERGPDSFLER KKSAPELVED LGLEHLLVNN ATGQSYVLVN ETLHPMPKGA VMGIPTKIAP   120
FMSTRLFSFS GKARAAMDFV LPASKPKEDQ SLGEFFRRRV GDEVVENLIE PLLSGIYAGD   180
IDRLSLMSTF PQFYQTEQKH RSLILGMKKT RPQGSGQQLT AKKQGQFQTL KTGLQTLVEE   240
LENQLKLTKV YKGTKVTNIS RGEKGCSIAL DNGMTLDADA AIVTSPHKSA AGMFPDLPAV   300
SQLKDMHSTS VANVALGFPQ EAVQMEHEGT GFVISRNSDF SITACTWTNK KWPHSAPEGK   360
TLLRAYVGKA GDESIVELSD NEIIKIVLED LKKVMKIKGE PEMTCVTRWN ESMPQYHVGH   420
KQRIKKVREA LAASYPGVYM TGASFEGVGI PDCIDQGKSA VSDVLAYLFE               470

SEQ ID NO: 175            moltype = AA  length = 475
FEATURE                   Location/Qualifiers
source                    1..475
                          mol_type = protein
                          note = Recombinant
                          organism = synthetic construct
SEQUENCE: 175
KKIAVIGGGI TGLSVAYYVR KLLREQGVNA GVTLVEQSDR LGGKIRSLRR DGFTIEQGPD    60
SMIARKPAAL ELIRELGLED KLAGTNPQAK RSYILHRGKF HPMPPGLMLG IPTQMWPMVK   120
TGLLSPAGKL RAAMDLLLPA RRGGGDESLG GFIRRRLGRE VLEQMTEPLL AGIYAGDTEQ   180
LSLKATFPQF MEMERKHRSL ILGLLAGKKQ PPRPGGSQVP LPKAAQTSMF LTLTGGLEGL   240
TEALEESLSE EKIITGQAVT GLSQQEAGYE LNLSGGERLN ADGVILAVPA FAAARLLDGV   300
PEAAYLERIR YVSVANLAFA YRREDVPHDL NGSGVLIPRG EGRMITAITW VSSKWLHSAP   360
GDKALLRAYI GRLGDEAWTA MCRADIERRV AAELRDLLGI AASPLFCELA ALPESMPQYP   420
VGHVERLEAL RGALCRAKPG LLLCGAGYAG VGIPDCIRQG KEAAESMAAY LRDGR         475

SEQ ID NO: 176            moltype = AA  length = 489
FEATURE                   Location/Qualifiers
source                    1..489
                          mol_type = protein
                          note = Recombinant
                          organism = synthetic construct
```

```
SEQUENCE: 176
RKLVVIGGGI TGLSAAFYAL KQADEEGQPI SVTIIEQSDR LGGKIQTLRK EGCVIEKGPD   60
SFLARKLPMI DLARDLGMDS ELVATNPHAK KTYILRRGKL YRMPPGLVLG IPTELGPFAK  120
TGLISPWGKL RAAMDLFIKP HPADEDESVG AFLDRRLGRE VTEHIAEPLL AGIYAGDLQA  180
LSLQATFPQF AQVERKHGGL IRGMKASRQA GQSVPGLPDV AKGTMFLTFR NGLTSLVERL  240
EETLRDRAEL CLGIGAEGFE KREDGTYLVR LSDGSRLQAD AVIVTTPSYH AASLLEEHVD  300
ASALQAIRHV SVANVVSVFD RKQVNNQFDG TGFVISRREG RAITACTWTS VKWPHTSRGD  360
KLIIRCYIGR AGDEERVDWP DEALKRTVRS ELRELLDIDI DPEFVEITRL RHSMPQYPVG  420
HVQAIRSLRD EVGRTLPGVF LAGQPYEGVG MPDCVRSGRD AAEEAAVSAMQ AMSTEPEAPA  480
EDAATGTAG                                                         489

SEQ ID NO: 177            moltype = AA   length = 469
FEATURE                   Location/Qualifiers
source                    1..469
                          mol_type = protein
                          note = Recombinant
                          organism = synthetic construct
SEQUENCE: 177
RRVVVVGGGL TGLSAAFYIR KHYREAGVEP VITLVEKSSS MGGMIETLHR DGFVIEKGPD   60
SFLARKTAMI DLAKELEIDH ELVSQNPESK KTYIMQRGKL HPMPAGLVLG IPTELRPFLR  120
SGLVSPAGKL RALMDFVIPP RRTTEDESLG YMIERRLGAE VLENLTEPLL AGIYAGDMRR  180
LSLQATFPQF GEVERDYGSL IRGMMTGRKP AETHTGTKRS AFLNFRQGLQ SLVHALVHEL  240
QDVDQRLNTA VKSLQRLDGA QTRYRVELGN GEMLEADDVV VTVPTYVASE LLKPHVDTAA  300
LDAINYVSVA NVVLAFEKKE VEHVFDGSGF LVPRKEGRNI TACTWTSTKW LHTSPDDKVL  360
LRCYVGRSGD EQNVELPDEA LTNLVLKDLR ETMGIEAVPI FSEITRLRKS MPQYPVGHLQ  420
HIAALREELG SKLPGVYIAG AGYEGVGLPD CIRQAKEMSV QATQELAAD               469

SEQ ID NO: 178            moltype = AA   length = 465
FEATURE                   Location/Qualifiers
source                    1..465
                          mol_type = protein
                          note = Recombinant
                          organism = synthetic construct
SEQUENCE: 178
KHLVIIGGGI TGLASAFYME KEIREKNLPL SVTLVEASPR VGGKIQTARK DGYIIERGPD   60
SFLERKKSAP ELVEDLGLEH LLVNNATGQS YVLVNETLHP MPKGAVMGIP TKIAPFMSTR  120
LFSFSGKARA AMDFVLPASK PKEDQSLGEF FRRRVGDEVV ENLIEPLLSG IYAGDIDRLS  180
LMSTFPQFYQ TEQKHRSLIL GMKKTRPQGS GQQLTAKKQG QFQTLKTGLQ TLVEELENQL  240
KLTKVYKGTK VTNISRGEKG CSIALDNGMT LDADAAIVTS PHKSAAGMFP DLPAVSQLKD  300
MHSTSVANVA LGFPQEAVQM EHEGTGFVIS RNSDFSITAC TWTNKKWPHS APEGKTLLRA  360
YVGKAGDESI VELSDNEIIK IVLEDLKKVM KIKGEPEMTC VTRWNESMPQ YHVGHKQRIK  420
KVREALAASY PGVYMTGASF EGVGIPDCID QGKSAVSDVL AYLFE                   465

SEQ ID NO: 179            moltype = AA   length = 473
FEATURE                   Location/Qualifiers
source                    1..473
                          mol_type = protein
                          note = Recombinant
                          organism = synthetic construct
SEQUENCE: 179
IAVIGGGITG LSVAYYVRKL LREQGVNAGV TLVEQSDRLG GKIRSLRRDG FTIEQGPDSM   60
IARKPAALEL IRELGLEDKL AGTNPQAKRS YILHRGKFHP MPPGLMLGIP TQMWPMVKTG  120
LLSPAGKLRA AMDLLLPARR GGGDESLGGF IRRRLGREVL EQMTEPLLAG IYAGDTEQLS  180
LKATFPQFME MERKHRSLIL GLLAGKKQPP RPGGSQVPLP KAAQTSMFLT LTGGLEGLTE  240
ALEESLSEEK IITGQAVTGL SQQEAGYELN LSGGERLNAD GVILAVPAFA AARLLDGVGP  300
AAYLERIRYV SVANLAFAYR REDVPHDLNG SGVLIPRGEG RMITAITWVS SKWLHSAPGD  360
KALLRAYIGR LGDEAWTAMC RADIERRVAA ELRDLLGIAA SPLFCELAAL PESMPQYPVG  420
HVERLEALRG ALCRAKPGLL LCGAGYAGVG IPDCIRQGKE AAESMAAYLR DGR          473

SEQ ID NO: 180            moltype = AA   length = 487
FEATURE                   Location/Qualifiers
source                    1..487
                          mol_type = protein
                          note = Recombinant
                          organism = synthetic construct
SEQUENCE: 180
LVVIGGGITG LSAAFYALKQ ADEEGQPISV TIIEQSDRLG GKIQTLRKEG CVIEKGPDSF   60
LARKLPMIDL ARDLGMDSEL VATNPHAKKT YILRRGKLYR MPPGLVLGIP TELGPFAKTG  120
LISPWGKLRA AMDLFIKPHP ADEDESVGAF LDRRLGREVT EHIAEPLLAG IYAGDLQALS  180
LQATFPQFAQ VERKHGGLIR GMKASRQAGQ SVPGLPDVAK GTMFLTFRNG LTSLVERLEE  240
TLRDRAELCL GIGAEGFEKR EDGTYLVRLS DGSRLQADAV IVTTPSYHAA SLLEEHVDAS  300
ALQAIRHVSV ANVVSVFDRK QVNNQFDGTG FVISRREGRA ITACTWTSVK WPHTSRGDKL  360
IIRCYIGRAG DEERVDWPDE ALKRTVRSEL RELLDIDIDP EFVEITRLRH SMPQYPVGHV  420
QAIRSLRDEV GRTLPGVFLA GQPYEGVGMP DCVRSGRDAA EAAVSAMQAM STEPEAPAED  480
AATGTAG                                                            487

SEQ ID NO: 181            moltype = AA   length = 467
FEATURE                   Location/Qualifiers
source                    1..467
```

```
                          mol_type = protein
                          note = Recombinant
                          organism = synthetic construct
SEQUENCE: 181
VVVVGGGLTG LSAAFYIRKH YREAGVEPVI TLVEKSSSMG GMIETLHRDG FVIEKGPDSF    60
LARKTAMIDL AKELEIDHEL VSQNPESKKT YIMQRGKLHP MPAGLVLGIP TELRPFLRSG   120
LVSPAGKLRA LMDFVIPPRR TTEDESLGYM IERRLGAEVL ENLTEPLLAG IYAGDMRRLS   180
LQATFPQFGE VERDYGSLIR GMMTGRKPAE THTGTKRSAF LNFRQGLQSL VHALVHELQD   240
VDQRLNTAVK SLQRLDGAQT RYRVELGNGE MLEADDVVVT VPTYVASELL KPHVDTAALD   300
AINYVSVANV VLAFEKKEVE HVFDGSGFLV PRKEGRNITA CTWTSTKWLH TSPDDKVLLR   360
CYVGRSGDEQ NVELPDEALT NLVLKDLRET MGIEAVPIFS EITRLRKSMP QYPVGHLQHI   420
AALREELGSK LPGVYIAGAG YEGVGLPDCI RQAKEMSVQA TQELAAD             467

SEQ ID NO: 182          moltype = AA  length = 463
FEATURE                 Location/Qualifiers
source                  1..463
                          mol_type = protein
                          note = Recombinant
                          organism = synthetic construct
SEQUENCE: 182
LVIIGGGITG LASAFYMEKE IREKNLPLSV TLVEASPRVG GKIQTARKDG YIIERGPDSF    60
LERKKSAPEL VEDLGLEHLL VNNATGQSYV LVNETLHPMP KGAVMGIPTK IAPFMSTRLF   120
SFSGKARAAM DFVLPASKPK EDQSLGEFFR RRVGDEVVEN LIEPLLSGIY AGDIDRLSLM   180
STFPQFYQTE QKHRSLILGM KKTRPQGSGQ QLTAKKQGQF QTLKTGLQTL VEELENQLKL   240
TKVYKGTKVT NISRGEKGCS IALDNGMTLD ADAAIVTSPH KSAAGMFPDL PAVSQLKDMH   300
STSVANVALG FPQEAVQMEH EGTGFVISRN SDFSITACTW TNKKWPHSAP EGKTLLRAYV   360
GKAGDESIVE LSDNEIIKIV LEDLKKVMKI KGEPEMTCVT RWNESMPQYH VGHKQRIKKV   420
REALAASYPG VYMTGASFEG VGIPDCIDQG KSAVSDVLAY LFE                463

SEQ ID NO: 183          moltype = DNA  length = 1329
FEATURE                 Location/Qualifiers
source                  1..1329
                          mol_type = genomic DNA
                          organism = Xanthomonas campestris
SEQUENCE: 183
atgcaaacac agcccgttat cattgccggc gccggtattg ccggactaag tatagcttac    60
gaattacagc agaaaggcat tccctatgaa atcatggagg cctcttccta tgcaggaggc   120
gttgtgaaat cattacatat tgatggttat gaactggatg ctggccctaa ttcgctggcc   180
gcatctgcag cattcatggc ttatatcgat caactggtt tgcaggacca ggtattggaa   240
gctgcggctg ccagtaagaa ccgctttctg tcagaaatg ataaattgca tgcagtatcg   300
ccacatccct ttaagatact gcagtcagca tatatcagtg gtggcgccaa gtggcgtctg   360
ttcacagaaa gatttcgaaa agcggccgct ccggaggggag aggaaacagt atcttccttt   420
gtgacccgcc gttttggaaa ggagatcaat gactacctt ttgaacccgt gctttctggt   480
atatatgcag gtaatcctga tctgatgtca gttggtgaag tactgcctat gctgccacaa   540
tgggagcaaa aatacggtag tgttacgcag ggactcctga agaataaagg agctatgggt   600
ggacgtaaga tcattgcctt taaaggaggt aatgcgcacac tgacaaacag attgcaatcc   660
ctgcttagcg gtaagataag atttaactgt gccgtaaccg gtgtaaccgg tggggcggac   720
gactatattg tacaatatac cgagaatggt aatacagcta tgctgaatgc atcccgtgtg   780
atattcacca ccctgcata cagtacagcc gtagctatac aggcacttga cgcttccctt   840
gctacacatc tcagcgatgt tccctatccc cgtatgggcg tactgcacct ggggtttgga   900
gcggaagccc ggcagaaagc accggcaggt tttggtttcc tggtgccgca tgctgcagga   960
aagcatttcc tgggcgctat ctgtaacagc gctatattcc cttcccgcgt accgacaggt  1020
aaagtgctgt ttacggtgtt cctgggtggc gcgagacaag aacagctgtt tgatcagctg  1080
gggcctgaaa agctacagca gacagtagtg aaagaactga tggaactgct gggcctgact  1140
acaccaccag aaatgcagcg tttagtgaa tggaacagac cgattccgca actaaatgta  1200
ggttatgcac agacgaggca gcagatagc gtttttgaac agcgttaccc gggcatcaga  1260
ttagcgggta actatgtgac cggagtggct gtaccgcta tcatacaggc cgcaaaaggg  1320
tactgttga                                                          1329

SEQ ID NO: 184          moltype = DNA  length = 1347
FEATURE                 Location/Qualifiers
source                  1..1347
                          mol_type = genomic DNA
                          organism = Chitinophaga pinensis
SEQUENCE: 184
atgtctgatc aacccgtatt gattgtcggc gccggcttat ccggattgag cattgcgtat    60
gaattgcaga aactgcaggt gccttaccag gtactggaag tttcgggtca tagcggcggc   120
gtgatgaaat cattacggaa agatggattt gaactggatg caggcgctaa tacaatcgca   180
gcttctctg aaatactggc atacttcaca tcactgggac tggaaaatga gatattgcag   240
gccaccgctg ccagcaagca ccggttcctg gtaagacggc ggcagttgca cgctgtttct   300
ccccatcctt tcaagatcat gtcgtctcct tacctgagca ggggcagtaa atggcggttg   360
tttaccgaac gttttcgcaa acctgttgtg gcaagcggag aagaaccgt caccgatttt   420
ataacaagaa ggtttaaccg ggagatagca gaatatgtgt ttgacccggt attatccggc   480
atatatgccg gcaatcccga ccagatgagc atagcggaat tattacctgc gttgccgcgc   540
tgggagcggg aatatgggag tgttaccaaa gggctgatga aagataaagg cgcaatgggc   600
ggccggaaga ttatcagttt taaaggtggt aaccagttgc tcacaaaccg tttgcagcaa   660
ttgctcacta ccccggtgcg ctttaattgt aaggtaaccg gtatcaccgc atccaatggc   720
ggctatattg taagcgctgt agaagatggc gtatcagaaa gttatactgc ttcaagggtg   780
atattaacca cacctgctta cagcgcgggca gcaactatta cgaatcttga tgctgctacc   840
```

-continued

```
gctgccttgt taaatgaaat tcattatccc cgtatgggcg tgctgcacct gggttttgac   900
gctactgcgt tgccgcagcc cctggatgga tttggtttcc tggtaccgaa tgctgaaaat   960
atgcatttcc tgggagcaat ctgcaacgct gcaatttcc cggataaggc gcctccggga  1020
aaaatcctct ttacggtatt cctgggagga gcaagacagg aaagtttgtt tgaccagatg  1080
acgcccgaag ctctgcaaca gcaggtagtt tcagaggtca tgtctttact gcatttatct  1140
gcgccgccgg taatgcagca tttcagtagc tggaataaag cgattccgca gttaaatgtg  1200
ggtcatgtta agttacggcg tgccgtggaa gcttttgaaa aaaaatatcc cggtattcac  1260
ctcagcggga attacctgca aggcgtagct atcccggctt tactgcaaca tgccgccgct  1320
ttggcggctt ccctgaagaa aaattaa                                      1347
```

SEQ ID NO: 185          moltype = DNA  length = 1335
FEATURE                 Location/Qualifiers
source                  1..1335
                        mol_type = other DNA
                        note = Recombinant
                        organism = synthetic construct
SEQUENCE: 185

```
caacccgtcc tcatcgttgg agctggtctc tccgggctct caatcgctta cgaactacag   60
aagctgcaag tccccttacca agtgctggag gtttctggac attctggtgg agtcatgaag  120
tcactccgga aggacggatt tgaactcgac gctggtgcca acaccatagc cacgtctccc  180
gagattcttg cgtactttac ctcactaggt cttgagaatg agatcctcca ggcgactgct  240
acttctaaac accgcttctt ggtgcggcga aggcaactgc acgccgtgag ccgcacccg   300
ttcaagatca tgtcatcgcc gtacctctgc cgtggctcca aatggaggct ctttactgag  360
cggtttcgga aacccgtcgt cgcttcgggc gaggagaccg tcaccgattt catcacgagg  420
agattcaacc gcgaaatagc ggagtatgtg ttcgaccctg ttctaagtgg gatctacgcc  480
gggaacccgg accaaatgag tattgctgag gtgttgcctg ccttgcctag gtgggaaagg  540
gagtacggat cagtgaccaa gggccttatg aaggataagg gtgcgatggg aggtcgaaag  600
atcatcagct ttaagggtgg caaccagcta cttacaaacc gcttacagca gctactcact  660
actccggtga gattcaattg caaggtgaca gggattacag ccagcaatgg cgggtacatc  720
gtgagcgctg ttgaggacgg cgtatctgag agctacaccg catctcgtgt gatcttgacc  780
acacccgctt actcagcagc ggctaccata actaaccttg atgcagccac tgcggcactg  840
ttgaacgaaa tccattatcc acgtatgggc gtgttacact tgggctttga tgcaactgcc  900
ttgccacagc cgctggacgg gttcggattt ctagtgccga acgcggagaa catgcacttc  960
ctgggagagcc a tctgcaatgc agccatcttc ccggacaagg ctccgcccgg caagatcctg  1020
tttacagtgt tcctcggagg cgcacgccag gagtcgctct tcgatcagat gactcctgag  1080
gctcttcagc agcaagtcgt tagtgaggtg atgagcttgt tgcacttgtc agctccaccg  1140
gtgatgcagc acttctcctc ctggaacaag gccatccctc aattgaacgt cgggcacgtg  1200
aagttgcggc gcgcggtaga ggcgttcgag aagaaatacc ctggaatcca tctctcgggc  1260
aactacctcc agggagttgc aataccagct ttactccagc acgccgcagc tttagctgct  1320
tctcttaaga agaac                                                   1335
```

SEQ ID NO: 186          moltype = DNA  length = 1413
FEATURE                 Location/Qualifiers
source                  1..1413
                        mol_type = genomic DNA
                        organism = Bacillus subtilis
SEQUENCE: 186

```
atgagtgacg gcaaaaaaca tgtagtcatc atcggcggcg gcattaccgg tttagccgcc   60
gccttctata tggaaaaaga aatcaaagaa aagaatctgc cgcttgaact gacgcttgtt  120
gaggcaagtc cgagagtcgg cggaaaaatc cagactgtca agaaggacgg ctatatcatc  180
gaaagagc cagactcatt tctggaacga aagaaaagcg ccccgcagct tgttaaagac  240
ttaggtcttg agcatttgct tgtcaacaat gcgaccggac aatcctatgt gcttgtaaac  300
cgcactctgc atccaatgcc gaagggcgct gtaatgggga taccgacaaa aattgcgccg  360
tttgtttcta cgggtctgtt ttctttgtct gggaaggcga gagctgctat ggatttcatc  420
ctgcctgcta gcaaaaacaa ggatgatcag tcattgggag aattcttccg cagacgtgtc  480
ggagatgaag tggtcgagaa cttaatcgag ccgcttctat cagggatcta cgcaggcgac  540
attgacaagc tcagcctgat gtcgacattc ccgcaatttt atcagacgga acaaaagcat  600
agaagcctga ttctcggcat gaaaaaaaca aggcctcaag gctcaggcca gcagctgacg  660
gcaaaaaaac aagggcagtt ccagactctg tcaaccggtt tgcagaccct tgtagaagag  720
atcgaaaagc agttaaagct gacgaaggtg tataaaggca caaagtgac caaactcagc  780
catagcggct ctggctattc gctcgaactg gataacggcg tcacacttga tgctgattca  840
gtaattgtga ctgctccgca taaagcggct gcgggaatgc tttctgagct tcctgccatt  900
tctcatttga aaaaatatgca ctccacatcc gtggcaaacg tcgctttagg tttccctgaa  960
ggctccgtcc aaatggagca tgagggcacg ggttttgtca ttcaagaaa cagtgacttt 1020
gcgatcacag cctgtacgtg gacgaataaa aaatggccgc acgcagcgcc ggaaggcaaa 1080
acgctgcttc gggcatatgt cggaaaagct ggagacgaat ccattgtcga tctatcagat 1140
aatgacatta tcaacattgt gttagaagac ttaaagaaag tcatgaacat aaacggcgag 1200
ccggaaatga catgtgtcac ccgatggcat gaaagcatgc cgcagtacca tgtcggccat 1260
aagcagcgta tcaaggagct gcgtgaagca cttgcacctg cgtatccggg tgtttatatg 1320
acaggcgctt ctttcgaagg tgtcggcatt cccgactgca ttgatcaagg aaaagctgcc 1380
gtgtctgacg cgcttaccta tttattcagc taa                               1413
```

SEQ ID NO: 187          moltype = DNA  length = 1413
FEATURE                 Location/Qualifiers
source                  1..1413
                        mol_type = genomic DNA
                        organism = Bacillus pumilus
SEQUENCE: 187

```
atgcatgaca atcaaaaaca ccttgtcatc attggcggtg gcatcactgg tttagccgcc   60
```

```
gccttctatt tggaaaagga agtcgaggaa aaaggtcttc cgattcaaat atcacttatt   120
gaagcgagcc ctaggctagg tggaaaaata caaacattat ataaagacgg ctacatcatt   180
gaacgtggac ctgattcatt tttagaaaga aaggtcagtg ggccgcagct tgcaaaagat   240
gtcggtctgt ccgatcagct cgtcaataat gaaactgggc aagcgtatgt actggtcaat   300
gaaaagcttc acccgatgcc aaaaggtgct gttatgggca ttccaactca aatcagccca   360
tttattacaa ctggtctttt ttcagttgcg ggaaaagcaa gagcggcgat ggatttcgtg   420
ttgccaaaaa gcaagcagac ggaagaccag tcgcttggtg aatttttttag aagacgtgtg   480
ggtgatgagg tcgttgagaa tttaattgag ccgcttctat caggcattta tgcagggggat   540
attgaccgtc tgagcttaat gtcgaccttc ccgcaatttt atcaaacaga acagcagcat   600
cgaagtttga ttcttgggat gaaaaaatca cagcagcatg cgaaagcgca gcaagtgact   660
gcgaaaaaac aaggacagtt ccaaacgatc aatcaaggat tgcagtcgct tgtgtgaagca   720
gtagaaggta agctcaagct gacaacggtc tataaaggga caaaagtcaa acaaattgaa   780
aaaacgatg gaggctatgg cttacaatta gacagcggtc aaacgctttt tgccgattca   840
gccattgtca cgactccgca tcaatcgatt tattccatgt ttcctaaaga agcagggcta   900
gagtatttgc atgacatgac ctctacttct gttgcaacag tagcactcgg ttttaaagat   960
gaggatgttc ataatgaata tgacggcact ggatttgtca tctcaagaaa cagtgatttc  1020
tctattacgg cctgtacatg gacaaacaaa aaatggccgc atactgctcc gaaaggaaaa  1080
acgctattgc gtgcgtatgt agggaaggct ggcgacgaat caattgtcga cagtcgac  1140
agtcaaatcg tcagcattgt gctagaagat ttaaagaaaa tcatggatat taaagcagat  1200
ccagaattga cgacagtgac tcgctggaag acaagtatgc cgcaatatca cgtcggtcat  1260
cagaaagcca tttcgaacat gcgagaaacg tttaagcaat catatcctgg tgtttatatt  1320
acaggtgctg ctttttgaagg tgtcggaatc cctgattgta ttgatcaagg aaaagccgcc  1380
atctcagagg ctgtatcgta tctattttca taa                               1413
```

SEQ ID NO: 188          moltype = DNA  length = 1413
FEATURE                 Location/Qualifiers
source                  1..1413
                        mol_type = genomic DNA
                        organism = Bacillus pumilus
SEQUENCE: 188

```
atgcatgaca atcaaaaaca ccttgtcatc attggcggtg gcatcactgg tttagccgcc    60
gccttctatt tggaaaagga agtcgaagaa aaaggtcttc ccattcaaat atctcttatt   120
gaagcgagcc ctaggctagg tggaaaaatc caaacattat ataaagacgg ctacatcatt   180
gaacgtgggc ctgattcatt tttagaaaga aaggtcagtg gaccgcagct ggcgaaagat   240
gtaggtctat ccgatcagct cgtcaataat gaaacagggc aggcgtatgt actagtcaat   300
gaaacccttc acccgatgcc aaaaggcgct gtcatgggta ttccaactca aatcagccca   360
ttcatcacaa ccggtctttt ttcagttgca ggaaaagcga gagccgcaat ggatttcgtc   420
ttgccaaaaa gcaagcaaac agaagatcag tcgctcggtg aattttttttag aagacgtgtc   480
ggtgatgaag tagttgagaa tttaatcgaa cctcttctat caggcattta tgcaggtgac   540
attgaccgtc tcagcttaat gtccaccttc ccgcagtttt atcaaacaga acaaaagcat   600
cgcagtttga ttcttgggat gaaaaaatca cagcagcatg cgaaagcgca gcaagtgaca   660
gcgaaaaaac aagggcagtt ccaaacgatc aatcaaggac ttcaagcgct tgttgaagca   720
gtagaaacga agctcaagct gacaacgatt tataaaggga caaaagtgac gcagattgaa   780
aaaacagatg ggggctacgg tgtgcagtta gacagcggtc aaacgctttt ggctgattca   840
gccattgtga caactccgca tcaatcgatc tattccatgt ttccaaaaga agcggggctt   900
gagtacttgc atgatatgac atctacttct gttgcaacgg ttgcactcgg ttttaaagaa   960
gaggatgttc ataatgaata tgacggtact ggttttgtca tctcaagaaa cagtgatttc  1020
tctattacag cttgtacgtg gacgaacaaa aaatggccgc atacagctcc taaaggaaaa  1080
acattattgc gtgcttatgt agggaaggct ggcgacgaat caattgtcga cagtcgac  1140
catcaaatcg tcagcattgt actggaggat ttgaagaaaa ttatggatat taaagcagat  1200
ccagaactga caacagtgac tcgctggaag acgagcatgc cgcaatatca cgtcggtcat  1260
caaaaagcca tttcgaacat gcgagaaacg tttaagcaat catatcctgg tgtttatatc  1320
acaggtgctg ctttttgaagg tgtcggaatc cctgattgta ttgatcaagg aaaagctgcc  1380
atttcagagg ctgtatctta tctattttca taa                               1413
```

SEQ ID NO: 189          moltype = DNA  length = 1329
FEATURE                 Location/Qualifiers
source                  1..1329
                        mol_type = other DNA
                        note = Recombinant
                        organism = synthetic construct
SEQUENCE: 189

```
atgcaaactc agcccgtcat aatagcgggc gctggcattg cgggcctttc tatcgcatac    60
gagctgcaac agaagggcat tccttacgaa attatggaag cctcgtccta cgccggaggc   120
gtggtcaagt cccttcacat tgatggctac gaactagacg ccggacctaa ttcacttgcc   180
gcgtccgctg ccttcatggc ctacatcgac caactcggac tccaagatca agtgcttgaa   240
gccgccgcag catccaagaa ccgcttcctc gtaagaaacg acaagctcca tgcagtctcg   300
ccgcaccgt ttaagatcct ccagtcggcc tacatcagtg gcggcgctaa gtggagattg   360
tttaccgaaa ggttccgcaa agctgcggct ccagaggtg gagacagt gagcagcttc   420
gtgacgagga ggtttggcaa ggagatcaac gactaccgt ttgaacccgt cttgtccggg   480
atctacgcgg gcaacccgga tttgatgagt gttggcgagg ttctgccgat gcttcctcaa   540
tgggagcaga agtacggcag cgttacacaa ggcttgttga agaataaggg cgcaatgggc   600
ggccgaaaga taatcgcttt caaggcgggg aatgccacac tgaccaaccg tcttcagtca   660
ctgctctcag gaaagatccg cttcaattgc gccgtgacgg gtgtcacacg aggcgcagac   720
gactacattg ttcagtacac tgagaatggc aataccgaa tgttgaatgc aagccgcgtg   780
atcttcacaa cacccgctta ctcaactgct gttgccatcc aggcgttgga cgccagcttg   840
gccactcacc tctctgatgt accctatcct cgcatgggtg tgttgcactt gggcttcggt   900
gctgaggcaa ggcagaaggc tcctgcgggc tttgggttct tggtcccaca cgcagccgga   960
aagcacttcc tgggagcaat ctgtaactcc gctatcttcc cttcgcgggt gcccactggc  1020
```

-continued

```
aaggtgttat tcaccgtgtt cttgggcggt gccagacagg agcaactgtt tgaccagcta    1080
ggccctgaga agttacaaca gacagtggtg aaggagctta tggaattgct gggcctaact    1140
acgccgccgg agatgcaacg attctctgag tggaatcgcg caataccgca acttaatgtt    1200
ggctacgccc agactcgtca gcagattggc gtattcgagc agcgctaccc tggcatccgc    1260
ttggccggga actatgtaac tggagtggcg gtgcccgcca ttatccaagc tgcaaagggc    1320
tattgctaa                                                            1329

SEQ ID NO: 190              moltype = DNA  length = 1320
FEATURE                     Location/Qualifiers
source                      1..1320
                            mol_type = other DNA
                            note = Recombinant
                            organism = synthetic construct
SEQUENCE: 190
cagcccgtca taatagcggg cgctggcatt gcgggccttt ctatcgcata cgagctgcaa    60
cagaagggca ttccttacga aattatggaa gcctcgtcct acgccggagg cgtggtcaag    120
tcccttcaca ttgatggcta cgaactagac gccggaccta attcacttgc cgcgtccgct    180
gccttcatgg cctacatcga ccaactcgga ctccaagatc aagtgcttga agccgccgca    240
gcatccaaga accgcttcct cgtaagaaac gacaagctcc atgcagtctc gccgcacccg    300
tttaagatcc tccagtcggc ctacatcagt ggcggcgcta agtggagatt gtttaccgaa    360
aggttccgca aagctgcggc tccagagggt gaggagacag tgagcagctt cgtgacgagg    420
aggtttggca aggagatcaa cgactacctg tttgaacccg tcttgtccgg gatctacgcg    480
ggcaacccgg atttgatgag tgttggcgag gttctgccga tgcttcctca atgggagcag    540
aagtacggca gcgttacaca aggcttgttg aagaataagg gcgcaatggg cggccgaaag    600
ataatcgctt tcaagggcgg gaatgccaca ctgaccaacc gtcttcagtc actgctctca    660
ggaaagatcc gcttcaattg cgccgtgacg ggtgtccaac gaggcgcaga cgactacatt    720
gttcagtaca ctgagaatgg caataccgca atgttgaatg caagccgcgt gatcttcaca    780
acacccgctt actcaactgc tgttgccatc caggcgttgg acgccagctt ggccactcac    840
ctctctgatg tacccatatcc tcgcatgggt gtgttgcact tgggcttcgg tgctgaggca    900
aggcagaagg ctcctgcggg ctttgggttc ttggtcccac gcagccgg aaagcacttc    960
ctgggagcaa tctgtaactc cgctatcttc ccttcgcggg tgcccactgg caaggtgtta    1020
ttcaccgtgt tcttgggcgg tgccagacag gagcaactgt ttgaccagct aggccctgag    1080
aagttacaac agacagtggt gaaggagctt atggaattgc tgggcctaac tacgccgccg    1140
gagatgcaac gattctctga gtggaatcgc gcaataccgc aacttaatgt tggctacgcc    1200
cagactcgtc agcagattgg cgtattcgag cagcgctacc ctggcatccg cttggccggg    1260
aactatgtaa ctggagtggc ggtgcccgcc attatccaag ctgcaaaggg ctattgctaa    1320

SEQ ID NO: 191              moltype = DNA  length = 1347
FEATURE                     Location/Qualifiers
source                      1..1347
                            mol_type = other DNA
                            note = Recombinant
                            organism = synthetic construct
SEQUENCE: 191
atgagcgacc agcccgtcct catcgttgga gctggtctct ccgggctctc aatcgcttac    60
gaactacaga agctgcaagt cccttaccaa gtgctggagg tttctggaca ttctggtgga    120
gtcatgaagt cactccggaa ggacggattt gaactcgacg ctggtgccaa caccatagcc    180
gcgtctcccg agattcttgc gtactttacc tcactaggtc ttgagaatga gatcctccag    240
gcgactgctg cttctaaaca ccgcttcttg gtgcggcgaa ggcaactgca cgccgtgagc    300
ccgcacccgt tcaagatcat gtcatcgccg tacctcagcc gtggtccaa atggcggctc    360
tttactgagc ggtttcggaa gcccgtcgtc gcttcgggca aggagaccgt caccgatttc    420
atcacgagga gattcaaccg cgaaatagcc gagtatgtgt tcgaccctgt tctaagcggg    480
atctacgccg ggaacccgga ccaaatgagt attgctgagg tgttgcctgc cttgcctagg    540
tgggaaaggg agtacggatc agtgaccaag ggccttatga aggataaggg tgcgatggga    600
ggtcgaaaga tcatcagctt taagggtggc aaccagctac ttacaaaccg cttacagcag    660
ctactcacta ctccggtgag attcaattgc aaggtgacac ggattacagc cagcaatggc    720
gggtacatcg tgagcgctgt tgaggacggc gtatctgaga gctacaccgc atctcgtgtg    780
atcttgacca caccccgctta ctcagcagcg gctaccataa ctaaccttga tgcagccact    840
gcggcactgt tgaacgaaat ccattatcca cgtatgagtg tgttacactt gggctttgat    900
gcaactgcct tgccacagcc gctggacggg ttcggatttc tagtgccgaa cgcggagaac    960
atgcacttcc tgggagccat ctgcaatgca gccatcttcc cggacaaggc tccgcccggc    1020
aagatcctgt ttacagtgtt cctcggaggc gcacgccagg agtcgctctt cgatcagatg    1080
actcctgagg ctcttcagca gcaagtcgtt agtgaggtga tgagcttgtt gcacttgtca    1140
gctccaccgg tgatgcagca cttctcctcc tggaacaagg ccatccctca attgaacgtc    1200
gggcacgtga agttgcggcg cgcggtagag cgttcgagga agaaataccc tggaatccat    1260
ctctcgggca actacctcca gggagttgca ataccagctt tactccagca cgccgcagct    1320
ttagctgctt ctcttaagaa gaactga                                        1347

SEQ ID NO: 192              moltype = DNA  length = 1413
FEATURE                     Location/Qualifiers
source                      1..1413
                            mol_type = other DNA
                            note = Recombinant
                            organism = synthetic construct
SEQUENCE: 192
atgtcggatg gcaagaagca cgtcgtcatc ataggcggtg ggatcactgg cttggccgct    60
gcattctaca tggagaagga gattaaggag aagaacctcc cacttgagct gacgctagtt    120
gaggccagtc ccagggtcgg cggcaagatc cagacggtca agaaggacgg gtacataatt    180
gaacgcggcc ctgacagctt cttagagcgc aagaaatcgg ctccgcagct agttaaggac    240
```

-continued

```
ttgggacttg agcacctgct cgtcaacaac gcgaccggac agtcgtacgt gctcgtgaac    300
cggacgctcc acccgatgcc gaagggcgct gtgatgggca ttccgaccaa gatagcacca    360
ttcgtgagta ccggcctatt cagcctttcc ggcaaggcaa gggctgcgat ggacttcatc    420
ttgcctgcct ctaagactaa ggacgatcag tccttgggcg agttcttccg ccgccgggtg    480
ggtgatgagg tggtggagaa cttaattgag ccgctcctat ctggaatcta cgctggtgac    540
atcgacaaac tgtctctgat gtccaccttt ccgcagttct accaaactga gcagaagcac    600
cgttcactta tcttgggaat gaagaagact agacctcaag gttcgggtca gcaactgacg    660
gccaagaaac agggtcagtt ccagacgcta agcaccgggc ttcagacact cgtggaggag    720
attgagaaac agctcaaact tactaaggtg tacaagggca cgaaggtgac aaagttatcc    780
cactccggca gcgggtactc cctggagttg gacaatggcg taacgttgga cgccgactca    840
gttatcgtga cagcgccgca taaggctgct gccgggatgt tgtcagaact cccggcgatt    900
tcccatctca agaacatgca cagtacctcg gttgccaacg tcgccctcgg attcccggaa    960
ggaagtgttc aaatggagca cgaaggcacg ggtttcgtaa tttccaggaa ctccgacttt   1020
gccatcaccg cttgtacttg gaccaacaag aagtggccac atgctgcgcc ggagggcaag   1080
acattgctca gagcttacgt cgggaaggcg ggcgacgagt caatcgtcga tcttagcgac   1140
aacgacatca ttaacattgt gctggaggac ttgaagaagg ttatgaacat caatggcgag   1200
ccagagatga cctgcgtgac ccgatggcac gagtctatgc cgcagtacca cgtcggtcac   1260
aagcagcgca tcaaggagtt gcgcgaggca ctcgcctcag cttaccctgg cgtgtacatg   1320
actggcgctt cgtttgaggg cgttggtatt cctgactgca tcgaccaggg aaaggcggcc   1380
gtcagtgacg cgctcaccta cctcttcagt tga                                1413
```

SEQ ID NO: 193          moltype = DNA  length = 1413
FEATURE                 Location/Qualifiers
source                  1..1413
                        mol_type = other DNA
                        note = Recombinant
                        organism = synthetic construct
SEQUENCE: 193

```
atgcacgaca accagaagca cctggtcata atcggaggcg gcataaccgg ccttgctgcg     60
gccttctacc tggagaagga ggtcgaggag aagggtctcc ctatccagat ttcattgatt    120
gaggcttcgc ctcggctggg agggaagatc cagacattgt acaaggacgg gtacatcatc    180
gagcgtggtc cagacagttt cctggagcgg aaggtcagcg gaccgcagct cgccaaggac    240
gtgggactta gcgaccaact ggtgaacaac gagacaggac aggcgtacgt cttggtgaat    300
gagaagttgc acccgatgcc taagggtgcc gtgatgggca tcccaacgca aatctcacct    360
ttcatcacca ccggactctt ctccgtggcc ggaaaggcaag gagctgcaat ggacttcgtt    420
ctgcctaagt cgaaacagac cgaagaccag tctctaggcg agttcttccg ccgccgtgtg    480
ggtgacgagg ttgtgga gaa cctcatcgag cctttgttgt ctgggatcta cgcgggcgac    540
atcgacagac ttagtctcat gagtaccttt ccgcaattct atcagacaga acagcagcat    600
cgaagtctca tactcgggat gaagaagtca caacaacatg caaaggccca gcaagttacc    660
gccaagaaac agggccagtt ccaaacgatc aaccagggcc tccagagctt ggtgaaggca    720
gtggagggaa agttgaagct caccaccgtt tacaaaggga caaaggttaa acagattgag    780
aagacgacg gcggttacgg gttacaattg gactccggac agactctctt cgctgattcc    840
gctatcgtaa ctactcctca ccagacatc tactctatgt tcccgaagga ggcgggcctg    900
gagtacctgc acgacatgac ttcaacgtct gtcgccaccg tggctttggg cttcaaggac    960
gaggacgtcc acaatgagta tgacgggacg ggattcgtta tcagtaggaa ctccgacttc   1020
agcatcaccg cctgcacgtg gaccaacaag aagtggccac acaccgcgcc caaagggaag   1080
acccttctga gggcatacgt gggcaaggcg ggcgacgaga gcatcgtcga gcaatctgat   1140
tctcagattg tttcaatcgt cctcgaagac ctcaagaaga tcatggacat caaggcagac   1200
ccggaactta ccaccgttac tcgatggaag acctcgatgc ctcagtatca cgtcgggcac   1260
cagaaggcaa tcagcaacat gagggagaca ttcaagcagt cgtatcctgg cgtgtacatt   1320
accggagcag cattcgaagg cgtaggaatc cctgactgca ttgaccaggg caaggctgct   1380
atctcagagg ccgtgtccta tctcttctcg tga                                1413
```

SEQ ID NO: 194          moltype = DNA  length = 1413
FEATURE                 Location/Qualifiers
source                  1..1413
                        mol_type = other DNA
                        note = Recombinant
                        organism = synthetic construct
SEQUENCE: 194

```
atgcacgaca accagaagca cctggtgata attggaggcg ggattaccgg cctagcagcc     60
gctttctatc tggagaagga ggtggaggag aagggcctcc cgatacagat ttcgctgatt    120
gaagcctctc cgcgcctggg cggcaagatc cagacattgt acaaggacgg gtacatcatt    180
gagcgcgggc ctgactcgtt cctggagcgg aaggtctccg gtcctcaact ggccaaagac    240
gtgggtcttt ccgatcagct tgtgaacaat gagaccggtc aggcttacgt cttggtcaac    300
gaaactctgc atcccatgcc taagggagcc gttatgggca ttccaacgca aatctctccg    360
ttcataacga ctgggctgtt cagcgttgcg ggcaaagcaa gggctgctat ggacttcgta    420
ctgccaaaga gtaagcagac cgaggaccag tccctcggcg agttcttccg ccgccgagtg    480
ggcgatgagg tggttgagaa tctaatcgaa ccgctgttgt cgggcatcta tgcgggcgac    540
atcgacaggc taagtcttat gtccactttc cctcagttct accagacaga gcagaaacac    600
aggagtctca tccttggaat gaagaagtcc cagcagcacg cgaaggctca gcaagtgacc    660
gccaagaagc aaggacagtt ccagaccatc aaccagggcc tacaggccct tgtcgaagcc    720
gttgagtcga agttaaagtt gacgacgatc tacaagggca ccaaggtgaa gcagattgag    780
aagactgacg gtggctatgg tgtgcaactc gattcgggcc aaacattgct cgctgactcc    840
gctatcgtca cgacgccaca ccagtcgatc tactcgatgt tcccgaagga ggcgggccta    900
gagtaccttc acgacatgac ctccacttcg gtcgccaccg ttgcactcgg ctttaaggag    960
gaggacgttc acaacgagta cgatggcacc ggattcgtga tctccaggaa ctcggacttc   1020
tcgattaccg cgtgcacgtg gacaaataag aagtggccgc acacagcgcc aaagggcaag   1080
acccttctgc gggcgtatgt gggcaaggcc ggtgacgaga gcattgtcga caatctgac    1140
```

-continued

```
catcagatcg tttctattgt tcttgaggat ctcaagaaga taatggacat taaggccgac   1200
cctgagctta ccacagtgac gaggtggaag acctcgatgc cgcagtatca cgtagggcac   1260
cagaaggcca tctccaacat gcgggagaca ttcaagcagt cgtaccctgg cgtgtacatt   1320
actggcgctg ctttcgaggg cgttggcatc ccggactgca tcgaccaggg caaggccgca   1380
atctcagagg cagtgtcgta cctgttcagc tag                                1413

SEQ ID NO: 195            moltype = DNA   length = 1329
FEATURE                   Location/Qualifiers
source                    1..1329
                          mol_type = other DNA
                          note = Recombinant
                          organism = synthetic construct
SEQUENCE: 195
atgcaaacgc aaccagtgat aatcgcgggc gctggcatcg ccggactttc cattgcgtac   60
gagctccagc agaagggtat cccgtacgag atcatggagg caagttccta tgccggcggc   120
gtcgtcaagt cactgcacat cgacgggtac gagctggacg cgggacccaa cagcctagcc   180
gcttccgctg ccttcatggc gtacatcgac cagctggggc tccaagacca agtcctcgag   240
gctgccgcgg cgagtaaaaa tcgctttctc gtggaggaacg acaagcttca cgctgtgtca   300
ccgcaccctt tcaaaatact tcaaagcgcc tacatctcgg gcggtgctaa gtggcggtta   360
ttcacggagc gttttaggaa ggccgccgct cccgaaggtg aggagactgt ttcctctttc   420
gtcacacgca ggttcggaaa ggagatcaac gattatctct ttgagcctgt tctcagcgga   480
atatacgccg gcaacccaga ccttatgagc gtcggagagg ttctccctat gctgccgcaa   540
tgggagcaaa agtatggttc tgtgacccaa ggcctactga agaataaggg ggcgatgggc   600
ggaagaaaga taattgcatt caagggggggt aatgccaccc ttacaaatcg cctgcaaagc   660
cttttgtcgg gaaaaatccg tttcaattgt gccgtcaccg gtgttacaag aggcgcagat   720
gattacatcg ttcagtacac cgagaacggt aataccgcca tgctaaacgc atctagggtg   780
attttcacaa ccccggccta ctcaactgcc gtcgccatcc aagccctcga cgccagcctg   840
gccactcatc tcagtgatgt gccttaccct cgtatggggg tattacatct tggcttcggg   900
gccgaagcgc gacagaaagc ccccgctgga tttggcttcc tagtccctca cgccgccggt   960
aaacattttc ttggcgccat ctgtaactcc gcaatcttcc catccagagt gcctactggc   1020
aaggttctgt ttactgtgtt cctgggcggt gcccgccagg agcagctatt cgaccaatta   1080
ggcccagaaa agtccaaca aaccgttgtg aaggaactaa tggagttgct cggactgacg   1140
acaccacccg agatgcagag gtttttctgag tggaaccgcg cgattccaca actcaacgtc   1200
gggtacgccc agacccggca acagataggg gttttcgagc agcgctatcc aggcattcga   1260
cttgctggta attacgtcac aggagtcgct gtgccagcca taatacaagc tgcaaagggg   1320
tattgctga                                                            1329

SEQ ID NO: 196            moltype = DNA   length = 1347
FEATURE                   Location/Qualifiers
source                    1..1347
                          mol_type = other DNA
                          note = Recombinant
                          organism = synthetic construct
SEQUENCE: 196
atgtcagacc aaccagtctt gattgttggg gccggcctct ctggcctgtc gattgcctac   60
gaactgcaga agctccaggt gccgtaccaa gtcctggagg tgtcgggcca tagcggcggt   120
gtcatgaaat cgctgcgtaa ggacggcttc gagttgacg cgggcgcgaa cacaatcgcg   180
gctagcccag aaatacttgc ttactttaca agtctgggtc tggagaatga gatcctccag   240
gctacagccg ctagcaaaca tcgattcctg gtgcgcaggc gacaactgca cgccgtcagt   300
ccacatccat tcaagataat gtcgagcccc tatttaagcc gcgggtccaa gtggaggctc   360
tttactgaaa gatttcgaaa accggtcgtc gctagcggag aagaaactgt tacagatttt   420
attactcgca ggttcaacag ggagattgca gaatatgtct tcgatccagt tctctcagga   480
atttacgcgg gcaacccaga ccagatgagc atcgctgaag tcctgcccgc gctccctcgg   540
tgggaacgag aatatggaag cgtcaccaaa ggtctcatga aggacaaggg ggccatgggc   600
ggtcggaaga tcatatcgtt taaaggcggg aaccagcttc tgactaaccg gctgcaacag   660
ctgctcacta caccagtgcg gtttaattgc aaagtcacag gtataaccggc tagtaatggc   720
ggctacattg tttcagcggt cgaagatggt gtgagcgagt catacaccgc ctcccgcgtg   780
atccttacca caccggccta ctcggcggca gctacaatca ccaatcttga cgcggctaca   840
gccgcattac tcaacgagat tcattatccc aggatggggg tcctccatct gggcttcgac   900
gcgacagctc ttccccagcc cttggatggc ttcgggtttc tggtcccgaa cgccgaaaac   960
atgcattttc tcggcgccat ttgcaacgcc gcgatcttcc cggataaggc cccgcctgga   1020
aaaatattgt tcactgtctt tcttggcggc gcacgccagg agtccctgtt cgaccaaatg   1080
accccagagg ctctgcagca gcaggtggtc tctgaggtga tgtcacttct gcacctttct   1140
gcacctccag tgatgcagca cttctcaagc tggaataaag ctatcccca gttgaacgtc   1200
ggccacgtga agcttcgtag ggcggtcgaa gcgttcgaaa agaagtatcc aggcattcac   1260
ctgtccggca actatctgca gggcgtcgca atcccggcgc tactccagca cgccgctgcg   1320
ctagccgcgt ctcttaagaa gaattag                                       1347

SEQ ID NO: 197            moltype = DNA   length = 1413
FEATURE                   Location/Qualifiers
source                    1..1413
                          mol_type = other DNA
                          note = Recombinant
                          organism = synthetic construct
SEQUENCE: 197
atgagtgacg ggaagaagca cgttgtgata atcggaggcg ggataaccgg cctcgccgcc   60
gccttctata tggagaagga aattaaggag aaaaacctcc cgctagagct gacgttggtg   120
gaagcgtcac caagggtcgg cggtaagatc cagaccgtca aaaaggatgg ctacatcatc   180
gagcgcggcc cggacagctt cctcgagcgg aagaagtccg caccccagtt agtcaaagac   240
```

-continued

```
ctcggcttgg aacacctttt ggtcaacaac gcgacaggtc agtcctatgt gcttgtgaat   300
cggacgctgc acccgatgcc taagggcgct gtcatgggta tccccacgaa gatcgcgccg   360
ttcgtatcga ccggcctgtt ctccctatca ggtaaggccc gcgctgccat ggactttatc   420
ctccctgcct cgaaaactaa agacgatcag tcactaggcg agttctttcg gcggcgagtg   480
ggtgacgagg tggtggagaa cctcatagaa cccctgctgt ccgggatcta cgctggagac   540
atcgacaagc tgagcctcat gtctactttt ccgcaatttt atcagaccga gcagaaacac   600
agatctctta tccttggcat gaagaagacc aggcctcagg ggtcgggtca acagctcaca   660
gcaaagaagc aagggcagtt ccaaaccctg agcacaggct tgcagaccct ggtcgaagaa   720
attgagaagc agctgaaatt aacgaaggtt tacaagggaa ccaaggtcac caaacttagt   780
cacagcggct cgggctacag cctagagctt gacaacggag tgactctgga cgcagacagc   840
gtgatcgtga cggcgcccca caaggctgcg gcgggaatgc tgagtgagct ccccgccata   900
agtcatctca agaacatgca ctcgacgtcg gtagccaatg tcgcgttggg gtttcccgag   960
ggtagcgtcc aaatggaaca cgaaggaact ggtttcgtca tatcccggaa ctctgacttc  1020
gcgatcacag cgtgcacttg gacgaataaa aagtggccac acgcagcgcc tgaggggaag  1080
acccttcttc gagcgtatgt gggcaaagcg ggcgatgaaa gcattgtgga tttatcggac  1140
aacgacatta tcaacatcgt actggaagac ctaaagaaag tcatgaacat aaacggcgaa  1200
ccggagatga catgcgtcac taggtggcac gagagcatgc cgcagtacca cgtggggcac  1260
aagcagcgca tcaaggaatt gagggcaggcc ctcgctagcg cgtaccctgg agtttacatg  1320
accggcgcca gttttgaggg tgtcggtatc cctgactgta tcgaccaggg taaggccgcg  1380
gtaagcgacg cattgacgta cctgttctca tga                               1413
```

SEQ ID NO: 198          moltype = DNA  length = 1413
FEATURE                 Location/Qualifiers
source                  1..1413
                        mol_type = other DNA
                        note = Recombinant
                        organism = synthetic construct
SEQUENCE: 198

```
atgcacgaca accagaagca tctggtcatc attggcgggg gcatcacggg cttggcagcc   60
gccttctacc tggagaagga ggtcgaggag aagggccttc cgattcaaat atctctgatt  120
gaggcgtctc cccgactcgg cgggaagatc cagaccctct ataaagacgg ctatataatt  180
gagcggggac cagattcttt cctggagcga aaggtctcgg gcccacagtt ggcgaaagat  240
gtcggcctct ccgatcaact cgtgaacaac gagaccgggc aggcctatgt tctggtgaac  300
gagaaattgc atcctatgcc taaggggggc gtcatgggaa taccaaccca aatatctccc  360
ttcataacaa ccggactgtt ctcggttgcc ggtaaggcca gggccgcgat ggacttcgtc  420
ctgccaaagt ctaagcagac ggaggaccag tccctcgggg aattttttcg ccgccgggtc  480
ggcgacgagg ttgtgggaaa cctgattgag ccgttgctgt ctggcatcta cgcaggcgat  540
atcgacaggc tgagccttat gtctacgttc ccgcaatttt atcagaccga gcagcagcac  600
cggtctctga tacttggcat gaagaaatca caacagcacg ccaaagcaca acaggttact  660
gctaagaagc aaggacaatt ccagacaatc aaccaagggt tgcagtccct cgtggaggcg  720
gtagaaggca aattgaaact caccaccgtc tacaagggca cgaaagttaa gcagatcgag  780
aaaacgggatg gcgggtacgg tctccagctc gatagcggcc agacactgtt cgccgactca  840
gcgatcgtca ccaccccca ccagtccatc tacagcatgt ccctaagga ggcggggtta  900
gaatacttac atgacatgac ctccacctcc gtcgccacag tagctctcgg cttcaaggac  960
gaggacgtgc acaacgaata cgacggtacc gggttcgtga tctcgcggaa ttcggacttc  1020
agtattactg cctgcacctg gacgaacaag aagtggccac acacagcacc caaaggtaag  1080
accttgctga gggcttatgt gggtaaggcg ggggacgaga gcatagtgga gcagtctgaa  1140
tcgcagatcg tcagcatcgt actggaagac ctgaagaaga tcatggacat caaggccgac  1200
ccggagttga ccaccgtcac acggtggaaa acctcaatgc cacaatatca tgtcggacat  1260
cagaaggcca tctccaacat gcgcgagacc ttcaagcagt cttacccggg cgtgtatatc  1320
accggagcgg ctttcgaggg ggtcggcatc cctgactgca tagaccaggg gaaggcggcc  1380
atcagcgagg ctgtgtcgta ccttttctcg tga                               1413
```

SEQ ID NO: 199          moltype = DNA  length = 1413
FEATURE                 Location/Qualifiers
source                  1..1413
                        mol_type = other DNA
                        note = Recombinant
                        organism = synthetic construct
SEQUENCE: 199

```
atgcatgaca accagaagca cctggttatc attggcggtg gcataaccgg gctcgccgcc   60
gccttttacc tggagaagga ggtggaggaa aaaggcctcc caatccagat cagtttgata  120
gaggcgagtc cgcgcttggg gggcaagatc cagactctgt ataaagatgg atacattatc  180
gagagcgggg cagacagctt cctggagcgc aaggtcccgg ggcctcagtt ggcgaaggat  240
gttgggttgt cagatcagct cgtgaacaac gaaacgggcc aggcgtatgt gttagtcaat  300
gaaactctgc accccatgcc caagggcgcg gtgatgggga tacccaccca gatcagtccc  360
ttcatcacaa ccggtctgtt ctcggtcgca gggaaggccc gagcggcgat ggattttgtc  420
ctgccaaagt cgaagcagac cgaggaccag agcctcgggg agtttttcag gcgcagagtt  480
ggcgatgagg tcgtcgagaa cctcattgag ccgcttctca gcgggattta tgcgggagac  540
atcgacaggc tctccctgat gtcaactttt ccgcagttct accagacgga gcaaaagcac  600
aggagcctga ttctgggaat gaagaagtca caacaacatg ctaaagccca gcaggtaact  660
gcaaagaagc agggtcagtt ccaaacaatc aatcaaggtc tccaggcact cgtcgaggcc  720
gtgggagtcaa agctaaagct gaccaccata tacaagggta ccaaagtgaa acaaatcgag  780
aagacagacg gcgggtacgg agtgcagctt gactccggca gaccctcct gccgactct  840
gcgatcgtga ccacgccgca ccagtccatc tactctatgt ccccaaggga ggccgggctc  900
gaatatttgc acgatatgac cagcaccagc gtcgctacgg tagcactcgg gttcaaggag  960
gaggacgtcc acaacgagta cgatggcact ggcttcgtga tcagccgtaa ctctgatttc  1020
agcatcactg catgcacatg gactaataag aaatggcccc acactgcacc caagggcaag  1080
acgctgctga gagcctacgt cgggaaggcc ggggacgagt ctattgtaga gcagagcgat  1140
```

```
caccagattg tgagtatcgt actggaggac ctgaaaaaga tcatggatat aaaggcggac   1200
ccagagctga ctaccgtgac ccgctggaaa acatccatgc cgcaatacca tgtgggccac   1260
caaaaagcga tctccaacat gcgggagacg ttcaagcaat cttatcccgg cgtgtacatc   1320
acgggagccg cgttcgaggg cgtgggcatc ccggattgca tcgatcaggg taaggctgcg   1380
atatcggagg ctgtcagtta cctgtttct tag                                 1413
```

```
SEQ ID NO: 200          moltype = DNA  length = 1434
FEATURE                 Location/Qualifiers
source                  1..1434
                        mol_type = genomic DNA
                        organism = Paenibacillus macerans
SEQUENCE: 200
gtgagcaaaa aaatcgccgt catcggcgga ggcataaccg ggttaagcgt ggcttattac   60
gtgcgtaaat tgctgcgtga acaggggta aacgctgagg ttaccctcgt ggaacagtcc   120
gatcggctgg gcggcaaaat ccgttcccta cgacgtgacg gctttacgat agaacagggc   180
ccggattcaa tgatcgcgcg caagcccgcc gcgctggaat tgatccggga actcgggctg   240
gaggataagc tggcgggaac gaatccgcag gcgaagcgaa gttatatatt gcatcgcggc   300
aaattccatc ccatgccgcc ggggctgatg ctcggcatac cgacgcaaat gtggccgatg   360
gtcaagacgg ggctgctctc tccggccggc aagctgcggg ccgcgatgga tctgctgctt   420
cccgcgcggc gcggcggcgg cgacgaatcg ctcggcggct tcatccgccg ccggctcggc   480
agagaagtgc tggagcagat gacggagccg cttctagccg gcatatatgc cggggacacc   540
gaacagctta gcttgaaagc gacgtttccg cagtttatgg agatggagcg caagcaccgc   600
agcctgatcc ttgggctgct ggccggcaaa aagcagccgc cgcggccggg gggaagccag   660
gtcccgctgc cgaaggccgc gcaaaccagc atgtttctga cgttgacggg cggttttggag   720
ggactgacgg aagcgctgga ggaatcgcta agcgaagaga aaataattac cggccaggcg   780
gtaaccggac tgtcgcagca agaggcgggt tatgagctta acttaagcgg gggcgagcgt   840
ttgaacgcgg acggagtcat tttggcagtt cctgcttttg ctgcggcccg gctattggat   900
ggcgttcccg aagccgctta cctggagcgg atccgttatg tgtccgtggc caatttagcc   960
ttcgcctacc ggcgggaaga cgttccgcac gatttgaacg gctccggccgt gcttatcccg   1020
cgcggggagg ggcgaatgat tacggccatt acctgggttt cttcgaaatg gctgcattcg   1080
gctcccggcg ataaagcgct gctgcgagcc tatatcggcc gcctgggcga cgaggcatgg   1140
accgcgatgt gcagggccga catcgagcgc cgggtggccg ccgagctgcg cgatttgctg   1200
ggcatcgccg ccagcccgct gttttgcgag ctcgccgctt tgccggagtc gatgccccaa   1260
tatccggtcg ggcatgtcga gcggcttgag gcgctgcgcg gggcattgtg ccgggcgaag   1320
ccggggctgc tgctgtgcgg cgcgggatat gccggccgtag gcattcccga ctgcatccgg   1380
cagggcaagg aagccgctga aagcatggcg gcttatttga gggatggacg gtga          1434
```

```
SEQ ID NO: 201          moltype = DNA  length = 1482
FEATURE                 Location/Qualifiers
source                  1..1482
                        mol_type = genomic DNA
                        organism = Paenibacillus thiaminolyticus
SEQUENCE: 201
atgaaagctc tgcggaaact tgtcgttatc ggtggcggaa ttacgggatt gagcgcggcg   60
ttctatcgc tgaagcaggc ggatgaagag gggcagccca tctccgttac catcatagag   120
caatcggacc gtctcggcgg gaagatacag accctgcgga aggaagggtg tgtcattgag   180
aaaggcccgg actccttcct cgcccggaag ctgccgatga tcgatttggc gcgcgaccgc   240
ggaatggatt ctgaattggt cgccacgaat ccgcatgcca aaaaaacata tatattgcgc   300
cggggcaagc tgtaccggat gccgcccggc ctcgtgctgg gcatcccgac ggagctgggg   360
ccgttcgcga agacagggct catctccccg tggggggaagc tgcgcgcggc tatggatctg   420
ttcatcaagc cgcatccggc ggatgaagat gaatccgttg gcgcgttcct ggacagacgg   480
ctcggacgcg aagtgacgga gcatattgcc gagccgctgc ttgccggcat ttatgccgga   540
gatttgcagg cgctgagcct gcaggccacc ttcccgcagt tcgcgcaggt ggagcggaag   600
cacggtggcc tgatacgcgg aatgaaggcg agccgccaag caggcaaatc ggtaccgggg   660
ctgccggatg tcgccaaagg aacgatgttc ctgacattcc gcaacggctt gacctcgctc   720
gtcgaacggc tggaggagac gctgcgggac cgggccgaat tgtgccttgg catcggcgcg   780
gaaggattcg agaagcggga ggacggaacg tatctggtgc gcttgagcga tgggagcagg   840
ctgcaggcgg atgccgtcat cgtgacgacg ccttcgtatc atgcggcatc cttgctcgag   900
gagcatgtca atgcgagcgc cttgcaggcg atccgtcatg tatccgtcgc gaatgtcgtc   960
agcgtgttcg atcgcaagca ggtcaataat cagttcgacg gcacagggt cgtcatctcg   1020
cgccgggaag gccgggcgat tacggcctgc acgtggacct cggtgaagtg gccgcatacg   1080
agccgcgggg acaagcttat tatccgctgc tacattggcc gggccggtga cgaggaacgg   1140
gtggactggc cggacgaggc gctcaagcgg acggtgcgca gcgagctgcg ggagctgctt   1200
gatatcgata tcgacccgga gttcgtcgag attacgcgcc ttcgccactc gatgccccag   1260
tatccggtcg gccatgtgca ggcgatccgc tcgctgaggg acgaggtggg gcgcacgctc   1320
ccaggcgtgt tcctggcagg acagccgtac gaaggggtcg gcatgcccga ttgcgttcgc   1380
agcggccgcg atgcggcgga agccgcggtt agcgcgatgc aggccatgag tacggagcca   1440
gaggcgccag ccgaggatgc cgctactgga acggcggggt aa                       1482
```

```
SEQ ID NO: 202          moltype = DNA  length = 1425
FEATURE                 Location/Qualifiers
source                  1..1425
                        mol_type = genomic DNA
                        organism = Paenibacillus polymyxa
SEQUENCE: 202
atgggtgata agaaacgccg tgttgttgtt gtcggcggtg gccttaccgg cctcagcgcg   60
gcattttata tccgcaagca ttaccgggaa gcaggagttg aacctgtgat tactttggtc   120
gagaaaagct cgtccatggg aggcatgatt gagacactgc accgggatgg atttgtgatt   180
gaaaaagggc ccgattcgtt cctggctcgc aaaacggcaa tgattgatct ggccaaagaa   240
```

-continued

```
ttggagatcg atcatgagct ggtaagtcag aatccggagt cgaagaaaac gtatatcatg    300
cagcgtggca agcttcatcc tatgccagca ggacttgttc tcggtattcc gacagaacta    360
agaccattct tgagaagtgg tttgtttct ccggcaggca aactgcgggc gttgatggat    420
tttgtcatcc cgccgcgtcg tacaacagag gatgaatcgc tcggttatat gattgaacgc    480
cgtcttggag cagaagtgct ggagaacttg acggaaccac tgctcgcgag aatctatgca    540
ggtgatatgc ggcgattgag cctccaggct accttcccgc agttcggaga agtagagcgc    600
gattacggca gcttgatccg gggcatgatg acggggcgca aaccggctga gacgcatacc    660
ggaacaaaac ggagcgcttt tttgaacttt cgccagggac ttcagagcct tgttcatgca    720
ctcgtccatg agttgcagga tgtggatcaa cgtctgaaca ctgcggtgaa atcgctgcaa    780
cgccttgatg gagcgcagac cagataccgt gttgaacttg gtaatgacga aatgcttgaa    840
gccgatgatg tagtggttac tgtgccgaca tatgtcgcgt cggagctgtt gaagcctcac    900
gtggacacag cggcactgga tgcgattaac tatgtgtctg tagccaatgt agtgctcgct    960
tttgagaaaa aagaggtgga gcatgtattc gacggatcgg gtttcctcgt tccgcggaaa   1020
gagggtcgga atattacggc ttgcacgtgg acatcgacaa aatggctgca taccagcccg   1080
gatgataaag tactgcttcg ctgttatgtt ggtcgctccg gtgacgaaca gaacgtagag   1140
cttccggatg aagcgctgac gaatctcgtt ctcaaagatc tgagagagac gatgggtatt   1200
gaagcagtgc cgatcttctc cgagattaca aggcttcgta aatccatgcc acagtatccg   1260
gtgggacacc ttcaacatat tgccgctctc cgtgaggagc ttggcagcaa attaccgggt   1320
gtgtacattg caggtgcagg ttatgagggc gtaggcttgc ctgattgcat cagacaagcg   1380
aaggaaatgt ctgttcaggc tacacaagag cttgcagcag attaa             1425

SEQ ID NO: 203          moltype = DNA  length = 1413
FEATURE                 Location/Qualifiers
source                  1..1413
                        mol_type = genomic DNA
                        organism = Bacillus atrophaeus
SEQUENCE: 203
atgagtgacg gcaaaaagca tcttgtcatc atcggcggcg gcatcacggg attggcctcc    60
gccttctata tggaaaaaga aatcagagag aaaaatttgc ctctttctgt gacgttagtc    120
gaagcaagcc cgagagttgg cgggaaaatt caaacggccc gcaaggacgg ttatattatt    180
gaaagagggc cggactcatt tttagaaaga aaaaaaagcg caccggagct tgtcgaagat    240
ttaggccttg agcatttgct tgtcaacaat gcgacggggc agtcttatgt gctggttaac    300
gaaacgcttc acccgatgcc aaagggcgct gttatgggca tacctactaa aatagcgcca    360
tttatgtcta ccggcttatt ttcattttcc ggcaaagcgc gcgcggctat ggatttcgtt    420
ttgcccgcaa gcaagccgaa ggaagatcag tccctggctg aattcttccg caggcgtgtc    480
ggtgacgaag ttgttgaaaa tttgattgag ccgctattat ccggcattta tgcgggtgac    540
attgacaggc tcagcctgat gtcgacgttc ccgcagtttt atcagaccga acaaaagcac    600
agaagcttga tcctcggcat gaaaaaaaca aggcctcagg gctccggaca gcggttaacg    660
gctaaaaaac aagggcaatt ccaaacctta aagaccggct tgcagacact cgtcgaagag    720
ctggaaaacc agctgaagct gacgaaggta tacaagggta caaaagtaac caatatcagc    780
cgcgggggaa agggctgctc catcgctctt gataacggga tgacgctgga tgccgatgca    840
gcgattgtaa cctcaccgca caaatcggct gccggaatgt ttccggatct gccagctgtc    900
agtcagttaa aagacatgca ctctacctct gtggcgaatg tcgcgcttgg ctttccacaa    960
gaggctgtcc aaatggaaca tgaaggaacg ggttttgtca tctcaagaaa cagtgatttt   1020
tcaataacgg cctgtacttg gacgaataaa aaatggccgc actctgctcc ggaaggcaaa   1080
acgctcctca gggcttatgt cggaaaagcg ggtgatgaat caatcgtcga actgtctgat   1140
aatgagatta tcaaaattgt attagaagac ctaaagaaag tcatgaaaat caaaggcgaa   1200
cctgaaatga cgtgcgtcac acgctggaat gagagtatgc cccaatatca tgtcggccac   1260
aaacagcgta taaaaaaagt gcgcgaagca ctggctgctt cctatccggg agtttacatg   1320
acgggcgctt cattcgaagg cgttgggatt ccggactgta tcgatcaagg gaaaagcgcc   1380
gtttcagacg tacttgctta tttattcggt tga                          1413

SEQ ID NO: 204          moltype = DNA  length = 1413
FEATURE                 Location/Qualifiers
source                  1..1413
                        mol_type = genomic DNA
                        organism = Bacillus atrophaeus
SEQUENCE: 204
atgagtgacg gcaaaaagca tcttgtcatc atcggcggcg gcatcacggg attggcctcc    60
gccttctata tggaaaaaga aatcagagag aaaaatttgc ctctttctgt gacgttagtc    120
gaagcaagcc cgagagttgg cgggaaaatt caaacggccc gcaaggacgg ttatattatt    180
gaaagagggc cggactcatt tttagaaaga aaaaaaagcg caccggagct tgtcgaagat    240
ttaggacttg agcatttgct tgtcaacaat gcgacggggc agtcttatgt gctggttaac    300
gaaacgcttc acccgatgcc aaagggcgct gttatgggca tacctactaa aatagcgcca    360
tttatgtcta cccgcttatt ttcattttcc ggcaaagcgc gcgcggctat ggatttcgtt    420
ttgcccgcaa gcaagccgaa ggaagatcag tccctgggtg aattcttccg caggcgtgtc    480
ggtgacgaag ttgttgaaaa tttgattgag ccgctattat ccggcattta tgcgggtgac    540
attgacagac tcagcctgat gtcgacgttc ccgcagtttt atcagaccga acaaagcac    600
agaagcttga tcctcggcat gaaaaaaaca aggcctcagg gctccggaca gcagttaacg    660
gctaaaaaac aagggcaatt ccaaacctta aagaccggct tgcagacact cgtcgaagag    720
ctggaaaacc agctgaaact gacgaaggta tacaagggta caaaagtaac caatatcagc    780
cgcgggggaa agggctgctc catcgctctt gataacggga tgacgctgga tgccgatgcc    840
gcgattgtga cctcaccgca caaatcggct gccggaatgt ttccggatct gccagctgtc    900
agccagttaa aagacatgca ctctacctct gtggcgaatg tcgcgcttgg ctttccacaa    960
gaggctgtcc aaatggaaca tgaaggaacg ggttttgtca tctcaagaaa cagtgatttt   1020
tcaataacgg cctgtacttg gacgaataaa aaatggccgc actctgctcc ggaaggcaaa   1080
acgctcctca gggcttatgt cggaaaagcg ggtgatgaat caatcgtcga actgtctgat   1140
aatgagatta tcaaaattgt attagaagac ctaaagaaag tcatgaaaat caaaggcgaa   1200
cctgaaatga cgtgcgtcac acgctggaat gagagtatgc cccaatatca tgtcggccac   1260
```

-continued

```
aaacagcgta taaaaaaagt gcgcgaagca ctggctgctt cctatccggg agtttacatg   1320
acgggcgctt cattcgaagg cgttgggatt ccggactgta tcgaccaagg gaaaagcgcc   1380
gtttcagacg tacttgctta tttattcgaa tga                                1413
```

```
SEQ ID NO: 205              moltype = DNA   length = 1434
FEATURE                     Location/Qualifiers
source                      1..1434
                            mol_type = other DNA
                            note = Recombinant
                            organism = synthetic construct
SEQUENCE: 205
atgtcaaaga agattgcagt cattggtggt gggataacag ggttgtccgt ggcctactac   60
gtgaggaagc tgcttcggga gcaaggcgtt aatgcgggcg ttaccctcgt cgagcaatcc   120
gaccgcctcg gcgggaagat tagatccttg agacgagacg gctttaccat tgagcaaggc   180
cctgactcta tgattgcacg taagcccgca gctctcgaac ttatccgtga gcttggtctg   240
gaggacaagt tggcgggcac aaaccctcaa gccaaacgct cctacatact gcaccgtggc   300
aagtttcatc cgatgccacc tgggctgatg ctcgggattc ccactcaaat gtggccaatg   360
gtcaagaccg ggctgctatc tccggccgga aagctacggg ctgcgatgga cctacttctt   420
cctgcaaggc gcggaggcgg cgacgaatca cttggtgggt ttatccggag gcggcttgga   480
cgtgaggtgt tggagcagat gaccgaacca ctccttgctg gaatctatgc tggcgacaca   540
gaacagcttt cacttaaagc gacctttcct caattcatgg agatggaaag gaaacatcgc   600
agtctcatcc ttggactatt ggctgggaag aaacagccac cgcgtcccgg tggtagccaa   660
gtgccgctcc caaaggccgc tcagaccagt atgttcttga cactcaccgg cgggttggaa   720
ggtctgaccg aagcactaga ggaaagccta tcagaggaga agataattac tggccaagca   780
gttaccggac tttcgcagca agaggccggg tatgagttaa atctctctgg cggagagaga   840
cttaatgcag acggagtgat cctcgcagtc ccagcgttcg ctgccgcccg acttcttgac   900
ggcgtgcctg aggccgccta cctagagcgc atccgctatg tcagtgttgc taatttggcg   960
ttcgcttaca ggcgtgagga cgtgcctcat gatctgaatg ggtccggcgt gttaatccct   1020
agaggtgaag ggaggatgat tacggccata acttgggttt cgtccaaatg gttgcattca   1080
gcaccggtg acaagggcact gctgagagcg tacattgggc gactaggtga tgaggcttgg   1140
acagccatgt gtagggccga catcgagcgt agagtcgccg ctgaactccg cgatctacta   1200
ggaattgccg ctagtccttt gttctgtgaa ctagccgcac tcccagaatc tatgccgcag   1260
tatccagtcg gtcacgtcga acgactcgaa gccttgcgag gagcattgtg tcgcgctaaa   1320
ccaggggttgt tgttgtgtgg tgccgggtac gctggcgttg gcattccaga ctgcattcgg   1380
caaggcaaag aagccgctga gtcgatggcg gcttatttga gggacggacg ctag          1434
```

```
SEQ ID NO: 206              moltype = DNA   length = 1482
FEATURE                     Location/Qualifiers
source                      1..1482
                            mol_type = other DNA
                            note = Recombinant
                            organism = synthetic construct
SEQUENCE: 206
atgaaggctc tgaggaaact tgtggtcatc ggcggaggga tcactgggct ttcggccgcc   60
ttctatgcac taaagcaagc cgatgaggaa gggcagccca tctcggtcac cataattgaa   120
cagagcgata ggctcggcgg aaagatccag acactccgca aggagggctg cgtaattgag   180
aagggcccgg attccttcct cgctaggaag ttgccgatca ttgatctagc tcgggatctt   240
ggcatggact ccgaattggt ggcgactaat ccgcacgcaa agaagactta catcttgagg   300
cgcggaaagc tctaccggat gcctccaggc ttagtgcttg gcatacctac ggaactagga   360
ccattcgcta agacagggct cattagccct tggggcaaac tccgcgccgc tatggatttg   420
ttcattaagc ctcatccagc cgatgaagac gaaagtgttg gcgctttcct ggacagacgt   480
ctcggtaggg aagtgaccga gcacattgcg gaacctttat tggcgggcat ctacgcgggc   540
gacttgcaag ccttaagcct tcaagccact ttcccacagt ttgcacaagt agagcgcaag   600
cacgggaggc tgatacgcgg tatgaaggcc agcagacagg ccggtcagtc cgtgcctggg   660
ctgccggacg tcgccaaggg tacgatgttc cttaccttct gcaacgggct taccagctta   720
gttgaaaggt tggaggaaac tctcagagac agggctgaac tctgtctggg catcggcgca   780
gaagggtttg agaaacgtga agatggaaca taccttgttc gactaagcga tggttcgagg   840
ctccaggccg acgcagtaat tgtcactacg ccgagctatc atgcggcatc cctgttggag   900
gagcatgtgg atgcttcggc cctccaggcc attcgtcatg taagcgttgc aaatgtcgtt   960
agcgtcttcg accgaaagca agtgaataac cagttcgacg gcacagggtt tgttatctca   1020
cggcgagaag gtcgcgcaat caccgcctgc acctggacat ccgtgaaatg gccgcatact   1080
tcgcgcggc acaaactgat tatccggtgc tacatcggta gggctggcga cgaggagcga   1140
gtggattggc ccgatgaagc tctcaagcgt actgtaagat cagaactgcg tgagttgctg   1200
gacattgaca ttgatccgga atttgtggag attacacgac tcaggcactc tatgcctcaa   1260
tacccagtcg gccacgtcca ggctatccgc tctttgaggg acgaggtcgg taggacttta   1320
ccgggcgtgt tccttgctgg gcaaccctac gaaggtgtgg gaatgcctga ctgtgtgagg   1380
tccgccggg atgccgccga agcagcagta agtgctatgc aagcaatgag tacagaacca   1440
gaagcaccgg cagaggacgc cgctactgga acggcgggtt ga                        1482
```

```
SEQ ID NO: 207              moltype = DNA   length = 1425
FEATURE                     Location/Qualifiers
source                      1..1425
                            mol_type = other DNA
                            note = Recombinant
                            organism = synthetic construct
SEQUENCE: 207
atgggagaca agaagcggag agttgttgtt gttggcggcg gcttgactgg cctaagcgcc   60
gccttctaca tccggaaaca ttatcgagaa gctggagttg agcccgtcat cacgcttgtt   120
gagaaatcta gctcgatggg agggatgatt gagacccttc ataggacgg gtttgtcatc   180
```

```
gagaagggcc cggacagttt cttggcacgg aagaccgcaa tgattgatct ggcgaaagag  240
ctggagattg accacgagtt ggtcagccag aatccagaat cgaagaagac ctacataatg  300
caacgtggaa agctgcaccc tatgccagcg ggacttgttc tgggcattcc caccgaattg  360
cgtcccttc tccggagcgg gcttgtctca cccgctggga agttgcgggc gctgatggac  420
ttcgtaatac cgccacgaag gacgaccgaa gatgagtcac tcgggtacat gatcgagcgc  480
cgactgggtg ccgaggtgtt ggagaacctc acagagccgt tgctcgctgg aatctacgct  540
ggcgacatga gaagattgtc cctccaggct acgtttccgc agttcggtga ggtggagcgc  600
gactacggct ccttaatcag aggaatgatg accggacgta agcctgcgga gacacacaca  660
gggaccaaga ggtctgcctt tctcaatttc agacagggtc tgcaatcact ggttcacgcc  720
ttagtccatg aactccagga tgtagatcag aggttaaata ctgcggtgaa gtcgcttcag  780
aggcttgacg gcgcacaaac ccgttatcgc gttgaactcg gcaatggcga aatgcttgag  840
gctgacgacg tggtggttac tgtaccaacc tacgtggcga gcgagcttct taagccgcac  900
gtggacacgg cggcgttaga cgctattaac tatgtgtcgg tggctaatgt agttcttgca  960
ttcgagaaga aggaagtaga gcacgtcttc gatggatcgg gcttcttggt gcctcggaag 1020
gagggaagga acataaccgc ctgcacctgg acttcgacca agtggctcca cacatcacca 1080
gatgacaagg ttctgttacg ttgttacgtg ggcagaagtg gagatgagca gaatgtggaa 1140
ctcccggatg aggcactcac taatctggtg cttaaggatc tgagagagac gatgggcatc 1200
gaggcggttc caatcttctc agagattacc cggctccgca agtcaatgcc gcagtaccca 1260
gtaggacatc tccagcacat cgccgcattg cgcgaggaac tcggctctaa gctaccagga 1320
gtgtacatcg ccggagcggg ctacgagggc gttggtcttc cggattgcat tcgccaggcc 1380
aaagaaatgt cagtccaggc aacgcaagaa ctcgctgccg actga          1425

SEQ ID NO: 208          moltype = DNA   length = 1413
FEATURE                 Location/Qualifiers
source                  1..1413
                        mol_type = other DNA
                        note = Recombinant
                        organism = synthetic construct
SEQUENCE: 208
atgagtgacg ggaagaagca cttggttata atcgggggg gaataaccgg cctggccagc  60
gctttctata tggagaagga gatccgggag aagaacttac ctctcagcgt gaccttggtg  120
gaggcatccc cgcgggtagg ggggaagatc cagactgctc gaaaggacgg ctatatcata  180
gagcgggggcc cggacagctt cctggagcgc aagaagtcgg cgcccgagtt agtcgaggac  240
ctcggtctcg agcacttact cgtaaacaac gctacagggc agtcttacgt cctcgtcaac  300
gaaacactgc acccgatgcc caaaggcgcg gtgatgggaa tccccactaa gattgcacct  360
ttcatgtcga ctggccttt cagcttcagt gggaaggcga gggcggcaat ggacttcgtc  420
ctgcccgcgt ccaagccgaa ggaggatcag agcctcggcg agttttccg caggcgagtt  480
ggggatgagg tcgtggaaaa cctcattgag cccttgctat ccggaatcta tgccggagac  540
atcgacaggc tcagccttat gtctactttc ccccagttct accagacaga gcaaaagcac  600
cgaagtttga tcctcgggat gaagaagacg cgtcctcagg ttctggtca gaggctaaca  660
gcaaagaagc agggtcaatt ccagacgctt aaaacagggc ttcaaacact tgtggaggaa  720
ctcgagaatc agcttaaact aaccaaagtg tacaagggca cgaaggtaac taacatcagc  780
cgcggtgaaa agggctgcag catcgcactt gacaacggga tgacactgga cgcggacgac  840
gcaatcgtca cgagcccca caaatcagcg gcgggaatgt tccccgacct tccggcggtc  900
agccagctga aagacatgca ctccacctcc gtcgcaaacg tcgcgctcgg cttcccgcag  960
gaggctgtcc agatggagca tgaggggact ggcttcgtta tcagcagaaa ttcggacttc 1020
agtatcacag cgtgcacttg gacaaacaag aaatggcctc acagccgacc tgagggggaag 1080
acacttttgc gagcgtacgt ggggaaagct ggggacgagt ccatagttga actaagcgac 1140
aacgagataa ttaagatcgt gcttgaggac cttaagaaag tgatgaagat aaagggcgag 1200
cccgaaatga catgcgtaac tagatggaat gagtccatgc cacagtacca cgtcgggcac 1260
aagcagcgta tcaaaaaggt cagggaggct ttggcggcct cacacccggg cgtatacatg 1320
accggtgcat ccttcgaggg ggtggggata ccagactgca tcgaccaagg caaatccgca 1380
gtctcagacg ttttggcata cttgttcggc tag               1413

SEQ ID NO: 209          moltype = DNA   length = 1413
FEATURE                 Location/Qualifiers
source                  1..1413
                        mol_type = other DNA
                        note = Recombinant
                        organism = synthetic construct
SEQUENCE: 209
atgtcggatg gcaagaagca cctcgtcatc atcggcgggg gtatcaccgg acttgcgtcc  60
gcgttctaca tggagaagga gatcagggag aagaacttgc ccctctcagt gaccctggtg  120
gaggcctcgc cccgtgttgg tggtaagatc cagacacggc gaaaagacgg ctacattatc  180
gagcgggggc ccgactcctt cctcgagagg aagaagtctg cccccgagct tgtcgaggac  240
ttgggggcttg agcacctcct cgtgaacaat gcgaccgggc agagctacgt tttggtgaac  300
gagaccctgc acccgatgcc caaggggagcc gtgatgggga tccctaccaa gatcgcgcct  360
ttcatgagca ctcgactttt ttcattcagc ggcaaggcca gagccgctat ggactttgtt  420
ctcccggctt ctaagcctaa ggaagaccag agtctaggcg aattcttcag gcgagagtc  480
ggcgatgagg ttgttgagaa ccttatagag ccattattgt caggtatata cgcaggagac  540
attgacaggc tgtctctcat gagtaccttc cctcaattct accagacgga gcagaaacac  600
aggagcctca tattgggggat gaagaagacg cgtcctcaag gaagcggaca gcagttgacg  660
gccaagaagc agggccagtt ccaaacgctc aagaccggac ttcagaccct cgtcgaggag  720
cttgagaacc agctaaagtt gacgaaagtt acaaggggca ctaaggtcac aaacatctcg  780
aggggcgaga agggatgcag catcgcgtta gacaacggga tgaccctaga cgctgacgca  840
gctattgtga ctagccccca taagtccgca gccggcatgt ttccagactt gccggccgtt  900
agccagttga aggacatgca ctcgaccagc gtggcaaacg tcgcattggg cttcccacag  960
gaggcggtgc agatggagca tgaggggacc ggattcgtga tctcaaggaa ttccgatttc 1020
tccattacgg catgtacctg gacaaacaaa aaatggcccc acagcgcccc agaagggaaa 1080
```

```
acactcctac gcgcttatgt tggcaaggcc ggcgatgagt caattgtgga gctctccgac   1140
aatgagatca tcaaaatcgt tcttgaagat cttaagaagg taatgaagat taaggggggaa   1200
ccggaaatga cgtgtgtgac aaggtggaac gagagtatgc cccaatatca cgtgggccac   1260
aagcagagga taaagaaggt gagggaggcg ttggcggcgt cttaccccgg cgtgtacatg   1320
acgggggctt cattcgaggg ggtgggcatc cccgactgca ttgaccaagg caaaagcgcg   1380
gtgtctgacg tgctcgcgta cctgttcgag tag                                1413

SEQ ID NO: 210              moltype = DNA   length = 1413
FEATURE                     Location/Qualifiers
source                      1..1413
                            mol_type = other DNA
                            note = Recombinant
                            organism = synthetic construct
SEQUENCE: 210
atgtccgacg ggaagaagca cctggtaatc atcggtggtg ggatcaccgg tctggcttca   60
gcgttctaca tggaaaagga gatccgggag aagaacttgc ccctttcggt gactctagtg   120
gaggcctctc cacgggtggg gggcaagatt cagaccgcgc gcaaggatgg ctacatcata   180
gagcgaggac cagactcatt cctagagcgt aagaagtccg cccccagagct cgtcgaggat   240
ctcggtctag agcacttgct agtgaataac gctacaggac agtcctacgt gctcgtgaac   300
gagacactac acccgatgcc taagggggct gtcatgggta taccgaccaa gatcgccccg   360
ttcatgtcca ctcgcctttt ctcgttctcg ggcaaagctc gggccgctat ggatttcgtc   420
ttgcctgcct cgaaaccgaa ggaggaccag tccttaggag agttcttccg cggcgagggat   480
ggcgacgagg tggtggagaa cttaatcgaa cccttgctct cggggatcta cgctggagac   540
attgatcgac tatcgcttat gtctacgttt cctcaatttt accagacgga gcagaagcac   600
cgtagcctca ttttgggtat gaagaagaca cggcctcaag gttcggggca gcagcttact   660
gccaagaagc agggccaatt ccagacactc aagaccggct tgcagactct agtggaggag   720
ctggagaatc aattgaagct gacaaaggtc tacaagggta ccaaggtgac aaacatatcg   780
cgtggcgaaa agggatgctc cattgccctc gacaacggta tgaccctcga cgccgacgca   840
gcgattgtga cgagcccaca caagagcgcc gcgggcatgt tcccggactt gcctgcagtg   900
tcacagctga aagacatgca ttctacatcc gtcgccaacg tcgccctggg ctttccccag   960
gaggctgtgc agatggagca cgaggggacg ggcttcgtta tcagccgcaa ctccgacttt   1020
tctattaccg cgtgcacatg gaccaacaag aagtggccgc acagcgctcc ggaggggaaa   1080
acacttctcc gagcatacgt aggcaaggcc ggggacgagt caattgttga gctctccgac   1140
aatgaaatca ttaaaatagt tctggaggat cttaagaagg taatgaagat aaaggggaa   1200
cctgaaatga cgtgtgttac ccgctggaat gagtcaatgc cccagtacca tgtgggacac   1260
aagcagagga taaagaaggt gagggaggcg ctcgctgcgt cctacccagg ggtctacatg   1320
acaggagcga gttttgaggg ggtgggtatt cccgactgta tcgaccaggg taagtcggca   1380
gtgtctgacg tgctcgctta cctattcgag tag                                1413

SEQ ID NO: 211              moltype = DNA   length = 1434
FEATURE                     Location/Qualifiers
source                      1..1434
                            mol_type = other DNA
                            note = Recombinant
                            organism = synthetic construct
SEQUENCE: 211
atgtcgaaga agatcgccgt tatcggtgga ggcattacag ggctctcggt cgcctactac   60
gtgcgtaagc tgcttcgtga gcaaggcgtc aacgctggtg tgacgctggt tgagcagtct   120
gatcgcctcg gtggaaaaat ccgtagcctt cgcagagacg ggttcacgat tgaacaagga   180
ccagattcca tgatcgcgcg caaacccgcg gcgttggagc taattcgaga actcggactc   240
gaggacagac tcgccggcac taacccacag gcaaagcggt cgtacatcct tcaccgacgg   300
aagttccacc cgatgccccc aggcctgatg ctcggcatcc cgacccagat gtggccgatg   360
gtcaagaccg ggctcctgtc tcccgcgggg aaactaaggg ccgctatgga cctcctcctc   420
cctgctcgga ggggcggcgg tgatgagagt ctcggggat ttatcaggcg gagattaggc    480
cgcgaggtac ttgagcaaat gaccgaacca ctgctcgcag gtatctatgc aggcgatacg   540
gaacaactgt ccttgaaagc aacatttcca caattcatgg agatggaaag aaaacatagg   600
tccctcatac tcggtcttct tgctggaaaa aagcaacctc cgagaccggg tggttcacaa   660
gtgcctctgc ctaaagcggc gcaaacttca atgttcctga ctctgacagg cgggctcgaa   720
ggcttaccg aagctctaga ggaatccttg tctgaggaaa aaataatcac cggccaggct    780
gttaccgggc ttagccaaca ggaagccggt tatgaactga acctttcagg tggagagagg   840
ttgaacgccg atgggtcat attggctgta ccggcgttcg ccgcggctcg cctgctggac    900
ggcgtccctg aggccgcgta tttggagcgc atacgctatg tttctgttgc gaacctcgct   960
tttgcatata gacgggaaga tgtgccccat gatcttaatg gttccggagt gttgatccca   1020
cgcggggagg gtcgaatgat aacggcaatt acttgggttt ccagcaagtg gttacattcg   1080
gctcctgggg ataaagctct tttgcgggca tacatcggac gtctcggcga cgaagcctgg   1140
acggccatgt gcagagccga cattgagcga cgggtcgctg cagagctgag agacttgttg   1200
ggcatagctg catctccatt gttctgcgag ctggctgcat tgcctgaaag catgccgcaa   1260
tatccagtag ggcatgtgga gcgcctcgaa gctctccgag gcgcgttgtg tagggcgaaa   1320
cctggactgc tgctctgcgg tgccggctat gcaggtgtgg gaattcctga ctgtatcagg   1380
caaggtaaag aagcggcaga gtccatggcc gcttacctta gggatgggcg ctag          1434

SEQ ID NO: 212              moltype = DNA   length = 1482
FEATURE                     Location/Qualifiers
source                      1..1482
                            mol_type = other DNA
                            note = Recombinant
                            organism = synthetic construct
SEQUENCE: 212
atgaaggcgc tgcggaagct ggtggtaatc ggggggggga tcacggggct gtcggccgcg   60
```

-continued

```
ttctacgcac tcaagcaggc cgacgaagag ggtcagccaa tttccgtaac gattatcgag   120
caatccgatc gacttggcgg caagatacag accctgagaa aggagggatg cgtcattgaa   180
aagggaccag attcatttct ggcgaggaag ctccccatga tcgatctggc gagagactta   240
ggcatggact cggagctggt ggccacaaat cctcatgcaa aaaagactta catcctacgg   300
cgcggtaagt tgtaccgcat gccaccgggc ctggtgttgg ggattcctac cgagttagga   360
cccttcgcga aaaccggact catcagcccc tgggggaaac ttcgagccgc gatggacctt   420
ttcatcaaac cacatccagc cgatgaagat gagtctgtgg gagctttttt agatagacgt   480
ttaggtcgcg aggtgacgga gcacatcgca gagccgctgc tcgccgggat atacgcaggc   540
gatcttcaag ctttgtcctt gcaagctacg ttccctcagt ggaacgcaaa   600
cacggaggtc tcatcagagg tatgaaagcg tctcgccaag ctggacagtc agtcccaggg   660
ctcccagatg tggccaaggg taccatgttt cttactttca gaaatggttt gactagcctg   720
gtggagcgtc tcgaagaaac ccttcgagat agagccgagc tctgtctggg tatcggtgca   780
gaggggtttg aaaaacggga agacggcacg taccttgttc gattatctga tggctccaga   840
ttgcaagccg acgccgttat agttaccaca ccatcatacc atgccgcctc cctactggag   900
gagcacgtcg acgccagcgc gttacaggct atccgccacg tatctgtagc caacgtggtg   960
agcgttttcg ataggaagca ggttaacaat cagtttgatg ggacaggttt tgttatctca   1020
agacgcgaag gcagggctat cactgcttgc acttggacct cagttaagtg gccgcatacc   1080
agccgggggg ataagttgat aatccggtgt tacattggtc gtgcaggaga tgaggagcgc   1140
gtggattggc cagacgaagc gctaaagcgg accgtgagaa gtgagcttcg cgagctgtta   1200
gacatagaca tagatcccga attcgtggaa attacacggt tgaggcactc tatgccacaa   1260
tacctgttg gtcatgtgca agctatacgg tccctgcgcg acgaagtagg ccggaccttg   1320
ccgggcgtgt ttcttgcggg tcagccgtat gagggggtg ggatgccaga ttgtgtgcgt   1380
tctggccgcg acgcggcaga ggctgccgta tcagccatgc aagccatgtc gacagaaccc   1440
gaagcccgg cggaagatgc agcgacagga actgcaggtt ag                        1482
```

```
SEQ ID NO: 213              moltype = DNA  length = 1425
FEATURE                     Location/Qualifiers
source                      1..1425
                            mol_type = other DNA
                            note = Recombinant
                            organism = synthetic construct
SEQUENCE: 213
atggggata agaagaggag ggtcgttgtc gtgggtgggg gactgaccgg actatcagcc   60
gcgttctaca ttagaaagca ctaccgagag gccggccgtgg agccggtgat cacgctggtc   120
gagaagtcga gttcgatggg cggaatgatc gagaccctac acagggacgg ctttgtgatt   180
gagaagggac cagatagctt ccttgcacgc aagacagcca tgatcgatct cgcaaaagag   240
ctcgagatag accacgaact ggtgtctcag aacccggagt ccaagaagac atatatcatg   300
cagagaggta aactacaccc catgccagcc gggttggttc taggaatacc taccgagctc   360
cgcccgtttt tgcgtagcgg tctcgtgagc cccgccggga agctgcgtgc gctaatggac   420
ttcgtgatcc cgcctcggcg aacgaccgaa gacgaatcgc tgggatacat gattgaacgg   480
cgattgggcg ctgaggtgct tgaaaatctt acggagcctc tgcttgcagg gatttatgcg   540
ggtgatatga ggcggttgtc tctccaggca acgttccac agttcggtga ggtagaacgc   600
gattacggct cactgatacg gggcatgatg accggtcgca agccgccga gacacacacc   660
ggtacaaaaa ggtcagcctt tcttaatttc cggcaagggt tacagtcact tgttcatgca   720
cttgtacacg aattgcagga cgtcgatcaa agacttaata ccgcagtgaa gagcctgcag   780
cgcctggatg gggcccaaac taggtaccgt gtggaattag gcaatggaga gatgctggag   840
gccgatagcg tggtggttca cgtcccaacg tacgtagctt ctgagctcct caagccccac   900
gttgacaccg cagctctgga tgcaatcaat tatgtgagcg tggctaatgt cgtcctggcc   960
tttgagaaga aggaagtgga gcatgtgttc gacggatcag ggttcttggt tccgagaaaa   1020
gagggcagga atatcacggc gtgcacttgg acttcgacaa aatggctcca cacctcccg   1080
gatgacaaag tacttctgcg atgctatgtg ggccgaagtg gtgatgagca gaatgtgagc   1140
ctccccgacg aggcactgac caacctcgtc ctcaaggacc taaggagac tatgggcatt   1200
gaggccgtgc caattttctc tgaaataaca cgcctgcgca agtccatgcc ccaataccct   1260
gtgggccatc ttcaacacat tgcggccctg cgggaagaac ttgggtctaa ctgccgggc   1320
gtgtacatag cgggcgccgg ttacgagggt gtcgggttgc ctgactgtat tagacaggca   1380
aaggaaatgt ccgtgcaagc aacccaagaa cttgctgctg actga                  1425
```

```
SEQ ID NO: 214              moltype = DNA  length = 1413
FEATURE                     Location/Qualifiers
source                      1..1413
                            mol_type = other DNA
                            note = Recombinant
                            organism = synthetic construct
SEQUENCE: 214
atgagtgacg gtaagaagca tttggtcatc atcggcggcg gcatcaccgg cttagcctcc   60
gccttctaca tggaaaagga gattcgggag aagaaccttc ccttgtcagt taccctggtg   120
gaggcctcgc cacgggtcgg gggtaaaatc cagacggccc ggaaggatgg ttatattatc   180
gagcgcggac ccgactcgtt cctcgagcgc aagaagagcg cacccgaact cgttgaggac   240
cttggcctcg aacatctcct cgttaacaat gcaactgatc agtcgtacgt cctggtcaac   300
gagacactcc atcccatgcc caagggcgcg gtgatgggca ttccgacgaa gattgcccct   360
tttatgtcga ctgctccttt cagcttctcg ggaaaggccc gtgccgctat ggacttcgtc   420
ctccctgcct cgaaaccgaa ggaggaccag tctcttggag aattttttag cgcgcagagtg   480
ggggacgagg ttgtggagaa tctgatcgaa ccgcttctga gcggaatcta tgcgggcgac   540
attgaccgac tctcactcat gagcaccttc ccacaattct accagacgga gcagaagcat   600
cggtcactca tcctggggat gaaaaaaacc cggcctcaag gatcaggaca aaggcttaca   660
gctaaaaagc aggggcagtt tcaaactctc aagacgggcc tgcagactct agtcgaggag   720
ttagaaaacc agttgaagtt gaccaaggtg tacaagggca cgaaagtgac aaacatcagc   780
cggggcgaaa agggttgttc aatcgcgttg gacaacggca tgaccctgga cgcagacgca   840
gcaatcgtga catcgcccca caagagtgct gcgggcatgt ccctgatct gccggcggtc   900
```

```
agccagctta aggatatgca ctcaacctcg gtggctaacg tggccttggg cttccctcag    960
gaggccgtcc aaatggagca cgaaggaacc ggctttgtta tcagccgtaa cagtgacttc   1020
tcgattaccg cttgtacctg gacgaacaag aagtggcctc acagcgcgcc agaagggaag   1080
accctcctgc gagcctacgt cggcaaggct ggtgacgagt cgatcgttga gttgtctgac   1140
aacgagatta tcaagatcgt acttgaagat ctcaagaagg tcatgaagat aaagggtgaa   1200
cccgagatga cttgcgttac tagatggaac gagtctatgc ctcagtatca cgtggggcac   1260
aagcagagga tcaagaaggt ccgggaggcc ttggctgcct cgtatccggg agtctacatg   1320
accggggcct catttgaggg agtcggtatc cccgactgca tcgaccaagg aaagtccgcc   1380
gtctctgacg tgttggctta tctattcggc tag                                1413

SEQ ID NO: 215          moltype = DNA  length = 1413
FEATURE                 Location/Qualifiers
source                  1..1413
                        mol_type = other DNA
                        note = Recombinant
                        organism = synthetic construct
SEQUENCE: 215
atgagcgacg gaaagaaaca tctcgtgatc atcgggggcg gaataacagg cctagcctcg    60
gcattctaca tggagaagga gatcagagag aaaaacctcc cgctctctgt gaccctggtg   120
gaggcttcac cgagagtggg cgggaagata cagacggcgc gcaaggatgg ctacataata   180
gagcggggc cagattcttt cctggagaga aaaaaaagcg ccccggaatt ggtggaggac   240
ctcggcctcg aacacctcct ggtgaataac gcaacagggc aaagctacgt actcgttaat   300
gagactctcc accccatgcc aaaaggggc gtgatgggaa tccccacaaa gatcgctcca   360
ttcatgagca ccaggttatt ctctttctct ggtaaagcta gggcagccat ggacttcgtc   420
ctgccagcct ccaaaccgaa agaagaccaa agcctcgggg aattcttccg ccggagggtg   480
ggcgacgagg tggttgagaa tttaattgaa cctctcctct caggtatata cgcaggggac   540
atcgaccgct tgtcgctgat gagcacctt ccgcagttct accagacgga gcagaagcat   600
cgctcactca ttcttggtat gaagaagact cgtccgcaag ggtctggcca gcagctgaca   660
gccaagaaac aggggcagtt ccaaactctt aagaccggcc tacagactct ggtggaggag   720
ctcgagaacc agctgaagct cacaaaggtt tacaaggca caaggtgac aaacatctca   780
agggggagga agggttgctc catcgcgctc gataacggca tgacactcga tgctgatgcc   840
gcgatagtaa ctagcccgca caagtcggcc gcgggaatgt tcccgacct ccccgcggtc   900
tcgcaactga aggacatgca ttccaccagc gtcgccaacg tagctctagg ctttcctcag   960
gaggcagtcc aaatggaaca cgagggcacg ggtttcgtaa tctcccgcaa cagcgacttc   1020
tcaatcactg cttgcacgtg gactaacaag aagtggccgc attcggcccc cgagggcaag   1080
acgcttcttc gagcatacgt gggtaaggct ggtgatgaga gtatcgtcga gctctcggac   1140
aacgagatca ttaagatcgt gttggaggac ttgaagaagg tgatgaaaat caagggggag   1200
ccggaaatga cttgcgtgac tcgctggaac gagagcatgc cgcagtacca cgttgggcat   1260
aagcagagga taaagaaagt tcgcgaagcg ctggccgcgt cttaccctgg agtgtatatg   1320
acgggagcct cctttgaggg tgtggggatc ccggactgca tcgaccaggg aaagtcagct   1380
gtctccgacg tgctggccta cttattcgag tga                                1413

SEQ ID NO: 216          moltype = DNA  length = 1428
FEATURE                 Location/Qualifiers
source                  1..1428
                        mol_type = other DNA
                        note = Recombinant
                        organism = synthetic construct
SEQUENCE: 216
aagaagattg cagtcattgg tggtgggata acagggttgt ccgtggccta ctacgtgagg    60
aagctgcttc gggagcaagg cgttaatgcg ggcgttaccc tcgtcgagca atccgaccgc   120
ctcggcggga agattagatc cttgagacga gacggcttta ccattgagca aggccctgac   180
tctatgattg cacgtaagcc cgcagctctc gaacttatcc gtgagcttgg tctggaggac   240
aagttggcgg gcacaaaccc tcaagccaaa cgctcctaca tactgcaccg tggcaagttt   300
catccgatgc cacctgggct gatgctcggg attcccactc aaatgtggcc aatggtcaag   360
accgggctgc tatctccggc cggaaagcta cgggctgcga tggacctact tcttcctgca   420
aggcgcggag cgcgcgacga atcacttggt gggtttatcc ggaggcggct tggacgtgag   480
gtgttggagc agatgaccga accactcctt gctggaatct atgctggcga cacagaacag   540
ctttcactta aagcgacctt tcctcaattc atggagatgg aaaggaaaca tcgcagtctc   600
atccttggac tattggctgg gaagaaacag ccaccgcgtc ccggtggtag ccaagtgccg   660
ctcccaaagg ccgctcagac cagtatgttc ttgacactca ccggcgggtt ggaaggtctg   720
accgaagcac tagaggaaag cctatcagag gagaagataa ttactggcca agcagttacc   780
ggactttcgc agcaagaggc cgggtatgag ttaaatctct ctggcggaga gagacttaat   840
gcagacggag tgatcctcgc agtcccagcg ttcgctgccg cccgacttct tgacggcgtg   900
cctgaggccg cctacctaga gcgcatccgc tatgtcagtg ttgctaattt ggcgttcgct   960
tacaggcgtg aggacgtgcc tcatgatctg aatgggtccg gcgtgttaat ccctagaggt   1020
gaagggagga tgattacggc cataacttgg gtttcgtcca aatggttgca ttcagcaccc   1080
ggtgacaagg cactgctgag agcgtacatt gggcgactag gtgatgaggc ttggacagcc   1140
atgtgtgagg ccgacatcga gcgtagagtc gccgctgaac tccgcgatct actaggaatt   1200
gccgctagtc ctttgttctg tgaactagcc gcactcccag aatctatgcc cagtatcca   1260
gtgggtcacg tcgaacgact cgaagccttg cgaggagcat tgtgtcgcgc taaccaggg   1320
ttgttgttgt gtggtgccgg gtacgctggc gttggcattc cagactgcat tcggcaaggc   1380
aaagaagccg ctgagtcgat ggcggcttat ttgagggacg gacgctag               1428

SEQ ID NO: 217          moltype = DNA  length = 1470
FEATURE                 Location/Qualifiers
source                  1..1470
                        mol_type = other DNA
                        note = Recombinant
```

```
                          organism = synthetic construct
SEQUENCE: 217
aggaaacttg tggtcatcgg cggagggatc actgggcttt cggccgcctt ctatgcacta   60
aagcaagccg atgaggaagg gcagcccatc tcggtcacca taattgaaca gagcgatagg   120
ctcggcggaa agatccagac actccgcaag gagggctgcg taattgagaa gggcccggat   180
tccttcctcg ctaggaagtt gccgatgatt gatctagctc gggatcttgg catggactcc   240
gaattggtgg cgactaatcc gcacgcaaag aagacttaca tcttgaggcg cggaaagctc   300
taccggatgc ctccaggctt agtgcttggc atacctacgg aactaggacc attcgctaag   360
acagggctca ttagcccttg gggcaaactc cgcgccgcta tggatttgtt cattaagcct   420
catccagccg atgaagacga aagtgttggc gctttcctgg acagacgtct cggtagggaa   480
gtgaccgagc acattgcgga accttttattg gcgggcatct acgcgggcga cttgcaagcc   540
ttaagccttc aagccacttt cccacagttt gcacaagtag agcgcaagca cggagggctg   600
atacgcggta tgaaggccag cagacaggcc ggtcagtccg tgcctgggct gccggacgtc   660
gccaagggta cgatgttcct tacctttcgc aacgggctta ccagcttagt tgaaaggttg   720
gaggaaactc tcagagacag ggctgaactc tgtctgggca tcggcgcaga agggtttgag   780
aaacgtgaag atgggaacata ccttgttcga ctaagcgatg gttcgaggct ccaggccgac   840
gcagtaattg tcactacgcc gagctatcat gcggcatccc tgttggagga gcatgtggat   900
gcttcggccc tccaggccat tcgtcatgta agcgttgcaa atgtcgttag cgtcttcgac   960
cgaaagcaag tgaataacca gttcgacggc acagggtttg ttatctcacg gcgagaaggt   1020
cgcgcaatca ccgcctgtac ctggacatcc gtgaaatggc cgcatacttc gcgcggcgac   1080
aaactgatta tccggtgcta catcggtagg gctggcgacg aggagcgagt ggattggccc   1140
gatgaagctc tcaagcgtac tgtaagatca gaactgcgtg agttgctgga cattgacatt   1200
gatccggaat ttgtggagat tacacgactc aggcactcta tgcctcaata cccagtcggc   1260
cacgtccagg ctatccgctc tttgagggac gaggtcggta ggactttacc gggcgtgttc   1320
cttgctgggc aaccctacga aggtgtggga atgcctgact gtgtgaggtc cggccgggat   1380
gccgccgaag cagcagtaag tgctatgcaa gcaatgagta cagaaccaga agcaccggca   1440
gaggacgccg ctactggaac ggcgggttga                                    1470

SEQ ID NO: 218           moltype = DNA  length = 1410
FEATURE                  Location/Qualifiers
source                   1..1410
                         mol_type = other DNA
                         note = Recombinant
                         organism = synthetic construct
SEQUENCE: 218
cggagagttg ttgttgttgg cggcggcttg actggcctaa gcgccgcctt ctacatccgg   60
aaacattatc gagaagctgg agttgagccc gtcatcacgc ttgttgagaa atctagctcg   120
atgggaggga tgattgagac ccttcatagg gacgggtttg tcatcgagaa gggccccggac   180
agtttcttgg cacggaagac cgcaatgatt gatctgccaa aagagctgga gattgaccac   240
gagttggtca gccagaatcc agaatcgaag aagacctaca taatgcaacg tggaaagctg   300
caccctatgc cagcgggact tgttctgggc attcccaccg aattgcgtcc ctttctccgg   360
agcgggcttg tctcacccgc tgggaagttg cgggcgctga tggacttcgt aataccgcca   420
cgaaggacga ccgaagatga gtcactcggg tacatgatcg agcgccgact gggtgccgaa   480
gtgttggaga acctcacaga gccgttgctc gctggaatct acgctggcga catgagaaga   540
ttgtccctcc aggctacgtt tccgcagttc ggtgaggtgg agcgcgacta cggctcctta   600
atcagaggaa tgatgaccgg acgtaagcct gcggagacac acacagggac caagaggtct   660
gcctttctca atttcagaca gggtctgcaa tcactggttc acgccttagt ccatgaactc   720
caggatgtag atcagaggtt aaatactgcg gtgaagtcgc ttcagaggct tgacggcgca   780
caaacccgtt atcgcgttga actcggcaat ggcgaaatgc ttgaggctga cgacgtggtg   840
gttactgtac caacctacgt ggcgagcgag cttcttaagc cgcacgtgga cacggcggcg   900
ttagacgcta ttaactatgt gtcggtggct aatgtagttc ttgcattcga gaagaaggaa   960
gtagagcacg tcttcgatgg atcgggcttc ttggtgcctc ggaaggaggg aaggaacata   1020
accgcctgca cctggacttc gaccaagtgg ctccacacat caccagatga caaggttctg   1080
ttacgttgtt acgtgggcag aagtggagat gagcagaatg tggaactccc ggatgaggca   1140
ctcactaatc tggtgcttaa ggatctgaga gagacgatgg gcatcgagg ggttccaatc   1200
ttctcagaga ttacccggct ccgcaagtca atgccgcagt acccagtagg acatctccag   1260
cacatcgccg cattgcgcga ggaactcggc tctaagctac caggagtgta catcgccgga   1320
gcgggctacg agggcgttgg tcttccggat tgcattcgcc aggccaaaga aatgtcagtc   1380
caggcaacgc aagaactcgc tgccgactga                                    1410

SEQ ID NO: 219           moltype = DNA  length = 1398
FEATURE                  Location/Qualifiers
source                   1..1398
                         mol_type = other DNA
                         note = Recombinant
                         organism = synthetic construct
SEQUENCE: 219
aagcacctgg taatcatcgg tggtgggatc accggtctgg cttcagcgtt ctacatggaa   60
aaggagatcc gggagaagaa cttgcccctt tcggtgactc tagtggaggc ctctccacgg   120
gtggggggca agattcagac cgcgcgcaag gatggctaca tcatagagcg aggaccagac   180
tcattcctag agcgtaagaa gtccgcccca gagctcgtcg aggatctcgg tctagagcac   240
ttgctagtga ataacgctac aggacagtcc tacgtgctcg tgaacgagac actacacccg   300
atgcctaagg gggctgtcat gggtataccg accaagatcg ccccgttcat gtccactcgc   360
ctttctcgt tctcgggcaa agctcgggcc gctatggatt tcgtcttgcc tgcctcgaaa   420
ccgaaggagg accagtcctt aggagagttc ttccgccgga gggtcggcga cgaggtggtg   480
gagaacttaa tcgaacccttt gctctcgggg atctcacgctg gagacattga tcgactatcg   540
cttatgtcta cgtttcctca attttaccag acggagcaga agcaccgtag cctcattttg   600
ggtatgaaga agacacggcc tcaaggttcg gggcagcagc ttactgccaa gaagcagggc   660
caattccaga cactcaagac cggcttgcag actctagtgg aggagctgga gaatcaattg   720
```

```
aagctgacaa aggtctacaa gggtaccaag gtgacaaaca tatcgcgtgg cgaaaaggga  780
tgctccattg ccctcgacaa cggtatgacc ctcgacgccg acgcagcgat tgtgacgagc  840
ccacacaaga gcgccgcggg catgttcccg gacttgcctg cagtgtcaca gctgaaagac  900
atgcattcta catccgtcgc caacgtcgcc ctgggctttc cccaggaggc tgtgcagatg  960
gagcacgagg ggacgggctt cgttatcagc cgcaactccg actttctat taccgcgtgc  1020
acatggacca acaagaagtg gccgcacagc gctccggagg ggaaaacact tctccgagca  1080
tacgtaggca aggccgggga cgagtcaatt gttgagctct ccgacaatga aatcattaaa  1140
atagttctgg aggatcttaa gaaggtaatg aagataaagg gggaacctga aatgacgtgt  1200
gttacccgct ggaatgagtc aatgccccag taccatgtgg gacacaagca gaggataaag  1260
aaggtgaggg aggcgctcgc tgcgtcctac ccaggggtct acatgacagg agcgagtttt  1320
gaggggggtgg gtattcccga ctgtatcgac cagggtaagt cggcagtgtc tgacgtgctc  1380
gcttacctat tcgagtag                                                1398
```

```
SEQ ID NO: 220         moltype = DNA  length = 1422
FEATURE                Location/Qualifiers
source                 1..1422
                       mol_type = other DNA
                       note = Recombinant
                       organism = synthetic construct
SEQUENCE: 220
attgcagtca ttggtggtgg gataacaggg ttgtccgtgg cctactacgt gaggaagctg  60
cttcgggagc aaggcgttaa tgcgggcgtt accctcgtcg agcaatccga ccgcctcggc  120
gggaagatta gatccttgag acgagacggc tttaccattg agcaaggccc tgactctatg  180
attgcacgta agcccgcagc tctcgaactt atccgtgagc ttggtctgga ggacaagttg  240
gcgggcacaa accctcaagc caaacgctcc tacatactgc accgtggcaa gtttcatccg  300
atgccacctg ggctgatgct cgggattccc actcaaatgt ggccaatggt caagaccggg  360
ctgctatctc cggccggaaa gctacgggct gcgatggacc tacttcttcc tgcaaggcgc  420
ggaggcggcg acgaatcact tggtgggttt atccggaggc ggcttggacg tgaggtgttg  480
gagcagatga ccgaaccact ccttgctgga atctatgctg gcgacacaga acagctttca  540
cttaaagcga cctttcctca attcatggag atggaaagga aacatcgcag tctcatcctt  600
ggactattgg ctgggaagaa acagccaccg cgtcccggtg gtagccaagt gccgctccca  660
aaggccgctc agaccagtat gttcttgaca ctcaccggcg ggttggaagg tctgaccgaa  720
gcactagagg aaagcctatc agaggagaag ataattactg gccaagcagt taccggactt  780
tcgcagcaag aggccgggta tgagttaaat ctctctggcg gagagagact taatgcagac  840
ggagtgatcc tcgcagtccc agcgttcgct gccgcccgac ttcttgacgg cgtgcctgag  900
gccgcctacc tagagcgcat ccgctatgtc agtgttgcta atttggcgtt cgcttacagg  960
cgtgaggacg tgcctcatga tctgaatggg tccggcgtgt taatccctag aggtgaaggg  1020
aggatgatta cggccataac ttgggtttcg tccaaatggt tgcattcagc acccggtgac  1080
aaggcactgc tgagagcgta cattgggcga ctaggtgatg aggcttggac agccatgtgt  1140
agggccgaca tcgagcgtag agtcgccgct gaactccgcg atctactagg aattgccgct  1200
agtcctttgt tctgtgaact agccgcactc ccagaatcta tgccgcagta tccagtgggt  1260
cacgtcgaac gactcgaagc cttgcgagga gcattgtgtc gcgctaaacc agggttgttg  1320
ttgtgtggtg ccgggtacgc tggcgttggc attccagact gcattcggca aggcaaagaa  1380
gccgctgagt cgatggcggc ttatttgagg gacggacgct ag                     1422
```

```
SEQ ID NO: 221         moltype = DNA  length = 1464
FEATURE                Location/Qualifiers
source                 1..1464
                       mol_type = other DNA
                       note = Recombinant
                       organism = synthetic construct
SEQUENCE: 221
cttgtggtca tcggcggagg gatcactggg ctttcggccg ccttctatgc actaaagcaa  60
gccgatgagg aagggcagcc catctcggtc accataattg aacagagcga taggctcggc  120
ggaaagatcc agacactccg caaggagggc tgcgtaattg agaagggccc ggattccttc  180
ctcgctagga agttgccgat gattgatcta gctcgggatc ttggcatgga ctccgaattg  240
gtggcgacta atccgcacgc aaagaagact tacatcttga ggcgcggaaa gctctaccgg  300
atgcctccag gcttagtgct tggcatacct acggaactag gaccattcgc taagacaggg  360
ctcattagcc cttggggcaa actccgcgcc gctatgatt tgttcattaa gcctcatcca  420
gccgatgaag acgaaagtgt tggcgctttc ctggacagac gtctcggtag ggaagtgacc  480
gagcacattg cggaaccttt attggcgggc atctacgcgg gcgacttgca agccttaagc  540
cttcaagcca ctttcccaca gtttgcacaa gtagagcgca agcacggagg ctgatacgc  600
ggtatgaagg ccagcagaca ggccggtcag tccgtgcctg ggctgccgga cgtcgccaag  660
ggtacgatgt tccttacctt tcgcaacggg cttaccagct tagttgaaag gttggaggaa  720
actctcagag acagggctga actcgtctg ggcatcggcg cagaagggtt tgagaaacgt  780
gaagatggaa cataccttgt tcgactaagc gatggttcga ggctccaggc cgacgcagta  840
attgtcacta cgccgagcta tcatgcggca tccctgttgg aggagcatgt ggatgcttcg  900
gccctccagg ccattcgtca tgtaagcgtt gcaaatgtcg ttagcgtctt cgaccgaaag  960
caagtgaata accagttcga cggcacaggg tttgttatct cacggcgaga aggtcgcgca  1020
atcaccgcct gtacctggac atccgtgaaa tggccgcata cttcgcgcgg cgacaaactg  1080
attatccggt gctacatcgg tagggctggc gacgaggagc gagtggattg cccgatgaa  1140
gctctcaagc gtactgtaag atcagaactg cgtgagttgc tggacattga cattgatccg  1200
gaatttgtgt agattacacg actcaggcac tctatgcctc aatacccagt cggccacgtc  1260
caggctatcc gctctttgag ggacgaggtc ggtaggactt taccgggcgt gttccttgct  1320
gggcaaccct acgaaggtgt gggaatgcct gactcgtgta ggtccggccg gatgccgcc  1380
gaagcagcag taagtgctat gcaagcaatg agtacagaac cagaagcacc ggcagaggac  1440
gccgctactg gaacggcggg ttga                                         1464
```

```
SEQ ID NO: 222         moltype = DNA  length = 1404
```

-continued

```
FEATURE              Location/Qualifiers
source               1..1404
                     mol_type = other DNA
                     note = Recombinant
                     organism = synthetic construct
SEQUENCE: 222
gttgttgttg ttggcggcgg cttgactggc ctaagcgccg ccttctacat ccggaaacat    60
tatcgagaag ctggagttga gcccgtcatc acgcttgttg agaaatctag ctcgatggga   120
gggatgattg agacccttca tagggacggg tttgtcatcg agaagggccc ggacagtttg   180
ttggcacgga agaccgcaat gattgatctg gcgaaagagc tggagattga ccacgagttg   240
gtcagccaga atccagaatc gaagaagacc tacataatgc aacgtggaaa gctgcaccct   300
atgccagcgg gacttgttct gggcattccc accgaattgc gtccctttct ccggagcggg   360
cttgtctcac ccgctgggaa gttgcgggcg ctgatggact tcgtaatacc gccacgaagg   420
acgaccgaag atgagtcact cgggtacatg atcgagcggc gactgggtgc cgaggtgttg   480
gagaacctca cagagccgtt gctcgctgga atctacgctg cgacatgag aagattgtcc     540
ctccaggcta cgtttccgca gttcggtgag gtggagcgcg actacggctc cttaatcaga   600
ggaatgatga ccggacgtaa gcctgcggag acacacacag ggaccaagag gtctgccttt   660
ctcaatttca gacagggtct gcaatcactg gttcacgcct tagtccatga actccaggat   720
gtagatcaga ggttaaatac tgcggtgaag tcgcttcaga ggcttgacgg cgcacaaacc   780
cgttatcgcg ttgaactcgg caatggcgaa atgcttgagg ctgacgacgt ggtggttact   840
gtaccaacct acgtggcgag cgagcttctt aagccgcacg tggacacggc ggcgttagac   900
gctattaact atgtgtcggt ggctaatgta gttcttgcat tcgagaagaa ggaagtagag   960
cacgtcttcg atggatcggg cttcttggtg cctcggaagg agggaaggaa cataaccgcc  1020
tgcacctgga cttcgaccaa gtggctccac acatcaccag atgacaaggt tctgttacgt  1080
tgttacgtgg gcagaagtgg agatgagcag aatgtgaac tcccggatga ggcactcact   1140
aatctggtgc ttaaggatct gagagagacg atgggcatcg gacgcggttcc aatcttctca  1200
gagattaccc ggctccgcaa gtcaatgccg cagtacccag taggacatct ccagcacatc  1260
gccgcattgc gcgaggaact cggctctaag ctaccaggag tgtacatcgc cggagcgggc  1320
tacgagggcg ttggtcttcc ggattgcatt cgccaggcca agaaatgtc agtccaggca   1380
acgcaagaac tcgctgccga ctga                                         1404

SEQ ID NO: 223         moltype = DNA   length = 1398
FEATURE                Location/Qualifiers
source                 1..1398
                       mol_type = other DNA
                       note = Recombinant
                       organism = synthetic construct
SEQUENCE: 223
aagcacctgg taatcatcgg tggtgggatc accggtctgg cttcagcgtt ctacatggaa    60
aaggagatcc gggagaagaa cttgcccctt tcggtgactc tagtggaggc ctctccacgg   120
gtggggggca agattcagac cgcgcgcaag gatggctaca tcatagagcg aggaccagac   180
tcattcctag agcgtaagaa gtccgcccca gagctcgtcg aggatctcgg tctagagcac   240
ttgctagtga ataacgctac aggacagtcc tacgtgctcg tgaacgagac actacaccgg   300
atgcctaagg gggctgtcat gggtataccg accaagatcg ccccgttcat gtccactcgc   360
ctttttctcgt tctcgggcaa agctcgggcc gctatggatt tcgtcttgcc tgcctcgaaa   420
ccgaaggagg accagtcctt aggagagttc ttccgccgga gggtcggcga cgaggtggtg   480
gagaacttaa tcgaaccctt gctctcgggg atctacgctg gagacattga tcgactatcg   540
cttatgtcta cgtttcctca attttaccag acggagcaga agcaccgtag cctcattttg   600
ggtatgaaga agacacggcc tcaaggttcg gggcagcagc ttactgccaa gaagcagggc   660
caattccaga cactcaagac cggcttgcag actctagtgg aggagctgga gaatcaattg   720
aagctgacaa aggtctacaa gggtaccaag gtgacaaaca tatcgcgtgg cagaaaggga   780
tgctccattg ccctcgacaa cggtatgacc ctcgacgccg acgcagcgat tgtgacgagc   840
ccacacaaga gcgccgcggg catgttcccg gacttgcctg cagtgtcaca gctgaaagac   900
atgcattcta catccgtcgc caacgtcgcc ctgggctttc cccaggaggc tgtgcagatg   960
gagcacgagg ggacgggctt cgttatcagc cgcaactccg acttttctat taccgcgtgc  1020
acatggacca acaagaagtg gccgcacagc gctccggagg ggaaaacact tctccgagca  1080
tacgtaggca aggccgggga cgagtcaatt gttgagctct ccgacaatga aatcattaaa  1140
atagttctgg aggatcttaa gaaggtaatg aagataaagg gggaacctga aatgacgtgt  1200
gttaccgct ggaatgagtc aatgccccag taccatgtgg gacacaagca gaggataaag    1260
aaggtgaggg aggcgctcgc tgcgtcctac ccagggggtct acatgacagg agcgagtttt  1320
gaggggtgg gtattcccga ctgtatcgac cagggtaagt cggcagtgtc tgacgtgctc   1380
gcttacctat cgagtag                                                 1398

SEQ ID NO: 224         moltype = AA   length = 445
FEATURE                Location/Qualifiers
source                 1..445
                       mol_type = protein
                       note = Recombinant
                       organism = synthetic construct
SEQUENCE: 224
QPVLIVGAGL SGLSIAYELQ KLQVPYQVLE VSGHSGGVMK SLRKDGFELD AGANTIAASP    60
EILAYFTSLG LENEILQATA ASKHRFLVRR RQLHAVSPHP FKIMSSPYLS RGSKWRLFTE   120
RFRKPVVASG EETVTDFITR RFNREIAEYV FDPVLSGIYA GNPDQMSIAE VLPALPRWER   180
EYGSVTKGLM KDKGAMGGRK IISFKGGNQL LTNRLQQLLT TPVRFNCKVT GITASNGGYI   240
VSAVEDGVSE SYTASRVILT TPAYSAAATI TNLDAATAAL LNEIHYPRMG VLHLGFDATA   300
LPQPLDGFGF LVPNAENMHF LGAICNAAIF PDKAPPGKIL FTVFLGGARQ ESLFDQMTPE   360
ALQQQVVSEV MSLLHLSAPP VMQHFSSWNK AIPQLNVGHV KLRRAVEAFE KKYPGIHLSG   420
NYLQGVAIPA LLQHAAALAA SLKKN                                         445
```

-continued

```
SEQ ID NO: 225         moltype = AA  length = 448
FEATURE                Location/Qualifiers
source                 1..448
                       mol_type = protein
                       note = Recombinant
                       organism = synthetic construct
SEQUENCE: 225
MSDQPVLIVG AGLSGLSIAY ELQKLQVPYQ VLEVSGHSGG VMKSLRKDGF ELDAGANTIA  60
TSPEILAYFT SLGLENEILQ ATATSKHRFL VRRRQLHAVS PHPFKIMSSP YLCRGSKWRL  120
FTERFRKPVV ASGEETVTDF ITRRFNREIA EYVFDPVLSG IYAGNPDQMS IAEVLPALPR  180
WEREYGSVTK GLMKDKGAMG GRKIISFKGG NQLLTNRLQQ LLTTPVRFNC KVTGITASNG  240
GYIVSAVEDG VSESYTASRV ILTTPAYSAA ATITNLDAAT AALLNEIHYP RMGVLHLGFD  300
ATALPQPLDG FGFLVPNAEN MHFLGAICNA AIFPDKAPPG KILFTVFLGG ARQESLFDQM  360
TPEALQQQVV SEVMSLLHLS APPVMQHFSS WNKAIPQLNV GHVKLRRAVE AFEKKYPGIH  420
LSGNYLQGVA IPALLQHAAA LAASLKKN                                     448

SEQ ID NO: 226         moltype = AA  length = 466
FEATURE                Location/Qualifiers
source                 1..466
                       mol_type = protein
                       note = Recombinant
                       organism = synthetic construct
SEQUENCE: 226
KKHVVIIGGG ITGLAAAFYM EKEIKEKNLP LELTLVEASP RVGGKIQTVK KDGYIIERGP  60
DSFLERKKSA PQLVKDLGLE HLLVNNATGQ SYVLVNRTLH PMPKGAVMGI PTKIAPFVST  120
GLFSLSGKAR AAMDFILPAS KTKDDQSLGE FFRRRVGDEV VENLIEPLLS GIYAGDIDKL  180
SLMSTFPQFY QTEQKHRSLI LGMKKTRPQG SGQQLTAKKQ GQFQTLSTGL QTLVEEIEKQ  240
LKLTKVYKGT KVTKLSHSGS GYSLELDNGV TLDADSVIVT APHKAAAGML SELPAISHLK  300
NMHSTSVANV ALGFPEGSVQ MEHEGTGFVI SRNSDFAITA CTWTNKKWPH AAPEGKTLLR  360
AYVGKAGDES IVDLSDNDII NIVLEDLKKV MNINGEPEMT CVTRWHESMP QYHVGHKQRI  420
KELREALASA YPGVYMTGAS FEGVGIPDCI DQGKAAVSDA LTYLFS                466

SEQ ID NO: 227         moltype = AA  length = 465
FEATURE                Location/Qualifiers
source                 1..465
                       mol_type = protein
                       note = Recombinant
                       organism = synthetic construct
SEQUENCE: 227
KHLVIIGGGI TGLAAAFYLE KEVEEKGLPI QISLIEASPR LGGKIQTLYK DGYIIERGPD  60
SFLERKVSGP QLAKDVGLSD QLVNNETGQA YVLVNEKLHP MPKGAVMGIP TQISPFITTG  120
LFSVAGKARA AMDFVLPKSK QTEDQSLGEF FRRRVGDEVV ENLIEPLLSG IYAGDIDRLS  180
LMSTFPQFYQ TEQQHRSLIL GMKKSQQHAK AQQVTAKKQG QFQTINQGLQ SLVEAVEGKL  240
KLTTVYKGTK VKQIEKTDGG YGLQLDSGQT LFADSAIVTT PHQSIYSMFP KEAGLEYLHD  300
MTSTSVATVA LGFKDEDVHN EYDGTGFVIS RNSDFSITAC TWTNKKWPHT APKGKTLLRA  360
YVGKAGDESI VEQSDSQIVS IVLEDLKKIM DIKADPELTT VTRWKTSMPQ YHVGHQKAIS  420
NMRETFKQSY PGVYITGAAF EGVGIPDCID QGKAAISEAV SYLFS                 465

SEQ ID NO: 228         moltype = AA  length = 465
FEATURE                Location/Qualifiers
source                 1..465
                       mol_type = protein
                       note = Recombinant
                       organism = synthetic construct
SEQUENCE: 228
KHLVIIGGGI TGLAAAFYLE KEVEEKGLPI QISLIEASPR LGGKIQTLYK DGYIIERGPD  60
SFLERKVSGP QLAKDVGLSD QLVNNETGQA YVLVNETLHP MPKGAVMGIP TQISPFITTG  120
LFSVAGKARA AMDFVLPKSK QTEDQSLGEF FRRRVGDEVV ENLIEPLLSG IYAGDIDRLS  180
LMSTFPQFYQ TEQHRSLIL GMKKSQQHAK AQQVTAKKQG QFQTINQGLQ ALVEAVESKL  240
KLTTIYKGTK VKQIEKTDGG YGVQLDSGQT LLADSAIVTT PHQSIYSMFP KEAGLEYLHD  300
MTSTSVATVA LGFKEEDVHN EYDGTGFVIS RNSDFSITAC TWTNKKWPHT APKGKTLLRA  360
YVGKAGDESI VEQSDHQIVS IVLEDLKKIM DIKADPELTT VTRWKTSMPQ YHVGHQKAIS  420
NMRETFKQSY PGVYITGAAF EGVGIPDCID QGKAAISEAV SYLFS                 465

SEQ ID NO: 229         moltype = DNA  length = 537
FEATURE                Location/Qualifiers
source                 1..537
                       mol_type = other DNA
                       note = Recombinant
                       organism = synthetic construct
SEQUENCE: 229
aaggccttgg tactgtactc gacgcgggac ggccagaccc acgcaattgc ttcatacatc  60
gcctcctgca tgaaggagaa ggccgaatgc gacgtgatcg acctcaccca cggggagcac  120
gtgaacctca cccaatacga tcaggtgcta atcggtgcag gtattcgtta cggccacttc  180
aacgccgtgc ttgacaagtt catcaagaga aacgtggatc aactgaacaa catgccaagc  240
gcgttcttct gcgtaaacct cacagcaagg aagcccgaga agcgtactcc ccagacaaac  300
ccttatgtcc gaaaattctt gcttgctacc ccctggcagc ccgcgttgtg cggagtgttc  360
gcaggggccc ttcggtaccc gcgataccgg tggatcgaca aggtgatgat ccagctaata  420
atgcggatga ctgggggaga gacagacacg agcaaggagg tcgagtacac ggattgggag  480
```

```
caggttaaga agttcgcgga ggatttttgca aagctatcgt acaagaaggc cctctag       537

SEQ ID NO: 230          moltype = DNA   length = 1338
FEATURE                 Location/Qualifiers
source                  1..1338
                        mol_type = other DNA
                        note = Recombinant
                        organism = synthetic construct
SEQUENCE: 230
cagcccgtcc tcatcgttgg agctggtctc tccgggctct caatcgctta cgaactacag       60
aagctgcaag tcccttacca agtgctggag gtttctggac attctggtgg agtcatgaag       120
tcactccgga aggacggatt tgaactcgac gctggtgcca acaccatagc cgcgtctccc       180
gagattcttg cgtactttac ctcactaggt cttgagaatg agatcctcca ggcgactgct       240
gcttctaaac accgcttctt ggtgcggcga aggcaactgc acgccgtgag cccgcacccg       300
ttcaagatca tgtcatcgcc gtacctcagc cgtggctcca aatggcggct ctttactgag       360
cggtttcgga agcccgtcgt cgcttcgggc gaggagaccg tcaccgattt catcacgagg       420
agattcaacc gcgaaatagc ggagtatgtg ttcgaccctg ttctaagcgg gatctacgcc       480
gggaacccgg accaaatgag tattgctgag gtgttgcctg ccttgcctag gtgggaaagg       540
gagtacggat cagtgaccaa gggccttatg aaggataagg gtgcgatggg aggtcgaaag       600
atcatcagct ttaagggtgg caaccagcta cttacaaacc gcttacagca gctactcact       660
actccggtga gattcaattg caaggtgaca gggattacag ccagcaatgg cgggtacatc       720
gtgagcgctg ttgaggacgg cgtatctgag agctacaccg catctcgtgt gatcttgacc       780
acacccgctt actcagcagc ggctaccata actaaccttg atgcagccac tgcggcactg       840
ttgaacgaaa tccattatcc acgtatgggc gtgttacact tgggctttga tgcaactgcc       900
ttgccacagc cgctggacgg gttcggattt ctagtgccga acgcggagaa catgcacttc       960
ctgggagcca tctgcaatgc agccatcttc ccggacaagg ctccgcccgg caagatcctg       1020
tttacagtgt tcctcggagg cgcacgccag gagtcgctct tcgatcagat gactcctgag       1080
gctcttcagc agcaagtcgt tagtgaggtg atgagcttgt tgcacttgtc agctccaccg       1140
gtgatgcagc acttctcctc ctggaacaag gccatccctc aattgaacgt cgggcacgtg       1200
aagttgcggc gcgcggtaga ggcgttcgag aagaaatacc ctggaatcca tctctcgggc       1260
aactacctcc agggagttgc aataccagct ttactccagc acgccgcagc tttagctgct       1320
tctcttaaga agaactga                                                     1338

SEQ ID NO: 231          moltype = DNA   length = 1344
FEATURE                 Location/Qualifiers
source                  1..1344
                        mol_type = other DNA
                        note = Recombinant
                        organism = synthetic construct
SEQUENCE: 231
atgagcgacc aacccgtcct catcgttgga gctggtctct ccgggctctc aatcgcttac       60
gaactacaga agctgcaagt cccttaccaa gtgctggagg tttctggaca ttctggtgga       120
gtcatgaagt cactccggaa ggacggattt gaactcgacg ctggtgccaa caccatagcc       180
acgtctcccg agattcttgc gtactttacc tcactaggtc ttgagaatga gatcctccag       240
gcgactgcta cttctaaaca ccgcttcttg gtgcggcgaa ggcaactgca cgccgtgagc       300
ccgcacccgt tcaagatcat gtcatcgccg tacctctgcc gtggctccaa atggaggctc       360
tttactgagc ggtttcggaa acccgtcgtc gcttcgggcg aggagaccgt caccgatttc       420
atcacgagga gattcaaccg cgaaatagcc gagtatgtgt tcgaccctgt tctaagtggg       480
atctacgccg ggaacccgga ccaaatgagt attgctgagg tgttgcctgc cttgcctagg       540
tgggaaaggg agtacggatc agtgaccaag ggccttatga aggataaggg tgcgatggga       600
ggtcgaaagg tcatcagctt taagggtggc aaccagctac ttacaaaccg cttacagcag       660
ctactcacta ctccggtgag attcaattgc aaggtgacag ggattacagc cagcaatggc       720
gggtacatcg tgagcgctgt tgaggacggc gtatctgaga gctacaccgc atctcgtgtg       780
atcttgacca cacccgctta ctcagcagcg gctaccataa ctaacttga tgcagccact       840
gcggcactgt tgaacgaaat ccattatcca cgtatgggcg tgttacactt gggctttgat       900
gcaactgcct tgccacagcc gctggacggg ttcggatttc tagtgccgaa cgcggagaac       960
atgcacttcc tgggagccat ctgcaatgca gccatcttcc cggacaaggc tccgcccggc       1020
aagatcctgt ttacagtgtt cctcggaggc gcacgccagg agtcgctctt cgatcagatg       1080
actcctgagg ctcttcagca gcaagtcgtt agtgaggtga tgagcttgtt gcacttgtca       1140
gctccaccgg tgatgcagca cttctcctcc tggaacaagg ccatccctca attgaacgtc       1200
gggcacgtga agttgcggcg cgcggtagag gcgttcgaga gaaatacccc tggaatccat       1260
ctctcgggca actacctcca gggagttgca ataccagctt tactccagca cgccgcagct       1320
ttagctgctc tcttaagaa gaac                                               1344

SEQ ID NO: 232          moltype = DNA   length = 1338
FEATURE                 Location/Qualifiers
source                  1..1338
                        mol_type = other DNA
                        note = Recombinant
                        organism = synthetic construct
SEQUENCE: 232
cagcccgtcc tcatcgttgg agctggtctc tccgggctct caatcgctta cgaactacag       60
aagctgcaag tcccttacca agtgctggag gtttctggac attctggtgg agtcatgaag       120
tcactccgga aggacggatt tgaactcgac gctggtgcca acaccatagc cacgtctctg       180
gagattcttg cgtactttac ctcactaggt cttgagaatg agatcctcca ggcgactgct       240
acttctaaac accgcttctt ggtgcggcga aggcaactgc acgccgtgag cccgcacccg       300
ttcaagatca tgtcatcgcc gtacctctgc cgtggctcca aatggaggct ctttactgag       360
cggtttcgga aacccgtcgt cgcttcgggc gaggagaccg tcaccgattt catcacgagg       420
agattcaacc gcgaaatagc ggagtatgtg ttcgaccctg ttctaagtgg gatctacgcc       480
```

```
gggaacccgg accaaatgag tattgctgag gtgttgcctg ccttgcctag gtgggaaagg   540
gagtacggat cagtgaccaa gggccttatg aaggataagg gtgcgatggg aggtcgaaag   600
atcatcagct ttaagggtgg caaccagcta cttacaaacc gcttacagca gctactcact   660
actccggtga gattcaattg caaggtgaca gggattacag ccagcaatgg cgggtacatc   720
gtgagcgctg ttgaggacgg cgtatctgag agctacaccg catctcgtgt gatcttgacc   780
acacccgctt actcagcagc ggctaccata actaaccttg atgcagccac tgcggcactg   840
ttgaacgaaa tccattatcc acgtatgggc gtgttacact tgggctttga tgcaactgcc   900
ttgccacagc cgctggacgg gttcggattt ctagtgccga acgcggagaa catgcacttc   960
ctgggagcca tctgcaatgc agccatcttc ccggacaagg ctccgcccgg caagatcctg  1020
tttacagtgt tcctcggagg cgcacgccag gagtcgctct tcgatcagat gactcctgag  1080
gctcttcagc agcaagtcgt tagtgaggtg atgagcttgt tgcacttgtc agctccaccg  1140
gtgatgcagc acttctcctc ctggaacaag gccatccctc aattgaacgt cgggcacgtg  1200
aagttgcggc gcgcggtaga ggcgttcgag aagaaatacc ctggaatcca tctctcgggc  1260
aactacctcc agggagttgc aataccagct ttactccagc acgccgcagc tttagctgct  1320
tctcttaaga agaactga                                               1338

SEQ ID NO: 233              moltype = DNA   length = 1401
FEATURE                    Location/Qualifiers
source                     1..1401
                           mol_type = other DNA
                           note = Recombinant
                           organism = synthetic construct
SEQUENCE: 233
aagaagcacg tcgtcatcat aggcggtggg atcactggct tggccgctgc attctacatg    60
gagaaggaga ttaaggagaa gaacctccca cttgagctga cgctagttga ggccagtccc   120
agggtcggcg gcaagatcca gacggtcaag aaggacggt acataattga acgcggccct   180
gacagcttct tagagcgcaa gaaatcggct ccgcagctag ttaaggactt gggacttgag   240
cacctgctcg tcaacaacgc gaccggacag tcgtacgtgc tcgtgaaccg gacgctccac   300
ccgatgccga agggcgctgt gatgggcatt ccgaccaaga tagcaccatt cgtgagtacc   360
ggcctattca gcctttccgg caaggcaagg gctgcgatgg acttcatctt gcctgcctct   420
aagactaagg acgatcagtc cttgggcgag ttcttccgcc gccgggtggg tgatgaggtg   480
gtggagaact taattgagcc gctcctatct ggaatctacg ctggtgacat cgacaaactg   540
tctctgatgt ccacctttcc gcagttctac caaactgagc agaagcaccg ttcacttatc   600
ttgggaatga agaagactag acctcaaggt tcgggtcagc aactgacggc caagaaacag   660
ggtcagttcc agacgctaag caccgggctt cagacactcg tggaggagat tgagaaacag   720
ctcaaactta ctaaggtgta caagggcacg aaggtgacaa agttatccca ctccggcagc   780
gggtactccc tggagttgga caatggcgta acgttggacg ccgactcagt tatcgtgaca   840
gcgccgcata aggctgctgc cgggatgttg tcagaactcc cggcgatttc ccatctcaag   900
aacatgacta gtacctcggt tgccaacgtc gccctcggat tcccggaagg aagtgttcaa   960
atggagcacg aaggcacggg tttcgtaatt tccaggaact ccgactttgc catcaccgct  1020
tgtacttgga ccaacaagaa gtggcctcat gctgcgccgg agggcaagac attgctcaga  1080
gcttacgtcg gaaggcgggc cgacgagtca atcgtcgatc ttagcgacaa cgacatcatt  1140
aacattgtgc tggaggactt gaagaaggtt atgaacatca agatgatgacc  1200
tgcgtgaccc gatggcacga gtctatgccg cagtaccacg tcggtcacaa gcagcgcatc  1260
aaggagttgc gcgaggcact cgcctcagct taccctggcg tgtacatgac tggcgcttcg  1320
tttgagggcg ttggtattcc tgactgcatc gaccaggggaa aggcggccgt cagtgacgcg  1380
ctcacctacc tcttcagttg a                                            1401

SEQ ID NO: 234              moltype = DNA   length = 1398
FEATURE                    Location/Qualifiers
source                     1..1398
                           mol_type = other DNA
                           note = Recombinant
                           organism = synthetic construct
SEQUENCE: 234
aagcacctgg tcataatcgg aggcggcata accggccttg ctgcggcctt ctacctggag    60
aaggaggtcg aggagaaggg tctccctatc cagatttcat tgattgaggc ttcgcctcgg   120
ctgggaggga agatccagac attgtacaag acgggtaca tcatcgagcg tggtccagac   180
agtttcctgg agcggaaggt cagcggaccg cagctcgcca aggacgtggg acttagcgac   240
caactggtga caacgacgac aggacaggcg tacgtcttgg tgaatgagaa gttgcacccg   300
atgcctaagg gtgccgtgat gggcatccca acgcaaatct cacctttcat caccaccgga   360
ctcttctccg tggccggaaa ggcacgagct gcaatggact tcgttctgcc taagtcgaaa   420
cagaccgaag accagtctct aggcgagttc ttccgccgcc gtgtgggtga cgaggttgtg   480
gagaacctca tcgagccttt gttgtctggg atctacgtgg cgacatcga cagacttagt   540
ctcatgagta cctttccgca attctatcag acagaacagc agcatcgaag tctcatactc   600
gggatgaaga agtcacaaca acatgcaaag gcccagcaag ttaccgccaa gaaacagggc   660
cagttccaaa cgatcaacca gggcctccag agcttggtgg aggcagtgga gggaaagttg   720
aagctcacca ccgtttacaa agggacaaag gttaaacaga ttgagaagac ggacggcggt   780
tacgggttac aattggactc cggacagact ctcttcgctg attccgctat cgtaactact   840
cctcaccaga gcatctactc tatgttcccg aaggaggcgg gcctggagta cctgcacgac   900
atgacttcaa cgtctgtcgc caccgtggct ttgggcttca aggacgagga cgtccacaat   960
gagtatgacg gacgggatt cgttatcagt aggaactccg acttcagcat caccgcctgc  1020
acgtggacca acaagaagtg gccacacacc gcgcccaaag gaagaccct tctgagggca  1080
tacgtgggca aggcggggcga cgagagcatc gtcgagcaat ctgattctca gattgtttca  1140
atcgtcctcg aagacctcaa gaagatcatg gacatcaagg cagaccggga acttaccacc  1200
gttactcgat ggaagacctc gatgcctcag tatcacgtcg gcaccagaa ggcaatcagc  1260
aacatgagg agacattcaa gcagtcgtat cctggccgtgt acattaccgg agcagcattc  1320
gaaggcgtag gaatccctga ctgcattgac caggggcaagg ctgctatctc agaggccgtg  1380
tcctatctct tctcgtga                                                1398
```

```
SEQ ID NO: 235            moltype = DNA   length = 1398
FEATURE                   Location/Qualifiers
source                    1..1398
                          mol_type = other DNA
                          note = Recombinant
                          organism = synthetic construct
SEQUENCE: 235
aagcacctgg tgataattgg aggcgggatt accggcctag cagccgcttt ctatctggag   60
aaggaggtgg aggagaaggg cctcccgata cagatttcgc tgattgaagc ctctccgcgc   120
ctgggcggca agatccagac attgtacaag gacgggtaca tcattgagcg cgggcctgac   180
tcgttcctgg agcggaaggt ctccggtcct caactggcca aagacgtggg tctttccgat   240
cagcttgtga acaatgagac cggtcaggct tacgtcttgg tcaacgaaac tctgcatccc   300
atgcctaagg gagccgttat gggcattcca acgcaaatct ctccgttcat aacgactggg   360
ctgttcagcg ttgcgggcaa agcaagggct gctatggact tcgtgctgcc aaagagtaag   420
cagaccgagg accagtccct cggcgagttc ttccgccgcc gagtgggcga tgaggtggtt   480
gagaatctaa tcgaaccgct gttgtcgggc atcatgcgg gcgacatcga caggctaagt   540
cttatgtcca cttttcccttca gttctaccag acagagcaga aacacaggag tctcatcctt   600
ggaatgaaga agtcccagca gcacgcgaag gctcagcaag tgaccgccaa gaagcaagga   660
cagttccaga ccatcaacca gggcctacag gcccttgtcg aagccgttga gtcgaagtta   720
aagttgacga cgatctacaa gggcaccaag gtgaagcaga ttgagaagac tgacggtggc   780
tatggtgtgc aactcgattc gggccaaaca ttgctcgctg actccgctat cgtcacgacg   840
ccacaccagt cgatctactc gatgttcccg aaggaggcgg gcctagagta ccttcacgac   900
atgacctcca cttcggtcgc caccgttgca ctcggcttta aggaggagga cgttcacaac   960
gagtacgatg gcaccggatt cgtgatctcc aggaactcgg acttctcgat taccgcgtgc   1020
acgtggacaa ataagaagtg gccgcacaca gcgccaaagg caagaccct tctgcgggcg   1080
tatgtgggca aggccggtga cgagagcatt gtcgaacaat ctgaccatca gatcgtttct   1140
attgttcttg aggatctcaa gaagataatg gacattaagg ccgaccctga gcttaccaca   1200
gtgacgaggt ggaagaccct cgatgccgcag tatcacgtag ggcaccagaa ggccatctcc   1260
aacatgcggg agacattcaa gcagtcgtac cctggcgtgt acattactgg cgctgctttc   1320
gagggcgttg gcatcccgga ctgcatcgac cagggcaagg ccgcaatctc agaggcagtg   1380
tcgtacctgt tcagctag                                                 1398

SEQ ID NO: 236            moltype = AA   length = 68
FEATURE                   Location/Qualifiers
source                    1..68
                          mol_type = protein
                          organism = Glycine max
SEQUENCE: 236
MATATTTATA AFSGVVSVGT ETRRIYSFSH LQPSAAFPAK PSSFKSLKLK QSARLTRRLD   60
HRPFVVRC                                                             68

SEQ ID NO: 237            moltype = AA   length = 56
FEATURE                   Location/Qualifiers
source                    1..56
                          mol_type = protein
                          note = Recombinant
                          organism = synthetic construct
SEQUENCE: 237
MATTTAAAAV TISIPKKPVF IRRPRLRGPV DCRGLHASDA IISNEAPTGT TISADC       56

SEQ ID NO: 238            moltype = AA   length = 76
FEATURE                   Location/Qualifiers
source                    1..76
                          mol_type = protein
                          organism = Eragrostis tef
SEQUENCE: 238
MAAAPPLAAD MVLPSPCPAA VAPTPVVAAA WGAARAGSVR CKATQLRMMR TGGPVAPVAG   60
RRRRAPLSVR CDASSR                                                    76

SEQ ID NO: 239            moltype = AA   length = 80
FEATURE                   Location/Qualifiers
source                    1..80
                          mol_type = protein
                          organism = Setaria italica
SEQUENCE: 239
MAAAPPLSAD ALSFLPSAAA PAAAAPTPVV AAAWGAARAA GSVRGKAALR MARRGSGLAP   60
VVGRRPRRPP LSVRCDATSR                                                80

SEQ ID NO: 240            moltype = AA   length = 84
FEATURE                   Location/Qualifiers
source                    1..84
                          mol_type = protein
                          organism = Acalypha ostryifolia
SEQUENCE: 240
MATTTATTSF SGVSICPPHQ TNRTSLFPPQ SLSFPSSKHG SLVNSVQFNR SRRARRNHFS   60
LTSITNAPRR KRLLSVRCDA SATS                                           84

SEQ ID NO: 241            moltype = AA   length = 78
```

-continued

```
FEATURE               Location/Qualifiers
source                1..78
                      mol_type = protein
                      organism = Adansonia digitata
SEQUENCE: 241
MAASSSSVVS FSGISLCSTH SISNKTYLFS AHPRISVSFP SKPNSLKSFK QLQLKKNGLF   60
EKFSRTSSRS FVVRCDAS                                                  78

SEQ ID NO: 242        moltype = AA  length = 82
FEATURE               Location/Qualifiers
source                1..82
                      mol_type = protein
                      organism = Taraxacum officinale
SEQUENCE: 242
MATTASFSGV RIHAPSSTCI DRTTLFAQPS VSFSSFSKPR RTTLRSLKLR SRSNDVLLRT   60
RTGDRFGGKS SRSFVVRCDA SS                                             82

SEQ ID NO: 243        moltype = AA  length = 77
FEATURE               Location/Qualifiers
source                1..77
                      mol_type = protein
                      organism = Amaranthus cruentus
SEQUENCE: 243
MATATTSFPG AYLRVPPKNG VRNALFSQSI VSIARNSRKP KSLKSLKLST NSFNFGLHKS   60
CRKGSKSGSF VVRCDAA                                                   77

SEQ ID NO: 244        moltype = AA  length = 80
FEATURE               Location/Qualifiers
source                1..80
                      mol_type = protein
                      organism = Amaranthus cruentus
SEQUENCE: 244
MAIATTSFPG TYLRVPPKNG VRNALFSRSV VSNGVNSRKP NSLESLKSSR NSSNVCLSTS   60
FGHYRKSSKS GSFFVRCNAA                                                80

SEQ ID NO: 245        moltype = AA  length = 80
FEATURE               Location/Qualifiers
source                1..80
                      mol_type = protein
                      organism = Amaranthus hypochondriacus
SEQUENCE: 245
MAIATTSFPG TYLRVPPKNG VRNALFSRSV VSNGVNSRKP NSLESLKSSR NSSNVCLSTS   60
FGHYRKSSKS GSFFVRCNAA                                                80

SEQ ID NO: 246        moltype = AA  length = 77
FEATURE               Location/Qualifiers
source                1..77
                      mol_type = protein
                      organism = Amaranthus palmeri
SEQUENCE: 246
MATATTSFPG AYLRVPPKNG VRNALFSQSI VSIALNSRKP KSFKSLKSSA NSCNFGLHKS   60
YRKGSKSGSF VVRCDAA                                                   77

SEQ ID NO: 247        moltype = AA  length = 80
FEATURE               Location/Qualifiers
source                1..80
                      mol_type = protein
                      organism = Amaranthus palmeri
SEQUENCE: 247
MATATTSFPG TYLRVPPKNG VRNALFSRSV VSNGVNSRKP NSLKSLKLSR NSSNVCLYTS   60
FGHYRKSSKS GSFIIRCNAA                                                80

SEQ ID NO: 248        moltype = AA  length = 77
FEATURE               Location/Qualifiers
source                1..77
                      mol_type = protein
                      organism = Amaranthus palmeri
SEQUENCE: 248
MATATTSFPG AYLRVPPKNG VRNALFSQSI VSIALNSRKP KSFKSLKSSA NSCNFGLHKS   60
YRKGSKSGSF VVRCDAA                                                   77

SEQ ID NO: 249        moltype = AA  length = 77
FEATURE               Location/Qualifiers
source                1..77
                      mol_type = protein
                      organism = Amaranthus palmeri
SEQUENCE: 249
MATATTSFPG AYLRVPPKNG VRNALFSQSI VSIALNSRKP KSFKSLKSSA NSCNFGLHKS   60
YRKGSKSGSF VVRCDAA                                                   77
```

-continued

```
SEQ ID NO: 250           moltype = AA  length = 80
FEATURE                  Location/Qualifiers
source                   1..80
                         mol_type = protein
                         organism = Amaranthus palmeri
SEQUENCE: 250
MATATTSFPG TYLRVPPKNG VRNALFSRSV VSNGVNSRKP KSLKSLKSSR NSSNVCLYTS   60
FGHYRKSSKS GSFIIRCNAA                                               80

SEQ ID NO: 251           moltype = AA  length = 80
FEATURE                  Location/Qualifiers
source                   1..80
                         mol_type = protein
                         organism = Amaranthus tuberculatus
SEQUENCE: 251
MATATTSFPG TYLRVPPKNG VRNALFSRSV VSNGVDSRKP NSLKSMKLSR NSSNVCLYTS   60
FGHYRKSSKS GSFIVRCNAA                                               80

SEQ ID NO: 252           moltype = AA  length = 80
FEATURE                  Location/Qualifiers
source                   1..80
                         mol_type = protein
                         organism = Amaranthus tuberculatus
SEQUENCE: 252
MATATTSFPG TYLRVPPKNG VRNALFSRSV VSNGVDSRKP NSLKSMKLSR NSSNVCLYTS   60
FGHYRKSSKS GSFIVRCNAA                                               80

SEQ ID NO: 253           moltype = AA  length = 80
FEATURE                  Location/Qualifiers
source                   1..80
                         mol_type = protein
                         organism = Amaranthus tuberculatus
SEQUENCE: 253
MATATTSFPG TYLRVPPKNG VRNALFSRSV VSNGVDSRKP NSLKSMKLSR NSSNVCLYTS   60
FGHYRKSSKS GSFIVRCNAA                                               80

SEQ ID NO: 254           moltype = AA  length = 80
FEATURE                  Location/Qualifiers
source                   1..80
                         mol_type = protein
                         organism = Amaranthus viridis
SEQUENCE: 254
MAIATTSFPG TYLRVPPKNG VRNALFSRSV VSNGVNSRKP NSLESLKSSR NSSNVCLSTS   60
FGHYRKGSKS GSFVVRCDAA                                               80

SEQ ID NO: 255           moltype = AA  length = 77
FEATURE                  Location/Qualifiers
source                   1..77
                         mol_type = protein
                         organism = Amaranthus viridis
SEQUENCE: 255
MATATTSFPG AYLRVPPKNG VRNALFSQSI VSIARNSRKP KSLKSLKLST NSFNFGLHKS   60
CRKGSKSGSF VVRCDAA                                                  77

SEQ ID NO: 256           moltype = AA  length = 71
FEATURE                  Location/Qualifiers
source                   1..71
                         mol_type = protein
                         organism = Ambrosia trifida
SEQUENCE: 256
MSTMSTLFHL PSSLCTDRTI TSSFAQPSVS VNSFSKPRRV ALRSLKLKTR SNDVLLRKSS   60
RSLVVRCDAS S                                                        71

SEQ ID NO: 257           moltype = AA  length = 87
FEATURE                  Location/Qualifiers
source                   1..87
                         mol_type = protein
                         organism = Conyza canadensis
SEQUENCE: 257
MATAAFSGVP CIDRTSLLSA QPSSSSSSSV VVCYSSFSKP GTTLLPSLKL KSSRNNNNSN   60
VFLFGNTRKT SRLSFLVRCD SSSSSSS                                       87

SEQ ID NO: 258           moltype = AA  length = 71
FEATURE                  Location/Qualifiers
source                   1..71
                         mol_type = protein
                         organism = Cucumis melo
SEQUENCE: 258
```

-continued

```
MAFSTAPFYA IGIRFPSHSS SISSTTNALI LKSPLALALT AKPKSPLLLK RNVGCQRFGR   60
NSRFVVRCDA S                                                        71

SEQ ID NO: 259           moltype = AA  length = 78
FEATURE                  Location/Qualifiers
source                   1..78
                         mol_type = protein
                         organism = Kochia scoparia
SEQUENCE: 259
MATATTSFPG AYLHLPPKNG VRNALFSQPI CSSNLNLKKP NSLKSVKLSR SSGNALFYKN   60
AKKNSKFGSL VVRCDAAG                                                 78

SEQ ID NO: 260           moltype = AA  length = 78
FEATURE                  Location/Qualifiers
source                   1..78
                         mol_type = protein
                         organism = Kochia scoparia
SEQUENCE: 260
MATATTSFPG AYLHLPPKNG VRNALFSQPI CSSNLNLKKP NSLKSVKLSR SSGNALFYKN   60
AKKNSKFGSL VVRCDAAG                                                 78

SEQ ID NO: 261           moltype = AA  length = 78
FEATURE                  Location/Qualifiers
source                   1..78
                         mol_type = protein
                         organism = Kochia scoparia
SEQUENCE: 261
MATATTSFPG AYLHLPPKNG VRNALFSQPI CSSNLNLKKP NSLKSVKLSR SSGNALFYKN   60
AKKNSKFGSL VVRCDAAG                                                 78

SEQ ID NO: 262           moltype = AA  length = 84
FEATURE                  Location/Qualifiers
source                   1..84
                         mol_type = protein
                         note = Rosa hybrid cultivar
                         organism = Rosa hybrida
SEQUENCE: 262
MASSTTSFAA SGVGLRLPQS VSTKCCSKAS LFPHPTLSLT FHARPQFFRG LASRQFNPNG   60
AFGTGSGRLG RTPNPFVVRS EASS                                          84

SEQ ID NO: 263           moltype = AA  length = 80
FEATURE                  Location/Qualifiers
source                   1..80
                         mol_type = protein
                         organism = Sedum album
SEQUENCE: 263
MAASAATITS SISAITPKPS SFSSSPSVTV PRFSVSCSAI PRPHKNPCSL KFRVKDSRFN   60
GIVKKRSNSN SFVVRCDTSS                                               80

SEQ ID NO: 264           moltype = AA  length = 79
FEATURE                  Location/Qualifiers
source                   1..79
                         mol_type = protein
                         organism = Sedum album
SEQUENCE: 264
MAADAATITA GITLTTARRS SSSIAPQFSV CCSAITNTQK NLSFLKLRVK DATLTTRIEG   60
IQKKRYNSAS FVVRCDASS                                                79

SEQ ID NO: 265           moltype = AA  length = 81
FEATURE                  Location/Qualifiers
source                   1..81
                         mol_type = protein
                         organism = Spinacia oleracea
SEQUENCE: 265
MATATTSFLG AYLRVPPNNG VRNALFSQPF LSLRIKSKRT KSLNSLKFTG DSSKILLFKC   60
SRPFEKGLKS GSFVVRCDAA G                                             81

SEQ ID NO: 266           moltype = AA  length = 79
FEATURE                  Location/Qualifiers
source                   1..79
                         mol_type = protein
                         organism = Allium cepa
SEQUENCE: 266
MAATSSATTH LPFFSPHTKH AKTNSFFASL PVSAYSTKNS ISFKALKAVR WSETFGQSKK   60
ANGFAKRKQF AVVRCDASS                                                79

SEQ ID NO: 267           moltype = DNA  length = 204
FEATURE                  Location/Qualifiers
source                   1..204
```

```
                        mol_type = genomic DNA
                        organism = Glycine max
SEQUENCE: 267
atggctactg ctactaccac agctaccgct gcattctctg gtgttgtgag tgttggaacc        60
gagacacgta gaatttactc tttctcacac ttgcaaccta gcgcagcctt ccctgccaag       120
ccatcatcct ttaagtcctt gaagctgaaa cagtcggcga ggcttacgag gcgcctcgat       180
catagaccct ttgtggtccg atgc                                               204

SEQ ID NO: 268        moltype = DNA  length = 168
FEATURE               Location/Qualifiers
source                1..168
                      mol_type = other DNA
                      note = Recombinant
                      organism = synthetic construct
SEQUENCE: 268
atggccacta ccacagcagc cgcggcggtc accatcagca ttcctaaaaa gcctgttttt        60
atccgccgcc cacgacttcg tgggcccgtc gactgcagag gcctgcatgc atccgacgca       120
atcatctcca acgaggcccc tacagggacg acaatctcgg ctgactgt                    168

SEQ ID NO: 269        moltype = DNA  length = 228
FEATURE               Location/Qualifiers
source                1..228
                      mol_type = genomic DNA
                      organism = Eragrostis tef
SEQUENCE: 269
atggcagccg cacctcccct agcagccgac atggtgttac catccccatg ccctgccgcg        60
gttgcaccta ccccagtggt tgcagctgct tggggtgcag cccgagctgg atctgttaga       120
tgtaaagcga cccaacttcg aatgatgaga actgggggcc ctgttgctcc agttgccggt       180
agacgacgac gagctccatt gagtgtacgt tgtgatgctt cctccaga                    228

SEQ ID NO: 270        moltype = DNA  length = 240
FEATURE               Location/Qualifiers
source                1..240
                      mol_type = genomic DNA
                      organism = Setaria italica
SEQUENCE: 270
atggctgccg ctcctcccct ctctgcagat gcactatcat tcctaccatc cgccgccgct        60
ccggcagccg ctgcaccaac acctgttgta gctgcggcat ggggagccgc acgagctgca       120
gggtcagtta gaggtaaagc tgctttgcgt atggctcgaa ggggtagtgg actggctcca       180
gtggttggaa gaagacctcg acgacctcct ctttcagtta gatgtgacgc aacatctcgt       240

SEQ ID NO: 271        moltype = DNA  length = 252
FEATURE               Location/Qualifiers
source                1..252
                      mol_type = genomic DNA
                      organism = Acalypha ostryifolia
SEQUENCE: 271
atggctacaa ccaccgcgac gacgtctttc tcgggcgtct cgatctgccc acctcaccag        60
acgaatcgca cctctttgtt tccgccccag tccttgtctt tccctccag taagcatggc        120
agtcttgtga actctgtgca attcaaccgt tcgcgacgcg ctagacgtaa tcacttcagc        180
ctcacttcca ttaccaatgc accgaggcgc aaaaggttac tatctgtccg gtgcgacgcg       240
agtgccacat ct                                                           252

SEQ ID NO: 272        moltype = DNA  length = 234
FEATURE               Location/Qualifiers
source                1..234
                      mol_type = genomic DNA
                      organism = Adansonia digitata
SEQUENCE: 272
atggcggcgt catcttcgtc cgtcgtgagc ttctcgggca tctcgttgtg cagtactcac        60
tcgatctcca acaagaccta tctattctcc gcccacccgc gcatttcggt gtcgttcccc       120
agtaagccca atagtttgaa gtccttcaag cagctccagc tgaagaagaa cggactcttt       180
gagaagttct ctcgtacctc cagtcggagc ttcgtggtga ggtgcgacgc gtcg            234

SEQ ID NO: 273        moltype = DNA  length = 246
FEATURE               Location/Qualifiers
source                1..246
                      mol_type = genomic DNA
                      organism = Taraxacum officinale
SEQUENCE: 273
atggctacaa ccgcgagctt ctcgggtgtt cgtattcacg cgccttcctc cacatgtatc        60
gaccggacca ctttattcgc ccagccttcg gtgagctttt cttcctttc caagccgagg        120
cgaacgacct tgaggtcgct gaagctaagg tcgaggtcca acgatgtgtt gcttcgcacc       180
cgcacaggta acagattcgg cggaaagagc tcacgttcat ttgttgtgcg ctgcgacgca       240
tcttct                                                                  246

SEQ ID NO: 274        moltype = DNA  length = 231
FEATURE               Location/Qualifiers
source                1..231
```

```
                                  mol_type = genomic DNA
                                  organism = Amaranthus cruentus
SEQUENCE: 274
atggcgaccg cgacgacctc gtttcccggc gcgtacctgc gcgtgccgcc caagaacggg    60
gttcgtaacg ccctctttag ccagtctatc gtgtcaatg cgcgcaactc tcggaaaccc   120
aaatcgctca aatcccttaa actatctacc aactccttta acttcggtct gcacaagtct   180
tgtcgaaagg gaagcaaatc cgggtcgttc gtagtgcgtt gtgacgcggc c           231

SEQ ID NO: 275          moltype = DNA   length = 240
FEATURE                 Location/Qualifiers
source                  1..240
                        mol_type = genomic DNA
                        organism = Amaranthus cruentus
SEQUENCE: 275
atggccatcg ccaccacgag ctttccggga acgtacctcc gggtgccgcc caagaacggc    60
gtccgaaacg ccctattcag tcgctccgtc gtgtctaatg gggtgaactc aaggaagccg   120
aactcgctgg agtcgcttaa atcgtcgagg aatagctcga acgtctgctt gagtacgtcg   180
ttcgggcatt accggaaatc gagtaagtcg ggctcgttct tcgttcggtg taacgccgcc   240

SEQ ID NO: 276          moltype = DNA   length = 240
FEATURE                 Location/Qualifiers
source                  1..240
                        mol_type = genomic DNA
                        organism = Amaranthus hypochondriacus
SEQUENCE: 276
atggccatcg ccacgacctc gttccccggc acgtacctgc gagtgccgcc caagaacggg    60
gtccggaacg cgctgttctc tcggtccgtg gtcagcaatg gtgttaattc acgaaagccg   120
aacagtctgg aatctctcaa gagcagtcga aactcctcca acgtctgcct ttcgaccagc   180
ttcggtcact accggaagtc tagtaagagc gggtcgttct ttgtccggtg taatgctgcc   240

SEQ ID NO: 277          moltype = DNA   length = 231
FEATURE                 Location/Qualifiers
source                  1..231
                        mol_type = genomic DNA
                        organism = Amaranthus palmeri
SEQUENCE: 277
atggcgacgg ccaccacctc gttccccggc gcatacctcc gcgtgccgcc caagaacggc    60
gtccgcaacg cactctttag ccagagcatc gtcagtatcg cccttaacag tcgcaagcct   120
aaatcgttca agtcactaaa gtcaagcgct aattcgtgca actttggact tcacaagtcc   180
taccgaaag gcagcaagtc tggcagcttc gtcgttcgtt gtgatgccgc c            231

SEQ ID NO: 278          moltype = DNA   length = 240
FEATURE                 Location/Qualifiers
source                  1..240
                        mol_type = genomic DNA
                        organism = Amaranthus palmeri
SEQUENCE: 278
atggccaccg ccaccacctc gttccccggc acgtacctgc gcgtgccgcc caagaacggc    60
gtcaggaacg cgctgtttag tcgctcagtc gtgtccaacg gggtgaactc acgaaagccc   120
aacagtttaa agagcttaaa actgtcgagg aactctagta atgtctgcct ctacacctcc   180
ttcggacact atcgaaagtc cagtaagtcg ggctcattca tcatccggtg caatgcggcc   240

SEQ ID NO: 279          moltype = DNA   length = 231
FEATURE                 Location/Qualifiers
source                  1..231
                        mol_type = genomic DNA
                        organism = Amaranthus palmeri
SEQUENCE: 279
atggccaccg caacaaccag cttccctggc gcgtaccttc gtgtgccgcc caagaacggc    60
gtccgcaatg cgctgtttag tcagtccatc gtgagtatcg ctctcaattc ccggaaacct   120
aagagctta agagcctaaa gtcgagcgct aattcttgca acttcgggct tcacaagagc   180
tatcggaaag ggtctaagag cgggtcattc gtcgtgcggt gcgacgcggc c            231

SEQ ID NO: 280          moltype = DNA   length = 231
FEATURE                 Location/Qualifiers
source                  1..231
                        mol_type = genomic DNA
                        organism = Amaranthus palmeri
SEQUENCE: 280
atggccacgg ccacgacctc gtttccgggt gcgtacctgc gagttccgcc caagaacggt    60
gtacggaacg ccttgttctc ccaatccatc gtgagcatcg ccctcaacag tcgcaaaccg   120
aagtcattca aatccctgaa aagttcggcc aatagctgta acttcgggct gcataagagt   180
taccgcaagg ggtcgaaatc cgggtcgttc gtcgtccggt gcgacgctgc g            231

SEQ ID NO: 281          moltype = DNA   length = 240
FEATURE                 Location/Qualifiers
source                  1..240
                        mol_type = genomic DNA
                        organism = Amaranthus palmeri
```

```
SEQUENCE: 281
atggcaactg ccacgacgtc ctttccggga acgtatctcc gcgtgccgcc caagaacggc   60
gtccgcaacg ccctgttctc acgatccgtc gttagcaatg gcgtcaatag ccgcaagcct  120
aagtccctga aatcgctcaa gtcgtcgcgc aactctagta atgtctgtct ctacacatcg  180
ttcggacatt accgcaaatc atccaaatcc ggctcgttca taatccggtg caatgcggct  240

SEQ ID NO: 282           moltype = DNA   length = 240
FEATURE                  Location/Qualifiers
source                   1..240
                         mol_type = genomic DNA
                         organism = Amaranthus tuberculatus
SEQUENCE: 282
atggcgacag cgaccacatc cttccctggc acttacctga gagtgccgcc caagaatggg   60
gtgagaaacg ccttgttcag ccgcagcgta gtctctaatg gggtggatag tcgcaaaccg  120
aatagcctca agagtatgaa gctcagccgc aacagctcaa atgtctgcct ctacacgagc  180
tttggccact accgaaagtc ctccaagtct gggtcgttca tcgtgcgctg taacgccgcg  240

SEQ ID NO: 283           moltype = DNA   length = 240
FEATURE                  Location/Qualifiers
source                   1..240
                         mol_type = genomic DNA
                         organism = Amaranthus tuberculatus
SEQUENCE: 283
atggccacgg ccaccacctc ctttcctggc acatacctcc gcgtccctcc caagaatggg   60
gtgcgaaacg cactctttag tagatcggtc gtttccaatg gtgtcgattc ccgcaagccg  120
aactccctca agtcgatgaa gctgtcccgc aactcatcga acgtttgcct ctatacctcg  180
tttgggcact accgcaagtc gagcaaatcg ggctcgttca ttgtccggtg taatgcagcc  240

SEQ ID NO: 284           moltype = DNA   length = 240
FEATURE                  Location/Qualifiers
source                   1..240
                         mol_type = genomic DNA
                         organism = Amaranthus tuberculatus
SEQUENCE: 284
atggcgacgg cgacaacctc gtttccggga acgtacctgc gcgtgccgcc caagaacggg   60
gtgcggaacg ccctgttcag ccgctccgtc gtgtccaatg gcgtcgattc gaggaagcct  120
aactcattga aatctatgaa gttgtctcgt aattccagca acgtttgcct ctacacctcg  180
ttcgggcatt accgcaagtc aagcaagtcc ggatcgttta tcgtgcggtg caacgctgcg  240

SEQ ID NO: 285           moltype = DNA   length = 240
FEATURE                  Location/Qualifiers
source                   1..240
                         mol_type = genomic DNA
                         organism = Amaranthus viridis
SEQUENCE: 285
atggccattg ccaccacgtc gtttcccggc acgtacctga gggttccgcc caagaacgga   60
gtccgcaacg cactgtttag tcgctccgtg gtgagtaacg gggtcaactc cagaaaacct  120
aattcgctgg agtcccttaa atcgagccgg aacagctcga acgtctgctt gtcaacctcc  180
tttggccact accggaaggg ctccaagtcg ggctcattcg tcgtgcggtg cgatgcggcg  240

SEQ ID NO: 286           moltype = DNA   length = 231
FEATURE                  Location/Qualifiers
source                   1..231
                         mol_type = genomic DNA
                         organism = Amaranthus viridis
SEQUENCE: 286
atggccaccg ccacgacgtc ctttcccggt gcgtatctgc gagtgcctcc caagaacggc   60
gtccggaacg cgctgttcag ccagtccatc gtgagcatcg cgcggaatag tcggaaacct  120
aagtcgctca aatccttgaa actgtcaacg aactctttca atttcgggtt gcataagtcc  180
tgccgaaagg gtagcaaatc cgggtctttc gttgtgcggt gcgacgcggc c            231

SEQ ID NO: 287           moltype = DNA   length = 213
FEATURE                  Location/Qualifiers
source                   1..213
                         mol_type = genomic DNA
                         organism = Ambrosia trifida
SEQUENCE: 287
atgagtacga tgtcaaccct atttcacctc ccgtctagcc tgtgtaccga caggacgatc   60
accagcagct tcgcacaacc gagcgtttcg gtcaactcgt tctcgaagcc gcgccgcgtc  120
gcgctccggt ccttaaagct caaaacgcga agtaatgacg tcctgctgcg gaaatcttca  180
cgttcgctag tcgtgcgttg cgacgccagc agc                               213

SEQ ID NO: 288           moltype = DNA   length = 261
FEATURE                  Location/Qualifiers
source                   1..261
                         mol_type = genomic DNA
                         organism = Conyza canadensis
SEQUENCE: 288
atggcgacgg ccgccttctc gggcgttccg tgcattgacc ggacatcact cctctccgcc   60
```

-continued

```
cagccatcgt cctcctcttc cagtagcgtc gtggtctgct actcctcctt tagcaagccg   120
ggcacgaccc tattgccgtc gttgaagctc aaaagcagcc gcaacaacaa caattcaaac   180
gtattcctct tcgggaacac caggaaaaca tcccgtctgt cattcctagt gcgctgcgat   240
tcctcatctt caagctctag c                                             261

SEQ ID NO: 289          moltype = DNA   length = 213
FEATURE                 Location/Qualifiers
source                  1..213
                        mol_type = genomic DNA
                        organism = Cucumis melo
SEQUENCE: 289
atggcgttta gcaccgcacc cttctacgca attggtatca gatttcccag ccatagctca   60
tcaatctcaa gcaccactaa cgccctcatc cttaaaagtc cactggcgtt agccctaacc   120
gctaagccga agtctcccct actcctcaag cgcaacgttg gctgccagcg attcgggcga   180
aactcccgct tcgtcgtgcg ctgcgatgcg tcc                                213

SEQ ID NO: 290          moltype = DNA   length = 234
FEATURE                 Location/Qualifiers
source                  1..234
                        mol_type = genomic DNA
                        organism = Kochia scoparia
SEQUENCE: 290
atggcgaccg ccacgacctc cttccccggc gcgtacctcc atctcccgcc caagaacggg   60
gtccgcaacg ccttgttctc tcaacccatc tgttcatcca acctcaacct caagaaacct   120
aactctctca aatcggtgaa gctgtcccgc agttccggca atgccctatt ctacaagaac   180
gccaagaaga atagtaagtt cggcagtctg tcgtgcgcgg gcgacgcggc ggga          234

SEQ ID NO: 291          moltype = DNA   length = 234
FEATURE                 Location/Qualifiers
source                  1..234
                        mol_type = genomic DNA
                        organism = Kochia scoparia
SEQUENCE: 291
atggccaccg cgacgaccag cttttcccggc gcgtatctgc acctcccgcc caagaacggc   60
gtgagaaacg cgctgttcag tcaaccgata tgctcgtcca atctcaacct caagaaaccc   120
aattctctga aaagcgtcaa actgtcgcgt agtagcggca atgcgctgtt ctacaagaac   180
gccaagaaga atagcaagtt cgggtcgctc gtggtgcgct cgacgcggc gggc          234

SEQ ID NO: 292          moltype = DNA   length = 234
FEATURE                 Location/Qualifiers
source                  1..234
                        mol_type = genomic DNA
                        organism = Kochia scoparia
SEQUENCE: 292
atggccacag ccaccacgtc cttccctggg gcctacctac atctcccgcc caagaatggc   60
gtgcgaaacg cgctgttcag tcagcctata tgcagcagta atcttaacct caagaagcct   120
aattccctca agtcagtgaa actgagccgg tctagcggga acgcgctgtt ctacaagaac   180
gccaaaaaga atagcaagtt cggctcgctc gtggtccggt gcgacgcggc gggc          234

SEQ ID NO: 293          moltype = DNA   length = 252
FEATURE                 Location/Qualifiers
source                  1..252
                        mol_type = genomic DNA
                        note = Rosa hybrid cultivar
                        organism = Rosa hybrida
SEQUENCE: 293
atggcgtcat cgaccacttc gttcgccgcc agtggagttg gattgcggct ccctcagtcc   60
gtgagcacga agtgctgctc taaagcgtca ttgttcccac accccacact atcgttgacc   120
ttccacgcta ggccacagtt cttttagagg cttggcgtctc gccagttcaa tccaaacgga   180
gcgtttggga cgggctccgg acggctgggc cggacaccaa atccgtttgt cgtcagaagc   240
gaagcgagtt ct                                                       252

SEQ ID NO: 294          moltype = DNA   length = 240
FEATURE                 Location/Qualifiers
source                  1..240
                        mol_type = genomic DNA
                        organism = Sedum album
SEQUENCE: 294
atggcggcga gcgcggctac gatcacctcc agcatatcgg cgattacccc gaagccgtcg   60
tccttctcaa gcagcccttc ggtcaccgtg ccccgattct ctgtgtcgtg cagcgcgata   120
ccgcgtccac acaagaatcc ctgctcgttg aagttccggg tgaaggactc acggtttaac   180
ggaattgtca agaagcgcag taacagcaac tcattcgtag tacgttgtga cacttcctcg   240

SEQ ID NO: 295          moltype = DNA   length = 237
FEATURE                 Location/Qualifiers
source                  1..237
                        mol_type = genomic DNA
                        organism = Sedum album
SEQUENCE: 295
```

-continued

```
atggccgccg acgcagctac cattacggcg ggtatcactc tcacgacggc ccgccgctcc     60
tcctccagta ttgcgccgca gttctcggtg tgttgctcag cgattaccaa cacgcaaaaa    120
aatctgagct tcctcaagtt gcgcgtgaaa gacgccacct tgactacacg gattgagggt    180
attcagaaga agcggtacaa ctccgcgtcc ttcgtcgtca gatgcgacgc gagcagc       237

SEQ ID NO: 296          moltype = DNA  length = 243
FEATURE                 Location/Qualifiers
source                  1..243
                        mol_type = genomic DNA
                        organism = Spinacia oleracea
SEQUENCE: 296
atggccactg ccacgacgtc ctttctcggc gcttacttgc gggtgccgcc caacaatggc     60
gtgaggaatg cgctgttcag tcaaccgttc ctgtcgcttc gcattaagtc caaacgcact    120
aagagcctca actcgttgaa attcacagga gactcaagta agattctgct gtttaagtgc    180
tcccggccgt ttgagaaggg gcttaaatcc ggctcgttcg tggtgcgctg cgacgcggcc    240
ggt                                                                  243

SEQ ID NO: 297          moltype = DNA  length = 237
FEATURE                 Location/Qualifiers
source                  1..237
                        mol_type = genomic DNA
                        organism = Allium cepa
SEQUENCE: 297
atggcggcaa cgagctccgc gaccactcac ctcccttttt tcagcccgca caccaaacac     60
gcaaagacaa actctttctt cgcgtccctt ccggtcagcg cctactccac gaaaaactct    120
atcagtttca aggcgctcaa ggccgtgcga tggagcgaga ccttcgggca atcgaagaag    180
gccaatggtt ttgccaaaag gaagcaattt gccgtcgtgc ggtgcgatgc gagttca       237
```

METHODS AND COMPOSITIONS FOR GENE EXPRESSION IN PLANTS

REFERENCE TO RELATED APPLICATION

This application is a divisional of U.S. patent application Ser. No. 16/931,427, filed Jul. 16, 2020, which is a divisional of U.S. patent application Ser. No. 15/660,660, filed Jul. 26, 2017, now U.S. Pat. No. 10,745,712, which claims the benefit of U.S. provisional application No. 62/368,840, filed Jul. 29, 2016, each of which is herein incorporated by reference in their entireties.

INCORPORATION OF SEQUENCE LISTING

A computer readable form of a sequence listing is filed with this application by electronic submission and is incorporated into this application by reference in its entirety. The sequence listing is contained in the file named MONS397US_ST25, which is 330 kilobytes in size (measured in operating system MS Windows) and was created on Jul. 14, 2017.

BACKGROUND OF THE INVENTION

Field of the Invention

The invention relates generally to the fields of agriculture, plant biotechnology, and molecular biology. More specifically, the invention relates to compositions for recombinant protein expression in transgenic plants and methods of use thereof.

Description of Related Art

Agricultural crop production often utilizes crops with modified genomes, including transgenic traits created using the methods of molecular biology. For example, a heterologous gene, also known as a transgene, can be introduced into a plant genome. Expression of the transgene in the plant confers a trait, such as herbicide-tolerance or insect control, on the plant. Successful expression of a transgene in a plant may be achieved by utilizing heterologous gene expression elements. One example of this is the use of a transit peptide operably linked to a recombinant protein to achieve subcellular localization of the recombinant protein and thus enhanced protein expression or function. A need therefore exists for novel transit peptides capable of effectively localizing recombinant proteins within plant cells.

SUMMARY OF INVENTION

In one aspect, the present invention provides a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266. In one embodiment, the heterologous herbicide-tolerance protein has herbicide-insensitive protoporphyrinogen oxidase activity. In another embodiment, the heterologous herbicide-tolerance protein comprises an amino acid sequence comprising at least 97 percent identity to a sequence selected from the group consisting of SEQ ID NOs:100-119, SEQ ID NOs:163-182, and SEQ ID NOs: 224-228. In a further embodiment, the DNA sequence encoding a transit peptide comprises a nucleic acid sequence comprising at least 97 percent identity to a sequence selected from the group consisting of SEQ ID NOs:54-99 and SEQ ID NOs:267-297. In still a further embodiment, the DNA sequence encoding a heterologous herbicide-tolerance protein comprises a nucleic acid sequence comprising at least 97 percent identity to a sequence selected from the group consisting of SEQ ID NOs:121-162 and SEQ ID NOs:183-223, SEQ ID NOs:229-235. In yet a further embodiment, the recombinant DNA molecule further comprises a heterologous promoter operably linked to the DNA sequence encoding a transit peptide.

In another aspect, the present invention provides a DNA construct comprising a DNA molecule provided herein, such as a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266, operably linked to a heterologous promoter. In one embodiment, the heterologous herbicide-tolerance protein has herbicide-insensitive protoporphyrinogen oxidase activity. In another embodiment, the heterologous herbicide-tolerance protein comprises an amino acid sequence selected from the group consisting of SEQ ID NOs:100-119, SEQ ID NOs:163-182, and SEQ ID NOs:224-228. In still another embodiment, the DNA construct is present in the genome of a transgenic plant, seed, or cell.

In a further aspect, the present invention provides a transgenic plant, seed, or cell comprising a recombinant DNA molecule provided herein, such as a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs: 236-266. In one embodiment, the plant, seed, or cell is tolerant to at least one PPO herbicide. In another embodiment, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100. In a further embodiment, the transgenic plant, seed, or cell is tolerant to at least a second herbicide.

In another aspect, the present invention provides a recombinant protein comprising in operable linkage: a) a transit peptide comprising an amino acid sequence comprising at least 95 percent identity to a sequence selected from the group consisting of SEQ ID NOs:4-49 and SEQ ID NOs: 236-266; and b) a heterologous herbicide-tolerance protein. In one embodiment, the heterologous herbicide-tolerance protein has herbicide-insensitive protoporphyrinogen oxidase activity. In a further aspect, the present invention provides a transgenic plant, seed, or cell comprising the recombinant protein provided herein.

In yet another aspect, the present invention provides, a method for producing an herbicide-tolerant plant comprising the steps of: a) transforming a plant cell with a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs: 236-266; and b) regenerating therefrom an herbicide-tolerant plant that comprises the DNA molecule. In one embodiment, the heterologous herbicide-tolerance protein comprises an amino acid sequence selected from the group consisting of SEQ ID NOs:100-119, SEQ ID NOs:163-182, and SEQ ID NOs:224-228. In another embodiment, the method further comprises the step of crossing the regenerated plant with itself or with a second plant to produce one or more progeny plants. In yet another embodiment, the method may further comprise the step of selecting a progeny plant that is tolerant to at least one PPO herbicide. In certain embodiments, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

In a further aspect, the present invention provides a method for producing an herbicide-tolerant transgenic plant or seed comprising crossing a plant comprising a recombinant DNA molecule provided herein with itself or a second plant to produce an herbicide-tolerant transgenic plant or seed. In certain embodiments, the recombinant DNA molecule comprises a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266.

In yet a further aspect, the present invention provides a method for expressing a heterologous herbicide-tolerance protein in a plant or cell, the method comprising growing a plant or cell that comprises a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266, wherein the growing results in expression of the heterologous herbicide-tolerance protein. In one embodiment, the heterologous herbicide-tolerance protein has herbicide-insensitive protoporphyrinogen oxidase activity.

In another aspect, the present invention provides a method for controlling or preventing weed growth in a plant growth area comprising applying an effective amount of at least one PPO herbicide to a plant growth area that comprises a transgenic plant or seed as provided herein, such as a transgenic plant or seed comprising a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs: 236-266, wherein the transgenic plant or seed is tolerant to the PPO herbicide. In certain embodiments, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

In a further aspect, the present invention provides method for controlling the growth of herbicide tolerant weeds comprising: a) cultivating in a plant growth area a plant or seed provided herein, for instance a plant or seed comprising a recombinant DNA molecule comprising a DNA sequence encoding a transit peptide operably linked to a DNA sequence encoding a heterologous herbicide-tolerance protein, wherein the transit peptide comprises an amino acid sequence comprising at least 97 percent identity to a sequence selected from the group consisting of SEQ ID NOs:4-49 and SEQ ID NOs:236-266; and b) applying a PPO herbicide and at least one other herbicide to the plant growth area, wherein the plant or seed is tolerant to the PPO herbicide and the at least one other herbicide. In certain embodiments, the PPO herbicide is selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100. In another embodiment, the other herbicide to which to plant or seed is tolerant is selected from the group consisting of: an ACCase inhibitor, an ALS inhibitor, an EPSPS inhibitor, a synthetic auxin, a photosynthesis inhibitor, a glutamine synthetase inhibitor, a HPPD inhibitor, a PPO inhibitor, and a long-chain fatty acid inhibitor. In further embodiments, the ACCase inhibitor is an aryloxyphenoxy propionate or a cyclohexanedione; the ALS inhibitor is a sulfonylurea, imidazolinone, triazolopyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthetase inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the very long-chain fatty acid inhibitor is a chloroacetamide, an oxyacetamide, or a pyrazole.

In yet a further aspect, the present invention provides a recombinant DNA molecule comprising a DNA sequence encoding a transit peptide operably linked to a DNA sequence encoding a heterologous herbicide-tolerance protein, wherein the transit peptide comprises an amino acid sequence comprising at least 95 percent identity to a sequence selected from the group consisting of SEQ ID NOs:236-266. In one embodiment, the heterologous herbicide-tolerance protein has herbicide-insensitive protoporphyrinogen oxidase activity. In another embodiment, the heterologous herbicide-tolerance protein comprises an amino acid sequence comprising at least 95 percent identity to a sequence selected from the group consisting of SEQ ID NOs:100-119, SEQ ID NOs:163-182, and SEQ ID NOs: 224-228. If a further embodiment, the DNA sequence encoding a transit peptide comprises a nucleic acid sequence comprising at least 95 percent identity to a sequence selected from the group consisting of SEQ ID NOs:267-297. In yet another embodiment, the DNA sequence encoding a heterologous herbicide-tolerance protein comprises a nucleic acid sequence comprising at least 95 percent identity to a sequence selected from the group consisting of SEQ ID NOs:121-162 and SEQ ID NOs:183-223, SEQ ID NOs:229-235. In still a further embodiment, the recombinant DNA molecule further comprises a heterologous promoter operably linked to the DNA sequence encoding a transit peptide.

BRIEF DESCRIPTION OF THE SEQUENCES

SEQ ID NOs:1-2 and SEQ ID NO:236 are amino acid sequences of the *Arabidopsis thaliana* albino and pale green (APG6) transit peptide.

SEQ ID NO:3 is the amino acid sequence of the cotton 12G088600TP transit peptide.

SEQ ID NOs:4-49 and SEQ ID NOs:237-266 are amino acid sequences of transit peptides.

SEQ ID NOs:50-52 and SEQ ID NO:267 are nucleic acid sequences encoding the APG6 transit peptide.

SEQ ID NO:53 is the nucleic acid sequence encoding the cotton 12G088600TP transit peptide.

SEQ ID NOs:54-99 and SEQ ID NOs:268-297 are exemplary nucleic acid sequences encoding SEQ ID NOs:4-49 and SEQ ID NOs:237-266, respectively.

SEQ ID NOs:100-119 are amino acid sequences of HemG protoporphyrinogen oxidases.

SEQ ID NO:120 is the amino acid sequence of the wild-type protoporphyrinogen oxidase from *Amaranthus tuberculatus* (waterhemp) (WH).

SEQ ID NOs:121-162 and SEQ ID NO:229 are exemplary nucleic acid sequences encoding SEQ ID NOs:100-119.

SEQ ID NOs:163-182 and SEQ ID NOs:224-228 are amino acid sequences of HemY protoporphyrinogen oxidases.

SEQ ID NOs:183-223 and SEQ ID NOs:230-235 are exemplary nucleic acid sequences encoding SEQ ID NOs:163-182 and SEQ ID NOs:224-228.

DETAILED DESCRIPTION

The following descriptions and definitions are provided to better define the invention and to guide those of ordinary skill in the art in the practice of the invention. Unless otherwise noted, terms are to be understood according to conventional usage by those of ordinary skill in the relevant art.

Operably linking a transit peptide to a heterologous protein utilizes the transgenic plant cell's protein localization system to achieve sub-cellular localization of the heterologous protein. The transit peptide is removed from the heterologous protein in a processing step during translocation of the heterologous protein into an organelle. The properties of the combination of a specific transit peptide with a specific heterologous protein when expressed in a plant can be unpredictable and surprising. For example, the efficiency of sub-cellular localization and the efficiency of processing (removal of the transit peptide from the heterologous protein) varies and may be affected by the amino acid sequence of the transit peptide, the heterologous protein, or both. These variables affect the function and levels of a heterologous protein and thus affect the phenotype of a transgenic cell, plant, or seed comprising the heterologous protein. Various transit peptides are known in the art for use in transgenic plants, but in view of the variability in the efficiencies of sub-cellular localization and processing and the continuing development of new transgenic traits, novel transit peptides are needed.

The invention provides novel, recombinant DNA molecules for effectively targeting heterologous proteins within plant cells. Effective targeting of a heterologous protein involves efficient sub-cellular localization of the transit peptide and heterologous protein combination and processing of the transit peptide from the heterologous protein. Although transit peptides for localizing heterologous proteins within cells are known, the degree of localization and processing for any transit peptide and heterologous protein combination varies. Localization and processing affect the expression level and function of a heterologous protein and thus affect the phenotype of the cell, plant, or seed comprising the heterologous protein. For example, inefficient localization and processing of a transit peptide and herbicide-tolerance protein combination can result in poor herbicide-tolerance for a transgenic plant.

The invention overcomes these obstacles by providing novel recombinant DNA molecules capable of providing efficient targeting of a protein through improved localization and processing. Recombinant DNA molecules of the invention comprise a DNA sequence encoding a transit peptide operably linked to a DNA sequence encoding a heterologous protein. In one example, recombinant DNA molecules of the invention include, but are not limited to, a recombinant DNA molecule comprising a DNA sequence encoding a transit peptide operably linked to a DNA sequence encoding an herbicide-tolerant protoporphyrinogen oxidase. Compositions and methods for using these recombinant DNA molecules are also provided.

Recombinant Molecules

As used herein, the term "recombinant" refers to a non-natural DNA, protein, cell, seed, or organism that is the result of genetic engineering and was created by human intervention. A "recombinant DNA molecule" is a DNA molecule that does not naturally occur and as such is the result of human intervention, such as a DNA molecule comprised of a combination of at least two DNA sequences heterologous to each other. An example of a recombinant DNA molecule is a DNA molecule provided herein encoding a transit peptide of the present invention, such as a transit peptide comprising a sequence selected from the group consisting of SEQ ID NOs:4-49 and SEQ ID NOs:236-266, operably linked to a DNA molecule encoding an herbicide-tolerance protein of the present invention, such as a protoporphyrinogen oxidase comprising a sequence selected from the group consisting of SEQ ID NOs:100-119, 163-182, and 224-228. A "recombinant protein" is a protein produced as a result of human intervention that does not naturally occur. An example of a recombinant protein is a protein provided herein comprising a transit peptide of the present invention, such as a transit peptide comprising a sequence selected from the group consisting of SEQ ID NOs:4-49 and SEQ ID NOs:236-266, operably linked to a heterologous protein, such as an herbicide-tolerance protein of the present invention, for instance, a protoporphyrinogen oxidase comprising a sequence selected from the group consisting of SEQ ID NOs:100-119, 163-182, and 224-228. A recombinant cell, seed, or organism is a cell, seed, or organism comprising transgenic or heterologous DNA or protein, for example a transgenic plant cell, seed, plant, or plant part comprising a heterologous DNA molecule or heterologous protein of the invention.

As used herein, the term "isolated DNA molecule" means that the DNA molecule is present alone or in combination with other compositions but is not within its natural environment. A DNA molecule of the invention is an isolated DNA molecule so long as the DNA molecule is not within the DNA of the organism at the genomic location in which it naturally occurs. For example, a recombinant DNA molecule comprising a protein-coding DNA sequence and heterologous transit peptide DNA sequence is considered isolated when it is found in a context that is not the genome in which both the protein-coding DNA sequence and the heterologous transit peptide DNA sequence are naturally found (such as the genome of a transgenic plant, seed, plant part, or cell).

As used herein, the term "genetic engineering" refers to the creation, modification, or production of a DNA molecule, protein, cell, or organism using the techniques of biotechnology (such as molecular biology, protein biochemistry, bacterial transformation, and plant transformation).

Genetic engineering is thus a result of human intervention. For example, genetic engineering may be used to create a recombinant DNA molecule encoding a transit peptide comprising a sequence selected from the group consisting of SEQ ID NOs:4-49 and SEQ ID NOs:236-266 operably linked to a DNA molecule encoding an herbicide-tolerance protein, such as a protoporphyrinogen oxidase comprising a sequence selected from the group consisting of SEQ ID NOs:100-119, 163-182, and 224-228 using one or more of the techniques of molecular biology, such as gene cloning, DNA ligation, and DNA synthesis. Such a recombinant DNA molecule optionally may further comprise a heterologous promoter functional in a plant cell.

As used herein, "herbicide-tolerance" or "herbicide-tolerant" with respect to a protein means the ability to maintain at least some of its activity or function in the presence of an herbicide. For example, a protoporphyrinogen oxidase (PPO) is herbicide-tolerant if it maintains at least some of its enzymatic activity in the presence of one or more PPO herbicide(s). Herbicide-tolerance can be measured by any means known in the art. For example, enzymatic activity of a protoporphyrinogen oxidase can be measured by an enzymatic assay in which the production of the product of protoporphyrinogen oxidase or the consumption of the substrate of protoporphyrinogen oxidase in the presence of one or more PPO herbicide(s) is measured via fluorescence, high performance liquid chromatography (HPLC), or mass spectrometry (MS). Another example of an assay for measuring enzymatic activity of a protoporphyrinogen oxidase is a bacterial assay, such as the growth assays described herein, whereby a recombinant protoporphyrinogen oxidase is expressed in a bacterial cell otherwise lacking PPO activity and the ability of the recombinant protoporphyrinogen oxidase to complement this knockout phenotype is measured. Herbicide-tolerance may be complete or partial insensitivity to an herbicide, and may be expressed as a percent (%) tolerance or insensitivity to a PPO herbicide. As used herein, an "herbicide-tolerant protoporphyrinogen oxidase" exhibits herbicide-tolerance in the presence of one or more PPO herbicide(s).

As used herein, "herbicide-tolerance" or "herbicide-tolerant" with respect to an organism, plant, seed, tissue, part, or cell means the organism, plant, seed, tissue, part, or cell's ability to resist the effects of an herbicide when applied. For example, an herbicide-tolerant plant can survive or continue to grow in the presence of the herbicide. The herbicide-tolerance of a plant, seed, plant tissue, plant part, or cell may be measured by comparing the plant, seed, plant tissue, plant part, or cell to a suitable control. For example, the herbicide-tolerance may be measured or assessed by applying an herbicide to a plant comprising a recombinant DNA molecule encoding a protein capable of conferring herbicide-tolerance (the test plant) and a plant not comprising the recombinant DNA molecule encoding the protein capable of conferring herbicide-tolerance (the control plant) and then comparing the plant injury of the two plants, where herbicide-tolerance of the test plant is indicated by a decreased injury rate as compared to the injury rate of the control plant. An herbicide-tolerant plant, seed, plant tissue, plant part, or cells exhibits a decreased response to the toxic effects of an herbicide when compared to a control plant, seed, plant tissue, plant part, or cell. As used herein, an "herbicide-tolerance trait" is a transgenic trait imparting improved herbicide-tolerance to a plant as compared to the wild-type plant. Contemplated plants which might be produced with an herbicide-tolerance trait of the present invention could include, for instance, any plant including crop plants such as soybean (*Glycine max*), maize (*Zea mays*), cotton (*Gossypium* sp.), wheat (*Triticum* spp.), and *Brassica* plants, among others.

As used herein, a "hemG knockout strain" means an organism or cell of an organism, such as *E. coli*, that lacks HemG activity to the extent that it is unable to grow on heme-free growth medium, or such that its growth is detectably impaired in the absence of heme relative to an otherwise isogenic strain comprising a functional HemG. A hemG knockout strain of, for instance, *E. coli* may be prepared in view of knowledge in the art, for instance in view of the *E. coli* hemG sequence (Ecogene Accession No. EG11485; Sasarman et al., "Nucleotide sequence of the hemG gene involved in the protoporphyrinogen oxidase activity of *Escherichia coli* K12" *Can J Microbiol* 39:1155-1161, 1993).

The term "transgene" refers to a DNA molecule artificially incorporated into an organism's genome as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecules provided by the invention.

As used herein, the term "heterologous" refers to the relationship between two or more things not normally associated in nature, for instance that are derived from different sources or not normally found in nature together in any other manner. For example, a DNA molecule or protein may be heterologous with respect to another DNA molecule, protein, cell, plant, seed, or organism if not normally found in nature together or in the same context. In certain embodiments, a first DNA molecule is heterologous to a second DNA molecule if the two DNA molecules are not normally found in nature together in the same context, and a protein is heterologous with respect to a second operably linked protein, such as a transit peptide, if such combination is not normally found in nature. In another embodiment, a recombinant DNA molecule encoding a transit peptide operably linked to a protoporphyrinogen oxidase is heterologous with respect to an operably linked promoter that is functional in a plant cell if such combination is not normally found in nature. A recombinant DNA molecule also may be heterologous with respect to a cell, seed, or organism into which it is inserted when it would not naturally occur in that cell, seed, or organism. A "heterologous protein" is a protein present in a plant, seed, cell, tissue, or organism in which it does not naturally occur or operably linked to a protein with which it is not naturally linked. An example of a heterologous protein is a protein comprising a sequence selected from the group consisting of SEQ ID NOs:4-49, 236-266, 100-119, 163-182, and 224-228 that is expressed in a plant, seed, cell, tissue, or organism in which it does not naturally occur, or that is operably linked to a second protein, such as a transit peptide or herbicide-tolerant protein, with which it is not naturally linked. In another example, a heterologous protein, such as a heterologous herbicide-tolerance protein, for instance a protoporphyrinogen oxidase may be introduced into a plant cell in which it does not naturally occur using the techniques of molecular biology and plant transformation.

As used herein, the term "protein-coding DNA molecule" refers to a DNA molecule comprising a DNA sequence that encodes a protein. As used herein, a "protein-coding DNA sequence" means a DNA sequence that encodes a protein. A protein-coding DNA sequence may be any DNA sequence that encodes a protein, for example a protein comprising a sequence selected from the group consisting of SEQ ID NOs:4-49, 236-266, 100-119, 163-182, and 224-228. As used herein, the term "protein" refers to a chain of amino acids linked by peptide (amide) bonds and includes both polypeptide chains that are folded or arranged in a biologically functional way and polypeptide chains that are not. A "sequence" means a sequential arrangement of nucleotides or amino acids. The boundaries of a protein-coding sequence are usually determined by a translation start codon at the 5'-terminus and a translation stop codon at the 3'-terminus.

As used herein, the term "herbicide-tolerance protein" means a protein capable of conferring herbicide-tolerance to a cell, tissue, plant part, seed, or organism. Examples of herbicide-tolerance proteins are well known in the art and include, but are not limited to, glyphosate-tolerant 5-enolypyruvyl shikimate 3-phosphate synthases (e.g., CP4-EPSPS, 2mEPSPS), glyphosate oxidoreductases (GOX), glyphosate N-acetyltransferases (GAT), herbicide-tolerant acetolactate synthases (ALS)/acetohydroxyacid synthases (AHAS), herbicide-tolerant 4-hydroxyphenylpyruvate dioxygenases (HPPD), dicamba monooxygenases (DMO), phosphinothricin acetyl transferases (PAT), herbicide-tolerant glutamine synthetases (GS), 2,4-dichlorophenoxyproprionate dioxygenases (TfdA), R-2,4-dichlorophenoxypropionate dioxygenases (RdpA), S-2,4-dichlorophenoxypropionate dioxygenases (SdpA), herbicide-tolerant protoporphyrinogen oxidases (PPO), and cytochrome P450 monooxygenases. For example, a protoporphyrinogen oxidase comprising an amino acid sequence selected from the group consisting of SEQ ID NOs:100-119, SEQ ID NOs:163-182, and SEQ ID NOs:224-228 is an herbicide-tolerant protein.

As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which may or may not be ultimately folded into proteins. A protein-coding DNA molecule may be operably linked to a heterologous promoter in a DNA construct for use in expressing the protein in a cell transformed with, and thus comprising, the recombinant DNA molecule or a portion thereof. As used herein, "operably linked" means two DNA or protein molecules linked in manner so that one may affect the function of the other. Operably-linked DNA molecules may be part of a single contiguous molecule and may or may not be adjacent. For example, a promoter is operably linked with a protein-coding DNA molecule in a DNA construct where the two DNA molecules are so arranged that the promoter may affect the expression of the transgene. In another embodiment, two or more protein molecules may be operably linked. For instance, a transit peptide may be operably linked to a heterologous protein, such as an herbicide-tolerant protein.

In one embodiment, the recombinant DNA molecules of the invention include a DNA sequence encoding a protoporphyrinogen oxidase (PPO) operably linked to a transit peptide sequence. As used herein, "protoporphyrinogen oxidase" or "PPO" means an oxidase capable of converting protoporphyrinogen IX to protoporphyrin IX. Such protoporphyrinogen oxidase are known in the art and include, for instance, the protein sequences provided as SEQ ID NOs: 100-119, SEQ ID NOs:163-182, and SEQ ID NOs:224-228.

In another embodiment, the recombinant DNA molecules of the invention include a DNA sequence encoding a transit peptide sequence operably linked to a heterologous nucleic acid sequence encoding a protein that has herbicide-tolerant protoporphyrinogen oxidase activity, whereby the transit peptide sequence facilitates localizing the protein molecule within the cell. Transit peptides are also known in the art as signal sequences, targeting sequences, targeting peptides, and localization sequences. An example of a transit peptide is a chloroplast transit peptide (CTP), a mitochondrial targeting sequence (MTS), or a dual chloroplast and mitochondrial targeting peptide. By facilitating protein localization within the cell, such as to the mitochondria or chloroplast, the transit peptide ensures localization of a protein to an organelle for optimal enzyme activity and may increase the accumulation of the protein and protect the protein from proteolytic degradation, and/or enhance the level of herbicide-tolerance, and thereby reduce levels of injury in the transgenic cell, seed, or organism after herbicide application. Upon translocation into the organelle, the transit peptide is typically cleaved from the protein, also referred to as processing. Transit peptide processing may be complete (meaning that the complete transit peptide is cleaved from the amino-terminal end of the protein), incomplete (meaning that one or more amino acids of the transit peptide remain on amino-terminal end of the protein), or result in removal one or more amino acids from the amino-terminal end of the protein. Complete processing of the transit peptide from a protoporphyrinogen oxidase increases the level of protein accumulation, thereby increasing PPO herbicide-tolerance and reducing levels of injury in the transgenic cell, seed, or organism after herbicide application. For example, transit peptides may comprise an amino acid sequence of the present invention, such as those provided by SEQ ID NOs: 1-49 and SEQ ID NOs:236-266. Such a transit peptide may be encoded by a nucleic acid sequence of the invention, for instance as provided by SEQ ID NOs:50-99 and SEQ ID NOs:267-297.

Recombinant DNA molecules of the present invention may be synthesized and modified by methods known in the art, either completely or in part, especially where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes DNA molecules and proteins having at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, and at least 99% sequence identity to any of the DNA molecule or protein sequences provided herein as SEQ ID NOs:1-297. As used herein, the term "percent sequence identity" or "% sequence identity" refers to the percentage of identical nucleotides or amino acids in a linear polynucleotide or protein sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, CA), MEGAlign (DNAStar Inc., 1228 S. Park St., Madison, WI 53715), and MUSCLE (version 3.6) (Edgar, *Nucleic Acids Research* 32(5):1792-7, 2004) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence, or a portion thereof, or to a longer sequence.

As used herein, a "DNA construct" is a recombinant DNA molecule comprising two or more heterologous DNA sequences. DNA constructs are useful for transgene expression and may be comprised in vectors and plasmids. DNA constructs may be used in vectors for transformation, that is the introduction of heterologous DNA into a host cell, to produce transgenic plants and cells, and as such may also be contained in the plastid DNA or genomic DNA of a transgenic plant, seed, cell, or plant part. As used herein, a "vector" means any recombinant DNA molecule that may be used for plant transformation. DNA molecules as set forth in the sequence listing, can, for example, be inserted into a vector as part of a construct having the DNA molecule operably linked to a gene expression element that functions in a plant to affect expression of the protein encoded by the DNA molecule. Methods for constructing DNA constructs and vectors are well known in the art. The components for a DNA construct, or a vector comprising a DNA construct, generally include one or more gene expression elements operably linked to a transcribable DNA sequence, such as the following: a promoter for the expression of an operably linked DNA, an operably linked protein-coding DNA molecule, and a 3' untranslated region. Gene expression elements useful in practicing the present invention include, but are not limited to, one or more of the following type of elements: promoter, 5' untranslated region, enhancer, leader, cis-acting element, intron, 3' untranslated region, and one or more selectable marker transgenes.

The DNA constructs of the invention may include a promoter operably linked to a protein-coding DNA molecule provided by the invention, whereby the promoter drives expression of the heterologous protein molecule. Promoters useful in practicing the present invention include those that function in a cell for expression of an operably linked polynucleotide, such as a bacterial or plant promoter. Plant promoters are varied and well known in the art and include those that are inducible, viral, synthetic, constitutive, temporally regulated, spatially regulated, and/or spatio-temporally regulated.

In one embodiment of the invention, a DNA construct provided herein includes a DNA sequence encoding a transit peptide that is operably linked to a heterologous DNA sequence encoding a protein that has herbicide-tolerant protoporphyrinogen oxidase activity, whereby the transit peptide sequence facilitates localizing the protein within the cell.

As used herein, "control" means an experimental control designed for comparison purposes. For example, a control plant in a transgenic plant analysis is a plant of the same type as the experimental plant (that is, the plant to be tested) but does not contain the transgenic insert, recombinant DNA molecule, or DNA construct of the experimental plant. Examples of control plants useful for comparison with transgenic plants include: for maize plants, non-transgenic LH244 maize (ATCC deposit number PTA-1173); for comparison with transgenic soybean plants: non-transgenic A3555 soybean (ATCC deposit number PTA-10207); for comparison with transgenic cotton plants: non-transgenic Coker 130 (Plant Variety Protection (PVP) Number 8900252); for comparison with transgenic canola or *Brassica napus* plants: non-transgenic *Brassica napus* variety 65037 Restorer line (Canada Plant Breeders' Rights Application 06-5517); for comparison with transgenic wheat plants: non-transgenic wheat variety Samson germplasm (PVP 1994).

As used herein, "wild-type" means a naturally occurring similar, but not identical, version. A "wild-type DNA molecule" or "wild-type protein" is a naturally occurring version of the DNA molecule or protein, that is, a version of the DNA molecule or protein pre-existing in nature. An example of a wild-type protein useful for comparison with the engineered proteins provided by the invention is the protoporphyrinogen oxidase from *Arabidopsis thaliana*. A "wild-type plant" is a non-transgenic plant of the same type as the transgenic plant, and as such is genetically distinct from the transgenic plant comprising the herbicide-tolerance trait. Examples of wild-type plants useful for comparison include: for transgenic maize plants, non-transgenic LH244 maize (ATCC deposit number PTA-1173); for comparison with transgenic soybean plants, non-transgenic A3555 soybean (ATCC deposit number PTA-10207); for comparison with transgenic cotton plants, non-transgenic Coker 130 (Plant Variety Protection Number 8900252); for comparison with transgenic canola or *Brassica napus* plants, non-transgenic *Brassica napus* variety 65037 Restorer line (Canada Plant Breeders' Rights Application 06-5517); for comparison with transgenic wheat plants, non-transgenic wheat variety Samson germplasm (PVP 1994).

Transgenic Plants & Herbicides

An aspect of the invention includes transgenic plant cells, transgenic plant tissues, transgenic plants, and transgenic seeds that comprise the recombinant DNA molecules provided by the invention. These cells, tissues, plants, and seeds comprising the recombinant DNA molecules exhibit tolerance to one or more PPO herbicide(s), and, optionally, tolerance to one or more additional herbicide(s).

Suitable methods for transformation of host plant cells for use with the current invention include virtually any method by which DNA can be introduced into a cell (for example, where a recombinant DNA construct is stably integrated into a plant chromosome) and are well known in the art. Exemplary methods for introducing a recombinant DNA construct into plants include the *Agrobacterium* transformation system and DNA particle-bombardment, both of which are well known to those of skill in the art. Another exemplary method for introducing a recombinant DNA construct into plants is insertion of a recombinant DNA construct into a plant genome at a pre-determined site by methods of site-directed integration. Site-directed integration may be accomplished by any method known in the art, for example, by use of zinc-finger nucleases, engineered or native meganucleases, TALE-endonucleases, or an RNA-guided endonuclease (for example a CRISPR/Cas9 system). Transgenic plants can be regenerated from a transformed plant cell by the methods of plant cell culture or by taking a cutting from a transgenic plant and rooting the cutting to establish a vegetative clone of the transgenic plant. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, typically using a SNP assay, DNA sequencing, or a thermal amplification assay that allows for the distinction between heterozygotes and homozygotes, referred to as a zygosity assay.

As used herein, "herbicide" is any molecule that is used to control, prevent, or interfere with the growth of one or more plants. Exemplary herbicides include acetyl-CoA carboxylase (ACCase) inhibitors (for example aryloxyphenoxy propionates and cyclohexanediones); acetolactate synthase (ALS) inhibitors (for example sulfonylureas, imidazolinones, triazolopyrimidines, and triazolinones); 5-enolpyruvyl-shikimate-3-phosphate synthase (EPSPS) inhibitors (for example glyphosate), synthetic auxins (for example phenoxys, benzoic acids, carboxylic acids, semicarbazones), photosynthesis (photosystem II) inhibitors (for example triazines, triazinones, nitriles, benzothiadiazoles, and ureas), glutamine synthetase (GS) inhibitors (for example glufosinate and bialaphos), 4-hydroxyphenylpyruvate dioxygenase (HPPD) inhibitors (for example isoxazoles, pyrazolones, and triketones), protoporphyrinogen oxidase (PPO) inhibitors (for example diphenylethers, N-phenylphthalimide, aryl triazinones, and pyrimidinediones), very long-chain fatty acid inhibitors (for example chloroacetamides, oxyacetamides, and pyrazoles), cellulose biosynthesis inhibitors (for example indaziflam), photosystem I inhibitors (for example paraquat), microtubule assembly inhibitors (for example pendimethalin), and phytoene desaturase (PDS) inhibitors (for example norflurazone), among others.

As used herein, a "PPO herbicide" is a chemical that targets and inhibits the enzymatic activity of a protoporphyrinogen oxidase (PPO), which catalyzes the dehydrogenation of protoporphyrinogen IX to form protoporphyrin IX, which is the precursor to heme and chlorophyll. Inhibition of protoporphyrinogen oxidase causes formation of reactive oxygen species, resulting in cell membrane disruption and ultimately the death of susceptible cells. PPO herbicides are well-known in the art and commercially available. Examples of PPO herbicides include, but are not limited to, diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen, its salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl) phenoxy]-2-pyridyloxy]acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, carfentrazone, its salts and esters, and sulfentrazone); oxazolidinediones (such as pentoxazone); N-phenylphthalimides (such as cinidon-ethyl, flumiclorac, flumiclorac-pentyl, and flumioxazin); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol. Protoporphyrinogen oxidases and cells, seeds, plants, and plant parts provided by the invention exhibit herbicide-tolerance to one or more PPO herbicide(s).

Plants, seeds, plant parts, plant tissues, and cells provided by the invention exhibit herbicide-tolerance to one or more PPO herbicide(s). PPO herbicide(s) may be applied to a plant growth area comprising the plants and seeds provided by the invention as a method for controlling weeds. Plants and seeds provided by the invention comprise an herbicide-tolerance trait and as such are tolerant to the application of one or more PPO herbicide(s). The herbicide application may be the recommended commercial rate (1×) or any fraction or multiple thereof, such as twice the recommended commercial rate (2×). Herbicide rates may be expressed as grams per hectare (g/h) or pounds per acre (lbs/acre), acid equivalent per pound per acre (lb ae/acre), acid equivalent per gram per hectare (g ae/ha), pounds active ingredient per acre (lb ai/acre), or grams active ingredient per hectare (g ai/ha) depending on the herbicide and the formulation. The herbicide application comprises at least one PPO herbicide. The plant growth area may or may not comprise weed plants at the time of herbicide application. An herbicidally effective dose of PPO herbicide for use in an area for controlling weeds should consist of a range from about 0.1× to about 30× label rate(s) over a growing season. The 1× label rate for some exemplary PPO herbicides is provided in Table 1. One (1) acre is equivalent to 2.47105 hectares and one (1) pound is equivalent to 453.592 grams. Herbicide rates can be converted between English and metric as: (lb ai/ac) multiplied by 1.12=(kg ai/ha) and (kg ai/ha) multiplied by 0.89= (lb ai/ac).

TABLE 1

Exemplary PPO Herbicides

| PPO Herbicide | Chemical Family | 1X Rate |
|---|---|---|
| acifluorfen | Diphenylethers | 420 g ai/ha |
| fomesafen | Diphenylethers | 420 g ai/ha |
| lactofen | Diphenylethers | 70-220 g ai/ha |
| fluoroglycofen-ethyl | Diphenylethers | 15-40 g ai/ha |
| oxyfluorfen | Diphenylethers | 0.28-2.24 kg ai/ha |
| flumioxazin | N-phenylphthalimide | 70-105 g ai/ha |
| azafenidin | Triazolinone | 240 g ai/ha |
| carfentrazone-ethyl | Triazolinone | 4-36 g ai/ha |
| sulfentrazone | Triazolinone | 0.1-0.42 kg ai/ha |
| fluthiacet-methyl | Thiadiazole | 3-15 g ai/ha |
| oxadiargyl | Oxadiazole | 50-150 g ai/ha |
| oxadiazon | Oxadiazole | 2.24-4.48 kg ai/ha |
| pyraflufen-ethyl | Phenylpyrazole | 6-12 g ai/ha |
| saflufenacil | Pyrimidine dione | 25-100 g/ha |
| S-3100 | Pyrimidine dione | 5-80 g/ha |

Herbicide applications may be sequentially or tank mixed with one, two, or a combination of several herbicides or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, a "weed" is any undesired plant. A plant may be considered generally undesirable for agriculture or horticulture purposes (for example, *Amaranthus* species) or may be considered undesirable in a particular situation (for example, a crop plant of one species in a field of a different species, also known as a volunteer plant).

The transgenic plants, progeny, seeds, plant cells, and plant parts of the invention may also contain one or more additional traits. Additional traits may be introduced by crossing a plant containing a transgene comprising the recombinant DNA molecules provided by the invention with another plant containing one or more additional trait(s). As used herein, "crossing" means breeding two individual plants to produce a progeny plant. Two plants may thus be crossed to produce progeny that contain the desirable traits from each parent. As used herein "progeny" means the offspring of any generation of a parent plant, and transgenic progeny comprise a DNA construct provided by the invention and inherited from at least one parent plant. Additional trait(s) also may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation or genome editing on a transgenic plant or plant cell). Such additional traits include, but are not limited to, increased insect resistance, increased water use efficiency, increased yield performance, increased drought resistance, increased seed quality, improved nutritional quality, hybrid seed production, and herbicide-tolerance, in which the trait is measured with respect to a wild-type plant. Exemplary additional herbicide-tolerance traits may include transgenic or non-transgenic tolerance to one or more herbicides such as ACCase inhibitors (for example aryloxyphenoxy propionates and cyclohexanediones), ALS inhibitors (for example sulfonylureas, imidazolinones, triazolopyrimidines, and triazolinones) EPSPS inhibitors (for example glyphosate), synthetic auxins (for example phenoxys, benzoic acids, carboxylic acids, semicarbazones), photosynthesis inhibitors (for example triazines, triazinones, nitriles, benzothiadiazoles, and ureas), glutamine synthesis inhibitors (for example glufosinate), HPPD inhibitors (for example isoxazoles, pyrazolones, and triketones), PPO inhibitors (for example diphenylethers, N-phenylphthalimide, aryl triazinones, and pyrimidinediones), and long-chain fatty acid inhibitors (for example chloroacetamindes, oxyacetamides, and pyrazoles), among others. Exemplary insect resistance traits may include resistance to one or more insect members within one or more of the orders of Lepidoptera, Coleoptera, Hemiptera, Thysanoptera, Diptera, Hymenoptera, and Orthoptera, among others. Such additional traits are well known to one of skill in the art; for example, and a list of such transgenic traits is provided by the United States Department of Agriculture's (USDA) Animal and Plant Health Inspection Service (*APHIS*).

A cell transformed with a polynucleotide of the present invention, such as an expression construct, may be selected for the presence of the polynucleotide or its encoded enzymatic activity before or after regenerating such a cell into a transgenic plant. Transgenic plants comprising such a polynucleotide may thus be selected for instance by identifying a transgenic plant that comprises the polynucleotide or the encoded enzymatic activity, and/or displays an altered trait relative to an otherwise isogenic control plant. Such a trait may be, for example, tolerance to a PPO herbicide.

Transgenic plants and progeny that contain a transgenic trait provided by the invention may be used with any breeding methods that are commonly known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and western blots) or by enzymatic function; plant part assays, such as leaf or root assays; and, by analyzing the phenotype of the whole plant. To analyze transit peptide processing in a transgenic plant or seed, assays such as Edman degradation sequencing or mass spectrometry analysis may be performed on the heterologous protoporphyrinogen oxidase protein obtained from the transgenic cell, plant, or seed and the resulting sequence data compared to that of the protoporphyrinogen oxidase protein.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly, a plant genotype lacking the desired transgenic trait may be referred to as an unconverted genotype, line, inbred, or hybrid.

As used herein, the term "comprising" means "including but not limited to".

Having described the invention in detail, it will be apparent that modifications, variations, and equivalent embodiments are possible without departing the scope of the invention defined in the appended claims. Furthermore, it should be appreciated that the examples in the present disclosure are provided as non-limiting examples.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit, and scope of the invention. More specifically, it will be apparent that certain agents which are both chemically and physiologically related may be substituted for the agents described herein with the same or similar result achieved. All such similar substitutes and modifications apparent to those skilled in the art are deemed to be within the spirit, scope, and concept of the invention as defined by the appended claims.

Example 1: Transit Peptide Discovery

Novel transit peptides were mined from a collection of plant sequence databases. Bioinformatic methods and tools, such as hidden Markov models (HMM), the Pfam database, and basic local alignment search tool (BLAST), were used to identify thousands of EST and genomic sequences predicted to encode proteins known to be localized to the chloroplast and mitochondria in plant cells, such as protoporphyrinogen oxidase and heat shock proteins. These sequences were then analyzed, and the sequence encoding the transit peptide was identified. Thousands of putative transit peptide sequences were identified and assessed for predicted efficacy and comparative sequence diversity. From these, 60 unique transit peptides were selected for cloning and testing in plant cells, with variants produced for some of these (indicated as "_var" herein). Table 2 provides the SEQ ID NO corresponding to the protein and nucleotide sequences of each transit peptide and variants thereof.

Recombinant DNA molecules encoding the transit peptides were synthesized using the sequence for each predicted transit peptide. DNA constructs were produced operably linking each transit peptide to a promoter and protein-coding sequence. These DNA constructs were then used to transform plant protoplasts. A protoplast assay was used with transformed plant protoplasts to test transit peptides for the functional activity of an operably linked herbicide-tolerance protein in the presence of the herbicide. Successful candidates were then advanced for plant transformation to enable transgenic plant testing.

TABLE 2

| Transit Peptides | | |
| --- | --- | --- |
| Transit Peptide | PRT SEQ ID NO | DNA SEQ ID NO |
| ADADI_1600 | 8 | 58 |
| ALLCE_3035 | 16, 37, 46, 47, 237 | 66, 87, 96, 97, 268 |
| AMACR_2643 | 33 | 83 |
| AMAGR_5230 | 29 | 79 |
| AMAPA_1826 | 12 | 62 |
| AMAPA_4787 | 18 | 68 |
| AMBTR_1537 | 30 | 80 |
| ANDGE_6461 | 26 | 76 |
| BRANA_6036 | 31 | 81 |
| BRANA_9788 | 7 | 57 |
| CAMSA_6215 | 21, 41 | 71, 91 |
| CANRO_3271 | 24 | 74 |
| CANRO_3976 | 4, 35 | 54, 85 |
| CONCA_4103 | 11 | 61 |
| CUCME_4756 | 22, 39, 48 | 72, 89, 98 |
| DIGSA_5107 | 17 | 67 |
| DIGSA_5109 | 27 | 77 |
| ERATE_2090 | 25 | 75 |
| ERATE_4149 | 23, 36, 45 | 73, 86, 95 |
| ERATE_4824 | 28 | 78 |
| KOCSC_1672 | 14 | 64 |
| NICBE_5162 | 6 | 56 |
| ROSHY_6783 | 32 | 82 |
| ROSHY_8873 | 9 | 59 |
| SEDAL_8241 | 20 | 70 |
| SENOB_8832 | 5, 44 | 55, 94 |
| SETIT_2080 | 15 | 65 |
| SPIOL_0401 | 19 | 69 |
| SPIOL_0410 | 13 | 63 |
| TAROF_2111 | 34, 42, 38, 43 | 84, 92, 88, 93 |
| XANST_27 | 10, 40, 49 | 60, 90, 99 |
| ERATE_3481 | 238 | 269 |
| SETIT_9796 | 239 | 270 |
| ACAOS_3432 | 240 | 271 |
| ADADI_0544 | 241 | 272 |
| TAROF_9570 | 242 | 273 |
| AMACR_2380 | 243 | 274 |
| AMACR_2381 | 244 | 275 |
| AMAHY_5254 | 245 | 276 |
| AMAPA_22810 | 246 | 277 |
| AMAPA_2811 | 247 | 278 |
| AMAPA_6265_1 | 248 | 279 |

TABLE 2-continued

| Transit Peptides | | |
| --- | --- | --- |
| Transit Peptide | PRT SEQ ID NO | DNA SEQ ID NO |
| AMAPA_6265_2 | 249 | 280 |
| AMAPA_2906 | 250 | 281 |
| AMARU_1762 | 251 | 282 |
| AMARU_1763 | 252 | 283 |
| AMARU_1764 | 253 | 284 |
| AMAVI_1826 | 254 | 285 |
| AMAVI_1827 | 255 | 286 |
| AMBTR_6334 | 256 | 287 |
| CONCA_3910 | 257 | 288 |
| CUCME_3420 | 258 | 289 |
| KOCSC_5431 | 259 | 290 |
| KOCSC_9516 | 260 | 291 |
| KOCSC_0438 | 261 | 292 |
| ROSHY_3269 | 262 | 293 |
| SEDAL_6599 | 263 | 294 |
| SEDAL_6601 | 264 | 295 |
| SPIOL_1551 | 265 | 296 |
| ALLCE_6618 | 266 | 297 |

Example 2: PPO Enzyme Discovery

Novel microbial HemG and HemY protoporphyrinogen oxidases that are tolerant to PPO herbicides were identified from microbial sequence databases using bioinformatic methods and a novel herbicide bacterial screening system. This screening system used a growth assay of the hemG knockout *E. coli* strain in LB liquid medium with a PPO herbicide to confirm protoporphyrinogen oxidase activity for an enzyme and to identify protoporphyrinogen oxidases that were not sensitive to the PPO herbicide. Briefly, a hemG knockout *E. coli* strain was transformed with a bacterial expression vector containing a putative protoporphyrinogen oxidase and cultured in LB liquid medium. Purified crystalline form of one of five different PPO herbicides (acifluorfen (1 mM), flumioxazin (0.5 mM), lactofen (0.5 mM), fomesafen (1 mM), and S-3100 (100 microM), representing three different PPO chemistry subclasses, was added to the medium. Recombinant proteins were expressed and the *E. coli* growth rates were measured. Growth curves (OD600) were measured for the different variants in the presence and absence of the PPO herbicides at selected time-points from time zero to twenty-four hours. The growth of a transformed hemG knockout *E. coli* strain in LB medium in the presence of a PPO herbicide indicated that the gene used to transform the *E. coli* encoded an herbicide-tolerant protoporphyrinogen oxidase. The hemG knockout *E. coli* strain expressing the waterhemp (WH) protoporphyrinogen oxidase (SEQ ID NO:120), which is sensitive to all five PPO herbicides, was used as a control to confirm that the assay could distinguish between sensitive and tolerant protoporphyrinogen oxidases for each of the herbicides.

Protoporphyrinogen oxidases that are herbicide-tolerant proteins are provided as SEQ ID NOs:100-119, SEQ ID NOs:163-182, and SEQ ID NOs:224-228 and shown in Table 3. The DNA sequence encoding a protoporphyrinogen oxidase can include at the 5' end a codon for a methionine, commonly known as a start codon, or this codon (and optionally a few amino-terminal amino acids, for example 2 to 7), can be eliminated to facilitate operable linkage of a transit peptide sequence to the 5' end of the coding sequence. DNA sequences encoding a protoporphyrinogen oxidase can optionally be synthesized that are optimized for expression in a monocot or dicot. Table 3 provides for each protoporphyrinogen oxidase DNA sequences that are optimized for expression in monocots and dicots.

TABLE 3

| | | | Dicot | Monocot |
| | | Bacterial | optimized | optimized |
| | Protein | DNA SEQ | DNA SEQ | DNA SEQ |
| Name | SEQ ID NO | ID NO | ID NO | ID NO |
|---|---|---|---|---|
| H_N10 | 103, 112 | 124 | 134, 143 | 156 |
| H_N20 | 101, 111 | 122 | 132, 142, 151 | 154 |
| H_N30 | 104, 113 | 125 | 135, 144 | 157 |
| H_N40 | 105, 114 | 126 | 136, 145 | 158 |
| H_N50 | 106, 115 | 127 | 137, 146 | 159 |
| H_N60 | 102 | 123 | 133 | 155 |
| H_N70 | 107 | 128 | 138 | 160 |
| H_N90 | 100, 110, 117, 118 | 121 | 131, 141, 148, 149, 150, 229 | 153 |
| H_N100 | 108, 116, 119 | 129 | 139, 147, 152 | 161 |
| H_N110 | 109 | 130 | 140 | 162 |
| WH PPO | 120 | n/a | n/a | n/a |
| R2N30 | 163, 164 | 183 | 189, 190 | 195 |
| R2N40 | 165, 224 | 184 | 191, 230 | 196 |
| R2N40opt | 166, 225 | 185 | 231, 232 | n/a |
| R2N70 | 167, 226 | 186 | 192, 233 | 197 |
| R2N90 | 168, 227 | 187 | 193, 234 | 198 |
| R2N100 | 169, 228 | 188 | 194, 235 | 199 |
| R1N473 | 170, 175, 179 | 200 | 205, 216, 220 | 211 |
| R1N533 | 171, 176, 180 | 201 | 206, 217, 221 | 212 |
| R1N171 | 172, 177, 181 | 202 | 207, 218, 222 | 213 |
| R1N311 | 173 | 203 | 208 | 214 |
| R1N333 | 174, 178, 182 | 204 | 209, 210, 219, 223 | 215 |

Example 3: Transit Peptide and Protoporphyrinogen Oxidase Testing in Protoplasts Transit peptides operably linked to a protoporphyrinogen oxidase were tested in plant protoplasts for PPO herbicide-tolerance. Plant transformation vectors were constructed comprising a recombinant DNA molecule encoding the H_N90 protoporphyrinogen oxidase operably linked to a transit peptide. The vectors were then used to transform plant protoplasts, which were assessed for sensitivity to PPO herbicides.

Plant transformation vectors were produced comprising (i) fixed expression elements (a promoter and 3'UTR) operably linked to a transit peptide operably linked to the H_N90 protoporphyrinogen oxidase. Using this, 68 transit peptides were tested and direct comparisons were made by the use of the same protoporphyrinogen oxidase and other expression elements in each vector. Control vectors with the same fixed expression elements were produced comprising (i) H_N90 protoporphyrinogen oxidase without any transit peptide (H_N90 Control) or (ii) Green Fluorescent Protein (GFP) without a transit peptide (GFP Control).

Soybean protoplasts were transformed using standard methods and grown in the presence of the PPO herbicide S-3100 at 1.0 microM concentration. Protoplasts were then assayed for PPO herbicide tolerance, expressed relative to the GFP control (allowing derivation of a relative tolerance score to enable comparisons between experiments). Assays were done in two batches, indicated as Experiment No. 1 or Experiment No. 2. The assays were done in four replications, relative tolerance scores were averaged for each transit peptide, and standard error was calculated (SE). Any targeting peptide scoring a relative tolerance score of 50 or higher was considered highly efficacious for providing efficient sub-cellular localization and processing when operably linked to an herbicide-tolerance protein and a score of 40-50 indicates very good for providing efficient sub-cellular localization and processing when operably linked to an herbicide-tolerance protein. The GFP Control assays had a tolerance score of 0, confirming that the soybean protoplasts were not tolerant to the PPO herbicide in the absence of an herbicide-tolerance protein. The H_N90 Control assays had a tolerance score of 24 (Experiment 1, SE 4) and 11 (Experiment 2, SE 4), while several of the transit peptides provide higher tolerance scores, indicating that an effective transit peptide can increase the herbicide tolerance of the plant protoplasts. For example, ADADI_0544 and KOCSC_9516 scored as highly efficacious targeting peptides and AMAPA_62652 scored as a very good targeting peptide. Data are provided in Table 4.

TABLE 4

| Protoplast Assay Results | | | |
|---|---|---|---|
| Transit Peptide | Tolerance score | SE | Experiment |
| ADADI_0544 | 62 | 2 | 1 |
| KOCSC_9516 | 60 | 1 | 1 |
| ALLCE_3035_var | 56 | 4 | 1 |
| CAMSA_6215 | 56 | 3 | 1 |
| AMAPA_2810 | 56 | 3 | 1 |
| ALLCE_6618 | 56 | 2 | 1 |
| AMARU_1764 | 56 | 3 | 1 |
| AMBTR_6334 | 56 | 1 | 1 |
| SETIT_9796 | 55 | 5 | 1 |
| AMACR_2381 | 55 | 2 | 1 |
| AMAVI_1827 | 54 | 4 | 1 |
| CONCA_3910 | 54 | 1 | 1 |
| ERATE_3481 | 53 | 2 | 1 |
| ROSHY_3269 | 53 | 5 | 1 |
| AMAPA_6265_1 | 53 | 2 | 1 |
| AMAHY_5254 | 52 | 4 | 1 |
| SEDAL_6599 | 52 | 2 | 1 |
| AMACR_2380 | 51 | 3 | 1 |
| CUCME_3420 | 51 | 3 | 1 |
| AMARU_1762 | 51 | 5 | 1 |
| SEDAL_6601 | 50 | 5 | 1 |
| KOCSC_5431 | 48 | 4 | 1 |
| AMAPA_6265_2 | 47 | 2 | 1 |
| KOCSC_0438 | 47 | 3 | 1 |
| AMAPA_2811 | 46 | 3 | 1 |
| AMAVI_1826 | 45 | 4 | 1 |
| ACAOS_3432 | 44 | 2 | 1 |
| SPIOL_1551 | 43 | 4 | 1 |
| AMAPA_2906 | 43 | 2 | 1 |
| TAROF_9570 | 41 | 3 | 1 |
| AMARU_1763 | 40 | 8 | 1 |
| None - H_N90 Control | 24 | 4 | 1 |
| None - GFP | 0 | 4 | 1 |
| ADADI_0544 | 60 | 1 | 2 |
| SPIOL_1551 | 53 | 3 | 2 |
| KOCSC_9516 | 51 | 4 | 2 |
| ROSHY_3269 | 49 | 4 | 2 |
| AMACR_2381 | 48 | 3 | 2 |
| CAMSA_6215 | 46 | 2 | 2 |
| CUCME_4756_var | 46 | 1 | 2 |
| CUCME_3420 | 46 | 3 | 2 |
| CONCA_3910 | 45 | 4 | 2 |
| AMAGR_5230 | 43 | 2 | 2 |
| SENOB_8832 | 43 | 1 | 2 |
| KOCSC_1672 | 42 | 3 | 2 |
| CONCA_4103 | 36 | 5 | 2 |
| ADADI_1600 | 36 | 4 | 2 |
| BRANA_9788 | 33 | 1 | 2 |
| CUCME_4756 | 33 | 4 | 2 |
| ANDGE_6461 | 33 | 2 | 2 |
| ALLCE_3035 | 33 | 3 | 2 |
| AMAPA_4787 | 30 | 2 | 2 |
| TAROF_2111 | 28 | 3 | 2 |
| ROSHY_6783 | 26 | 4 | 2 |
| CANRO_3976 | 25 | 4 | 2 |
| TAROF_2111_var | 25 | 5 | 2 |

TABLE 4-continued

Protoplast Assay Results

| Transit Peptide | Tolerance score | SE | Experiment |
|---|---|---|---|
| XANST__27__var | 24 | 2 | 2 |
| NICBE__5162 | 24 | 3 | 2 |
| XANST__27 | 22 | 3 | 2 |
| SPIOL__0401 | 22 | 2 | 2 |
| ERATE__2090 | 22 | 1 | 2 |
| SPIOL__0410 | 21 | 2 | 2 |
| CANRO__3271 | 20 | 2 | 2 |
| AMAPA__1826 | 20 | 2 | 2 |
| DIGSA__5109 | 20 | 2 | 2 |
| DIGSA__5107 | 17 | 2 | 2 |
| ERATE__4149 | 15 | 4 | 2 |
| SETIT__2080 | 14 | 2 | 2 |
| ROSHY__8873 | 12 | 4 | 2 |
| AMBTR__1537 | 12 | 6 | 2 |
| SEDAL__8241 | 11 | 6 | 2 |
| None - H__N90 Control | 11 | 4 | 2 |
| ERATE__4824 | 9 | 5 | 2 |
| ALLCE__3035__var | 8 | 1 | 2 |
| None - GFP | 0 | 4 | 2 |
| AMACR__2643 | 0 | 4 | 2 |

Example 4: Transit Peptide and Protoporphyrinogen Oxidase Testing in Soybean Transit peptides operably linked to protoporphyrinogen oxidases were tested in transgenic soybean plants for PPO herbicide-tolerance. Plant transformation vectors were constructed comprising a DNA construct comprising a recombinant DNA molecule optimized for dicot expression and encoding a protoporphyrinogen oxidase operably linked to a transit peptide. The plant transformation vectors were then used to transform soybean, and the plants were regenerated and assessed for their sensitivity to a PPO herbicide.

The genes encoding the seven HemG protoporphyrinogen oxidases H_N10, H_N20, H_N30, H_N40, H_N50, H_N90, and H_N100 were operably linked to thirty-seven different transit peptides and cloned into a base plant transformation vector as described in Example 3. This permitted the side-by-side comparison of seven different HemG protoporphyrinogen oxidases with thirty-seven different transit peptides using the same promoter and 3'UTR elements in every DNA construct. These plant transformation vectors were used to transform soybean excised embryos (germplasm A3555) using *A. tumefaciens* and standard methods known in the art. Four hundred explants were inoculated for each construct. A sterile PPO herbicide solution was used for herbicide-tolerance testing. The herbicide solution consisted of 0.3 g of S-3100 in crop oil concentrate (5.0 mL) and 495 mL of deionized water.

At five weeks post-transformation, plants were sprayed with two passes of the sterile PPO herbicide solution at a 20 g/ha rate. For each DNA construct tested, four containers each with 30-40 individually transformed plants were tested. The treated plantlets then received at least 15 hours of light exposure post spray each day for four days. At the end of day four post application of S-3100, the treated plantlets were photographed and scored on a visual scale of green coloration (green coloration was representative of healthy photosynthetic plant tissue as compared to photo-bleached tissue) versus damage. The scoring values were 0 for poor tolerance, high damage, low green coloration; 1 for some tolerance, average damage, moderate green coloration; and 2 for good tolerance, low damage, high green coloration. The scoring for each construct is presented in Table 5, where n.d. indicates the analysis was not conducted. The results indicate that several constructs provided tolerance to the PPO herbicide.

TABLE 5

Tolerance score at 5 weeks in soybean

| Transit Peptide | H__N10 | H__N20 | H__N30 | H__N40 | H__N50 | H__N90 | H__N100 |
|---|---|---|---|---|---|---|---|
| APG6 | n.d. | 0 | 2 | 2 | 1 | 2 | 2 |
| 12G088600TP | n.d. | 0 | 0 | 1 | 1 | 2 | 1 |
| CANRO__3976 | 1 | 1 | n.d. | 1 | 1 | 2 | 1 |
| SENOB__8832 | n.d. | 1 | n.d. | 2 | 1 | 1 | n.d. |
| NICBE__5162 | n.d. | n.d. | n.d. | n.d. | 0 | 1 | n.d. |
| BRANA__9788 | 0 | 1 | 0 | n.d. | 2 | 2 | 2 |
| ADADI__1600 | n.d. | 2 | 1 | 2 | 1 | 2 | 2 |
| ROSHY__8873 | 0 | 1 | 1 | 2 | 1 | 0 | 0 |
| XANST__27 | 1 | 1 | 1 | 0 | 1 | 1 | 0 |
| CONCA__4103 | n.d. | n.d. | 0 | n.d. | 1 | 2 | 1 |
| AMAPA__1826 | n.d. | 1 | 1 | 1 | 0 | 2 | 0 |
| SPIOL__0410 | 1 | 2 | 1 | 1 | 1 | 2 | 2 |
| KOCSC__1672 | 1 | 2 | 1 | 1 | 1 | 2 | 0 |
| SETIT__2080 | 0 | 0 | n.d. | 2 | 1 | 2 | 1 |
| ALLCE__3035 | n.d. | 1 | 1 | 2 | 2 | 2 | 2 |
| DIGSA__5107 | 1 | 1 | n.d. | n.d. | 0 | 1 | 1 |
| AMAPA__4787 | n.d. | 2 | 1 | 1 | 1 | 2 | 1 |
| SPIOL__0401 | 1 | 1 | 0 | 1 | 1 | 2 | 1 |
| SEDAL__8241 | 0 | 1 | 0 | 1 | 0 | 1 | 1 |
| CAMSA__6215 | 0 | 2 | n.d. | n.d. | n.d. | 2 | 2 |
| CUCME__4756 | 0 | 0 | n.d. | 2 | 1 | 1 | 0 |
| ERATE__4149 | 1 | 1 | n.d. | n.d. | 2 | 2 | 2 |
| CANRO__3271 | 1 | 1 | n.d. | 1 | 1 | 1 | 2 |
| ERATE__2090 | 0 | 1 | 1 | 0 | 1 | 1 | 0 |
| ANDGE__6461 | n.d. | 1 | n.d. | 2 | 2 | 1 | 1 |
| DIGSA__5109 | 0 | 1 | 0 | 1 | 1 | 0 | n.d. |
| ERATE__4824 | 1 | 1 | 0 | 1 | 1 | 1 | 1 |
| AMAGR__5230 | n.d. | 1 | 0 | 1 | 1 | 2 | 1 |
| AMBTR__1537 | n.d. | 1 | 1 | 1 | 1 | 1 | 1 |
| BRANA__6036 | n.d. | 1 | n.d. | 1 | 1 | 1 | 1 |

TABLE 5-continued

| Transit Peptide | Tolerance score at 5 weeks in soybean | | | | | | |
|---|---|---|---|---|---|---|---|
| | H_N10 | H_N20 | H_N30 | H_N40 | H_N50 | H_N90 | H_N100 |
| ROSHY__6783 | 1 | 1 | n.d. | 1 | 0 | 0 | 1 |
| AMACR__2643 | n.d. | 0 | n.d. | 1 | 1 | 0 | 2 |
| TAROF__2111 | 1 | 1 | 1 | 0 | 1 | 2 | 1 |
| CANRO__3976__var | n.d. | n.d. | n.d. | n.d. | n.d. | n.d. | n.d. |
| ERATE__4149__var | n.d. | n.d. | n.d. | n.d. | 0 | 2 | 0 |
| ALLCE__3035__var | n.d. | n.d. | n.d. | n.d. | n.d. | 1 | 1 |
| TAROF__2111__var | 0 | n.d. | n.d. | n.d. | 0 | 2 | 1 |
| CUCME__4756__var | n.d. | n.d. | n.d. | n.d. | n.d. | n.d. | n.d. |
| XANST__27__var | n.d. | n.d. | n.d. | n.d. | 0 | n.d. | n.d. |

The plantlets in the non-sprayed containers corresponding to constructs having a score of 2 were then transplanted at approximately seven weeks post-transformation and grown as R0 plants using standard methods known in the art. A selection of plantlets corresponding to non-tolerant scores of 0 and 1 were also grown to serve as negative controls. The R0 plants were grown in a greenhouse under long-day nursery conditions (18 hours of light at 80° F. then 6 hours of dark at 74° F.) for approximately four additional weeks. At eleven weeks post-transformation, the R0 plants were sprayed with two passes of the same herbicide solution described above for a final application rate of 20 g/ha. For each DNA construct tested, 15-30 individually transformed plants were tested. Herbicide injury ratings were visually scored based on the amount of above ground tissue injury with 0% being no visible injury and 100% being complete death of the plant. Non-transgenic control plants scored injury ratings of greater than 30%. Marginal tolerance was 30% injury or less, good tolerance is 20% injury or less, and excellent tolerance was considered 10% injury or less.

Scores were collected seven days after treatment and averaged for all plants for each DNA construct.

The results of the herbicide-tolerance application at eleven weeks to the R0 plants confirmed the low percent injury rating scores observed at five weeks. For the eleven-week evaluation, any injury rating of 30% or above was equivalent to non-transgenic soybean injury ratings. Several of the constructs stood out as providing very good tolerance to the herbicide application. For example, APG6 (SEQ ID NO:1) with PPO H_N90 (SEQ ID NO:110) had only 3% injury, APG6 (SEQ ID NO:1) with PPO H_N30 (SEQ ID NO:113) or APG6 (SEQ ID NO:1) with PPO H_N40 (SEQ ID NO:114) each had only 5% injury; transit peptide CAMSA_6215 (SEQ ID NO:21) with PPO H_N90 (SEQ ID NO:110) had only 5% injury. In contrast, transit peptide AMACR_2643 (SEQ ID NO:33) with the PPO H_N90 (SEQ ID NO:110) had an injury score of 50%. Data are provided in Table 6, where n.d. indicates the analysis was not conducted.

TABLE 6

| Transit Peptide | Tolerance score at 11 weeks in soybean | | | | | |
|---|---|---|---|---|---|---|
| | H_N20 | H_N30 | H_N40 | H_N50 | H_N90 | H_N100 |
| APG6 | n.d. | 5 | 5 | n.d. | 3 | 15 |
| 12G088600TP | n.d. | n.d. | n.d. | n.d. | 35 | n.d. |
| CANRO__3976 | n.d. | n.d. | n.d. | n.d. | 30 | n.d. |
| SENOB__8832 | n.d. | n.d. | 15 | n.d. | n.d. | n.d. |
| NICBE__5162 | n.d. | n.d. | n.d. | n.d. | n.d. | n.d. |
| BRANA__9788 | 25 | n.d. | n.d. | 40 | 25 | 30 |
| ADADI__1600 | 20 | n.d. | 40 | n.d. | 15 | 30 |
| ROSHY__8873 | n.d. | n.d. | 30 | n.d. | 40 | n.d. |
| XANST__27 | n.d. | 35 | n.d. | 40 | 30 | n.d. |
| CONCA__4103 | n.d. | n.d. | n.d. | n.d. | 30 | 35 |
| AMAPA__1826 | n.d. | 35 | n.d. | n.d. | 30 | n.d. |
| SPIOL__0410 | 20 | n.d. | n.d. | n.d. | 30 | 50 |
| KOCSC__1672 | 20 | n.d. | 15 | 40 | 15 | n.d. |
| SETIT__2080 | n.d. | n.d. | 35 | 40 | 25 | n.d. |
| ALLCE__3035 | 30 | 35 | 30 | 40 | 35 | 30 |
| DIGSA__5107 | n.d. | n.d. | n.d. | n.d. | 35 | n.d. |
| AMAPA__4787 | 25 | n.d. | n.d. | 40 | 15 | n.d. |
| SPIOL__0401 | n.d. | n.d. | n.d. | n.d. | 30 | n.d. |
| SEDAL__8241 | n.d. | n.d. | n.d. | n.d. | n.d. | n.d. |
| CAMSA__6215 | 20 | n.d. | n.d. | n.d. | 5 | 35 |
| CUCME__4756 | n.d. | n.d. | 35 | n.d. | 25 | n.d. |
| ERATE__4149 | n.d. | n.d. | n.d. | 40 | 30 | 30 |
| CANRO__3271 | n.d. | n.d. | n.d. | n.d. | 30 | 35 |
| ERATE__2090 | n.d. | n.d. | n.d. | n.d. | n.d. | n.d. |
| ANDGE__6461 | n.d. | n.d. | 15 | 35 | n.d. | n.d. |
| DIGSA__5109 | n.d. | 35 | n.d. | n.d. | 40 | n.d. |
| ERATE__4824 | n.d. | n.d. | n.d. | n.d. | 35 | n.d. |
| AMAGR__5230 | n.d. | n.d. | n.d. | n.d. | 30 | 35 |
| AMBTR__1537 | 30 | n.d. | n.d. | n.d. | n.d. | 40 |
| BRANA__6036 | n.d. | n.d. | n.d. | n.d. | n.d. | n.d. |
| ROSHY__6783 | n.d. | n.d. | n.d. | n.d. | n.d. | n.d. |
| AMACR__2643 | n.d. | n.d. | n.d. | n.d. | 50 | 40 |

TABLE 6-continued

| Tolerance score at 11 weeks in soybean | | | | | | |
| --- | --- | --- | --- | --- | --- | --- |
| Transit Peptide | H_N20 | H_N30 | H_N40 | H_N50 | H_N90 | H_N100 |
| TAROF_2111 | n.d. | n.d. | n.d. | n.d. | 25 | n.d. |
| CANRO_3976_var | n.d. | n.d. | n.d. | n.d. | n.d. | n.d. |
| ERATE_4149_var | n.d. | n.d. | n.d. | n.d. | 35 | n.d. |
| ALLCE_3035_var | n.d. | n.d. | n.d. | n.d. | 15 | 35 |
| TAROF_2111_var | n.d. | n.d. | n.d. | n.d. | 15 | n.d. |
| CUCME_4756_var | n.d. | n.d. | n.d. | n.d. | n.d. | n.d. |
| XANST_27_var | n.d. | n.d. | n.d. | n.d. | n.d. | n.d. |

The genes encoding ten HemY protoporphyrinogen oxidases R2N30, R2N40, R2N40opt, R2N70, R2N90, R2N100, R1N473, R1N533, R1N171, R1N311, and R1N33 were operably linked to thirty-nine different transit peptides and cloned into a base plant transformation vector as described in Example 3. This permitted the side-by-side comparison of ten different HemY protoporphyrinogen oxidases with thirty-nine different transit peptides using the same promoter and 3'UTR elements in every DNA construct. These plant transformation vectors were used to transform soybean excised embryos (germplasm A3555) using *A. tumefaciens* and standard methods known in the art. Four hundred explants were inoculated for each construct. A sterile PPO herbicide solution was used for herbicide-tolerance testing. The herbicide solution consisted of 0.3 g of S-3100 in crop oil concentrate (5.0 mL) and 495 mL of deionized water.

At five weeks post-transformation, for each DNA construct four containers (each with 30-40 individually trans-formed plants) were sprayed with two passes of the sterile PPO herbicide solution for a final application rate of 20 g/ha. The treated plantlets then received at least 15 hours of light exposure post spray each day for four days. At the end of day four post application of S-3100, the treated plantlets were photographed and scored on a visual scale of green coloration (green coloration was representative of healthy photosynthetic plant tissue as compared to photo-bleached tissue) versus damage. The scoring values were 0 for poor tolerance, high damage, low green coloration; 1 for some tolerance, average damage, moderate green coloration; and 2 for good tolerance, low damage, high green coloration. The scoring for each construct is presented in Table 7, where n.d. indicates the analysis was not conducted. The results indicate that several constructs provided tolerance to the PPO herbicide.

TABLE 7

| Tolerance score at 5 weeks in soybean | | | | | | | | | | |
| --- | --- | --- | --- | --- | --- | --- | --- | --- | --- | --- |
| Transit Peptide | R1N171 | R1N473 | R1N533 | R2N30 | R2N40 | R2N40opt | R2N70 | R2N90 | R2N100 | R1N333 |
| APG6 | 0 | 2 | 0 | 2 | n.d. | 1 | n.d. | n.d. | 0 | n.d. |
| 12G088600TP | 0 | 0 | 2 | n.d. | n.d. | n.d. | 2 | 0 | 0 | 0 |
| CANRO_3976 | 0 | 1 | 0 | 1 | n.d. | n.d. | 1 | n.d. | 0 | 0 |
| SENOB_8832 | n.d. | 1 | 0 | 2 | n.d. | 0 | 0 | n.d. | 0 | 0 |
| NICBE_5162 | 1 | n.d. | n.d. | n.d. | 1 | 1 | n.d. | 0 | 0 | n.d. |
| BRANA_9788 | n.d. | 1 | 1 | n.d. | n.d. | 1 | 0 | n.d. | 0 | 0 |
| ADADI_1600 | 0 | 1 | 0 | 1 | n.d. | 2 | n.d. | n.d. | n.d. | 0 |
| ROSHY_8873 | 1 | 1 | n.d. | 2 | 0 | 1 | 0 | 1 | 1 | 0 |
| XANST_27 | 1 | 1 | n.d. | 2 | 0 | 0 | n.d. | 1 | n.d. | 1 |
| CONCA_4103 | 1 | 1 | 1 | 2 | n.d. | n.d. | n.d. | 0 | 1 | n.d. |
| AMAPA_1826 | 0 | 0 | 0 | 2 | n.d. | 1 | n.d. | n.d. | n.d. | 0 |
| SPIOL_0410 | 0 | 1 | 0 | 1 | n.d. | 2 | n.d. | 1 | 0 | 1 |
| KOCSC_1672 | 0 | 0 | 0 | n.d. | n.d. | 0 | n.d. | 0 | n.d. | 0 |
| SETIT_2080 | n.d. | 1 | 1 | 1 | n.d. | n.d. | n.d. | 0 | 1 | 0 |
| ALLCE_3035 | 1 | 1 | 1 | 2 | n.d. | 1 | n.d. | n.d. | 0 | 0 |
| DIGSA_5107 | 1 | 1 | 2 | 2 | n.d. | 1 | 0 | 0 | n.d. | 0 |
| AMAPA_4787 | 0 | 1 | n.d. | 1 | n.d. | 1 | n.d. | n.d. | 0 | 0 |
| SPIOL_0401 | 0 | 0 | 0 | 1 | n.d. | 0 | n.d. | 1 | 1 | 0 |
| SEDAL_8241 | 1 | 0 | 1 | n.d. | 2 | 1 | n.d. | 1 | 1 | 0 |
| CAMSA_6215 | 0 | 1 | 1 | 2 | n.d. | 1 | n.d. | 0 | n.d. | n.d. |
| CUCME_4756 | 0 | 0 | n.d. | 1 | n.d. | n.d. | 0 | 1 | 0 | 0 |
| ERATE_4149 | n.d. | 1 | 2 | 1 | n.d. | n.d. | n.d. | 0 | 0 | 0 |
| CANRO_3271 | 1 | 1 | 1 | 1 | n.d. | n.d. | n.d. | 1 | 0 | 1 |
| ERATE_2090 | n.d. | 0 | 2 | 2 | n.d. | n.d. | n.d. | 0 | 0 | 0 |
| ANDGE_6461 | 0 | 1 | 0 | 2 | n.d. | 1 | n.d. | n.d. | 0 | 0 |
| DIGSA_5109 | 1 | 0 | 1 | 1 | n.d. | 1 | n.d. | n.d. | 1 | 0 |
| ERATE_4824 | 0 | 1 | 0 | n.d. | n.d. | 2 | n.d. | 0 | 0 | 1 |
| AMAGR_5230 | 0 | 2 | 0 | 2 | n.d. | n.d. | n.d. | 0 | 1 | 0 |
| AMBTR_1537 | 0 | 0 | 1 | 1 | n.d. | 0 | n.d. | 0 | 0 | 1 |
| BRANA_6036 | 1 | 1 | n.d. | 1 | n.d. | 0 | n.d. | 0 | 0 | 0 |
| ROSHY_6783 | 1 | 1 | 1 | 1 | 0 | 0 | 1 | 0 | 1 | 1 |
| AMACR_2643 | 0 | 1 | 1 | 1 | n.d. | 0 | n.d. | 0 | 0 | 0 |
| TAROF_2111 | 0 | 2 | 0 | n.d. | 2 | 1 | 0 | 0 | 0 | 0 |
| CANRO_3976_var | n.d. | n.d. | n.d. | 0 | 1 | n.d. | n.d. | n.d. | n.d. | 1 |
| ERATE_4149_var | 0 | 0 | 1 | 1 | 1 | 1 | n.d. | n.d. | n.d. | n.d. |
| ALLCE_3035_var | n.d. | n.d. | 0 | 1 | 1 | n.d. | n.d. | n.d. | 0 | 1 |

TABLE 7-continued

| Transit Peptide | Tolerance score at 5 weeks in soybean | | | | | | | | | |
|---|---|---|---|---|---|---|---|---|---|---|
| | R1N171 | R1N473 | R1N533 | R2N30 | R2N40 | R2N40opt | R2N70 | R2N90 | R2N100 | R1N333 |
| TAROF_2111_var | 0 | 0 | 0 | 1 | 1 | 2 | n.d. | n.d. | 0 | n.d. |
| CUCME_4756_var | n.d. | n.d. | 2 | n.d. | 2 | n.d. | n.d. | n.d. | n.d. | n.d. |
| XANST_27_var | 1 | 1 | 2 | 1 | 2 | 1 | n.d. | n.d. | n.d. | n.d. |

The plantlets in the non-sprayed containers corresponding to constructs having a score of 2 were then transplanted at approximately seven weeks post-transformation and grown as R0 plants using standard methods known in the art. A selection of plantlets corresponding to non-tolerant scores of 0 and 1 were also grown to serve as negative controls. The R0 plants were grown in a greenhouse under long-day nursery conditions (18 hours of light at 80° F. then 6 hours of dark at 74° F.) for approximately four additional weeks. At eleven weeks post-transformation, the R0 plants were sprayed with two passes of the same herbicide solution described above for a final application rate of 20 g/ha. For each DNA construct tested, 15-30 individually transformed plants were tested. Herbicide injury ratings were visually 30% injury or less, good tolerance is 20% injury or less, and excellent tolerance was considered 10% injury or less. Scores were collected seven days after treatment and averaged for all plants for each DNA construct.

The results of the herbicide-tolerance application at eleven weeks to the R0 plants confirmed the low percent injury rating scores observed at five weeks. For the eleven-week evaluation, any injury rating of 30% or above was equivalent to non-transgenic soybean injury ratings. A few of the constructs stood out as providing very good tolerance to the herbicide application. For example, transit peptide ANDGE_6461 (SEQ ID NO:26) with R2N30 (SEQ ID NO:163) had only 7% injury. Data are provided in Table 8, where n.d. indicates the analysis was not conducted.

TABLE 8

| Transit Peptide | Tolerance score at 11 weeks in soybean | | | | | | | |
|---|---|---|---|---|---|---|---|---|
| | R1N171 | R1N473 | R1N533 | R2N30 | R2N40 | R2N40opt | R2N70 | R1N333 |
| APG6 | n.d. | 30 | n.d. | 17 | n.d. | 20 | n.d. | n.d. |
| 12G088600TP | n.d. | n.d. | 40 | n.d. | n.d. | n.d. | 30 | n.d. |
| CANRO_3976 | n.d. | n.d. | n.d. | n.d. | n.d. | n.d. | n.d. | n.d. |
| SENOB_8832 | n.d. | n.d. | n.d. | 25 | n.d. | n.d. | n.d. | n.d. |
| NICBE_5162 | n.d. | n.d. | n.d. | n.d. | n.d. | n.d. | n.d. | n.d. |
| BRANA_9788 | n.d. | 35 | n.d. | n.d. | n.d. | n.d. | n.d. | n.d. |
| ADADI_1600 | n.d. | n.d. | n.d. | 25 | n.d. | 30 | n.d. | n.d. |
| ROSHY_8873 | n.d. | n.d. | n.d. | 35 | n.d. | 30 | n.d. | 35 |
| XANST_27 | n.d. | n.d. | n.d. | 20 | n.d. | 25 | n.d. | 35 |
| CONCA_4103 | n.d. | n.d. | n.d. | 25 | n.d. | n.d. | n.d. | n.d. |
| AMAPA_1826 | n.d. | n.d. | n.d. | 25 | n.d. | n.d. | n.d. | n.d. |
| SPIOL_0410 | n.d. | n.d. | n.d. | n.d. | n.d. | 35 | n.d. | n.d. |
| KOCSC_1672 | n.d. | n.d. | n.d. | n.d. | n.d. | n.d. | n.d. | n.d. |
| SETIT_2080 | n.d. | n.d. | n.d. | 20 | n.d. | n.d. | n.d. | 35 |
| ALLCE_3035 | n.d. | n.d. | n.d. | 25 | n.d. | n.d. | n.d. | n.d. |
| DIGSA_5107 | 30 | 40 | 35 | 35 | n.d. | n.d. | n.d. | n.d. |
| AMAPA_4787 | n.d. | n.d. | n.d. | 25 | n.d. | n.d. | n.d. | n.d. |
| SPIOL_0401 | n.d. | n.d. | n.d. | 15 | n.d. | n.d. | n.d. | n.d. |
| SEDAL_8241 | n.d. | n.d. | n.d. | n.d. | 20 | n.d. | n.d. | n.d. |
| CAMSA_6215 | n.d. | n.d. | n.d. | 15 | n.d. | 20 | n.d. | n.d. |
| CUCME_4756 | n.d. | n.d. | n.d. | n.d. | n.d. | n.d. | n.d. | n.d. |
| ERATE_4149 | n.d. | n.d. | 35 | 25 | n.d. | n.d. | n.d. | n.d. |
| CANRO_3271 | n.d. | n.d. | n.d. | n.d. | n.d. | n.d. | n.d. | n.d. |
| ERATE_2090 | n.d. | n.d. | 35 | 15 | n.d. | n.d. | n.d. | n.d. |
| ANDGE_6461 | n.d. | n.d. | n.d. | 7 | n.d. | n.d. | n.d. | n.d. |
| DIGSA_5109 | n.d. | n.d. | n.d. | n.d. | n.d. | n.d. | n.d. | n.d. |
| ERATE_4824 | n.d. | n.d. | n.d. | n.d. | n.d. | 25 | n.d. | n.d. |
| AMAGR_5230 | n.d. | 35 | n.d. | 35 | n.d. | n.d. | n.d. | n.d. |
| AMBTR_1537 | n.d. | n.d. | n.d. | n.d. | n.d. | n.d. | n.d. | n.d. |
| BRANA_6036 | n.d. | n.d. | n.d. | 25 | n.d. | n.d. | n.d. | n.d. |
| ROSHY_6783 | n.d. | n.d. | n.d. | n.d. | n.d. | n.d. | n.d. | n.d. |
| AMACR_2643 | n.d. | n.d. | n.d. | n.d. | n.d. | n.d. | n.d. | n.d. |
| TAROF_2111 | n.d. | 40 | n.d. | n.d. | 20 | n.d. | n.d. | n.d. |
| CANRO_3976_var | n.d. | n.d. | n.d. | n.d. | n.d. | n.d. | n.d. | n.d. |
| ERATE_4149_var | n.d. | n.d. | n.d. | n.d. | n.d. | n.d. | n.d. | n.d. |
| ALLCE_3035_var | n.d. | n.d. | n.d. | 25 | n.d. | n.d. | n.d. | n.d. |
| TAROF_2111_var | n.d. | n.d. | n.d. | n.d. | n.d. | 25 | n.d. | n.d. |
| CUCME_4756_var | n.d. | n.d. | 35 | n.d. | 25 | n.d. | n.d. | n.d. |
| XANST_27_var | n.d. | 30 | 35 | n.d. | n.d. | n.d. | n.d. | n.d. | scored based on the amount of above ground tissue injury with 0% being no visible injury and 100% being complete death of the plant. Non-transgenic control plants scored injury ratings of greater than 30%. Marginal tolerance was The genes encoding the HemG protoporphyrinogen oxidase H_N90 was operably linked to 44 different transit peptides and cloned into a base plant transformation vector as described in Example 3. This permitted the side-by-side comparison of different transit peptides using the same promoter, herbicide-tolerance protein, and 3'UTR elements in every DNA construct. These plant transformation vectors were used to transform soybean excised embryos (germplasm AG3555) using *A. tumefaciens* and standard methods known in the art. Four hundred to 4,5000 individual transgenic plants were tested for each construct. A sterile PPO herbicide solution was used for herbicide-tolerance testing. The herbicide solution consisted of 0.3 g of S-3100 in crop oil concentrate (5.0 mL) and 495 mL of deionized water.

At five weeks post-transformation, plants were sprayed with two passes of the sterile PPO herbicide solution for a final application rate of 20 g/ha. For each DNA construct tested, 400 to 4,5000 replications were done. The treated plantlets then received at least 15 hours of light exposure post spray each day for four days. At the end of day four post-application of S-3100, the treated plantlets were scored for percentage of relative pass frequency (defined as the percentage of all the individual plants for a DNA construct that visually display tolerance to the herbicide application relative to control transgenic plants sprayed with a surfactant only solution.). Plantlets in the non-sprayed containers were transplanted at approximately seven weeks post-transformation and grown as R0 plants. The R0 plants were grown in a greenhouse under long-day nursery conditions (18 hours of light at 80° F. then 6 hours of dark at 74° F.) for approximately four additional weeks. At eleven to twelve weeks post-transformation, the R0 plants were sprayed with two passes of the same herbicide solution described above at a 20 g/ha rate. For each DNA construct tested, 15-45 replications were done. Herbicide injury ratings were collected three to seven days after treatment. For the eleven-week evaluation, the percentage of plants at or below 10% injury and at or below 20% injury was recorded. At the herbicide application rates tested, transgenic plants expressing the protoporphyrinogen oxidase H_N90 without any operably linked transit peptide (PPO Control), produced a zero plants with 20% injury or less. Several of the transit peptides operably linked to the H_N90 herbicide tolerance protein stood out as providing excellent or very good tolerance to the herbicide application. For example, at the eleven-week spray over 50% of plants had an injury score at or below 20% when expressing H-N90 operably linked to ALLCE_3035 (57%), KOCSC_9516 (59%), CAMSA_6215 (69%), ROSHY_3269 (70%), ADADI_0544 (75%), CUCME_3420 (80%), SPIOL_1551 (85%), CUCME_4756 (89%), or CONCA_3910 (90%). Data are provided in Table 9.

TABLE 9

| | Tolerance score at 5 and 11 weeks in soybean | | |
| --- | --- | --- | --- |
| Transit Peptide | 5 week spray relative pass frequency | 11 week spray % plants at ≤10% | 11 week spray % plants at ≤20% |
| CUCME_4756 | 27% | 0% | 0% |
| CANRO_3271 | 23% | 0% | 0% |
| DIGSA_5109 | 24% | 0% | 0% |
| CAMSA_6215 | 68% | 62% | 69% |
| AMACR_2381 | 30% | 0% | 0% |
| ROSHY_3269 | 54% | 25% | 70% |
| CUCME_3420 | 51% | 20% | 80% |
| ADADI_0544 | 30% | 20% | 75% |
| SPIOL_1551 | 40% | 70% | 85% |
| NICBE_5162 | 9% | 0% | 0% |
| CUCME_4756 | 28% | 26% | 89% |
| BRANA_9788 | 11% | 0% | 0% |
| SPIOL_0410 | 18% | 0% | 0% |
| XANST_0027 | 22% | 0% | 0% |

TABLE 9-continued

| | Tolerance score at 5 and 11 weeks in soybean | | |
| --- | --- | --- | --- |
| Transit Peptide | 5 week spray relative pass frequency | 11 week spray % plants at ≤10% | 11 week spray % plants at ≤20% |
| SETIT_2080 | 3% | 0% | 0% |
| ERATE_4149 | 3% | 0% | 0% |
| TAROF_2111 | 3% | 0% | 0% |
| CONCA_4103 | 26% | 0% | 0% |
| CANRO_3976 | 6% | 0% | 0% |
| AMACR_2643 | 3% | 0% | 0% |
| SPIOL_0401 | 6% | 0% | 0% |
| ADADI_1600 | 30% | 0% | 0% |
| ANDGE_6461 | 47% | 0% | 0% |
| ERATE_2090 | 11% | 0% | 0% |
| 12G088600TP | 13% | 0% | 0% |
| ALLCE_3035 | 5% | 0% | 0% |
| SENOB_8832 | 52% | 0% | 0% |
| TAROF_2111 | 66% | 0% | 0% |
| ROSHY_8873 | 10% | 0% | 0% |
| KOCSC_1672 | 25% | 12% | 24% |
| AMBTR_1537 | 2% | 0% | 0% |
| AMAPA_1826 | 7% | 0% | 0% |
| BRANA_6036 | 5% | 0% | 0% |
| CONCA_3910 | 40% | 60% | 90% |
| AMAPA_4787 | 6% | 0% | 0% |
| ROSHY_6783 | 0% | 0% | 0% |
| ALLCE_3035 | 26% | 35% | 57% |
| ERATE_4824 | 12% | 0% | 0% |
| AMAGR_5230 | 2% | 0% | 0% |
| SEDAL_8241 | 5% | 0% | 0% |
| DIGSA_5107 | 11% | 0% | 0% |
| KOCSC_9516 | 27% | 16% | 59% |
| XANST_0027_var | 3% | 0% | 0% |
| APG6 | 60% | 30% | 63% |
| None - PPO Control | 1% | 0% | 0% |

Example 5: Transit Peptide and Protoporphyrinogen Oxidase Testing in Corn

Transit peptides operably linked to protoporphyrinogen oxidases were tested in transgenic corn plants for PPO herbicide-tolerance. Plant transformation vectors were constructed comprising a DNA construct comprising a recombinant DNA molecule optimized for monocot expression and encoding a protoporphyrinogen oxidase operably linked to a transit peptide. The plant transformation vectors were then used to transform corn, and the regenerated plants were assessed for their sensitivity to a PPO herbicide.

The genes encoding the protoporphyrinogen oxidase H_N90 was operably linked to fourteen different transit peptides and cloned into base plant transformation vectors with a variety of promoters and 3' UTR elements. The use of the same protoporphyrinogen oxidase in each DNA construct permitted the side-by-side comparison of different transit peptides. A plant transformation vector was also produced with the protoporphyrinogen oxidase H_N90 without any operably linked transit peptide (PPO Control). These plant transformation vectors were used to transform corn using *A. tumefaciens* and standard methods known in the art. Regenerated R0 plants were grown and then screened to access the degree of tolerance exhibited to applications of S-3100 (40 to 80 g/ha rate) at approximately 10-14 weeks post-transformation. Tolerance was visually accessed 3 to 10 days following application of the herbicide. Sprayed plants are scored on the percent of injury to the entire above-ground part of the plant following herbicide treatment, relative to controls. For each DNA construct tested, 10 to 120 plants were tested and the injury rate was averaged. The percentage of R0 plants passing at a 20% injury or less score was recorded. Any DNA construct producing transgenic plants with 50% or more having 20% or less injury was considered a highly tolerant DNA construct. Any DNA construct producing transgenic plants with 20% or more having 20% or less injury was considered a tolerant DNA construct. At the herbicide application rates tested (S-3100 at 40 to 80 g/ha), transgenic plants expressing the protoporphyrinogen oxidase H_N90 without any operably linked transit peptide (PPO Control), with XANST_27 or with ALLCE_3035 produced zero plants with 20% injury or less. However, several of the transit peptides produced transgenic plants expressing the protoporphyrinogen oxidase H_N90 that were highly tolerant or tolerant: ADADI_0544 (41%), ANDGE_6461 (60%), CAMSA_6215 (60% and 41% pass), CONCA_3910 (36% and 45%), ROSHY_3269 (64% and 74%), SPIOL_1551 (50% and 55%), SETIT_9796 (55%). Data are provided in Table 10.

TABLE 10

Tolerance score in corn

| Promoter | Transit Peptide | 3'UTR | Percent with 20% or less injury |
|---|---|---|---|
| A | SETIT_9796 | E | 55% |
| A | ACAOS_3432 | E | 37% |
| A | ADADI_0544 | E | 41% |
| A | TAROF_9570 | E | 29% |
| A | ALLCE_6618 | E | 31% |
| D | ROSHY_3269 | H | 74% |
| B | ROSHY_3269 | F | 64% |
| D | CONCA_3910 | H | 36% |
| B | CONCA_3910 | F | 45% |
| D | SPIOL_1551 | H | 55% |
| B | SPIOL_1551 | F | 50% |
| D | CAMSA_6215 | H | 41% |
| B | CAMSA_6215 | F | 60% |
| B | ANDGE_6461 | F | 60% |
| B | ADADI_1600 | F | 11% |
| D | XANST_27_var | H | 0% |
| C | XANST_27_var | G | 0% |
| A | ALLCE_3035 | E | 0% |
| B | ALLCE_3035 | F | 0% |
| C | None - PPO Control | G | 0% |

Example 6: Transit Peptide and Protoporphyrinogen Oxidase Testing in Cotton

Transit peptides operably linked to protoporphyrinogen oxidases were tested in transgenic cotton plants for PPO herbicide-tolerance. Plant transformation vectors were constructed comprising a DNA construct comprising a recombinant DNA molecule optimized for dicot expression and encoding a protoporphyrinogen oxidase operably linked to a transit peptide. The plant transformation vectors were then used to transform cotton, and the regenerated plants were assessed for their sensitivity to a PPO herbicide.

The genes encoding the protoporphyrinogen oxidases H_N20 and H_N90 were operably linked to four different transit peptides and cloned into a base plant transformation vector as described in Example 3. This permitted the side-by-side comparison of different transit peptides using the same promoter and 3'UTR elements in every DNA construct. These plant transformation vectors were used to transform cotton using *A. tumefaciens* and standard methods known in the art. Regenerated plants were grown and then screened to access the degree of tolerance exhibited to applications of S-3100 (20 g/ha rate) at approximately 11 to 12 weeks post-transformation. Tolerance was visually accessed 3 to 10 days following application of the herbicide. Sprayed plants are scored on the percent of injury to the entire above-ground part of the plant following herbicide treatment, relative to controls. For each DNA construct tested, 10-15 replications were tested and the average injury rate was averaged. An average injury score of 50% or less was considered a highly herbicide-tolerant DNA construct, and an average injury score greater than 50% but less than 80% was considered a marginally herbicide-tolerant DNA construct. An average injury score at or above 80% was considered indistinguishable from control plants. Transgenic cotton plants expressing the protoporphyrinogen oxidase H_N90 operably linked to CAMSA_6215 produced plants that were highly herbicide-tolerant with an average injury score of 38%. Transgenic cotton plants expressing the protoporphyrinogen oxidase H_N90 operably linked to AMAPA_4787 produced plants that were marginally herbicide-tolerant with an average injury score of 63%.

What is claimed is:

1. A recombinant DNA molecule comprising a DNA sequence encoding a transit peptide operably linked to a DNA sequence encoding a heterologous protoporphyrinogen oxidase, wherein the transit peptide comprises an amino acid sequence having at least 97 percent identity to SEQ ID NO:265.

2. The recombinant DNA molecule of claim 1, wherein the heterologous protoporphyrinogen oxidase has herbicide insensitive protoporphyrinogen oxidase activity.

3. The recombinant DNA molecule of claim 1, wherein the heterologous protoporphyrinogen oxidase comprises an amino acid sequence having at least 97 percent identity to a sequence selected from the group consisting of SEQ ID NOs: 100-119, SEQ ID NOs: 163-182, and SEQ ID NOs: 224-228.

4. The recombinant DNA molecule of claim 1, wherein the DNA sequence encoding the transit peptide comprises a nucleic acid sequence having at least 97 percent identity to SEQ ID NO:296.

5. The recombinant DNA molecule of claim 1, wherein the DNA sequence encoding the heterologous protoporphyrinogen oxidase comprises a nucleic acid sequence having at least 97 percent identity to a sequence selected from the group consisting of SEQ ID NOs: 121-162, SEQ ID NOs: 183-223, and SEQ ID NOs: 229-235.

6. The recombinant DNA molecule of claim 1, further comprising a heterologous promoter operably linked to the DNA sequence encoding the transit peptide.

7. A DNA construct comprising the DNA molecule of claim 1, wherein said DNA molecule is operably linked to a heterologous promoter.

8. The DNA construct of claim 7, wherein the heterologous protoporphyrinogen oxidase has herbicide-insensitive protoporphyrinogen oxidase activity.

9. The DNA construct of claim 7, wherein the heterologous protoporphyrinogen oxidase comprises an amino acid sequence selected from the group consisting of SEQ ID NOs: 100-119, SEQ ID NOs: 163-182, and SEQ ID NOs: 224-228.

10. A transgenic plant, seed, or cell comprising the DNA construct of claim 7.

11. A transgenic plant, seed, or cell comprising the recombinant DNA molecule of claim 1.

12. The transgenic plant, seed, or cell of claim 11, wherein the plant, seed, or cell is tolerant to at least one PPO inhibiting herbicide.

13. The transgenic plant, seed, or cell of claim 12, wherein the PPO inhibiting herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, tiafenacil, 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione, and S-3100.

14. The transgenic plant, seed, or cell of claim 12, wherein the transgenic plant, seed, or cell is tolerant to at least one additional herbicide.

15. A method for producing an herbicide tolerant plant comprising the steps of:
   a) transforming a plant cell with the recombinant DNA molecule of claim 1; and
   b) regenerating therefrom an herbicide tolerant plant that comprises the DNA molecule.

16. The method of claim 15, further comprising the step of crossing the regenerated plant with itself or with a second plant to produce one or more progeny plants.

17. The method of claim 15, wherein the heterologous protoporphyrinogen oxidase comprises an amino acid sequence selected from the group consisting of SEQ ID NOs: 100-119, SEQ ID NOs: 163-182, and SEQ ID NOs: 224-228.

18. The method of claim 16, further comprising the step of selecting a progeny plant that is tolerant to at least one PPO inhibiting herbicide.

19. The method of claim 17, wherein the PPO inhibiting herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, tiafenacil, 1,5-dimethyl-6-thioxo-3-(2,2,7-trif-luoro-3,4-dihydro-3-oxo-4-prop-2-ynyl-2H-1,4-benzo-xazin-6-yl)-1,3,5-triazinane-2,4-dione, and S-3100.

20. A method for controlling or preventing weed growth in a plant growth area comprising applying an effective amount of at least one PPO inhibiting herbicide to a plant growth area that comprises the transgenic plant or seed of claim 12, wherein the transgenic plant or seed is tolerant to the PPO inhibiting herbicide.

21. The method of claim 20, wherein the PPO inhibiting herbicide is selected from the group consisting of: acifluo-rfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, tiafenacil, 1,5-dimethyl-6-thioxo-3-(2,2,7-trif-luoro-3,4-dihydro-3-oxo-4-prop-2-ynyl-2H-1,4-benzo-xazin-6-yl)-1,3,5-triazinane-2,4-dione, and S-3100.

22. A method for controlling the growth of herbicide tolerant weeds comprising:
  a) cultivating in a plant growth area the plant or seed of claim 14; and
  b) applying a PPO inhibiting herbicide and at least one additional herbicide to the plant growth area, wherein the plant or seed is tolerant to the PPO inhibiting herbicide and the at least one additional herbicide.

23. The method of claim 22, wherein the PPO inhibiting herbicide is selected from the group consisting of acifluo-rfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, tiafenacil, 1,5-dimethyl-6-thioxo-3-(2,2,7-trif-luoro-3,4-dihydro-3-oxo-4-prop-2-ynyl-2H-1,4-benzo-xazin-6-yl)-1,3,5-triazinane-2,4-dione, and S-3100.

24. The method of claim 22, wherein the at least one additional herbicide is selected from the group consisting of: an ACCase inhibitor, an ALS inhibitor, an EPSPS inhibitor, a synthetic auxin, a photosynthesis inhibitor, a glutamine synthetase inhibitor, a HPPD inhibitor, and a long-chain fatty acid inhibitor.

25. The method of claim 24, wherein the ACCase inhibitor is an aryloxyphenoxy propionate or a cyclohexanedione;

the ALS inhibitor is a sulfonylurea, imidazolinone, triazo-lopyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthetase inhibitor is glufosinate; the HPPD inhibitor is an isoxazole, a pyrazolone, or a triketone; or the very long-chain fatty acid inhibitor is a chloroacetamide, an oxyacetamide, or a pyra-zole.

26. A recombinant DNA molecule comprising a DNA sequence encoding a transit peptide operably linked to a DNA sequence encoding a heterologous protoporphyrino-gen oxidase, wherein the transit peptide comprises an amino acid sequence having at least 95 percent identity to SEQ ID NO:265.

27. The recombinant DNA molecule of claim 26, wherein the heterologous protoporphyrinogen oxidase has herbicide insensitive protoporphyrinogen oxidase activity.

28. The recombinant DNA molecule of claim 26, wherein the heterologous protoporphyrinogen oxidase comprises an amino acid sequence having at least 95 percent identity to a sequence selected from the group consisting of SEQ ID NOs: 100-119, SEQ ID NOs: 163-182, and SEQ ID NOs: 224-228.

29. The recombinant DNA molecule of claim 26, wherein the DNA sequence encoding the transit peptide comprises a nucleic acid sequence having at least 95 percent identity to SEQ ID NO:296.

30. The recombinant DNA molecule of claim 26, wherein the DNA sequence encoding the heterologous herbicide protoporphyrinogen oxidase comprises a nucleic acid sequence having at least 95 percent identity to a sequence selected from the group consisting of SEQ ID NOs: 121-162, SEQ ID NOs: 183-223, and SEQ ID NOs: 229-235.

31. The recombinant DNA molecule of claim 26, further comprising a heterologous promoter operably linked to the DNA sequence encoding the transit peptide.

* * * * *